United States Patent
Steeneck et al.

(10) Patent No.: US 11,078,168 B2
(45) Date of Patent: Aug. 3, 2021

(54) SUBSTITUTED N-HYDROXYAMIDINOHETEROCYCLES AS MODULATORS OF INDOLEAMINE 2,3-DIOXYGENASE

(71) Applicant: PHENEX DISCOVERY VERWALTUNGS-GMBH, Heidelberg (DE)

(72) Inventors: Christoph Steeneck, Heidelberg (DE); Olaf Kinzel, Heidelberg (DE); Simon Anderhub, Basel (CH); Martin Hornberger, Ladenburg (CH); Gerald Kleymann, Bad Salzuflen (DE); Thomas Hoffmann, Speyer (DE)

(73) Assignee: Phenex Discovery Verwaltungs-GmbH, Heidelberg (DE)

( * ) Notice: Subject to any disclaimer, the term of this patent is extended or adjusted under 35 U.S.C. 154(b) by 0 days.

(21) Appl. No.: 16/346,505

(22) PCT Filed: Nov. 3, 2017

(86) PCT No.: PCT/EP2017/078187
§ 371 (c)(1),
(2) Date: Apr. 30, 2019

(87) PCT Pub. No.: WO2018/083241
PCT Pub. Date: May 11, 2018

(65) Prior Publication Data
US 2019/0292160 A1    Sep. 26, 2019

(30) Foreign Application Priority Data

Nov. 3, 2016  (EP) ..................... 16002334
Aug. 31, 2017 (EP) ..................... 17001467

(51) Int. Cl.
| C07D 271/08 | (2006.01) |
| C07D 417/12 | (2006.01) |
| A61K 31/4245 | (2006.01) |
| C07D 413/12 | (2006.01) |
| A61K 45/06 | (2006.01) |

(52) U.S. Cl.
CPC ......... C07D 271/08 (2013.01); C07D 413/12 (2013.01); C07D 417/12 (2013.01); *A61K 45/06* (2013.01)

(58) Field of Classification Search
CPC . C07D 271/08; C07D 417/12; A61K 31/4245
See application file for complete search history.

(56) References Cited

U.S. PATENT DOCUMENTS

2018/0362482 A1† 12/2018 Han
2019/0152932 A1†  5/2019 Wang
2019/0169140 A1†  6/2019 Zhang

FOREIGN PATENT DOCUMENTS

| CN | 105646389 A | 6/2016 |
| CN | 106565696  * | 4/2017 |
| CN | 106565696 A | 4/2017 |
| EP | 3196197 A1 | 7/2017 |
| EP | 3495354 A1 | 6/2019 |
| WO | 2006/122150 A1 | 11/2006 |
| WO | 2008/036653 A2 | 3/2008 |
| WO | 2008/058178 A1 | 5/2008 |
| WO | 2010/005958 A2 | 1/2010 |
| WO | 2014066834 A1 | 5/2014 |
| WO | 2016041489 A1 | 3/2016 |
| WO | WO2017106062  * | 6/2017 |

OTHER PUBLICATIONS

'Cancer Prevention Overview', http://www.cancer.gov/cancertopics/pdq/prevention/overview/patient, accessed Nov. 14, 2012 (Year: 2012).*
English machine translation of CN 106565696, Apr. 2017, p. 1-58 (Year: 2017).*
International Search Report and Written Opinion dated Dec. 12, 2017, issued in corresponding International Application No. PCT/EP2017/078187, filed Nov. 3, 2017, 11 pages.
Peterson, A.C., et al., "Evaluation of Functionalized Tryptophan Derivatives and Related Compounds as Competitive Inhibitors of Indoleamine 2,3-Dioxygenase," Medicinal Chemistry Research 3(8):531-544, Jan. 1994.
Communication pursuant to Rule 114(2) dated Feb. 18, 2020, issued in corresponding European Application No. 17791708.5, filed Nov. 3, 2017, 1 page.
Observations of Opponent, dated Feb. 20, 2020, issued in corresponding European Application No. 17791708.5, filed Nov. 3, 2017, 21 pages.
U.S. Appl. No. 62/267,335 published by WIPO with the publication of WO2017106062 on Jun. 22, 2017 at https://patentscope.wipo.int/search/docs2/pct/     WO2017106062/pdf/zMa7mrDxFNla5Ynuv2tpilvNh75hT92kZnUpsdEkT6yEgBmHo_u_ASHBkxyhUBTEron1P7w8uS84xx
msoXWxpscZ6kmHLEZSJ4lWeDH7msS1YX91Q-7HNEDF1lZVAuEM?docId=id00000038273107.†

(Continued)

*Primary Examiner* — Karen Cheng
(74) *Attorney, Agent, or Firm* — Christensen, O'Connor Johnson Kindness PLLC

(57) ABSTRACT

The invention provides modulators of indoleamine 2,3-dioxygenase (IDO1) and their use in the prophylaxis and/or treatment of IDO1-mediated diseases. Specifically, the present invention provides compounds according to Formula (I) an enantiomer, diastereomer, tautomer or pharmaceutically acceptable salt thereof.

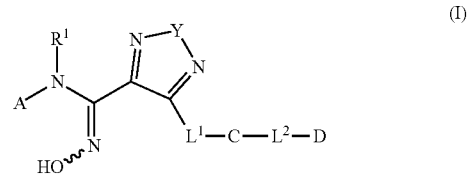

(I)

17 Claims, No Drawings

(56) References Cited

OTHER PUBLICATIONS

Chinese patent application CN201610631523.5 published by WIPO with the publication of WO2018024208 on Feb. 8, 2018 at https://patentscope.wipo.int/search/docs2/pct/WO2018024208/pdf/3g0plGatPn5oEX20Z5sPWvbZO-vB0Rpp9hlSRfCr6VskXaw7li7VN8IOCCOZIEIwoeLm7tR9QDzTFS4FpJfeUsLa58_1FStJpdG7wuunoemaq9Txw8wKD8-7yKO9qJ45?docId=id00000041171979.†

\* cited by examiner
† cited by third party

SUBSTITUTED N-HYDROXYAMIDINOHETEROCYCLES AS MODULATORS OF INDOLEAMINE 2,3-DIOXYGENASE

The present invention relates to novel compounds which act as modulators of indoleamine 2,3-dioxygenase (IDO1) and to the use of said compounds in the prophylaxis and/or treatment of diseases or conditions mediated by indoleamine 2,3-dioxygenase. The invention further relates to pharmaceutical compositions comprising the novel compounds.

Tryptophan is an essential amino acid and naturally serves as a building block for proteins. The majority of adult Tryptophan intake is not utilized for protein synthesis though, but channeled into two conversion pathways. The first pathway leading to the production of Serotonine degrades approximately 1% of ingested Tryptophan, whereas the majority of ~90% of Tryptophan fuels the so called Kynurenine pathway (Le Floc'h et al.; Amino Acids. 2011; 41(5):1195-205).

The Kynurenine pathway of Tryptophan degradation is initialized by a specific set of enzymes, including Indoleamine 2,3-dioxygenase 1 (IDO1) and Tryptophan 2,3-dioxygenase (TDO2). The product of this reaction, N-Formylkynurenine is subsequently converted to Kynurenine which can be further metabolized to such diverse products as Xanthurenic acid, Anthranilic acid or Nicotinamide to name a few (Stone, Darlington; Nat Rev Drug Discov. 2002; 1(8):609-20).

Under physiological conditions the expression of TDO is restricted to the liver (Bertazzo et al.; Biochim Biophys Acta. 2001; 15;1527(3):167-75) and the brain (Miller et al.; Neurobiol Dis. 2004; 15(3):618-29). IDO1 in contrast is found in a variety of tissues such as lung, digestive tract, uterus and secondary lymphoid organs (Théate et al.; Cancer Immunol Res. 2015; 3(2):161-72) and is readily (further) induced by pro inflammatory cytokines (Taylor, Feng; FASEB J. 1991; 5(11):2516-22 1991).

Initially, IDO1 has been implicated in a protective role in fetal rejection. Mice, treated with the IDO1 inhibitor 1-Methyl-Tryptophan lost their allogeneic concepti in a T cell dependent manner (Munn et al.; Science. 1998; 281 (5380):1191-3).

It was then conceived that IDO1 creates an immunosuppressive environment by catabolizing Tryptophan, thereby locally depleting this amino acid and creating immune privilege sites. Tryptophan depletion is most likely sensed through the General Control Nonderepressable Kinase 2 (GCN2) and leads to activation of the integrated stress response of cells (Munn et al.; Immunity. 2005; 22(5):633-42) with consecutive inhibition of T cell proliferation (Munn et al.; J Exp Med. 1999; 189(9):1363-72). Additionally, a low Tryptophan environment also sensitizes activated T cells to apoptosis via Fas (Lee et al.; Immunology. 2002; 107(4):452-60). More recently, the mechanism of how IDO1 can lead to immune suppression has been expanded, focusing on the catabolites of Tryptophan enzymatic conversion by IDO1, collectively called Kynurenines. It has been demonstrated that Kynurenine, 3-Hydroxykynurenine, 3-Hydroxyanthranilic acid and Quinolinic acid led to dose dependent inhibition of T cell proliferation (Terness et al.; J Exp Med. 2002; 196(4):447-57). In part, this may be due to cell type specific apoptosis of Thymocytes in response to incubation with the aforementioned Tryptophan metabolites (Fallarino et al.; Cell Death Differ. 2002; 9(10):1069-77).

The immune suppression observed concurrently with IDO1 expression is also associated with an increase in T cells displaying a regulatory phenotype (Treg). Treg cells are important to maintain immune homeostasis and induce immune tolerance to avoid inappropriate immune response as is the case in autoimmune disease (Sakaguchi et al.; Eur J Immunol. 2007; 37 Suppl 1:S116-23). In mice, expression of the transcription factor FOXP3 is an important marker for regulatory T cells (Fontenot et al.; Nat Immunol. 2003; 4(4):330-6) and co-cultivation of murine naïve CD4+ T cells with IDO positive Dendritic cells led to a remarkable increase in FOXP3 expression of the CD4+ population. This polarization could be mimicked by incubation of naïve CD4+ T cells in low Tryptophan medium supplemented with Kynurenines and was shown to be dependent on GCN2 (Fallarino et al.; Transpl Immunol. 2006; 17(1):58-60). In humans, AML patients with elevated levels of IDO1 also displayed an increase in circulating Treg cells. Analogous to the situation in mice, human CD3+ cells were polarized towards a regulatory phenotype in an IDO1 dependent manner when co-cultivated with IDO1 positive cells derived from AML patients (Curti et al.; Blood. 2007; 109(7):2871-7).

Several Kynurenines such as Kynurenine itself, 3-Hydroxykynurenine and Kynurenic acid also serve as ligands for the Aryl Hydrocarbon Receptor (AHR) albeit with differentially reported efficacies (DiNatale et al.; Toxicol Sci. 2010; 115(1):89-97, Mezrich et al.; J Immunol® 2010; 185(6):3190-8). This is of particular interest because firstly, the AHR has been implicated in the transcriptional regulation of IDO1 via a self-sustaining autocrine feed-forward loop with the AHR acting either directly on IDO1 transcription (Li et al.; J Immunol® 2016; 197(3):962-70) or with IL-6 as mediator (Litzenburger et al.; Oncotarget. 2014; 5(4):1038-51). Secondly, because the polarization of naïve CD4+ T cells towards Treg cells by Kynurenines is dependent on the AHR (Kimura et al.; Proc Natl Acad Sci USA. 2008 Jul. 15; 105(28):9721-6, Mezrich et al.; J Immunol, 2010; 185(6):3190-8).

Whether the depletion of Tryptophan or the generation of Kynurenines or the combined action of both is the key in creating an immune suppressive environment needs to be further investigated. The net result though, is a key factor not only for immune homeostasis in healthy individuals but also for how tumors can escape immune surveillance.

The importance of IDO1 for cancer development is supported by several lines of evidence. IDO1 has been detected in most human tumors, such as prostate, pancreas, lung, ovarian, colorectal cancer, melanoma and leukemia (Uyttenhove et al.; Nat Med. 2003;9(10):1269-74; Hanagiri et al.; J Clin Cell Immunol 2014, 5:5, Okamoto et al.; Clin Cancer Res. 2005; 11(16):6030-9; Ferdinande et al.; Br J Cancer. 2012; 106(1):141-7, Brody et al.; Cell Cycle. 2009; 8(12):1930-4, Chamuleau et al.; Haematologica. 2008; 93(12):1894-8, Theate et al.; Cancer Immunol Res. 2015; 3(2):161-72). Interestingly, IDO1 positive cells were also often found in immune cells in the tumor stroma and adjoining tumor draining lymph nodes (Astigiano et al.; Neoplasia. 2005; 7(4):390-6, Chen et al.; Breast Cancer Res. 2014; 16(4):410, Polak et al.; Br J Cancer. 2007; 96(12): 1879-87, Theate et al.; Cancer Immunol Res. 2015; 3(2): 161-72). A negative correlation of IDO1 expression either in tumor or in stromal cells with markers of disease progression has been observed in most of these cases.

Apart from these correlative analysis, elegant studies using mouse models underpinned the importance of IDO1 in tumor immune escape. When immunogenic mouse tumor cells lacking IDO1 were injected into immune competent mice, no tumor growth was observed. In contrast, if the cells constitutively expressed IDO1, tumors grew as expected. Pharmacologic inhibition of IDO1 in turn, resulted in a marked reduction of tumor outgrowth. As indicated above, this effect was dependent on the hosts' immune system, as immune compromised mice injected with the IDO1 positive and negative cell lines developed tumors to the same extent. Also, lower numbers of CD8+ T cells were found in mice injected with IDO1 positive cells in comparison to mice injected with IDO1 negative cells (Uyttenhove et al.; Nat Med. 2003;9(10):1269-74).

Although tumor derived IDO1 is a decisive factor for immune escape, research also investigated the role of IDO1 in immune cells. Munn et al. found a subset of plasmacytoid Dendritic cells in Tumor draining lymph nodes expressing IDO1. Although these cells comprised less than 1% of all lymph node cells they acted as potent and dominant suppressors of T cell proliferation (Munn et al.; J Clin Invest. 2004; 114(2): 280-290). The relative contribution of IDO1 from immune cells versus tumor derived IDO1 is still under debate. Koblish et al. observed that pharmacologic inhibition of IDO1 reduced tumor size, when IDO1 positive tumor cells were transplanted into immune competent IDO1−/− mice (Koblish et al.; Mol Cancer Ther. 2010; 9(2):489-98). In contrast, Banerjee et al. reported no effect on tumor size when using a syngeneic mouse tumor model in IDO1 negative mice and administration of an IDO1 inhibitor (Banerjee et al.; Oncogene. 2008; 27(20):2851-7). Both studies though, were able to demonstrate the efficacy of IDO inhibitors in preclinical mouse models as single agents. Moreover, synergistic or additive effects were observed when IDO1 inhibitors where used in combination with chemotherapeutics, irradiation, tumor vaccines or immune checkpoint inhibitors (Muller et al.; Nat Med. 2005; 11(3): 312-9, Hou et al.; Cancer Res. 2007 Jan. 15; 67(2):792-801, Sharma et al.; Blood. 2009 Jun. 11; 113(24):6102-11, Spranger et al.; J Immunother Cancer. 2014; 2:3)

The studies referenced herein did not report any potent toxicity of IDO1 inhibition and it is of interest to note that IDO knockout mice are viable and exhibit no major abnormal phenotype apart from defects in acquired tolerance (Mellor et al.; J Immunol. 2003; 171(4):1652-5). Therefore it seems unlikely that IDO1 inhibition in humans will encounter profound dose limiting toxicities.

Apart from its relevance for tumor immune evasion, IDO1 is implicated in a plethora of other medical conditions.

Throughout HIV disease progression, an altered Th17/Treg balance has been observed, favoring the latter in later stages. Favre et al. were able to demonstrate a crucial role for the Kynurenine 3-Hydroxykynurenine in this process and it is therefore hypothesized that patients with HIV may benefit from IDO1 inhibition together with antiretroviral therapy (Favre et al.; Sci Transl Med. 2010 May 19; 2(32): 32ra36.).

IDO1 also seems to be involved in disorders of the central nervous system because its downstream products 3-Hydroxykynurenine and quinolinic acid act as neurotoxins (Okuda et al.; J Neurochem. 1998; 70(1):299-307, Schwarcz et al.; Science. 1983; 219(4582):316-8). Thereby, IDO1 is also implicated in the disease development of Huntington's disease, Amyotrophic lateral sclerosis, Alzheimer's disease, Parkinson's disease and Schizophrenia (Thevandavakkam et al.; CNS Neurol Disord Drug Targets. 2010; 9(6):791-800; Chen et al.; Neurotox Res. 2010; 18(2):132-42; Guillemin et al.; Neuropathol Appl Neurobiol. 2005; 31(4):395-404; Lim et al.; Prog Neurobiol. 2016;pii: S0301-0082(15)30055-1, Kegel et al.; Int J Tryptophan Res. 2014; 7: 15-22).

IDO1 inhibitors may therefore be of high potential value for the treatment of HIV and CNS disorders and the reported preclinical data on efficacy against tumors either alone or in combination with other drugs validate the use of IDO1 inhibitors as a treatment option for antineoplastic therapies.

Compounds acting as IDO1 inhibitors are known in the art. WO 2006/122150 discloses compounds with a N-hydroxyamidino motif as potential modulators of IDO1. The efficacy of compounds having said motif is demonstrated e.g. in WO 2008/036642, WO 2008/036643, WO 2008/036652, WO 2008/036653 and WO 2008/05178.

The compounds detailed herein and compositions thereof as well as the methods described will serve to meet the future need for potent IDO1 inhibitors.

It is the object of the present invention to provide novel compounds which are suitable as potent IDO1 inhibitors.

Said object is solved by compounds according to formula (I)

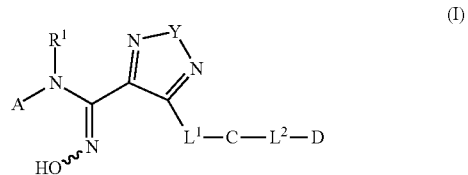

wherein A, C, D, $L^1$, $L^2$, $R^1$ and Y are defined as below.

It is further an object of the present invention to provide compounds according to formula (I) for use in the prophylaxis and/or treatment of diseases and conditions mediated by indoleamine 2,3-dioxygenase.

The present invention further relates to the use of the compounds according to formula (I) for the preparation of a medicament for the treatment and/or prophylaxis of a disease or condition mediated by indoleamine 2,3-dioxygenase.

Moreover, the present invention also relates to a method for treating or preventing a disease or condition mediated by indoleamin3 2,3-dioxygenase, the method comprising administering an effective amount of a compound according to formula (I) to a patient in need thereof.

Accordingly, the present invention provides a compound represented by Formula (I)

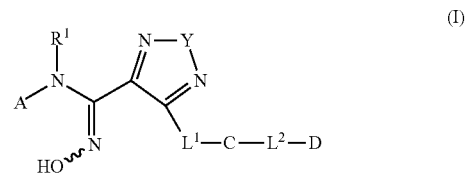

an enantiomer, diastereomer, tautomer or pharmaceutically acceptable salt thereof wherein A is $C_{3-10}$-cycloalkyl, 3 to 10-membered heterocycloalkyl containing 1 to 5 heteroatoms independently selected from the group consisting of N, O and S, or 6- to 10-membered mono- or bicyclic aryl or 5- to 14-membered mono- or bicyclic heteroaryl containing 1 to 5 heteroatoms independently selected from the group consisting of N, O and S, wherein cycloalkyl, heterocycloalkyl, aryl and heteroaryl are unsubstituted or substituted with 1 to 7 substituents independently selected from the group consisting of halogen, OH, oxo, CN, $C_{1-6}$-alkyl, O—$C_{1-6}$-alkyl, C(O)O$R^2$, S(O)—C$_{1-6}$-alkyl, S(O)$_2$—C$_{1-6}$-alkyl, N(R$^2$)$_2$, C(O)N(R$^2$)$_2$, S(O)$_2$N(R$^2$)$_2$ and C$_{3-6}$-cycloalkyl, wherein alkyl and cycloalkyl are unsubstituted or substituted with 1 to 3 substituents independently selected from the group consisting of halogen, C$_{1-3}$-alkyl, OH, CN, oxo and OS(O)$_2$CH$_3$; or wherein two adjacent substituents complete a 3- to 8-membered saturated or partially unsaturated ring containing carbon atoms and optionally containing 1 to 3 heteroatoms selected from O, S, N, S(O), S(O)$_2$ or NR$^2$, wherein the ring is unsubstituted or substituted with 1 to 7 substituents independently selected from the group consisting of halogen, OH, oxo, CN, C$_{1-6}$-alkyl, O—C$_{1-6}$-alkyl, C(O)OR$^2$, S(O)—C$_{1-6}$-alkyl, S(O)$_2$—C$_{1-6}$-alkyl, N(R$^2$)$_2$, C(O)N(R$^2$)$_2$, S(O)$_2$N(R$^2$)$_2$ and C$_{3-6}$-cycloalkyl, wherein alkyl and cycloalkyl are unsubstituted or substituted with 1 to 3 substituents independently selected from the group consisting of halogen, C$_{1-3}$-alkyl, OH, CN, oxo and OS(O)$_2$CH$_3$.

R$^1$ is hydrogen or C$_{1-6}$-alkyl;

R$^2$ is independently selected from the group consisting of hydrogen, C$_{1-6}$-alkyl, halo-C$_{1-6}$-alkyl and hydroxy-C$_{1-6}$-alkyl;

Y is O or S;

L$^1$ is —O—, —S—, —S(O)—, —S(O)$_2$—, or —S(O)(=NR$^3$)—;

R$^3$ is hydrogen or C$_{1-6}$-alkyl,

C is a bond, C$_{1-6}$-alkylene, C$_{2-6}$-alkenylene, C$_{2-6}$-alkynylene, C$_{0-6}$-alkylene-C$_{3-6}$-cycloalkylene, C$_{0-6}$-alkylene-3 to 10-membered-heterocycloalkylene, C$_{0-6}$-alkylene-C$_{6-10}$-aryl or C$_{0-6}$-alkylene-5-to 14-membered mono- or bicyclic heteroaryl, wherein alkylene, alkenylene and alkynylene are unsubstituted or substituted with 1 to 3 substituents independently selected from C$_{1-6}$-alkyl, halo-C$_{1-6}$-alkyl, halogen, OH, OR$^2$, N(R$^2$)$_2$, C$_{3-6}$-cycloalkyl, and 3- to 8-membered heterocycloalkyl;

L$^2$ is a bond, C$_{0-6}$-alkylene-NR$^2$—C$_{0-6}$-alkylene, C$_{0-6}$-alkylene-O—C$_{0-6}$-alkylene, C$_{0-6}$-alkylene-S—C$_{0-6}$-alkylene, C$_{0-6}$-alkylene-S(O)—C$_{0-6}$-alkylene, C$_{0-6}$-alkylene-S(O)$_2$—C$_{0-6}$-alkylene, C$_{0-6}$-alkylene-C(O)NR$^2$—C$_{0-6}$-alkylene, C$_{0-6}$-alkylene-NR$^2$C(O)—C$_{0-6}$-alkylene, C$_{0-6}$-alkylene-NR$^2$C(=NR$^2$)—C$_{0-6}$-alkylene, C$_{0-6}$-alkylene-C(=NR$^2$)NR$^2$—C$_{0-6}$-alkylene, C$_{0-6}$-alkylene-S(O)—NR$^2$—C$_{0-6}$-alkylene, C$_{0-6}$-alkylene-NR$^2$—S(O)—C$_{0-6}$-alkylene, C$_{0-6}$-alkylene-S(O)$_2$—NR$^2$—C$_{0-6}$-alkylene, C$_{0-6}$-alkylene-NR$^2$—S(O)$_2$—C$_{0-6}$-alkylene, C$_{0-6}$-alkylene-NR$^2$—S(=NR$^2$)(O)—C$_{0-6}$-alkylene, C$_{0-6}$-alkylene-NR$^2$—C(O)—NR$^2$—C$_{0-6}$-alkylene, C$_{0-6}$-alkylene-C(O)—C$_{0-6}$-alkylene, C$_{0-6}$-alkylene-NR$^2$—C(O)C(O)—NR$^2$—C$_{0-6}$-alkylene, C$_{0-6}$-alkylene-NR$^2$—C(O)—CR$^3$R$^4$—C(O)—NR$^2$—C$_{0-6}$-alkylene, C$_{0-6}$-alkylene-NR$^2$—C(O)—C R$^3$R$^4$—NR$^2$—C$_{0-6}$-alkylene, C$_{0-6}$-alkylene-NR$^2$—C(O)—O—C$_{0-6}$-alkylene, C$_{0-6}$-alkylene-O—C(O)—NR$^2$—C$_{0-6}$-alkylene or

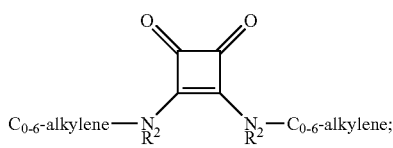

wherein alkylene may be unsubstituted or substituted with 1 to 3 substituents independently selected from C$_{1-6}$-alkyl, halo-C$_{1-6}$-alkyl, halogen, OH, OR$^2$, N(R$^2$)$_2$, C$_{3-6}$-cycloalkyl and 3- to 8-membered heterocycloalkyl;

wherein C$_{3-6}$-cycloalkyl and 3- to 8-membered heterocycloalkyl are unsubstituted or substituted with 1 to 3 substituents independently selected from halogen, OH, C$_{1-3}$-alkyl and halo-C$_{1-3}$-alkyl;

R$^4$ is hydrogen, OH, N(R$^2$)$_2$, C$_{1-6}$-alkyl, halo-C$_{1-6}$-alkyl or OH—C$_{1-6}$-alkyl, or R$^3$ and R$^4$ form a 3- to 6-membered cycloalkyl ring or 3- to 6-membered heterocycloalkyl ring having 1 or 2 heteroatoms independently selected from O, N and S, wherein cycloalkyl and heterocycloalkyl is unsubstituted or substituted by 1 to 4 substituents independently selected from halogen or hydroxy;

D is hydrogen, C$_{1-6}$-alkyl, C$_{1-6}$-fluoroalkyl, N(R$^2$)$_2$, C(O)OH, CN, C(O)OR$^2$, CH(NH$_2$)C(O)OH, S(O)$_2$C$_{1-6}$-alkyl, S(O)C$_{1-6}$-alkyl, S(O)$_2$N(R$^2$)$_2$, NR$^2$S(O)$_2$N(R$_2$), NR$^2$S(O)$_2$C$_{1-6}$-alkyl, C(O)N(R$^2$)$_2$, S(O)(=NR$^2$)C$_{1-6}$-alkyl, C$_{3-6}$ cycloalkyl, 4- to 8-membered mono- or bicyclic heterocycloalkyl containing 1, 2 or 3 heteroatoms independently selected from the group consisting of O, S and N, C$_{6-10}$-aryl, or 5- to 10-membered mono- or bicyclic heteroaryl containing 1, 2, 3 or 4 heteroatoms selected from O, S and N, wherein cycloalkyl, heterocycloalkyl, aryl and heteroaryl are unsubstituted or substituted with 1 to 7 substituents independently selected from the group consisting of halogen, OH, oxo, CN, C$_{1-6}$-alkyl, halo-C$_{1-6}$-alkyl, hydroxy-C$_{1-6}$-alkyl, O—C$_{1-6}$-alkyl, C$_{0-6}$-alkylene-C(O)OR$^2$, S(O)—C$_{1-6}$-alkyl, S(O)$_2$—C$_{1-6}$-alkyl, N(R$^2$)$_2$, C(O)N(R$^2$)$_2$, S(O)$_2$N(R$^2$)$_2$, NR$^2$S(O)$_2$NR$^2$, C$_{3-6}$-cycloalkyl, 3- to 6-membered heterocycloalkyl, S(O)(=NR$^2$)R$^2$, S(O)(=NR$^2$)N(R$^2$)$_2$ and heteroaryl wherein alkyl, alkylene, cycloalkyl, heterocycloalkyl and heteroaryl are unsubstituted or substituted with 1 to 3 substituents independently selected from the group consisting of halogen, OH, CN, NH$_2$, oxo and OS(O)$_2$CH$_3$;

with the proviso that (a) when L$^2$ represents —O— then D is not S(O)$_2$N(R$^2$)$_2$, and (b) when C represents a bond then D is not hydrogen.

In a preferred embodiment in combination with any of the above or below embodiments, A is C$_{3-10}$-cycloalkyl, 3 to 10-membered heterocycloalkyl containing 1 to 5 heteroatoms independently selected from the group consisting of N, O and S, or 6- to 10-membered mono- or bicyclic aryl wherein cycloalkyl, heterocycloalkyl and aryl are unsubstituted or substituted with 1 to 7 substituents independently selected from the group consisting of halogen, OH, oxo, CN, C$_{1-6}$-alkyl, O—C$_{1-6}$-alkyl, C(O)OR$^2$, S(O)—C$_{1-6}$-alkyl, S(O)$_2$—C$_{1-6}$-alkyl, N(R$^2$)$_2$, C(O)N(R$^2$)$_2$, S(O)$_2$N(R$^2$)$_2$ and C$_{3-6}$-cycloalkyl, wherein alkyl and cycloalkyl are unsubstituted or substituted with 1 to 3 substituents independently selected from the group consisting of halogen, C$_{1-3}$-alkyl, OH, CN, oxo and OS(O)$_2$CH$_3$; or wherein two adjacent substituents complete a 3- to 8-membered saturated or partially unsaturated ring containing carbon atoms and optionally containing 1 to 3 heteroatoms selected from O, S, N, S(O), S(O)$_2$ or NR$^2$, wherein the ring is unsubstituted or substituted with 1 to 7 substituents independently selected from the group consisting of halogen, OH, oxo, CN, C$_{1-6}$-alkyl, O—C$_{1-6}$-alkyl, C(O)OR$^2$, S(O)—C$_{1-6}$-alkyl, S(O)$_2$—C$_{1-6}$-alkyl, N(R$^2$)$_2$, C(O)N(R$^2$)$_2$, S(O)$_2$N(R$^2$)$_2$ and C$_{3-6}$-cycloalkyl, wherein alkyl and cycloalkyl are unsubstituted or substituted with 1 to 3 substituents independently selected from the group consisting of halogen, C$_{1-3}$-alkyl, OH, CN, oxo and OS(O)$_2$CH$_3$ $R^1$ is hydrogen or $C_{1-6}$-alkyl;

$R^2$ is independently selected from the group consisting of hydrogen, $C_{1-6}$-alkyl, halo-$C_{1-6}$-alkyl and hydroxy-$C_{1-6}$-alkyl;

Y is O or S;

$L^1$ is —O—, —S—, —S(O)—, —S(O)$_2$—, or —S(O)(=NR$^3$)—;

$R^3$ is hydrogen or $C_{1-6}$-alkyl,

C is a bond, $C_{1-6}$-alkylene, $C_{2-6}$-alkenylene, $C_{2-6}$-alkynylene, $C_{0-6}$-alkylene-$C_{3-6}$-cycloalkylene, $C_{0-6}$-alkylene-3 to 10-membered-heterocycloalkylene, $C_{0-6}$-alkylene-$C_{6-10}$-aryl or $C_{0-6}$-alkylene-5- to 14-membered mono- or bicyclic heteroaryl, wherein alkylene, alkenylene and alkynylene are unsubstituted or substituted with 1 to 3 substituents independently selected from $C_{1-6}$-alkyl, halo-$C_{1-6}$-alkyl, halogen, OH, OR$^2$, N(R$^2$)$_2$, $C_{3-6}$-cycloalkyl, and 3- to 8-membered heterocycloalkyl;

$L^2$ is a bond, $C_{0-6}$-alkylene-NR$^2$—$C_{0-6}$-alkylene, $C_{0-6}$-alkylene-O—$C_{0-6}$-alkylene, $C_{0-6}$-alkylene-S—$C_{0-6}$-alkylene, $C_{0-6}$-alkylene-S(O)—$C_{0-6}$-alkylene, $C_{0-6}$-alkylene-S(O)$_2$—$C_{0-6}$-alkylene, $C_{0-6}$-alkylene-C(O)NR$^2$—$C_{0-6}$-alkylene, $C_{0-6}$-alkylene-NR$^2$C(O)—$C_{0-6}$-alkylene, $C_{0-6}$-alkylene-NR$^2$C(=NR$^2$)—$C_{0-6}$-alkylene, $C_{0-6}$-alkylene-C(=NR$^2$)NR$^2$—$C_{0-6}$-alkylene, $C_{0-6}$-alkylene-S(O)—NR$^2$—$C_{0-6}$-alkylene, $C_{0-6}$-alkylene-NR$^2$—S(O)—$C_{0-6}$-alkylene, $C_{0-6}$-alkylene-S(O)$_2$—NR$^2$—$C_{0-6}$-alkylene, $C_{0-6}$-alkylene-NR$^2$—S(O)$_2$—$C_{1-6}$-alkylene, $C_{0-6}$-alkylene-NR$^2$—S(O)$_2$—NR$^2$—$C_{1-6}$-alkylene, $C_{0-6}$-alkylene-NR$^2$—S(=NR$^2$)(O)—$C_{0-6}$-alkylene, $C_{0-6}$-alkylene-NR$^2$—C(O)—NR$^2$—$C_{0-6}$-alkylene, $C_{0-6}$-alkylene-C(O)—$C_{0-6}$-alkylene, $C_{0-6}$-alkylene-NR$^2$—C(O)C(O)—NR$^2$—$C_{0-6}$-alkylene, $C_{0-6}$-alkylene-NR$^2$-0(O)—CR$^3$R$^4$—C(O)—NR$^2$—$C_{0-6}$-alkylene, $C_{0-6}$-alkylene-NR$^2$—C(O)—O—$C_{0-6}$-alkylene, $C_{0-6}$-alkylene-O—C(O)—NR$^2$—$C_{0-6}$-alkylene or

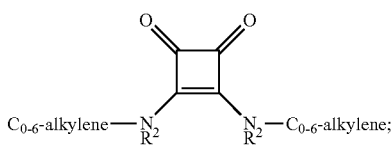

wherein alkylene may be unsubstituted or substituted with 1 to 3 substituents independently selected from $C_{1-6}$-alkyl, halo-$C_{1-6}$-alkyl, halogen, OH, OR$^2$, N(R$^2$)$_2$, $C_{3-6}$-cycloalkyl and 3- to 8-membered heterocycloalkyl;

wherein $C_{3-6}$-cycloalkyl and 3- to 8-membered heterocycloalkyl are unsubstituted or substituted with 1 to 3 substituents independently selected from halogen, OH, $C_{1-3}$-alkyl and halo-$C_{1-3}$-alkyl;

$R^4$ is hydrogen, OH, N(R$^2$)$_2$, $C_{1-6}$-alkyl, halo-$C_{1-6}$-alkyl or OH—$C_{1-6}$-alkyl, or $R^3$ and $R^4$ form a 3- to 6-membered cycloalkyl ring or 3- to 6-membered heterocycloalkyl ring having 1 or 2 heteroatoms independently selected from O, N and S;

D is hydrogen, $C_{1-6}$-alkyl, $C_{1-6}$-fluoroalkyl, N(R$^2$)$_2$, C(O)OH, CH(NH$_2$)C(O)OH, S(O)$_2C_{1-6}$-alkyl, S(O)$_2$N(R$^2$)$_2$, C(O)N(R$^2$)$_2$, $C_{3-6}$ cycloalkyl, 4- to 6-membered heterocycloalkyl containing 1, 2 or 3 heteroatoms independently selected from the group consisting of O, S and N, $C_{6-10}$-aryl, or 5- to 10-membered mono- or bicyclic heteroaryl containing 1, 2, 3 or 4 heteroatoms selected from O, S and N, wherein cycloalkyl, heterocycloalkyl, aryl and heteroaryl are unsubstituted or substituted with 1 to 7 substituents independently selected from the group consisting of halogen, OH, oxo, CN, $C_{1-6}$-alkyl, hydroxy-$C_{1-6}$-alkyl, O—$C_{1-6}$-alkyl, $C_{0-6}$-alkylene-C(O)OR$^2$, S(O)—$C_{1-6}$-alkyl, S(O)$_2$—$C_{1-6}$-alkyl, N(R$^2$)$_2$, C(O)N(R$^2$)$_2$, S(O)$_2$N(R$^2$)$_2$, NR$^2$S(O)$_2$NR$^2$ and $C_{3-6}$-cycloalkyl, wherein alkyl, alkylene and cycloalkyl, are unsubstituted or substituted with 1 to 3 substituents independently selected from the group consisting of halogen, OH, CN, NH$_2$, oxo and OS(O)$_2$CH$_3$;

with the proviso that (a) when $L^2$ represents —O— then D is not S(O)$_2$N(R$^2$)$_2$, and (b) when C represents a bond then D is not hydrogen.

In a preferred embodiment in combination with any of the above or below embodiments, A is $C_{3-6}$-cycloalkyl, 3 to 6-membered heterocycloalkyl containing 1 to 3 heteroatoms independently selected from the group consisting of N, O and S, phenyl or 5- or 6-membered heteroaryl containing 1 to 3 heteroatoms independently selected from the group consisting of N, O and S, wherein cycloalkyl, heterocycloalkyl, phenyl and heteroaryl are unsubstituted or substituted with 1 to 7 substituents independently selected from the group consisting of halogen, OH, oxo, CN, $C_{1-6}$-alkyl, O—$C_{1-6}$-alkyl, C(O)OR$^2$, S(O)—$C_{1-6}$-alkyl, S(O)$_2$—$C_{1-6}$-alkyl, N(R$^2$)$_2$, C(O)N(R$^2$)$_2$, S(O)$_2$N(R$^2$)$_2$ and $C_{3-6}$-cycloalkyl, wherein alkyl and cycloalkyl are unsubstituted or substituted with 1 to 3 substituents independently selected from the group consisting of halogen, $C_{1-3}$-alkyl, OH, CN, oxo and OS(O)$_2$CH$_3$; or wherein two adjacent substituents complete a 3- to 8-membered saturated or partially unsaturated ring containing carbon atoms and optionally containing 1 to 3 heteroatoms selected from O, S, N, S(O), S(O)$_2$ or NR$^2$, wherein the ring is unsubstituted or substituted with 1 to 7 substituents independently selected from the group consisting of halogen, OH, oxo, CN, $C_{1-6}$-alkyl, O—$C_{1-6}$-alkyl, C(O)OR$^2$, S(O)—$C_{1-6}$-alkyl, S(O)$_2$—$C_{1-6}$-alkyl, N(R$^2$)$_2$, C(O)N(R$^2$)$_2$, S(O)$_2$N(R$^2$)$_2$ and $C_{3-6}$-cycloalkyl, wherein alkyl and cycloalkyl are unsubstituted or substituted with 1 to 3 substituents independently selected from the group consisting of halogen, $C_{1-3}$-alkyl, OH, CN, oxo and OS(O)$_2$CH$_3$.

In an equally preferred embodiment in combination with any of the above or below embodiments, A is $C_{3-6}$-cycloalkyl, 3- to 6-membered heterocycloalkyl containing 1 to 3 heteroatoms independently selected from O, S and N, or phenyl wherein cycloalkyl, heterocycloalkyl and phenyl are unsubstituted or substituted with 1 to 7 substituents independently selected from the group consisting of halogen, OH, oxo, CN, $C_{1-6}$-alkyl, O—$C_{1-6}$-alkyl, C(O)OR$^2$, S(O)—$C_{1-6}$-alkyl, S(O)$_2$—$C_{1-6}$-alkyl, N(R$^2$)$_2$, C(O)N(R$^2$)$_2$, S(O)$_2$N(R$^2$)$_2$ and $C_{3-6}$-cycloalkyl, wherein alkyl and cycloalkyl are unsubstituted or substituted with 1 to 3 substituents independently selected from the group consisting of halogen, $C_{1-3}$-alkyl, OH, CN, oxo and OS(O)$_2$CH$_3$ or wherein two adjacent substituents complete a 3- to 8-membered saturated or partially unsaturated ring containing carbon atoms and optionally containing 1 to 3 heteroatoms selected from O, S, N, S(O), S(O)$_2$ or NR$^2$, wherein the ring is unsubstituted or substituted with 1 to 7 substituents independently selected from the group consisting of halogen, OH, oxo, CN, $C_{1-6}$-alkyl, O—$C_{1-6}$-alkyl, C(O)OR$^2$, S(O)—$C_{1-6}$-alkyl, S(O)$_2$—$C_{1-6}$-alkyl, N(R$^2$)$_2$, C(O)N(R$^2$)$_2$, S(O)$_2$N(R$^2$)$_2$ and $C_{3-6}$-cycloalkyl, wherein alkyl and cycloalkyl are unsubstituted or substituted with 1 to 3 substituents independently selected from the group consisting of halogen, $C_{1-3}$-alkyl, OH, CN, oxo and OS(O)$_2$CH$_3$.

In a more preferred embodiment in combination with any of the above or below embodiments, cycloalkyl, heterocycloalkyl and phenyl are unsubstituted or substituted with 1 to 5 substituents independently selected from the group consisting of halogen, OH, CN, $C_{1-6}$-alkyl, O—$C_{1-6}$-alkyl and $C_{3-6}$-cycloalkyl, wherein alkyl and cycloalkyl are unsubstituted or substituted with 1 to 3 substituents independently selected from the group consisting of halogen, $C_{1-3}$-alkyl and OH.

In an equally more preferred embodiment in combination with any of the above or below embodiments, cycloalkyl, heterocycloalkyl, phenyl and the 5- or 6-membered heteroaryl containing 1 to 3 heteroatoms independently selected from N, O and S are unsubstituted or substituted with 1 to 5 substituents independently selected from the group consisting of halogen, OH, CN, $C_{1-6}$-alkyl, O—$C_{1-6}$-alkyl and $C_{3-6}$-cycloalkyl, wherein alkyl and cycloalkyl are unsubstituted or substituted with 1 to 3 substituents independently selected from the group consisting of halogen, $C_{1-3}$-alkyl and OH.

In an even more preferred embodiment in combination with any of the above or below embodiments, A is phenyl which is unsubstituted or substituted with 1 to 3 substituents independently selected from the group consisting of F, Cl, Br, $CH_3$, $CH_2CH_3$, $CH_2F$, $CHF_2$, $CF_3$, $OCH_3$, $OCH_2F$, $OCHF_2$, $OCF_3$, $CH_2OH$, and $C_{3-6}$-cycloalkyl which is unsubstituted or substituted with 1 substituent selected from halogen and $C_{1-3}$-alkyl.

In a further even more preferred embodiment in combination with any of the above below embodiments, A is pyridine or pyrimidine which is unsubstituted or substituted with 1 to 3 substituents independently selected from the group consisting of F, Cl, Br, $CH_3$, $CH_2OH_3$, $CH_2F$, $CHF_2$, $CF_3$, $OCH_3$, $OCH_2F$, $OCHF_2$, $OCF_3$, $CH_2OH$, and $C_{3-6}$-cycloalkyl which is unsubstituted or substituted with 1 substituent selected from halogen and $C_{1-3}$-alkyl.

In a further more preferred embodiment in combination with any of the above or below embodiments, A is selected from

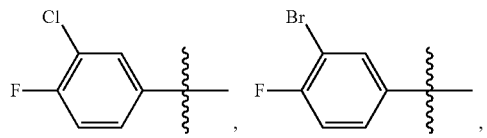


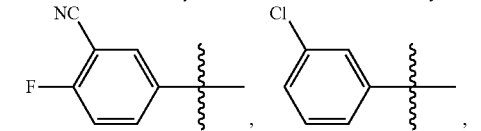


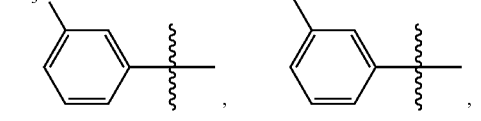

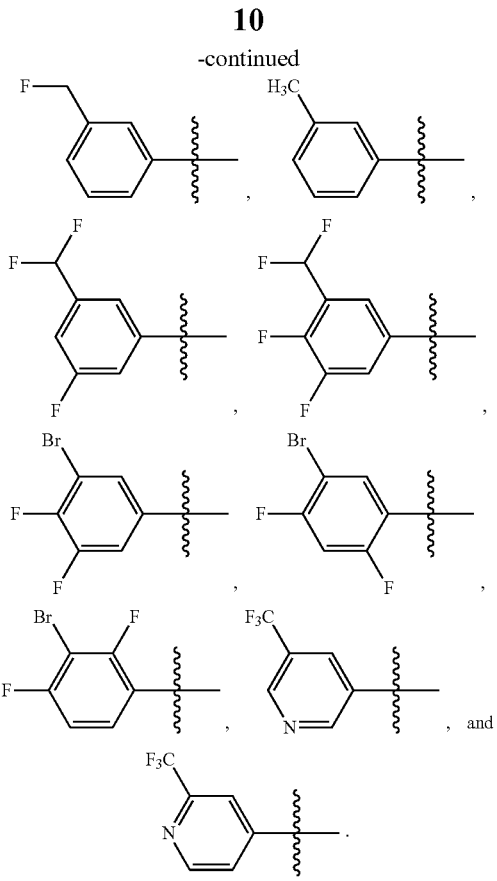

In an additional more preferred embodiment in combination with any of the above or below embodiments, A is selected from

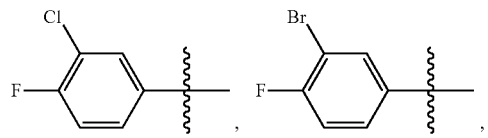

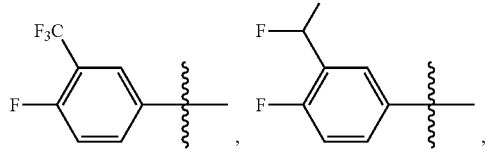

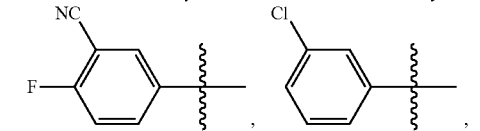

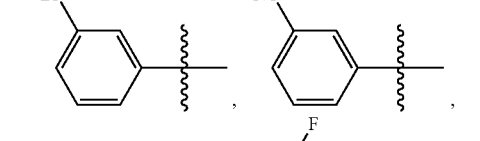

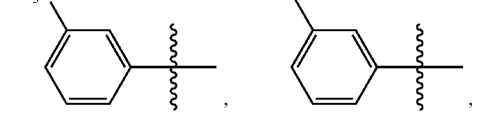

-continued

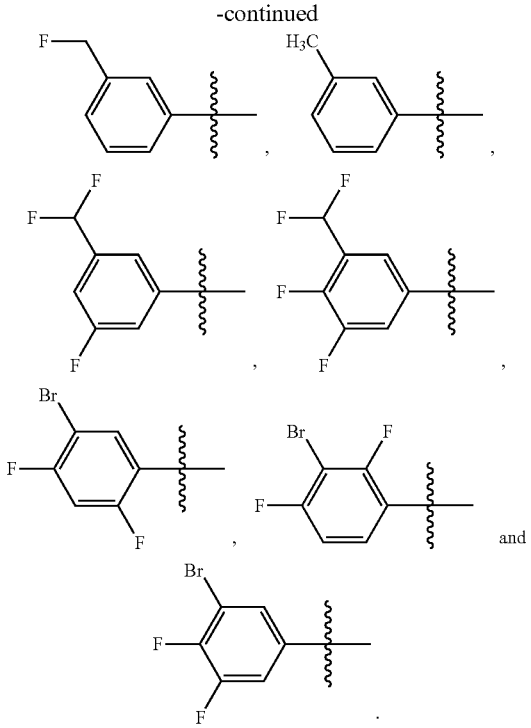

In a further more preferred embodiment in combination with any of the above or below embodiments, A is selected from

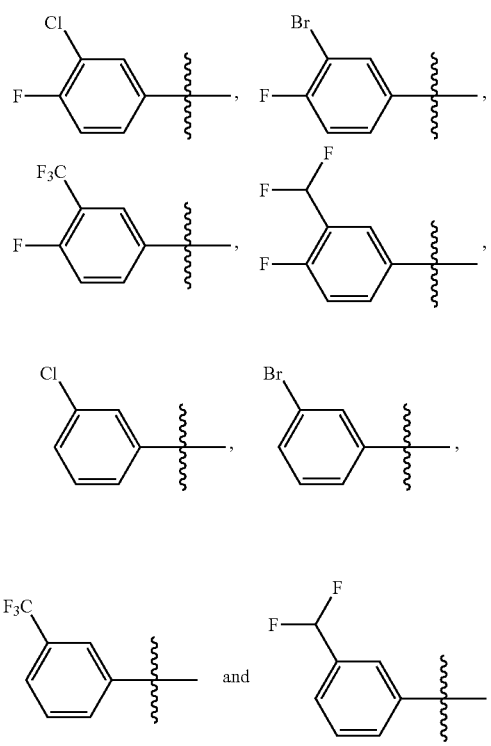

In a further equally more preferred embodiment in combination with any of the above or below embodiments, A is selected from

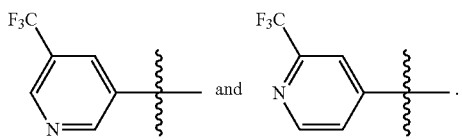 [SMILES: *c1cncc(C(F)(F)F)c1 ; *c1ccnc(C(F)(F)F)c1]

In a preferred embodiment in combination with any of the above or below embodiments, $R^1$ is hydrogen.

In a further preferred embodiment in combination with any of the above or below embodiments, Y is —O—.

In a preferred embodiment in combination with any of the above or below embodiments, $L^1$ is —O— or —S—. In a more preferred embodiment in combination with any of the above or below embodiments, $L^1$ is —O—. In an equally more preferred embodiment in combination with any of the above or below embodiments, $L^1$ is —S—.

In a preferred embodiment in combination with any of the above or below embodiments, $L^1$ is S, S(O) or $S(O)_2$. In a more preferred embodiment in combination with any of the above or below embodiments, $L^1$ is S(O). In an equally more preferred embodiment in combination with any of the above or below embodiments, $L^1$ is $S(O)_2$.

In a preferred embodiment in combination with any of the above or below embodiments, C is a bond, $C_{1-6}$-alkylene, $C_{0-6}$-alkylene-$C_{3-6}$-cycloalkylene, $C_{0-6}$-alkylene-3- to 10-membered-heterocycloalkylene, $C_{0-6}$-alkylene-$C_{6-10}$-aryl, or $C_{0-6}$-alkylene-5- to 14-membered mono- or bicyclic heteroaryl, wherein alkylene is unsubstituted or substituted with 1 to 3 substituents independently selected from $C_{1-6}$-alkyl, halo-$C_{1-6}$-alkyl, halogen, OH, $OR^2$, $N(R^2)_2$, $C_{3-6}$-cycloalkyl, and 3- to 8-membered heterocycloalkyl.

In an equally preferred embodiment in combination with any of the above or below embodiments C is a bond, $C_{1-6}$-alkylene, $C_{2-6}$-alkenylene, $C_{2-6}$-alkynylene, wherein alkylene, alkenylene and alkynylene are unsubstituted or substituted with 1 to 3 substituents independently selected from $C_{1-6}$-alkyl, halo-$C_{1-6}$-alkyl, halogen, OH, $OR^2$, $N(R^2)_2$, $C_{3-6}$-cycloalkyl, and 3- to 8-membered heterocycloalkyl.

In a more preferred embodiment in combination with any of the above or below embodiments C is a bond, $C_{1-6}$-alkylene, wherein alkylene is unsubstituted or substituted with 1 to 3 substituents independently selected from $C_{1-6}$-alkyl, halo-$C_{1-6}$-alkyl, halogen, OH, $OR^2$, $N(R^2)_2$, $C_{3-6}$-cycloalkyl, and 3- to 8-membered heterocycloalkyl.

In a most preferred embodiment in combination with any of the above or below embodiments C is selected from

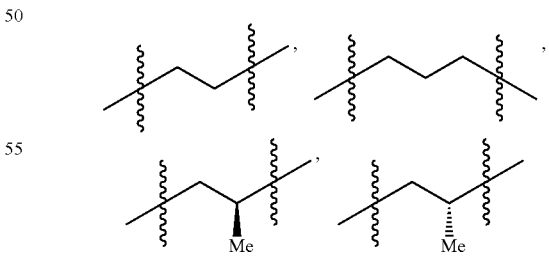

In a preferred embodiment in combination with any of the above or below embodiments, $L^2$ is a $C_{0-6}$-alkylene-S—$C_{0-6}$-alkylene, $C_{0-6}$-alkylene-S(O)—$C_{0-6}$-alkylene, $C_{0-6}$-alkylene-$S(O)_2$—$C_{0-6}$-alkylene, $C_{0-6}$-alkylene-$NR^2C(O)$—$C_{0-6}$-alkylene, $C_{0-6}$-alkylene-$NR^2C(=NR^2)$—$C_{0-6}$-alkylene, $C_{0-6}$-alkylene-$C(=NR^2)NR^2$—$C_{0-6}$-alkylene, $C_{0-6}$-alkylene-S(O)—$NR^{2-C}_{0-6}$-alkylene, $C_{0-6}$-alkylene- NR²—S(O)—C₀₋₆-alkylene, C₀₋₆-alkylene-S(O)₂—NR²—C₀₋₆-alkylene, C₀₋₆-alkylene-NR²—S(O)₂—C₁₋₆-alkylene, C₀₋₆-alkylene-NR²—S(O)₂—NR²—C₁₋₆-alkylene, C₀₋₆-alkylene-NR²—S(=NR²)(O)—C₀₋₆-alkylene, C₀₋₆-alkylene-NR²—C(O)—NR²—C₋₀₋₆-alkylene, C₀₋₆-alkylene-NR²—C(O)C(O)—NR²—C₀₋₆-alkylene, C₀₋₆-alkylene-NR²—C(O)—CR³R⁴—C(O)—NR²—C₀₋₆-alkylene, C₀₋₆-alkylene-NR²—C(O)—CR³R⁴—NR²—C₀₋₆-alkylene, C₀₋₆-alkylene-O—C(O)—NR²—C₀₋₆-alkylene or

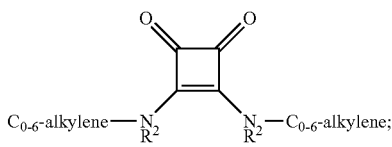

wherein alkylene may be unsubstituted or substituted with 1 to 3 substituents independently selected from C₁₋₆-alkyl, halo-C₁₋₆-alkyl, halogen, OH, OR², N(R²)₂, C₃₋₆-cycloalkyl and 3- to 8-membered heterocycloalkyl;

wherein C₃₋₆-cycloalkyl and 3- to 8-membered heterocycloalkyl are unsubstituted or substituted with 1 to 3 substituents independently selected from halogen, OH, C₁₋₃-alkyl and halo-C₁₋₃-alkyl;

R³ is hydrogen or C₁₋₆-alkyl,

R⁴ is hydrogen, OH, N(R²)₂, C₁₋₆-alkyl, halo-C₁₋₆-alkyl or OH—C₁₋₆-alkyl, or R³ and R⁴ form a 3- to 6-membered cycloalkyl ring or 3- to 6-membered heterocycloalkyl ring having 1 or 2 heteroatoms independently selected from O, N and S, wherein cycloalkyl and heterocycloalkyl is unsubstituted or substituted by 1 to 4 substituents independently selected from halogen or hydroxy.

In a preferred embodiment in combination with any of the above or below embodiments, L² is a bond, C₀₋₆-alkylene-NR²—C₀₋₆-alkylene, C₀₋₆-alkylene-O—C₀₋₆-alkylene, C₀₋₆-alkylene-S—C₀₋₆-alkylene, C₀₋₆-alkylene-S(O)—C₀₋₆-alkylene, C₀₋₆-alkylene-S(O)₂—C₀₋₆-alkylene, C₀₋₆-alkylene-C(O)NR²—C₀₋₆-alkylene, C₀₋₆-alkylene-NR²C(O)—C₀₋₆-alkylene, C₀₋₆-alkylene-NR²C(=NR²)—C₀₋₆-alkylene, C₀₋₆-alkylene-C(=NR²)NR²—C₀₋₆-alkylene, C₀₋₆-alkylene-S(O)—NR²—C₀₋₆-alkylene, C₀₋₆-alkylene-NR²—S(O)—C₀₋₆-alkylene, C₀₋₆-alkylene-S(O)₂—NR²—C₀₋₆-alkylene, C₀₋₆-alkylene-NR²—S(O)₂—C₀₋₆-alkylene, C₀₋₆-alkylene-NR²—S(O)₂—NR²—C₀₋₆-alkylene, C₀₋₆-alkylene-NR²—S(=NR²)(O)—C₀₋₆-alkylene, C₀₋₆-alkylene-NR²—C(O)—NR²—C₋₀₋₆-alkylene, C₀₋₆-alkylene-C(O)—C₀₋₆-alkylene, C₀₋₆-alkylene-NR²—C(O)C(O)—NR²—C₀₋₆-alkylene, C₀₋₆-alkylene-NR²—C(O)—CR³R⁴—C(O)—NR²—C₀₋₆-alkylene, C₀₋₆-alkylene-NR²—C(O)—O—C₀₋₆-alkylene, C₀₋₆-alkylene-O—C(O)—NR²—C₀₋₆-alkylene or

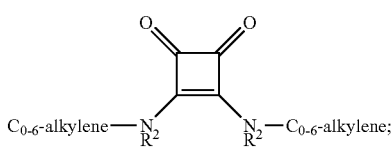

wherein alkylene may be unsubstituted or substituted with 1 to 3 substituents independently selected from C₁₋₆-alkyl, halo-C₁₋₆-alkyl, halogen, OH, OR², N(R²)₂, C₃₋₆-cycloalkyl and 3- to 8-membered heterocycloalkyl;

wherein C₃₋₆-cycloalkyl and 3- to 8-membered heterocycloalkyl are unsubstituted or substituted with 1 to 3 substituents independently selected from halogen, OH, C₁₋₃-alkyl and halo-C₁₋₃-alkyl;

R⁴ is hydrogen, OH, N(R²)₂, C₁₋₆-alkyl, halo-C₁₋₆-alkyl or OH—C₁₋₆-alkyl, or

R³ and R⁴ form a 3- to 6-membered cycloalkyl ring or 3- to 6-membered heterocycloalkyl ring having 1 or 2 heteroatoms independently selected from O, N and S.

In a more preferred embodiment in combination with any of the above or below embodiments, L² is a bond, C₀₋₆-alkylene-NR²—C₀₋₆-alkylene, C₀₋₆-alkylene-S—C₀₋₆-alkylene, C₀₋₆-alkylene-S(O)—C₀₋₆-alkylene, C₀₋₆-alkylene-S(O)₂—C₀₋₆-alkylene, C₀₋₆-alkylene-C(O)NR²—C₀₋₆-alkylene, C₀₋₆-alkylene-NR²C(O)—C₀₋₆-alkylene, C₀₋₆-alkylene-NR²C(=NR²)—C₀₋₆-alkylene, C₀₋₆-alkylene-C(=NR²)NR²—C₀₋₆-alkylene, C₀₋₆-alkylene-S(O)—NR²—C₀₋₆-alkylene, C₀₋₆-alkylene-NR²—S(O)—C₀₋₆-alkylene, C₀₋₆-alkylene-S(O)₂—NR²—C₀₋₆-alkylene, C₀₋₆-alkylene-NR²—S(O)₂—C₀₋₆-alkylene, C₀₋₆-alkylene-NR²—S(O)₂—NR²—C₀₋₆-alkylene, C₀₋₆-alkylene-NR²—S(=NR²)(O)—C₀₋₆-alkylene, C₀₋₆-alkylene-NR²—C(O)—NR²—C₋₀₋₆-alkylene, C₀₋₆-alkylene-C(O)—C₀₋₆-alkylene, C₀₋₆-alkylene-NR²—C(O)C(O)—NR²—C₀₋₆-alkylene, C₀₋₆-alkylene-NR²—C(O)—CR³R⁴—C(O)—NR²—C₀₋₆-alkylene, C₀₋₆-alkylene-NR²—C(O)—O—C₀₋₆-alkylene, C₀₋₆-alkylene-O—C(O)—NR²—C₀₋₆-alkylene or

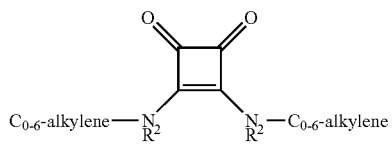

wherein alkylene may be unsubstituted or substituted with 1 to 3 substituents independently selected from C₁₋₆-alkyl, halo-C₁₋₆-alkyl, halogen, OH, OR², N(R²)₂, C₃₋₆-cycloalkyl and 3- to 8-membered heterocycloalkyl, wherein C₃₋₆-cycloalkyl and 3- to 8-membered heterocycloalkyl are unsubstituted or substituted with 1 to 3 substituents independently selected from halogen, OH, C₁₋₃-alkyl and halo-C₁₋₃-alkyl.

In a further preferred embodiment in combination with any of the above or below embodiments, L² is a C₀₋₆-alkylene-S—C₀₋₆-alkylene, C₀₋₆-alkylene-S(O)—C₀₋₆-alkylene, C₀₋₆-alkylene-S(O)₂—C₀₋₆-alkylene, C₀₋₆-alkylene-NR²C(O)—C₀₋₆-alkylene, C₀₋₆-alkylene-NR²C(=NR²)—C₀₋₆-alkylene, C₀₋₆-alkylene-C(=NR²)NR²—C₀₋₆-alkylene, C₀₋₆-alkylene-S(O)—NR²—C₀₋₆-alkylene, C₀₋₆-alkylene-NR²—S(O)—C₀₋₆-alkylene, C₀₋₆-alkylene-S(O)₂—NR²—C₀₋₆-alkylene, C₀₋₆-alkylene-NR²—S(O)₂—C₁₋₆-alkylene, C₀₋₆-alkylene-NR2—S(O)₂—NR²—C₁₋₆-alkylene, C₀₋₆-alkylene-NR²—S(=NR²)(O)—C₀₋₆-alkylene, C₀₋₆-alkylene-NR²—C(O)—NR²—C₋₀₋₆-alkylene, C₀₋₆-alkylene-NR²—C(O)C(O)—NR²—C₀₋₆-alkylene, C₀₋₆-alkylene-NR²—C(O)—CR³R⁴—C(O)—NR²—C₀₋₆-alkylene, C₀₋₆-alkylene-O—C(O)—NR²—C₀₋₆-alkylene or

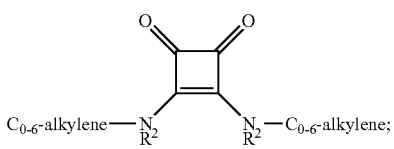

wherein alkylene may be unsubstituted or substituted with 1 to 3 substituents independently selected from C₁₋₆-alkyl, halo-C$_{1-6}$-alkyl, halogen, OH, OR$^2$, N(R$^2$)$_2$, C$_{3-6}$-cycloalkyl and 3- to 8-membered heterocycloalkyl;

wherein C$_{3-6}$-cycloalkyl and 3- to 8-membered heterocycloalkyl are unsubstituted or substituted with 1 to 3 substituents independently selected from halogen, OH, C$_{1-3}$-alkyl and halo-C$_{1-3}$-alkyl;

R$^3$ is hydrogen or C$_{1-6}$-alkyl,

R$^4$ is hydrogen, OH, N(R$^2$)$_2$, C$_{1-6}$-alkyl, halo-C$_{1-6}$-alkyl or OH—C$_{1-6}$-alkyl, or R$^3$ and R$^4$ form a 3- to 6-membered cycloalkyl ring or 3- to 6-membered heterocycloalkyl ring having 1 or 2 heteroatoms independently selected from O, N and S.

In a more preferred embodiment in combination with any of the above or below embodiments, L$^2$ is a bond, C$_{0-6}$-alkylene-NR$^2$—C$_{0-6}$-alkylene, C$_{0-6}$-alkylene-C(O)NR$^2$—C$_{0-6}$-alkylene, C$_{0-6}$-alkylene-NR$^2$C(O)—C$_{0-6}$-alkylene, C$_{0-6}$-alkylene-NR$^2$—S(O)—C$_{0-6}$-alkylene, C$_{0-6}$-alkylene-S(O)$_2$—NR$^2$—C$_{0-6}$-alkylene, C$_{0-6}$-alkylene-NR$^2$—C(O)C(O)—NR$^2$—C$_{0-6}$-alkylene or

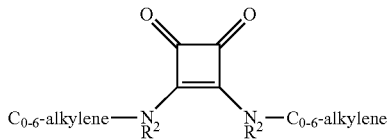

wherein alkylene may be unsubstituted or substituted with 1 to 3 substituents independently selected from C$_{1-6}$-alkyl, halo-C$_{1-6}$-alkyl, halogen, OH, OR$^2$, N(R$^2$)$_2$, C$_{3-6}$-cycloalkyl and 3- to 8-membered heterocycloalkyl, wherein C$_{3-6}$-cycloalkyl and 3- to 8-membered heterocycloalkyl are unsubstituted or substituted with 1 to 3 substituents independently selected from halogen, OH, C$_{1-3}$-alkyl and halo-C$_{1-3}$-alkyl.

In a preferred embodiment in combination with any of the above or below embodiments, D is hydrogen, C$_{1-6}$-fluoroalkyl, N(R$^2$)$_2$, C(O)OH, CN, C(O)OR$^2$, CH(NH$_2$)C(O)OH, S(O)$_2$C$_{1-6}$-alkyl, S(O)C$_{1-6}$-alkyl, S(O)$_2$N(R$^2$)$_2$, NR$^2$S(O)$_2$N(R$^2$)$_2$, NR$^2$S(O)$_2$C$_{1-6}$-alkyl, C(O)N(R$^2$)$_2$, S(O)(=NR$^2$)C$_{1-6}$-alkyl, C$_{3-6}$ cycloalkyl, 4- to 8-membered mono- or bicyclic heterocycloalkyl containing 1, 2 or 3 heteroatoms independently selected from the group consisting of O, S and N, C$_{6-10}$-aryl, or 5- to 10-membered mono- or bicyclic heteroaryl containing 1, 2, 3 or 4 heteroatoms selected from O, S and N, wherein cycloalkyl, heterocycloalkyl, aryl and heteroaryl are unsubstituted or substituted with 1 to 7 substituents independently selected from the group consisting of halogen, OH, oxo, CN, C$_{1-6}$-alkyl, halo-C$_{1-6}$-alkyl, hydroxy-C$_{1-6}$-alkyl, O—C$_{1-6}$-alkyl, C$_{0-6}$-alkylene-C(O)OR$^2$, S(O)—C$_{1-6}$-alkyl, S(O)$_2$—C$_{1-6}$-alkyl, N(R$^2$)$_2$, C(O)N(R$^2$)$_2$, S(O)$_2$N(R$^2$)$_2$, NR$^2$S(O)$_2$NR$^2$, C$_{3-6}$-cycloalkyl, 3- to 6-membered heterocycloalkyl, S(O)(=NR$^2$)R$^2$, S(O)(=NR$^2$)N(R$^2$)$_2$ and heteroaryl wherein alkyl, alkylene, cycloalkyl, heterocycloalkyl and heteroaryl are unsubstituted or substituted with 1 to 3 substituents independently selected from the group consisting of halogen, OH, CN, NH$_2$, oxo and OS(O)$_2$CH$_3$.

In an equally preferred embodiment in combination with any of the above or below embodiments, D is hydrogen, C$_{1-6}$-fluoroalkyl, N(R$^2$)$_2$, C(O)OH, CH(NH$_2$)C(O)OH, S(O)$_2$ C$_{1-6}$-alkyl, S(O)$_2$N(R$^2$)$_2$, C(O)N(R$^2$)$_2$, C$_{3-6}$ cycloalkyl, 4- to 6-membered heterocycloalkyl containing 1, 2 or 3 heteroatoms independently selected from the group consisting of O, S and N, C$_{6-10}$-aryl, or 5- to 10-membered mono- or bicyclic heteroaryl containing 1, 2, 3 or 4 heteroatoms selected from O, S and N, wherein cycloalkyl, heterocycloalkyl, aryl and heteroaryl are unsubstituted or substituted with 1 to 7 substituents independently selected from the group consisting of halogen, OH, oxo, CN, C$_{1-6}$-alkyl, hydroxy-C$_{1-6}$-alkyl, O—C$_{1-6}$-alkyl, C$_{0-6}$-alkylene-C(O)OR$^2$, S(O)—C$_{1-6}$-alkyl, S(O)$_2$—C$_{1-6}$-alkyl, NR$^2$, C(O)N(R$^2$)$_2$, S(O)$_2$N(R$^2$)$_2$, NR$^2$S(O)$_2$NR$^2$ and C$_{3-6}$-cycloalkyl, wherein alkyl, alkylene and cycloalkyl are unsubstituted or substituted with 1 to 3 substituents independently selected from the group consisting of halogen, OH, CN, NH$_2$, oxo and OS(O)$_2$CH$_3$.

In a preferred embodiment in combination with any of the above or below embodiments, D is C$_{1-3}$ alkyl, C$_{1-3}$ fluoroalkyl, N(R$^2$)$_2$, C(O)OH, CH(NH$_2$)C(O)OH, S(O)$_2$N(R$^2$)$_2$, S(O)$_2$C$_{1-6}$-alkyl, C(O)N(R$^2$)$_2$, C$_{3-6}$-cycloalkyl, 4- to 6-membered heterocycloalkyl containing 1, 2 or 3 heteroatoms independently selected from the group consisting of O, S and N, C$_{6-10}$-aryl, or 5- to 10-membered mono- or bicyclic heteroaryl containing 1, 2, 3 or 4 heteroatoms selected from O, S and N, wherein cycloalkyl, heterocycloalkyl, aryl and heteroaryl are unsubstituted or substituted with 1 to 7 substituents independently selected from the group consisting of halogen, OH, oxo, CN, C$_{1-6}$-alkyl, hydroxy-C$_{1-6}$-alkyl, O—C$_{1-6}$-alkyl, C$_{0-6}$-alkylene-C(O)OR$^2$, S(O)—C$_{1-6}$-alkyl, S(O)$_2$—C$_{1-6}$-alkyl, N(R$^2$)$_2$, C(O)N(R$^2$)$_2$, S(O)$_2$N(R$^2$)$_2$ and C$_{3-6}$-cycloalkyl, wherein alkyl, alkylene and cycloalkyl are unsubstituted or substituted with 1 to 3 substituents independently selected from the group consisting of halogen, OH, CN, NH$_2$, oxo and OS(O)$_2$CH$_3$.

In a preferred embodiment in combination with any of the above and below embodiments, -L$^2$-D is

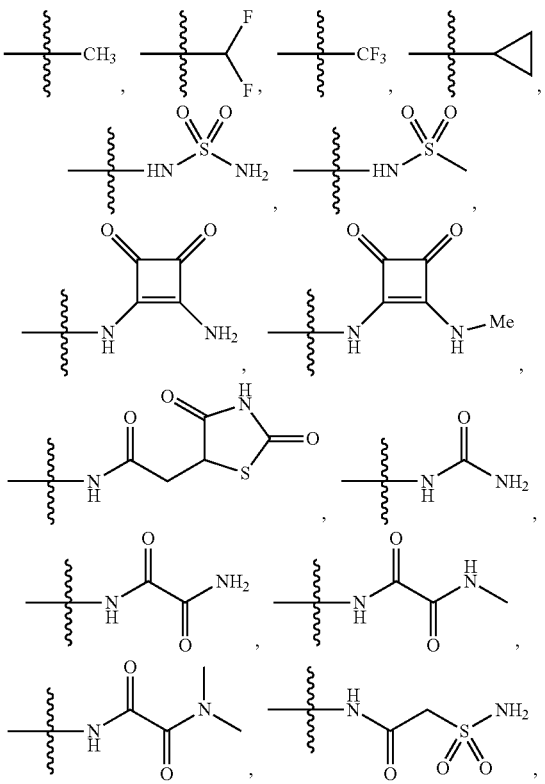

-continued
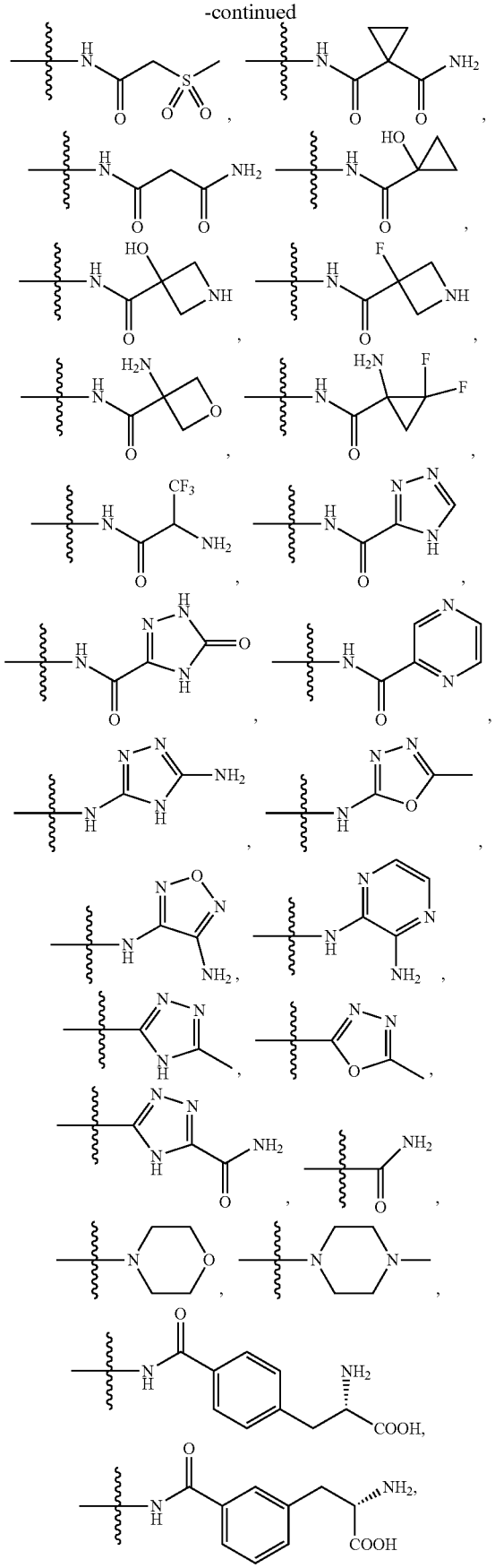
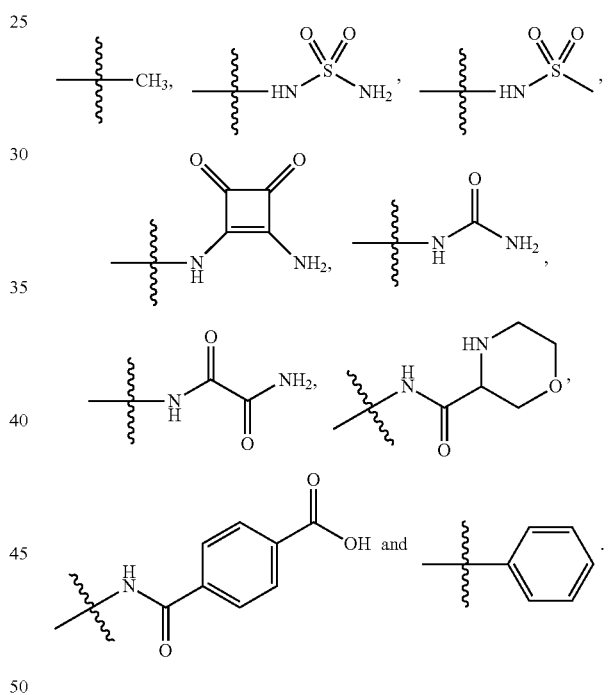
In a more preferred embodiment in combination with any of the above and below embodiments, -L²-D is
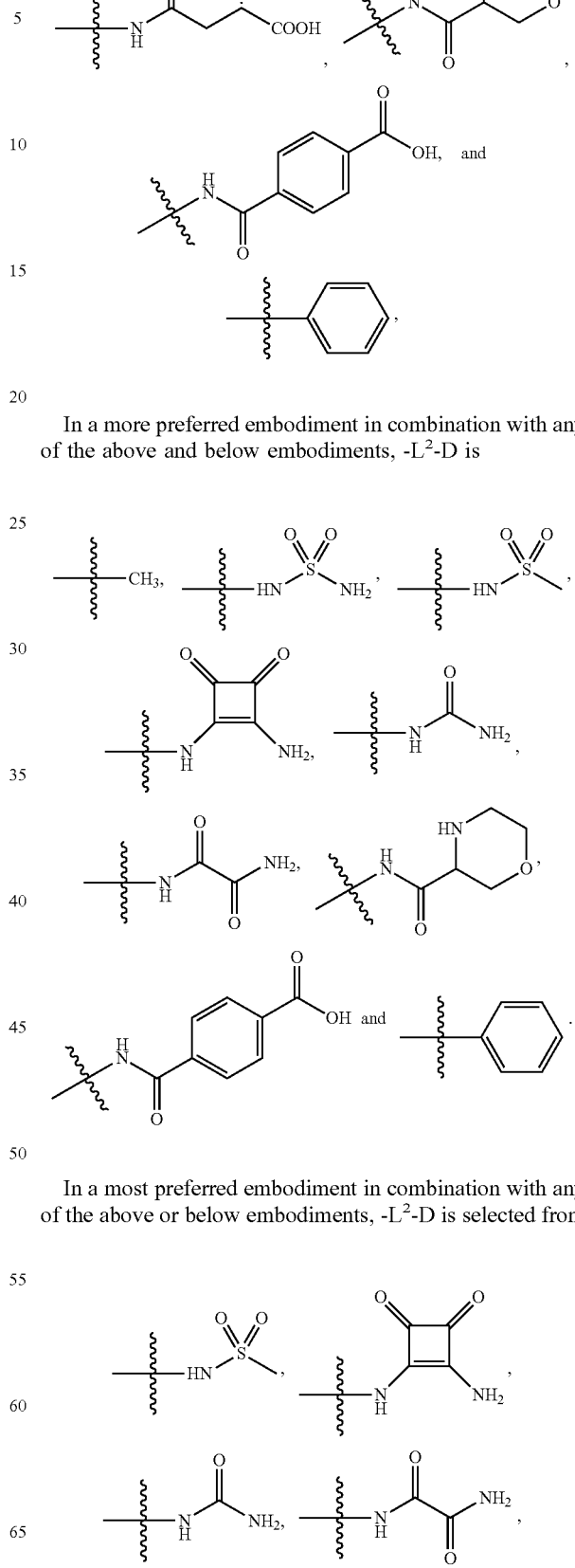
In a most preferred embodiment in combination with any of the above or below embodiments, -L²-D is selected from
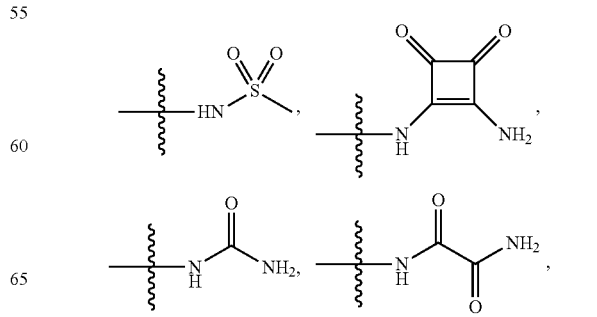

-continued

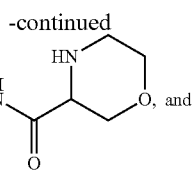

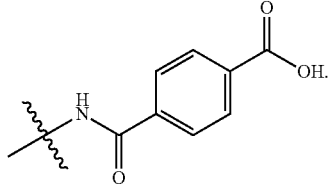

In an equally preferred embodiment in combination with any of the above or below embodiments, -L²-D is selected from

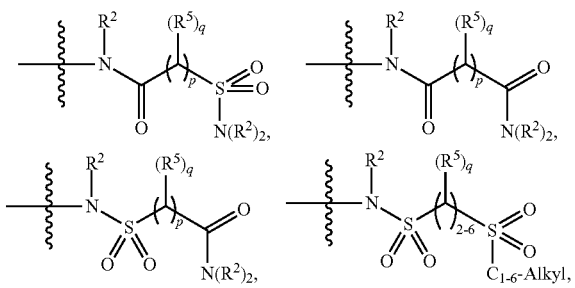

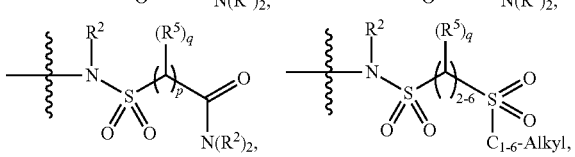

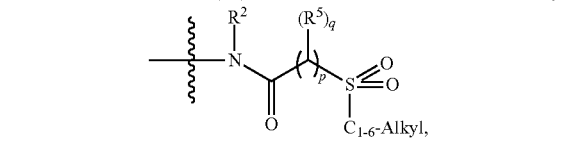

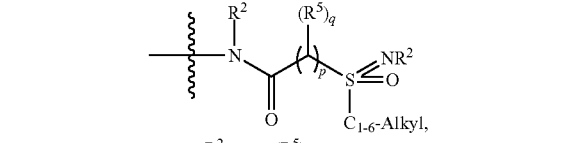

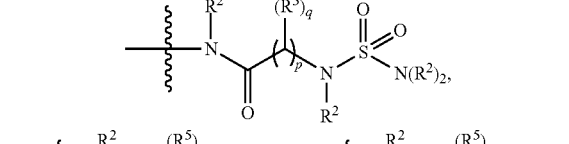

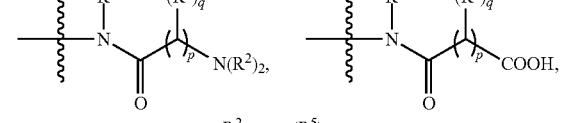

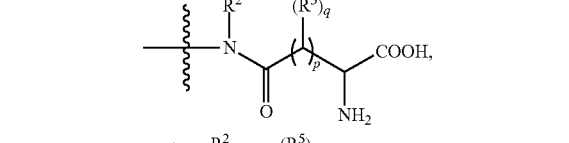

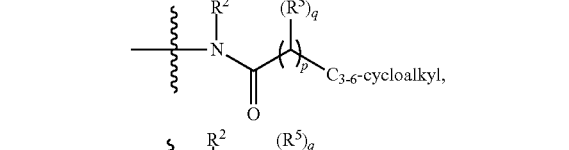

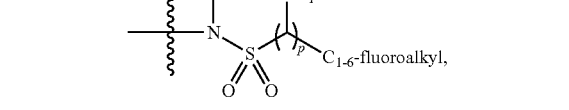

-continued

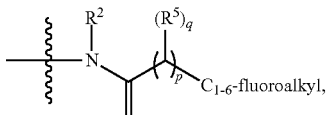

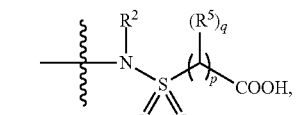

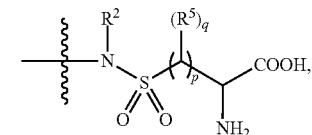

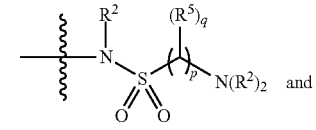

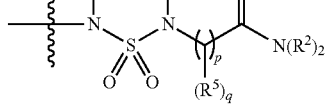

wherein $R^5$ is independently selected from the group consisting of halogen, $C_{1-6}$-alkyl, halo-$C_{1-6}$-alkyl and OH or two $R^5$ form a 3- to 6-membered cycloalkyl ring;

p is 1 to 6 and q is 0, 1, 2 or 3.

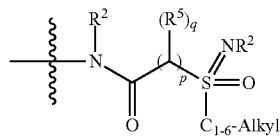

A preferred embodiment of the group are the following groups

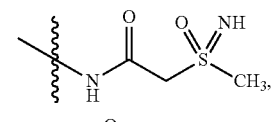

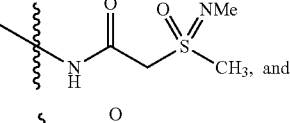

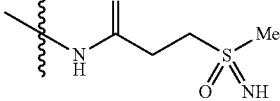

In a more preferred embodiment in combination with any of the above or below embodiments, -L²-D is selected from

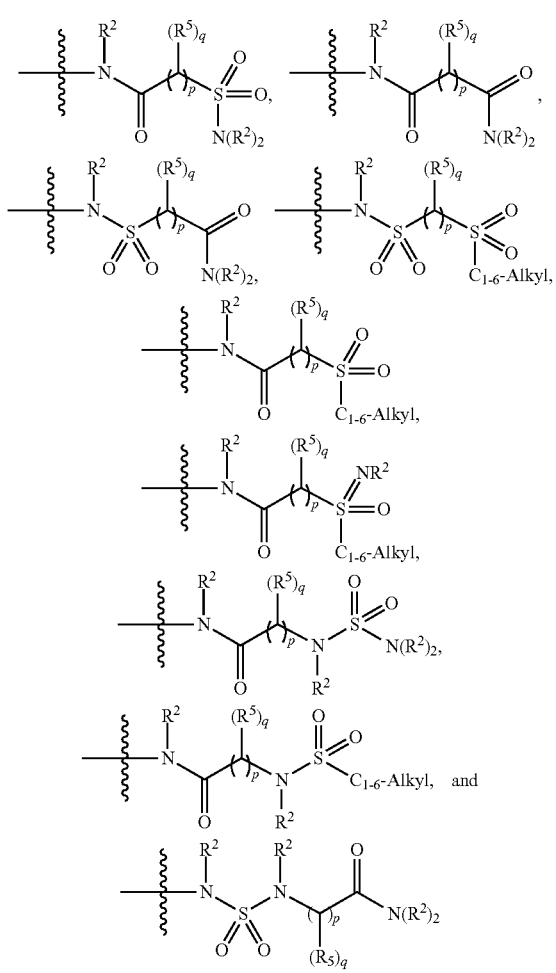

wherein
R⁵ is independently selected from the group consisting of halogen, $C_{1-6}$-alkyl, halo-$C_{1-6}$-alkyl, or two R⁵ form a 3- to 6-membered cycloalkyl ring;
p is 1 or 2
q is 0, 1, 2 or 3.

In a more preferred embodiment in combination with any of the above or below embodiments, -L²-D is selected from

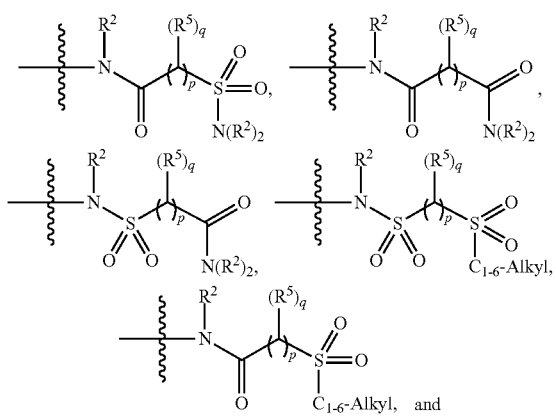

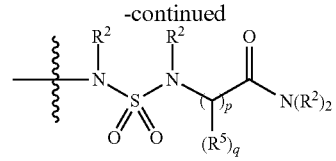

wherein
R⁵ is independently selected from the group consisting of halogen, $C_{1-6}$-alkyl, halo-$C_{1-6}$-alkyl, or two R⁵ form a 3- to 6-membered cycloalkyl ring;
p is 1 or 2
q is 0, 1, 2 or 3.

In a further more preferred embodiment in combination with any of the embodiments above or below, L²-D is selected from

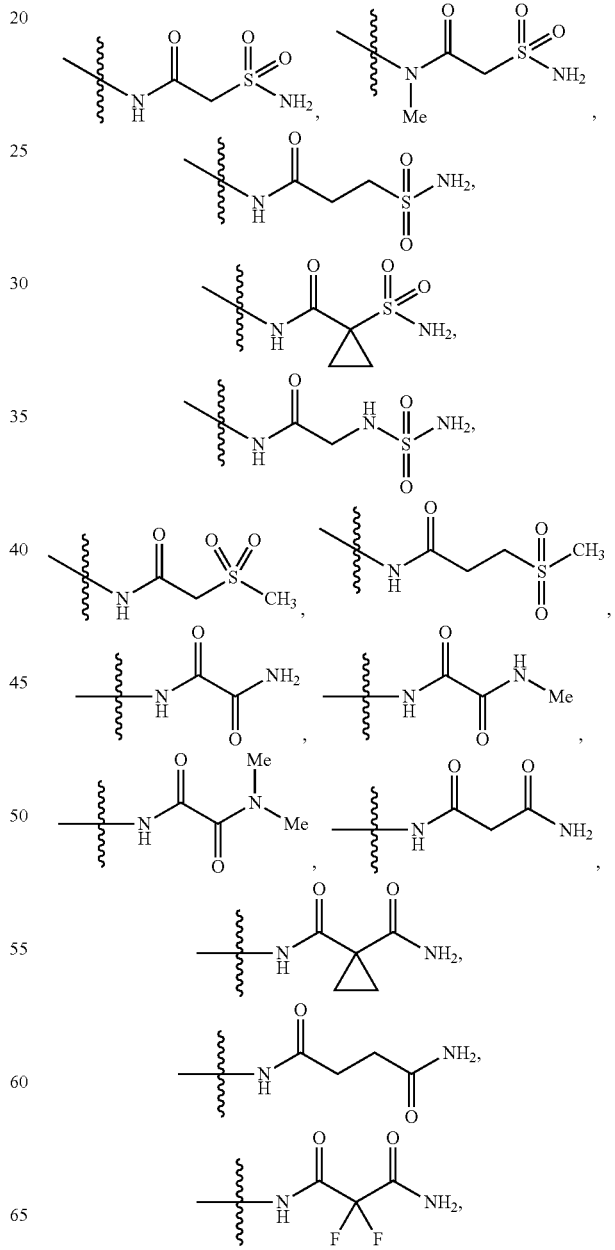

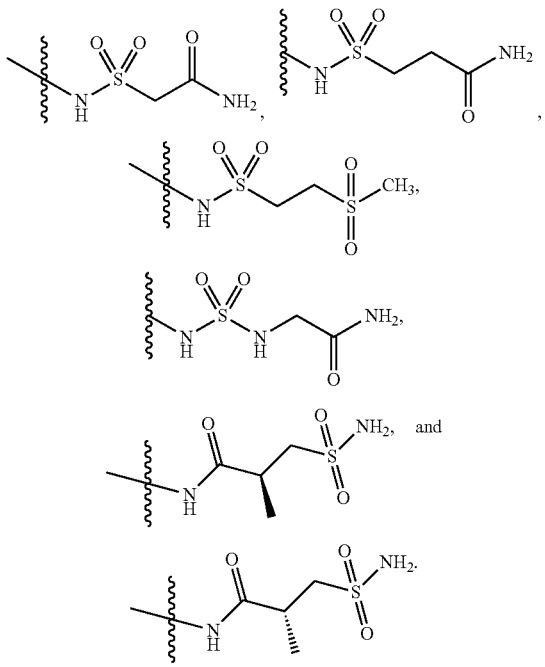

In an even more preferred embodiment in combination with any of the embodiments above or below, L²-D is selected from

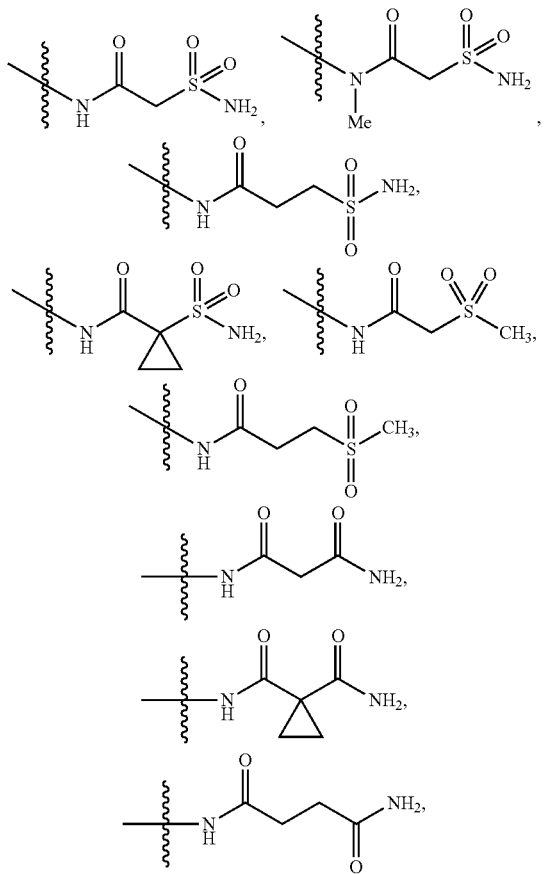

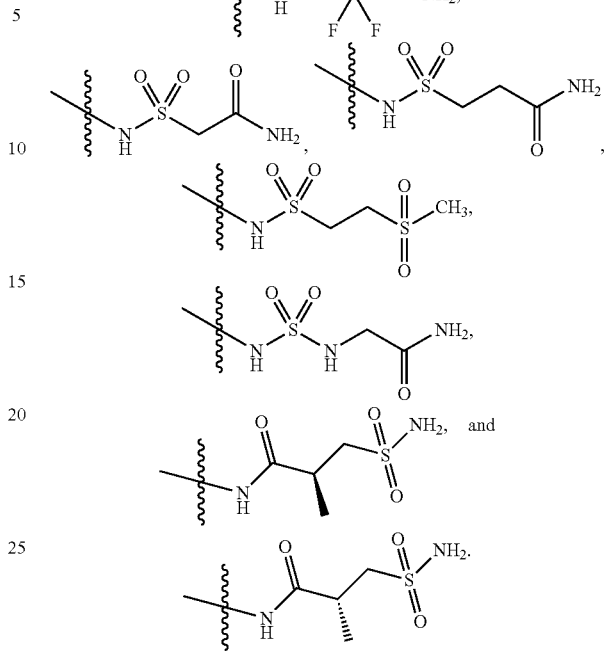

In a further equally preferred embodiment in combination with any of the above or below embodiments, L²-D is selected from

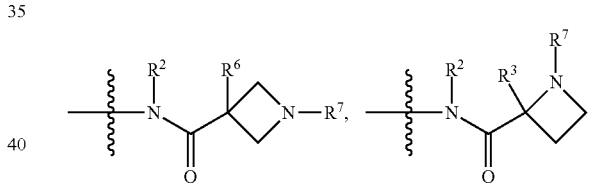

wherein R⁶ is selected from the group consisting of hydrogen, $C_{1-6}$-alkyl, hydroxy, halogen, $OR^2$, CN, and $C(O)N(R^2)_2$, and R⁷ is selected from the group consisting of hydrogen, $C_{1-6}$-alkyl, $C(O)NR^2$—$C_{1-6}$-alkyl, $C(O)C_{1-6}$-alkyl, and $S(O)_2 N(R^2)_2$ in combination with any of the above or below embodiments, -L²-D is selected from

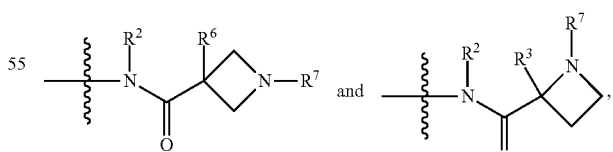

wherein

R⁶ is selected from the group consisting of hydroxy, halogen, $OR^2$, CN and $C(O)N(R^2)_2$; and R' is selected from the group consisting of $C(O)NR^2$—$C_{1-6}$-alkyl, $S(O)_2N(R^2)_2$, and $C(O)C_{1-6}$-alkyl.

In a more preferred embodiment in combination with any of the above or below embodiments, -L²-D is selected from

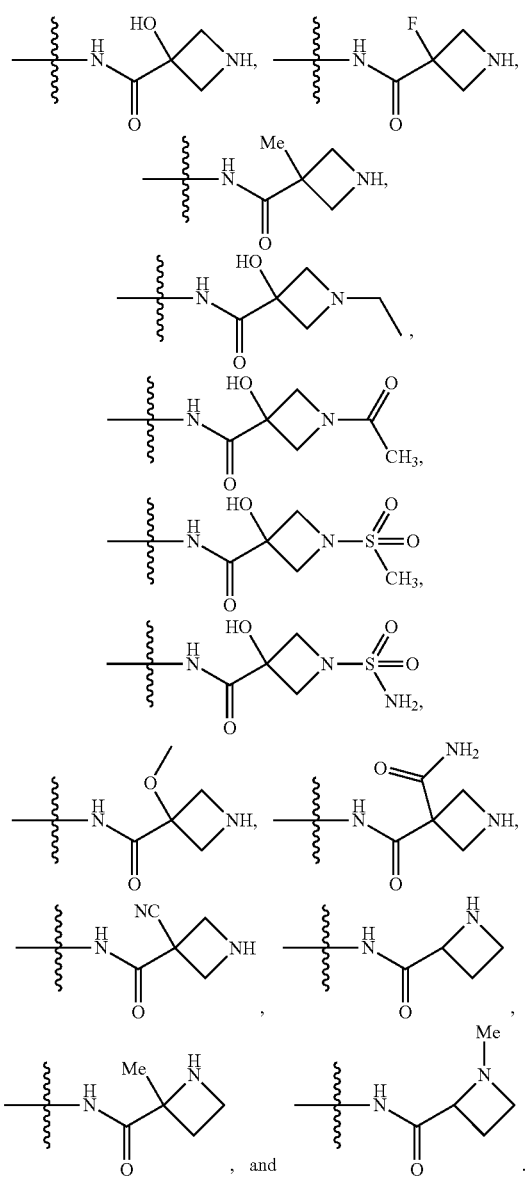

In a most preferred embodiment in combination with any of the above or below embodiments, -L²-D is selected from

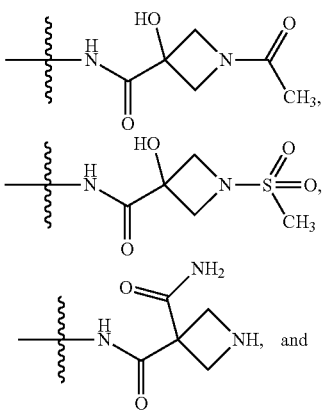

-continued

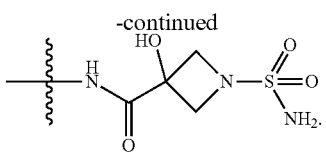

In a further equally preferred embodiment in combination with any of the above or below embodiments, L²-D is selected from

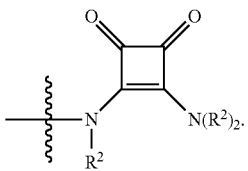

In a further equally more preferred embodiment in combination with any of the above or below embodiments, L²-D is selected from

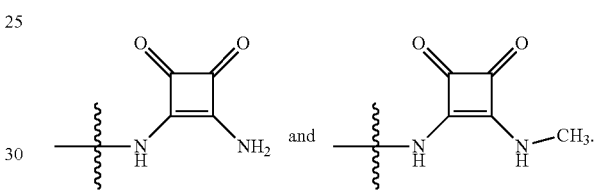

In a further equally preferred embodiment in combination with any of the above or below embodiments, L²-D is selected from

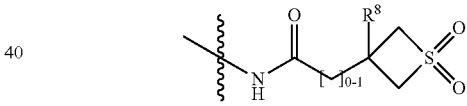

wherein $R^8$ is selected from the group consisting of hydrogen, $C_{1-6}$-alkyl, hydroxy, halogen, $OR^2$, CN, and $N(R^2)_2$.

In a further more preferred embodiment in combination with any of the above or below embodiments, L²-D is selected from

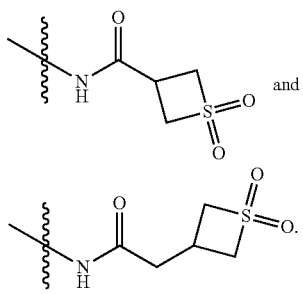

In a preferred embodiment in combination with any of the above or below embodiments, the compound according to formula (I) is selected from the group consisting of

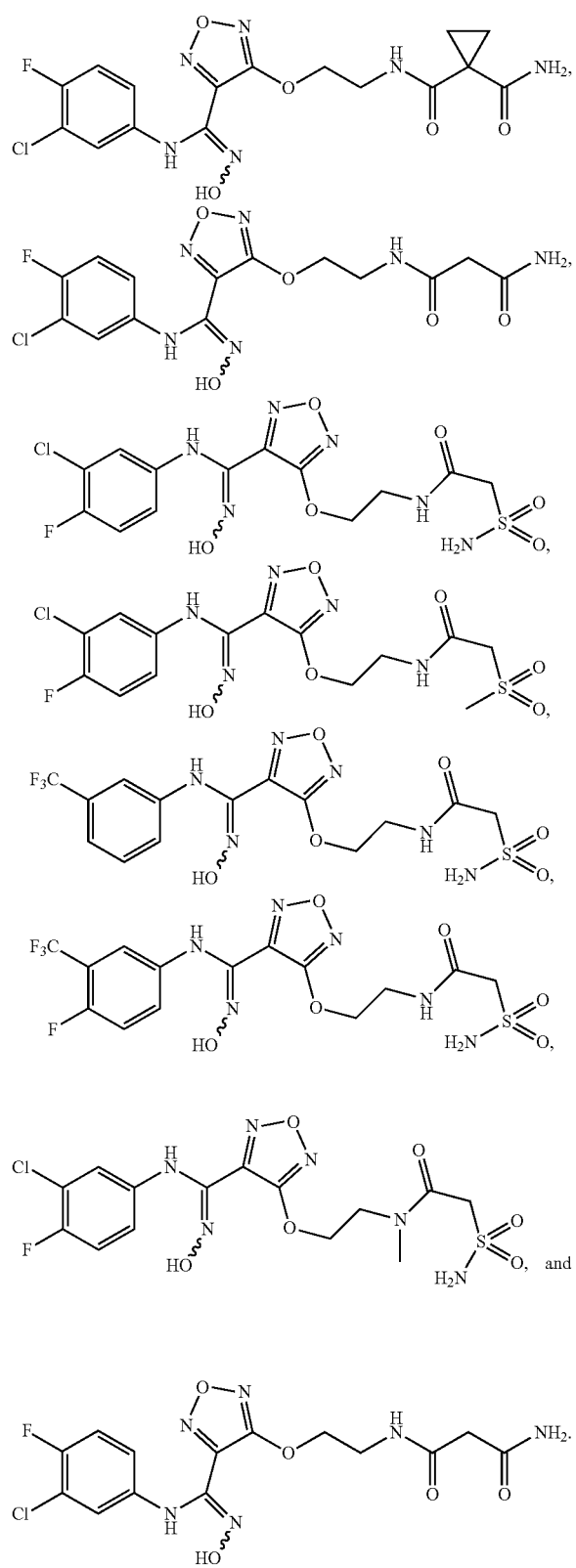
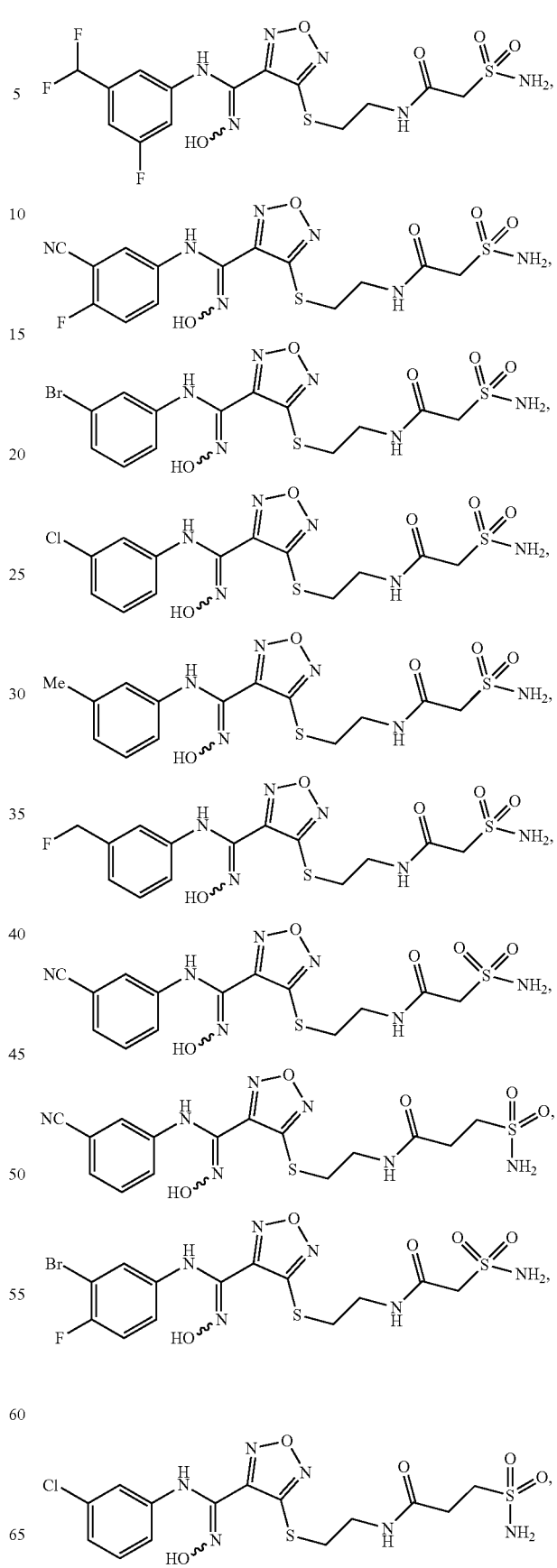
In an equally preferred embodiment in combination with any of the above or below embodiments, the compound according to formula (I) is selected from the group consisting of 29
-continued
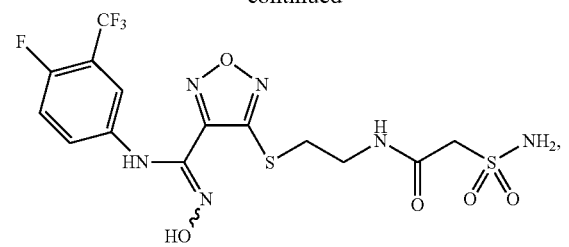
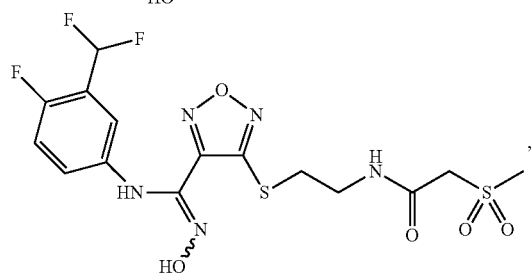
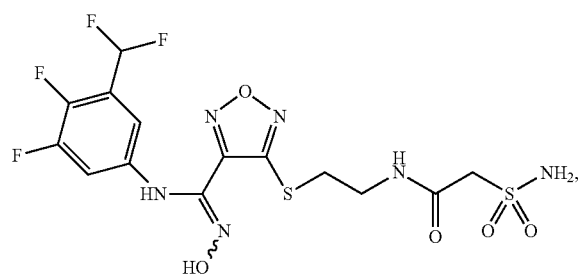
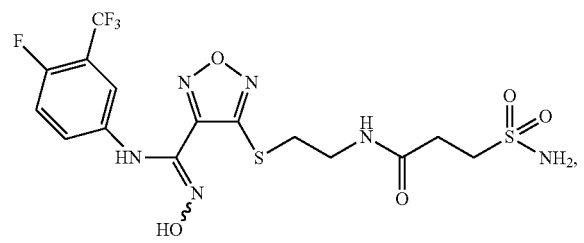
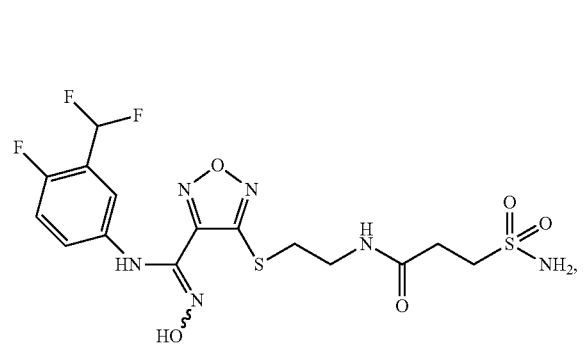
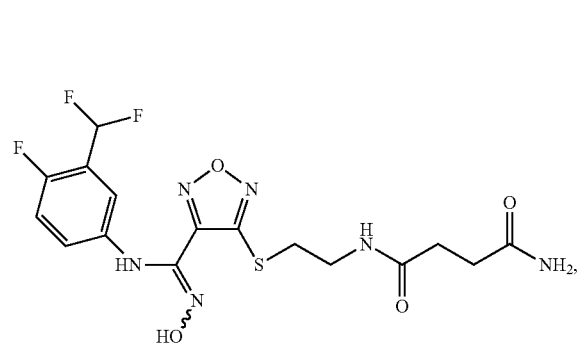
30
-continued
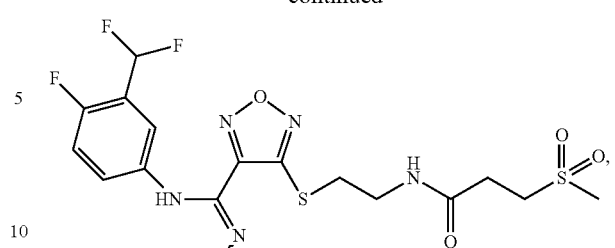
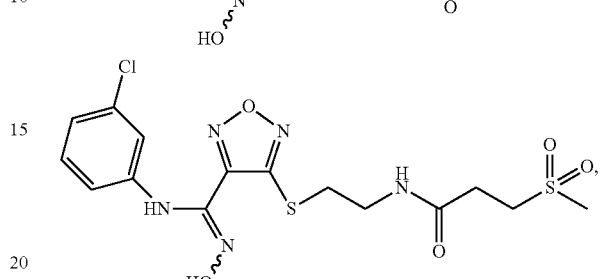
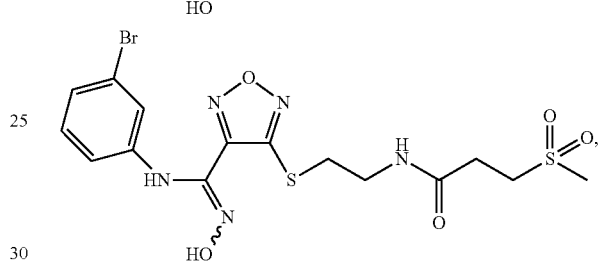
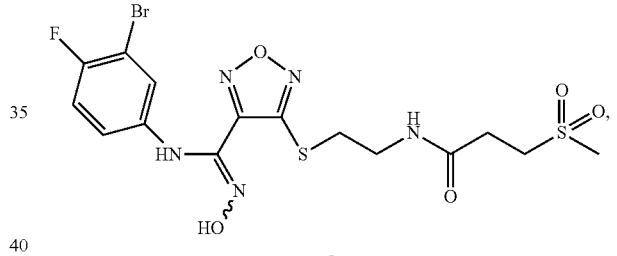
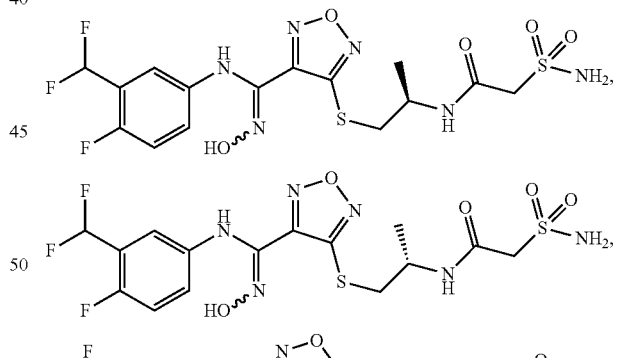
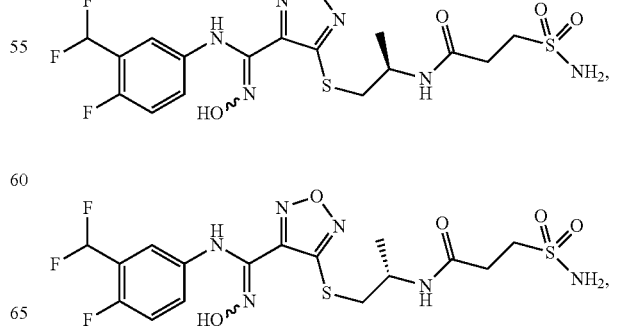

-continued
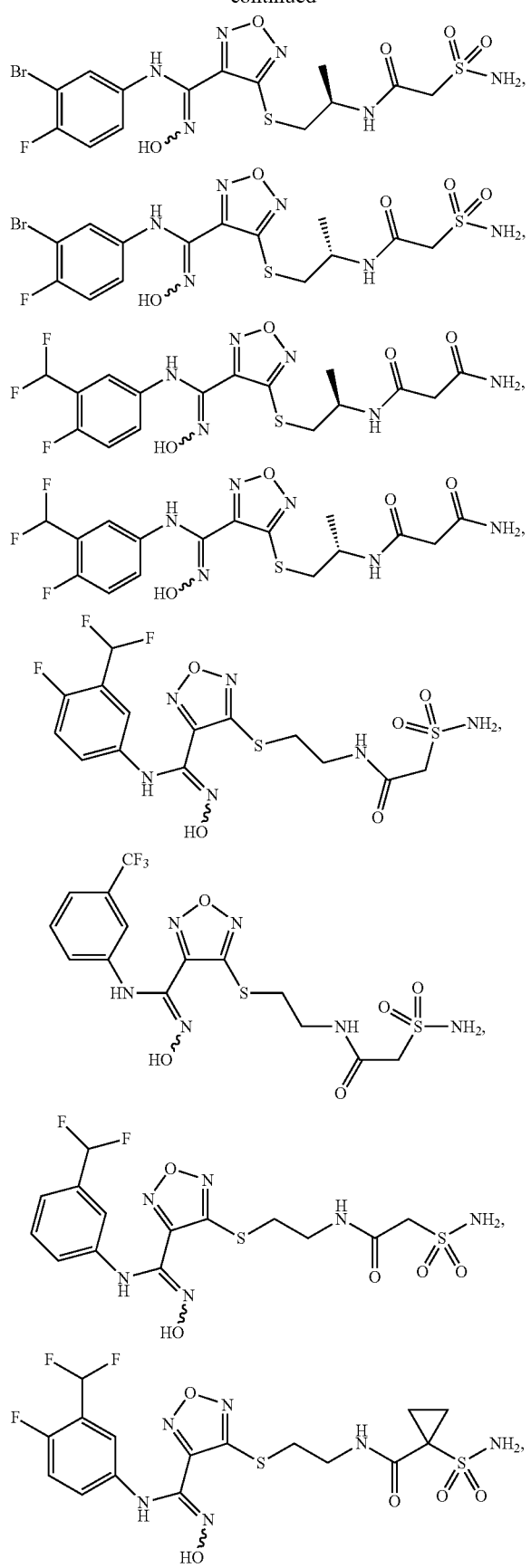
-continued
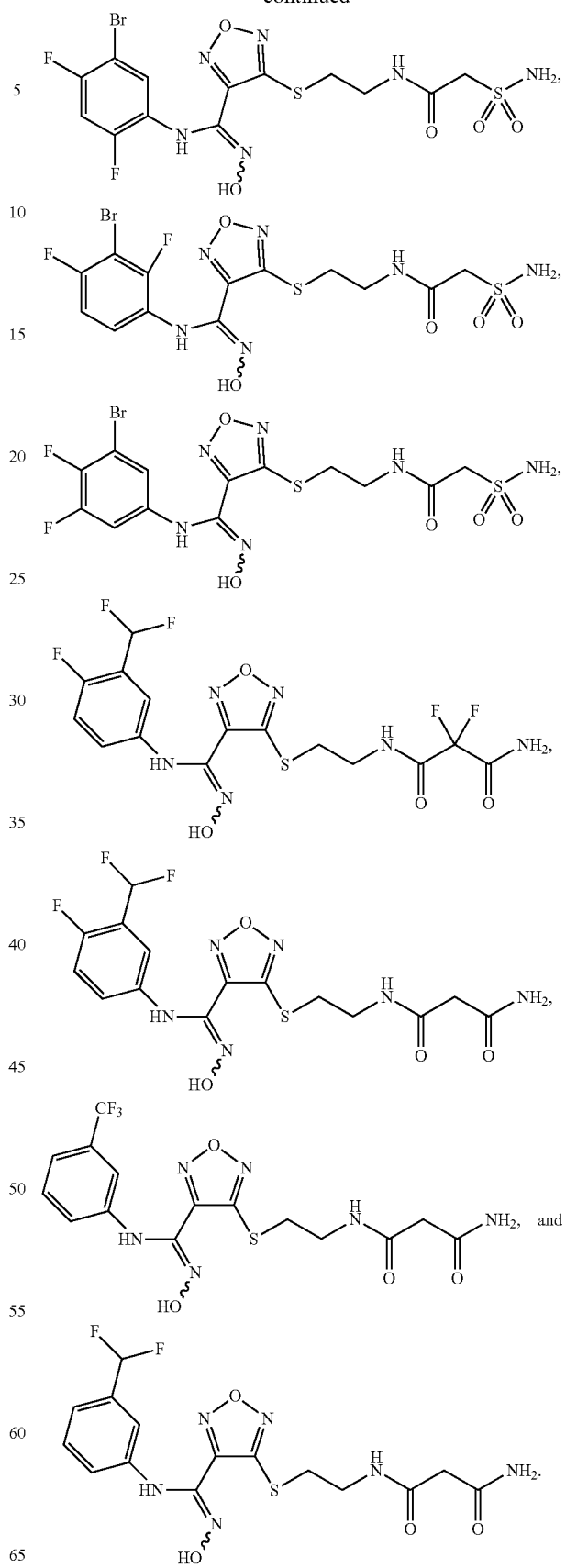

In a further equally preferred embodiment in combination with any of the above or below embodiments, the compound according to formula (I) is selected from the group consisting of

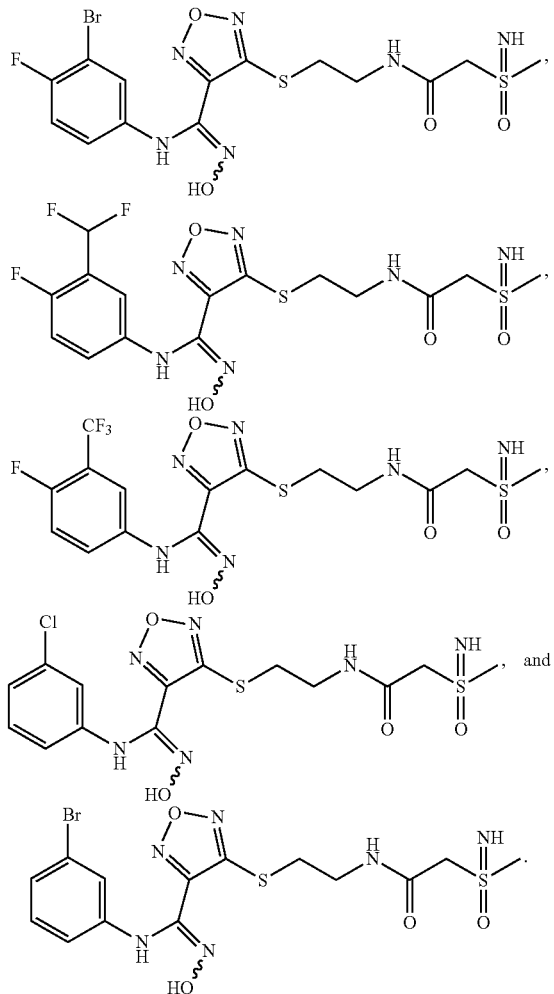

In the context of the present invention "$C_{1-6}$-alkyl" means a saturated alkyl chain having 1, 2, 3, 4, 5, or 6 carbon atoms which may be straight chained or branched. Examples thereof include methyl, ethyl, propyl, isopropyl, n-butyl, isobutyl, tert-butyl, n-pentyl, isopentyl, neopentyl and hexyl.

The term "halo-$C_{1-6}$-alkyl" means that one or more hydrogen atoms in the alkyl chain are replaced by a halogen. A preferred example thereof is $CF_3$.

"$C_{2-6}$-alkenyl" means an alkyl chain having 2, 3, 4, 5 or 6 carbon atoms which may be straight chained or branched, containing at least one carbon to carbon double bond. Examples thereof include ethenyl, propenyl, butenyl, pentenyl and hexenyl.

"$C_{2-6}$-alkynyl" means an alkyl chain having 2, 3, 4, 5 or 6 carbon atoms which may be straight chained or branched, containing at least one carbon to carbon triple bond. Examples thereof include ethynyl and propynyl.

A "$C_{0-10}$-alkylene" means that the respective group is divalent and connects the attached residue with the remaining part of the molecule. The same applies to the divalent $C_{3-6}$-cycloalkylene and heterocycloalkylene. Moreover, in the context of the present invention, "$C_0$-alkylene" is meant to represent a bond. An alkylene group may be straight chained or branched.

A $C_{3-10}$-cycloalkyl group or $C_{3-10}$-carbocycle means a saturated or partially unsaturated mono-, bi-, spiro-, or multicyclic ring system comprising 3, 4, 5, 6, 7, 8, 9, or 10 ring members. Examples include cyclopropyl, cyclobutyl, cyclopentyl, cyclohexyl, cyclohexenyl, bicyclo[2.2.2]octyl, bicyclo[2.2.1]heptyl, adamantyl, spiro[3.3]heptane and pentacyclo[4.2.0.0$^{2,5}$.0$^{3,8}$.0$^{4,7}$]octyl. Accordingly, a $C_{3-6}$-cycloalkyl group means a cycloalkyl ring having 3, 4, 5 or 6 carbon atoms. The $C_{3-10}$-cycloalkyl group can be connected to the remainder of the molecule via a bond or the cycloalkyl group may share a carbon at the attachment point with the remainder of the molecule. Illustrative examples of the attachment possibilities are shown below:

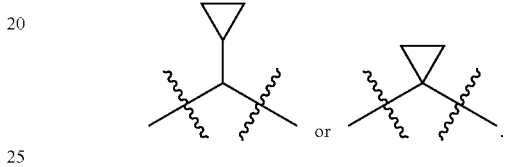

A 3- to 10-membered heterocycloalkyl group means a saturated or partially unsaturated mono-, bi-, spiro or multicyclic ring system having 3, 4, 5, 6, 7, 8, 9 or 10 ring members. Similarly, a 3- to 8-membered heterocycloalkyl group means a saturated or partially unsaturated mono-, bi-, spiro or multicyclic ring system having 3, 4, 5, 6, 7 or 8 ring members The heterocycloalkyl comprises 1, 2, 3, 4 or 5 heteroatoms, wherein the heteroatoms are independently selected from N, O, S, S(O) and S(O)$_2$. Examples thereof include epoxidyl, azetidinyl, oxetanyl, pyrrolidinyl, tetrahydrofuranyl, piperidinyl, piperazinyl tetrahydropyranyl, 1,4-dioxanyl, morpholinyl, 4-quinuclidinyl, 1,4-dihydropyridinyl, 2-azaspiro[3.3]heptane and 3,6-dihydro-2H-thiopyranyl. The heterocycloalkyl group can be connected to the remainder of the molecule via a carbon atom or nitrogen atom.

In the context of the present invention cycloalkylene and heterocycloalkylene means a cycloalkyl group and heterocycloalkyl group, respectively, that can be connected to the remainder of the molecule via the same or two different atoms. Examples thereof include

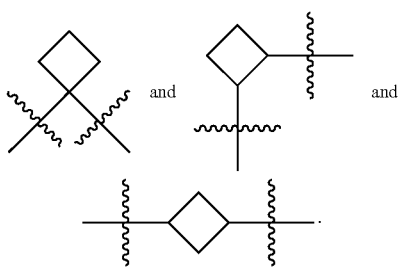

A 5-14-membered mono-, bi- or tricyclic heteroaromatic ring system (within the application also referred to as heteroaryl) containing up to 4 heteroatoms means a monocyclic heteroaromatic ring such as pyrrolyl, imidazolyl, furanyl, thiophenyl, pyridinyl, pyrimidinyl, pyrazinyl, pyrazolyl, oxazolyl, isoxazolyl, triazolyl, oxadiazolyl and thiadiazolyl. It further means a bi- or tricyclic ring system wherein the heteroatom(s) may be present in one or both rings including the bridgehead atoms. Examples thereof include quinolinyl, isoquinolinyl, quinoxalinyl, benzimidazolyl, benzisoxazolyl, benzodioxanyl, benzofuranyl, benzoxazolyl, indolyl, indolizinyl, pyrazolo[1,5-a]pyrimidinyl and dibenzo[b,d]furanyl. The nitrogen or sulphur atom of the heteroaryl system may also be optionally oxidized to the corresponding N-oxide, S-oxide or S,S-dioxide. If not stated otherwise, the heteroaryl system can be connected via a carbon or nitrogen atom. Examples for N-linked heterocycles are

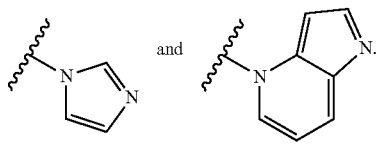 [SMILES: *n1ccnc1 ; *n1cccc2nccc1-2]

A 6-10-membered mono- or bicyclic aromatic ring system (within the application also referred to as aryl) means an aromatic carbon cycle such as phenyl or naphthyl.

Halogen is selected from fluorine, chlorine, bromine and iodine.

The compounds of the present invention are further intended to include all possible geometric isomers. Cis and trans geometric isomers of the compounds of the present invention are described and may be isolated as a mixture of isomers or as separated forms. A bond in a structure diagram represented by a wavy line "⁓" is intended to indicate that the structure represents the cis or the trans isomer, or a mixture of the cis and trans isomers in any ratio.

Compounds of the present invention also include tautomeric forms. Tautomeric forms result from the swapping of a single bond with an adjacent double bond together with the concomitant migration of a proton.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids.

The compounds of the present invention which contain one or more basic groups, i.e. groups which can be protonated can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Further the compounds of the present invention may be present in the form of solvates, such as those which include as solvate water, or pharmaceutically acceptable solvates, such as alcohols, in particular ethanol.

The compounds of the present invention are useful as inhibitors of IDO1. Hence, they are potential therapeutic agents for the prophylaxis and/or treatment of IDO1-mediated diseases or conditions such as cancer, viral and bacterial infections such as HIV infection, depression, neurodegenerative diseases such as Alzheimer's disease and Hunting-ton's disease, trauma, age-related cataracts, organ transplantation, asthma, rheumatoid arthritis, multiple sclerosis, inflammatory bowel disease, psoriasis, and systemic lupus erythematosus.

In a preferred embodiment, the compounds are used in the prophylaxis and/or treatment of cancer.

Furthermore, the present invention provides pharmaceutical compositions comprising at least one compound of the present invention, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing at least one compound of the present invention and a pharmaceutically acceptable excipient.

The pharmaceutical composition of the present invention may additionally comprise one or more other compounds as active ingredients like a prodrug compound or other therapeutic agents.

Additional therapeutic agents are preferably selected from known cancer therapeutics. Examples thereof include PD-1 agent, PD-L1 agent, CTLA-4 agent as well as chemotherapeutic agents, anticancer vaccines and cytokine therapy. The compounds of the present invention may also be administered to a patient while the patient undergoes irradiation therapy.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, emulsions and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing IDO mediated conditions for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

Abbreviations

Herein and throughout the application, the following abbreviations may be used.
Ac acetyl
br broad
d doublet
m multiplet
rt room temperature
CDI 1,1'-carbonyldiimidazole
DCM dichloromethane
DIBAL-H diisobutylaluminum hydride
DIPEA N, N-diisopropylethylamine
DMF N, N-dimethylformamide
DMSO dimethyl sulfoxide
EDC 1-ethyl-3-(3-dimethylaminopropyl)carbodiimide
Et$_2$O diethyl ether
EtOAc ethyl acetate
HATU O-(7-azabenzotriazol-1-yl)-N,N,N',N'-tetramethyluronium hexafluorophosphate
HOBt 1-hydroxybenzotriazole
HPLC high performance liquid chromatography
MCPBA m-chloroperoxybenzoic acid
Ms methanesulfonyl
NCS N-chlorosuccinimide
PE petroleum ether
SFC supercritical fluid chromatography
t triplet
TFA trifluoroacetic acid
TEA triethylamine
THF tetrahydrofurane General Schemes The compounds of the present invention can be prepared by a combination of methods known in the art including the procedures described in schemes 1-4 below. The following reaction schemes are only meant to represent examples of the invention and are in no way meant to be a limit of the invention.

Scheme 1 describes the preparation of alkoxy substituted 1,2,5-oxadiazoles of the present invention. Diethyl 2-oxosuccinate A-1 can be treated with hydroxylamine hydrochloride to give the carboxylic acid intermediate A-2. Esterification using concentrated sulfuric acid in methanol followed by base catalysed alkylation gives intermediate A-4, which can be saponified to the corresponding carboxylic acid A-5. Potassium permanganate oxidation gives carboxylic acid A-6 which can be converted to the aldehyde intermediate A-7 via Weinreb amide reduction. A sequence of oxime formation followed by chlorination with NCS gives the carbimidoyl chloride A 8. Reaction with an appropriate aniline affords compounds of structure A-9. Compounds of structure A-9 can be further converted via a sequence of hydroxyamidine protection using CDI (A-10) followed by transformations of the substituent Q into Q' by standard reactions known to persons skilled in the art (A-11) and deprotection of A-11 using sodium hydroxide to give compounds of structure A-12.

Scheme 2 describes the preparation of alkylthio substituted 1,2,5-oxadiazoles as well as the corresponding sulfoxides, sulfones and sulfoximines. 4-Nitro-1,2,5-oxadiazole-3-carbonitrile (B-1) reacts in a nucleophilic substitution with a thiol in presence of a base to the thioether intermediate B-2. Nitrile reduction with DIBAL-H gives the aldehyde intermediate B-3, which is converted to the carbimidoyl chloride B-5 via treatment with hydroxylamine followed by chlorination using NCS. Reaction with an appropriate aniline affords compounds of structure B-6. Treatment of B-6 with an excess of MCPBA gives the corresponding sulfon compounds of structure B-7. Treatment of B-6 with one equivalent of MCPBA gives the corresponding sulfoxide compounds of structure B-8. Sulfoxides B-8 also serves as intermediate and can be converted to intermediate B-9 through treatment with MgO, PhI(OAc)$_2$ and Rh$_2$(OAc)$_4$ in the presence of 2,2,2-trifluoracetamide. Treatment with K$_2$O0$_3$ converts intermediate B-9 into compounds of structure B-10. Compounds of structure B-6 can be further converted via a sequence of hydroxyamidine protection using CDI (B-11) followed by transformations of the substituent Q into Q' by standard reactions known to persons skilled in the art (B-12) and deprotection of B-12 using sodium hydroxide to give compounds of structure B-13.

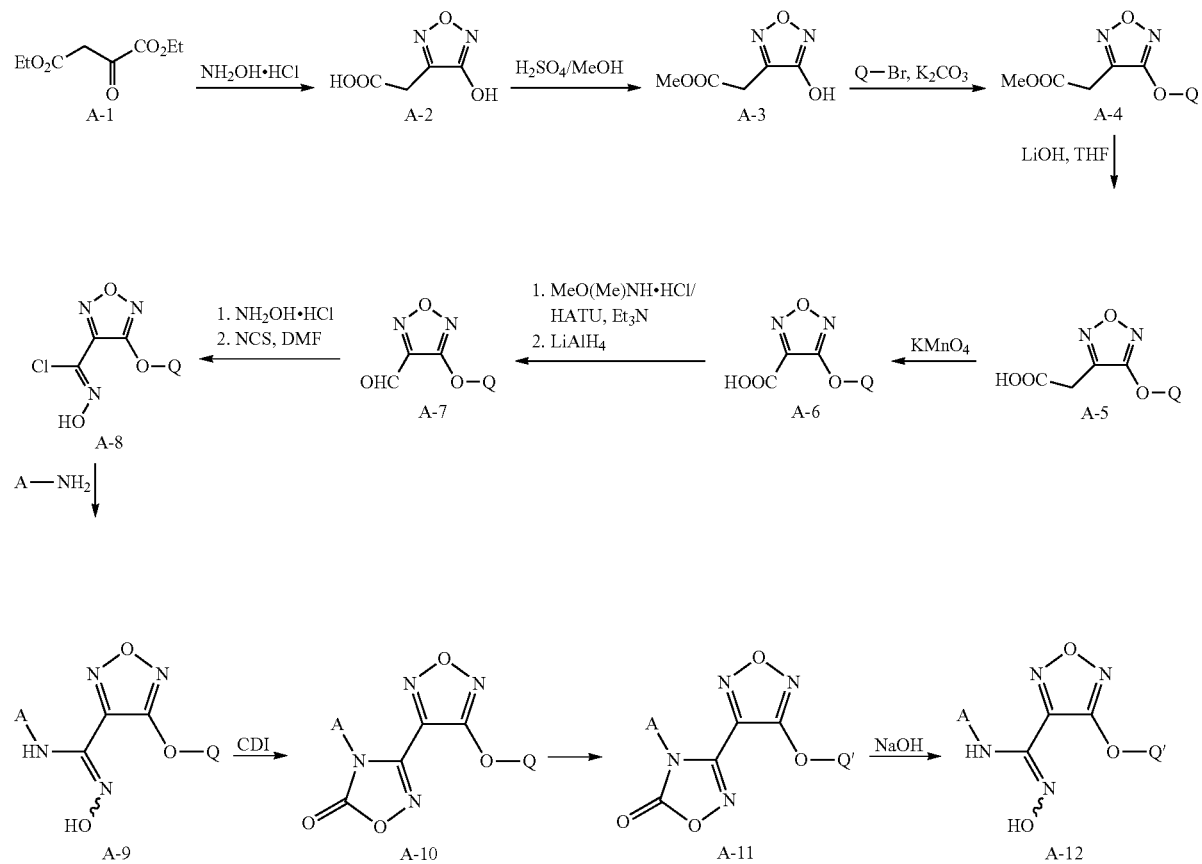

Q, Q' = —C—L$_2$—D or a residue with a functional group allowing the synthesis of —C—L$_2$—D

Scheme 2

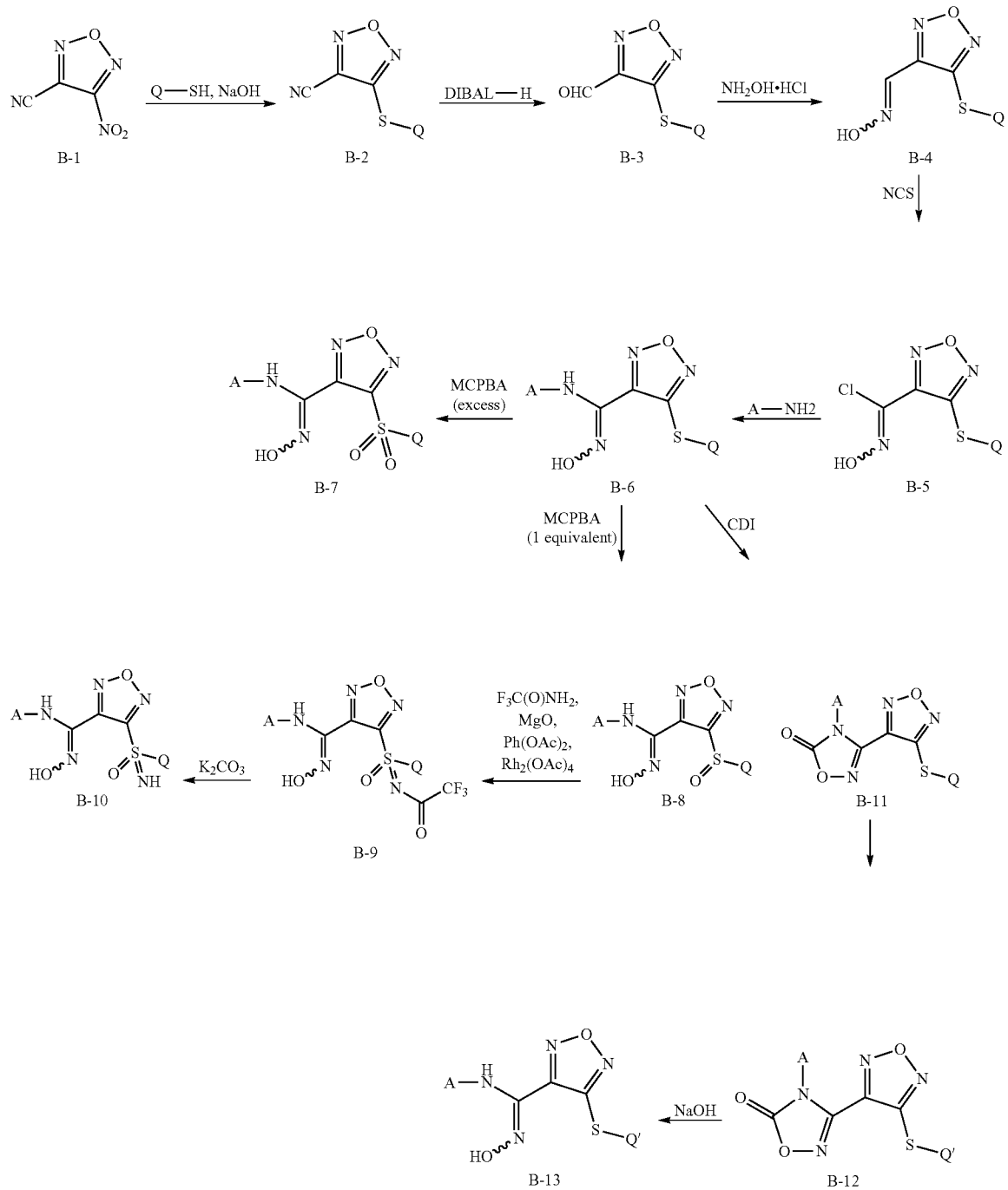

Q, Q' = —C—L$_2$—D or any residue with a functional
group allowing the synthesis of —C—L$_2$—D Scheme 3 describes the preparation of alkylthio substituted 1,2,5-thiadiazoles or 1,2,5-oxadiazoles. Amide coupling of 4-amino-1,2,5-thiadiazole-3-carboxylic acid or 4-amino-1,2,5-oxadiazole-3-carboxylic acid (C-1) with an appropriate aniline affords intermediate C-2. Amide C-2 is converted to the corresponding hydroxyamidine C-3 by treatment with phosphorous pentachloride and hydroxylamine. Treatment with CDI gives intermediate C-4 which is oxidised with hydrogen peroxide to the corresponding nitro compound C-5. Intermediate C-5 reacts in a nucleophilic substitution with a thiol in presence of a base to the thioether intermediate C-6. Compounds of structure C-6 can be further converted to intermediates of structure C-7 by transformations of the substituent Q into Q' using standard reactions known to persons skilled in the art. Deprotection of intermediate C-7 using sodium hydroxide can give compounds of structure C-8.

Scheme 3

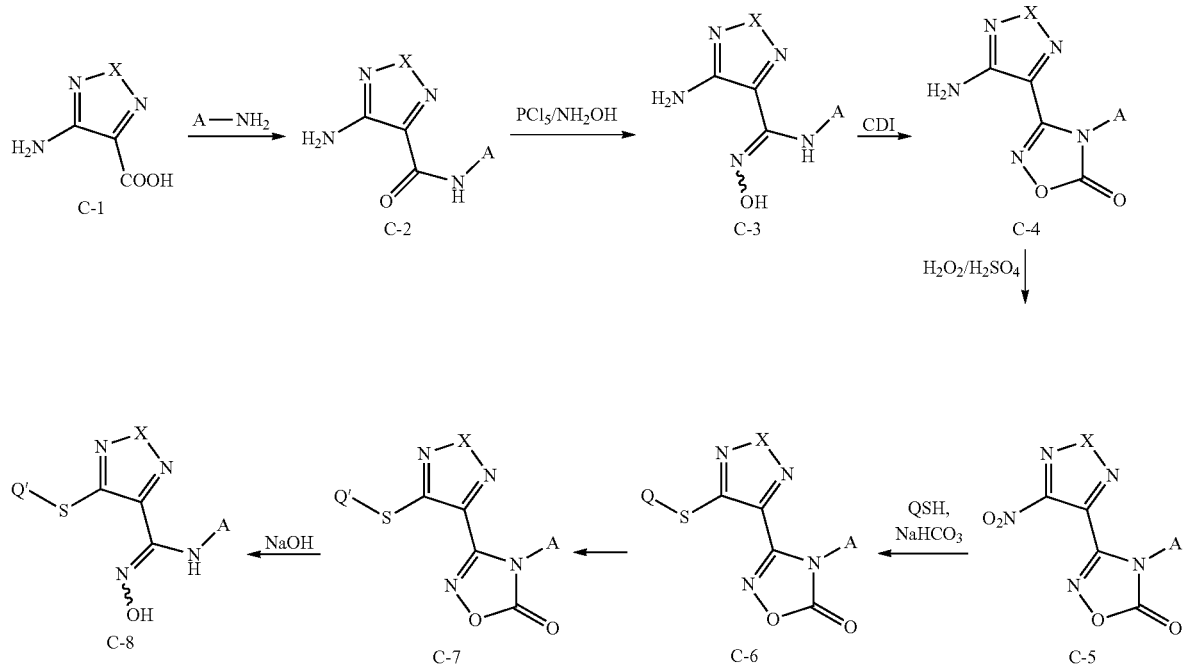

X = S or O
Q, Q' = —C—L₂—D or any residue with a functional
group allowing the synthesis of —C—L₂—D Scheme 4 describes an alternative synthetic route of alkoxy substituted 1,2,5-thiadiazoles or 1,2,5-oxadiazoles. Intermediate C-5 reacts in a nucleophilic substitution with alcohols in presence of a base, e.g. 30% aqueous NaOH to the ether intermediate C-9. Compounds of structure C-9 can be further converted to intermediates of structure C-10 by transformations of the substituent Q into Q' using standard reactions known to persons skilled in the art. Deprotection of intermediate C-10 using sodium hydroxide can give compounds of structure C-11.

Scheme 4

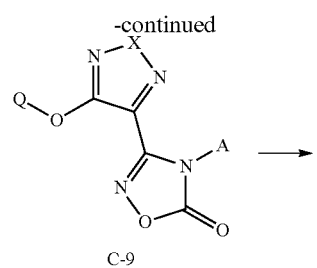

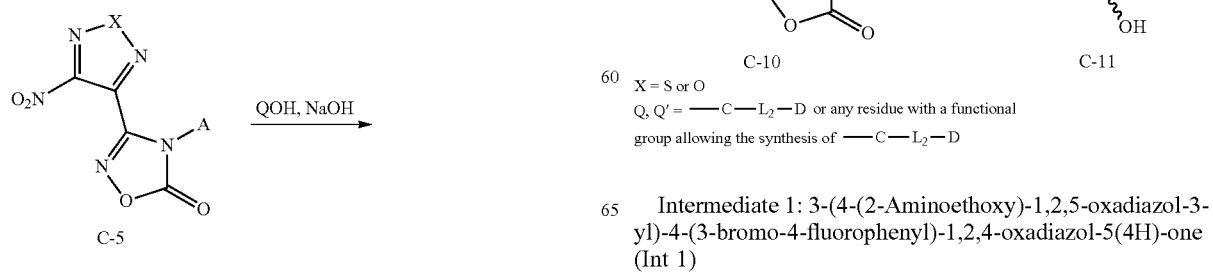

X = S or O
Q, Q' = —C—L₂—D or any residue with a functional
group allowing the synthesis of —C—L₂—D Intermediate 1: 3-(4-(2-Aminoethoxy)-1,2,5-oxadiazol-3-yl)-4-(3-bromo-4-fluorophenyl)-1,2,4-oxadiazol-5(4H)-one (Int 1)

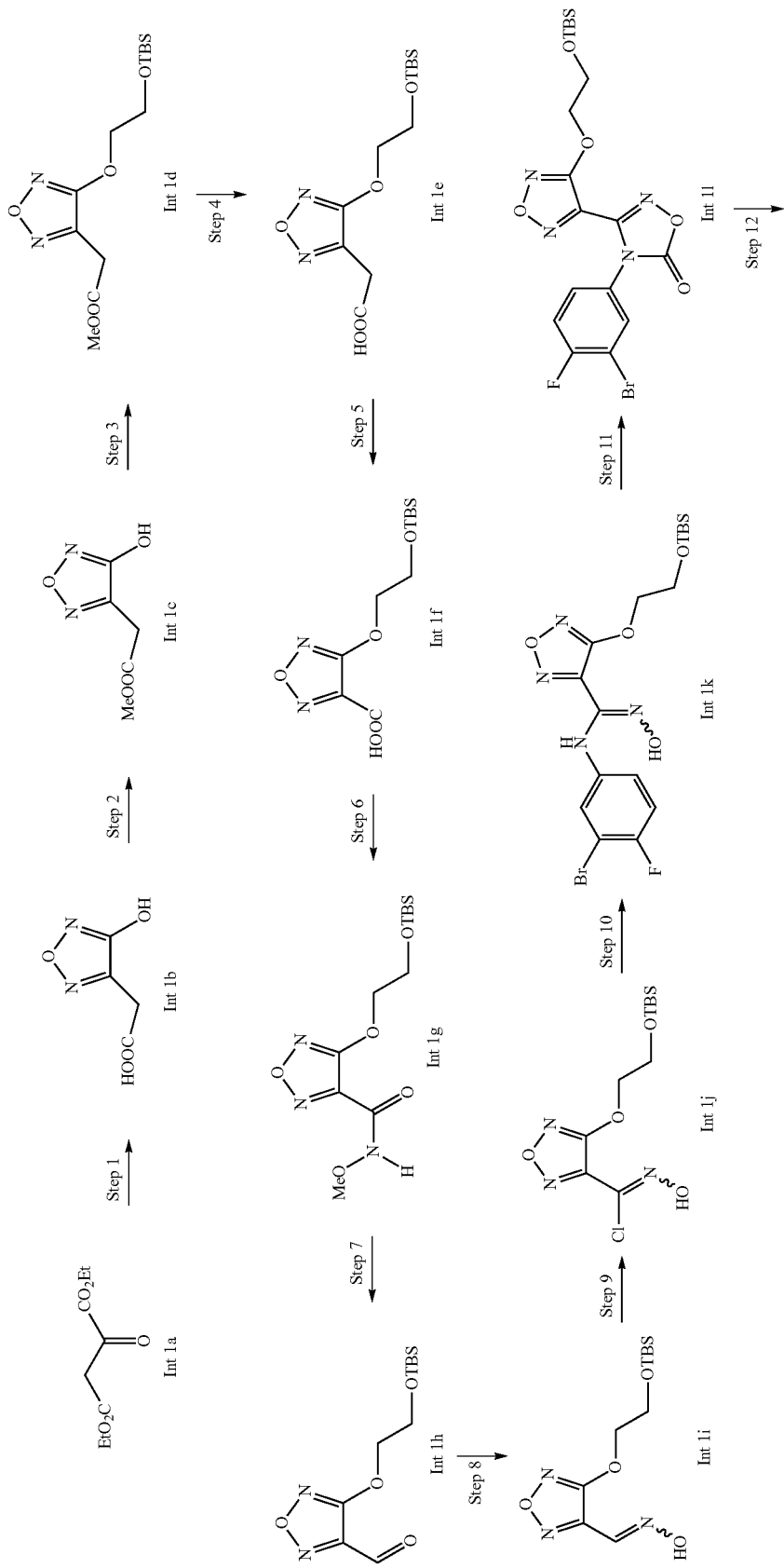

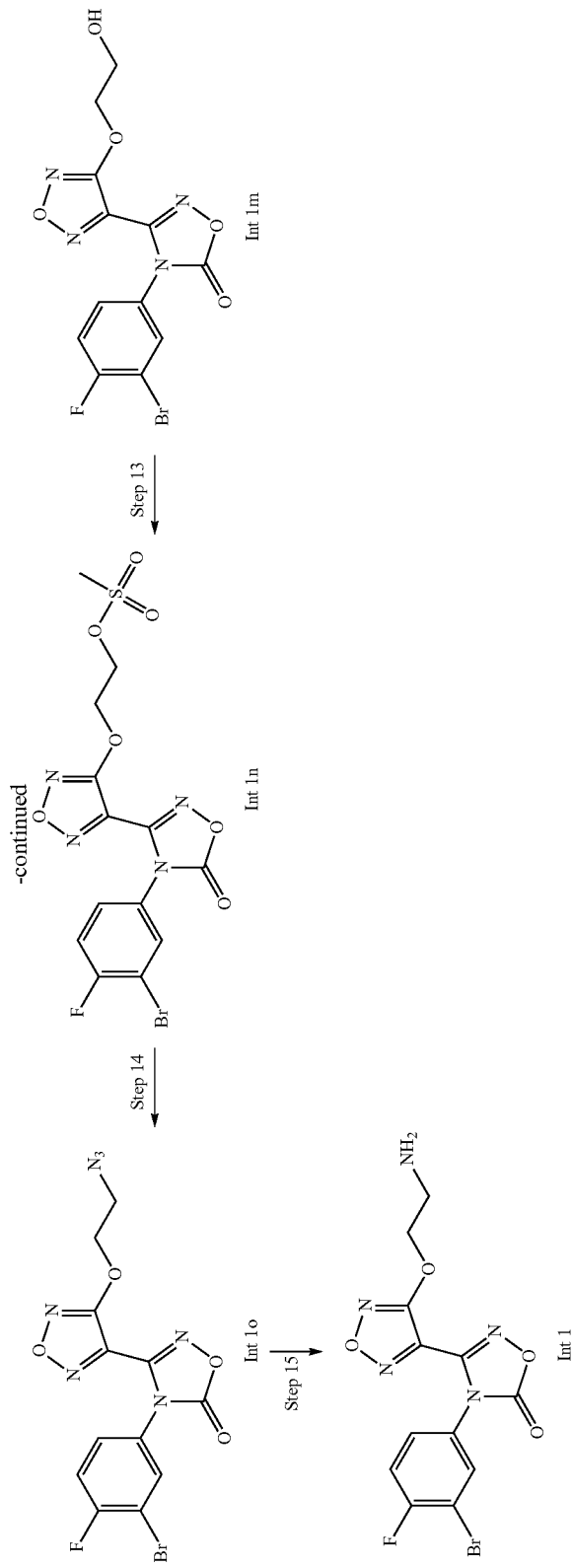

Step 1: 2-(4-Hydroxy-1,2,5-oxadiazol-3-yl)acetic acid (Int 1b)

To a solution of hydroxylamine hydrochloride (7.40 g, 106 mmol) and $Na_2CO_3$ (5.10 g, 47.8 mmol) in water (22 mL) was added diethyl 2-oxosuccinate (Int 1a) (10.0 g, 53.1 mmol). The mixture was stirred at rt for 8 h. NaOH (4.90 g, 122 mmol) in water (6 mL) was added and the mixture was heated to 90° C. for 3 d. The mixture was cooled below 5° C. and acidified to pH 1 with 5M $H_2SO_4$. The mixture was extracted with EtOAc (5×50 mL). The combined organic layers were washed with brine (30 mL), dried over anhydrous $MgSO_4$, filtered and concentrated to dryness to give the title compound as a yellow solid.

Step 2: Methyl 2-(4-hydroxy-1,2,5-oxadiazol-3-yl)acetate (Int 1c)

To a solution of 2-(4-hydroxy-1,2,5-oxadiazol-3-yl)acetic acid (Int 1b) (1.20 g, 8.33 mmol) in methanol (25 mL) was added concentrated $H_2SO_4$ (0.2 mL). The mixture was heated at reflux for 4 h. Water (50 mL) was added and the mixture was extracted with EtOAc (3×50 mL). The combined organic layers were dried over anhydrous $Na_2SO_4$, filtered and concentrated to dryness. The residue was purified by column chromatography to give the title compound as a colorless oil.

Step 3: Methyl 2-(4-(2-((tert-butyldimethylsilyl)oxy)ethoxy)-1,2,5-oxadiazol-3-yl)acetate (Int 1d)

Potassium carbonate (943 mg, 6.83 mmol) was added to a stirred solution of methyl 2-(4-hydroxy-1,2,5-oxadiazol-3-yl)acetate (Int 1c) (720 mg, 4.55 mmol) in DMF (20 mL). (2-Bromoethoxy)(tert-butyl)dimethylsilane (1.08 g, 4.56 mmol) was added dropwise at 80° C. over a period of 1 h. The mixture was cooled, water (50 mL) was added and the mixture was extracted with EtOAc (3×50 mL). The combined organic layers were dried over anhydrous $Na_2SO_4$, filtered and concentrated to dryness. The residue was purified by column chromatography to give the title compound as a colorless oil.

Step 4: 2-(4-(2-((tert-Butyldimethylsilyl)oxy)ethoxy)-1,2,5-oxadiazol-3-yl)acetic acid (Int 1e)

Methyl 2-(4-(2-((tert-butyldimethylsilyl)oxy)ethoxy)-1,2,5-oxadiazol-3-yl)acetate (Int 1d) (1.00 g, 3.16 mmol) was dissolved in THF (50 mL). $LiOH \cdot H_2O$ (664 mg, 15.8 mmol) and water (5 mL) were added. The mixture was stirred at rt for 2 h. The pH was adjusted to pH=6 by addition of 1M aqueous HCl. The mixture was extracted with DCM (3×50 mL). The combined organic layers were dried over anhydrous $Na_2SO_4$, filtered and concentrated to dryness to give the title compound as a colorless oil.

Step 5: 4-(2-((tert-Butyldimethylsilyl)oxy)ethoxy)-1,2,5-oxadiazole-3-carboxylic acid (Int 1f)

2-(4-(2-((tert-Butyldimethylsilyl)oxy)ethoxy)-1,2,5-oxadiazol-3-yl)acetic acid (Int 1e) (800 mg, 2.65 mmol) was dissolved in acetone (50 mL). $KMnO_4$ (837 mg, 5.30 mmol) was added dropwise over a period of 10 min at 0° C. The mixture was stirred at rt for 24 h. The pH of the mixture was adjusted to pH=7 using 1M HCl. The mixture was filtered and the solid was washed with dichloromethane. The filtrate was concentrated to dryness to give the title compound as a yellow oil.

Step 6: 4-(2-((tert-Butyldimethylsilyl)oxy)ethoxy)-N-methoxy-1,2,5-oxadiazole-3-carboxamide (Int 1g)

4-(2-((tert-Butyldimethylsilyl)oxy)ethoxy)-1,2,5-oxadiazole-3-carboxylic acid (Int 1f) (560 mg, 1.94 mmol) was dissolved in DMF (15 mL). HATU (1.11 g, 2.92 mmol) and TEA (0.80 mL, 5.83 mmol) were added and the mixture was stirred at rt for 30 min. N,O-Dimethylhydroxylamine hydrochloride (566 mg, 5.83 mmol) was added and the mixture was stirred at rt overnight. Water (20 mL) was added and the mixture was extracted with EtOAc (3×20 mL). The combined organic layers were dried over anhydrous $Na_2SO_4$, filtered, concentrated to dryness and the residue was purified by column chromatography (DCM/PE=1:2) to give the title compound as a white solid.

Step 7: 4-(2-((tert-Butyldimethylsilyl)oxy)ethoxy)-1,2,5-oxadiazole-3-carbaldehyde (Int 1h)

To a solution of 4-(2-((tert-butyldimethylsilyl)oxy)ethoxy)-N-methoxy-1,2,5-oxadiazole-3-carboxamide (Int 1g) (160 mg, 0.85 mmol) in THF (8 mL) at −78° C. was added dropwise $LiAlH_4$ (1M in THF, 0.34 mL, 0.34 mmol). The mixture was stirred at −78° C. for 2 h. $H_2O$ (10 mL) and brine (10 mL) were added and the mixture was warmed to rt. The mixture was partially concentrated under reduced pressure, diluted with EtOAc and filtered through a pad of Celite®. The aqueous layer was extracted with EtOAc (3×20 mL). The combined organic layers were washed with brine, dried over anhydrous $Na_2SO_4$, filtered and concentrated to dryness to give the title compound as a yellow solid.

Step 8: 4-(2-((tert-Butyldimethylsilyl)oxy)ethoxy)-1,2,5-oxadiazole-3-carbaldehyde oxime (Int 1i)

To a solution of 4-(2-((tert-butyldimethylsilyl)oxy)ethoxy)-1,2,5-oxadiazole-3-carbaldehyde (Int 1h) (100 mg, 0.78 mmol) in methanol/water (16 mL, 1:1) was added $NH_2OH \cdot HCl$ (70 mg, 1.02 mmol). $Na_2CO_3$ (50 mg, 0.47 mmol) in water (2 mL) was added and the mixture was stirred at rt for 30 min. Water (20 mL) was added and the formed precipitate was filtered off and washed with water to give the title compound which was used in the next step without further purification.

Step 9: 4-(2-((tert-Butyldimethylsilyl)oxy)ethoxy)-N-hydroxy-1,2,5-oxadiazole-3-carbimidoyl chloride (Int 1j)

To a solution of 4-(2-((tert-butyldimethylsilyl)oxy)ethoxy)-1,2,5-oxadiazole-3-carbaldehyde oxime (Int 1l) (88 mg, 0.61 mmol) in DMF (5 mL) was added NCS (98 mg, 0.74 mmol) at 0° C. The mixture was stirred at rt for 1 h. The mixture was poured into ice water (10 mL) and extracted with EtOAc (2×20 mL). The combined organic layers were washed with water and brine, dried over anhydrous $Na_2SO_4$, filtered, concentrated to dryness and the residue was purified by column chromatography (PE/EtOAc=5:1) to give the title compound as a white solid.

Step 10: N-(3-Bromo-4-fluorophenyl)-4-(2-((tert-butyldimethylsilyl)oxy)ethoxy)-N-hydroxy-1,2,5-oxadiazole-3-carboximidamide (Int 1k)

To a solution of 4-(2-((tert-butyldimethylsilyl)oxy)ethoxy)-N-hydroxy-1,2,5-oxadiazole-3-carbimidoyl chloride (Int 1j) (350 mg, 1.09 mmol) and 3-bromo-4-fluoroaniline (248 mg, 1.31 mmol) in H₂O/THF (40 mL, 1:1) was added NaHCO₃ (110 mg, 1.31 mmol). The mixture was stirred at 60° C. for 2 h. The mixture was diluted with EtOAc (25 mL). The organic layer was washed with water (10 mL) and brine (10 mL), dried over anhydrous Na₂SO₄, filtered and concentrated to dryness to give the title compound as a yellow solid.

Step 11: 4-(3-Bromo-4-fluorophenyl)-3-(4-(2-((tert-butyldimethylsilyl)oxy)ethoxy)-1,2,5-oxadiazol-3-yl)-1,2,4-oxadiazol-5(4H)-one (Int 1l)

A mixture of N-(3-bromo-4-fluorophenyl)-4-(2-((tert-butyldimethylsilyl)oxy)ethoxy)-N-hydroxy-1,2,5-oxadiazole-3-carboximidamide (Int 1k) (400 mg, 0.84 mmol), CDI (154 mg, 1.26 mmol), and EtOAc (15 mL) was heated to 60° C. for 20 min. The mixture was cooled to rt, diluted with EtOAc (20 mL), washed with water (10 mL) and brine (10 mL), dried over anhydrous Na₂SO₄, filtered and concentrated to dryness to give the title compound as a white solid.

Step 12: 4-(3-Bromo-4-fluorophenyl)-3-(4-(2-hydroxyethoxy)-1,2,5-oxadiazol-3-yl)-1,2,4-oxadiazol-5(4H)-one (Int 1m)

To a solution of 4-(3-bromo-4-fluorophenyl)-3-(4-(2-((tert-butyldimethylsilyl)oxy)ethoxy)-1,2,5-oxadiazol-3-yl)-1,2,4-oxadiazol-5(4H)-one (Int 1l) (300 mg, 0.60 mmol) in THF (10 mL) at 0° C. was added tetrabutylammonium fluoride (157 mg, 0.60 mmol). The mixture was stirred for 1 h at rt. Saturated NH₄Cl (10 mL) was added and the mixture was extracted with EtOAc (2×25 mL). The combined organic layers were washed with water and brine, dried over anhydrous Na₂SO₄, filtered and concentrated to dryness to give the title compound as a white solid.

Step 13: 2-((4-(4-(3-Bromo-4-fluorophenyl)-5-oxo-4,5-dihydro-1,2,4-oxadiazol-3-yl)-1,2,5-oxadiazol-3-yl)oxy)ethyl methanesulfonate (Int 1n)

To a solution of 4-(3-bromo-4-fluorophenyl)-3-(4-(2-hydroxyethoxy)-1,2,5-oxadiazol-3-yl)-1,2,4-oxadiazol-5(4H)-one (Int 1m) (185 mg, 0.48 mmol) in DCM (8 mL) methanesulfonyl chloride (0.05 mL, 0.48 mmol) was added at 0° C. in one portion. The mixture was stirred for 5 min at 0° C. and triethylamine (0.08 mL, 0.52 mmol) was added in one portion. After stirring for additional 10 min at 0° C. water (10 mL) was added. The mixture was extracted with EtOAc (2×10 mL), dried over anhydrous Na₂SO₄, filtered and concentrated to dryness to give the title compound as a yellow solid.

Step 14: 3-(4-(2-Azidoethoxy)-1,2,5-oxadiazol-3-yl)-4-(3-bromo-4-fluorophenyl)-1,2,4-oxadiazol-5(4H)-one (Int 1o)

2-((4-(4-(3-Bromo-4-fluorophenyl)-5-oxo-4,5-dihydro-1,2,4-oxadiazol-3-yl)-1,2,5-oxadiazol-3-yl)oxy)ethyl methanesulfonate (Int 1n) (200 mg, 0.43 mmol) was dissolved in DMF (5 mL). NaN₃ (37 mg, 0.56 mmol) was added and the mixture was heated at 80° C. for 2 h. Water (25 mL) was added and the mixture was extracted with EtOAc (3×20 mL). The combined organic layers were dried over anhydrous Na₂SO₄, filtered and concentrated to dryness to give the title compound as a yellow oil.

Step 15: 3-(4-(2-Aminoethoxy)-1,2,5-oxadiazol-3-yl)-4-(3-bromo-4-fluorophenyl)-1,2,4-oxadiazol-5(4H)-one (Int 1)

To a solution of 3-(4-(2-azidoethoxy)-1,2,5-oxadiazol-3-yl)-4-(3-bromo-4-fluorophenyl)-1,2,4-oxadiazol-5(4H)-one (Int 1o) (150 mg, 0.36 mmol) in methanol (4 mL) was added sodium iodide (328 mg, 2.19 mmol) and the mixture was stirred at rt for 5 min. A solution of chlorotrimethylsilane (236 mg, 2.19 mmol) in methanol (2 mL) was added dropwise and the mixture was stirred at rt for 40 min. The mixture was slowly poured into a solution of sodium thiosulfate (392 mg, 2.48 mmol) in water (10 mL) at 0° C. The precipitated solid was filtered off and washed with water to give the title compound as a white solid.

Intermediates 1/1 to 1/7

The following Intermediates were prepared similar as described for Intermediate 1 using the appropriate building blocks.

| Int. # | Building blocks | | Structure |
|---|---|---|---|
| Int 1/1 | 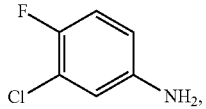 | 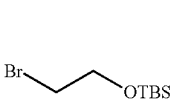 | 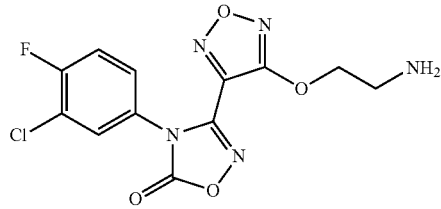 [SMILES: NCCOc1nonc1-c1noc(=O)n1-c1ccc(F)c(Cl)c1] |
| Int 1/2 | 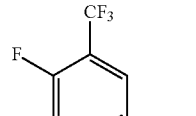 |  | 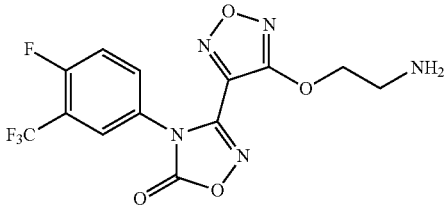 [SMILES: NCCOc1nonc1-c1noc(=O)n1-c1ccc(F)c(C(F)(F)F)c1] |

| Int. # | Building blocks | Structure |
|---|---|---|
| Int 1/3 | 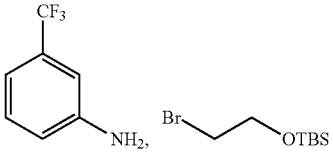 [SMILES: Nc1cccc(C(F)(F)F)c1 ; CC(C)(C)[Si](C)(C)OCCBr] | 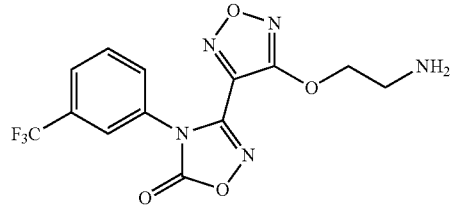 [SMILES: NCCOc1nonc1-c1noc(=O)n1-c1cccc(C(F)(F)F)c1] |
| Int 1/4 | 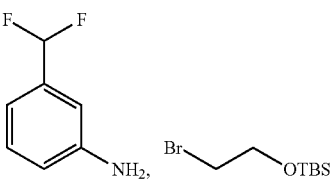 | 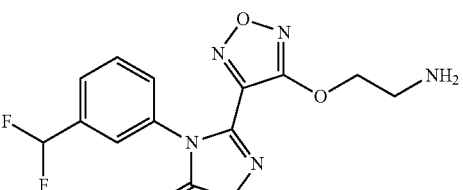 |
| Int 1/5 | 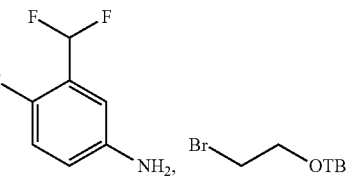 | 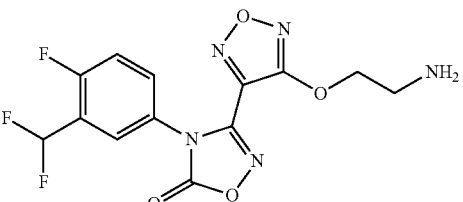 |
| Int 1/6 | 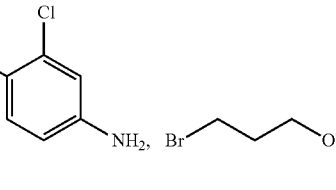 | 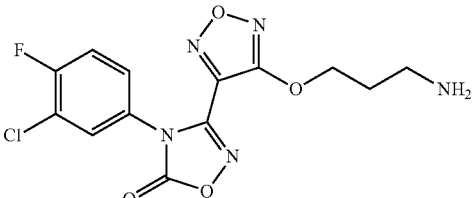 |
| Int 1/7 | 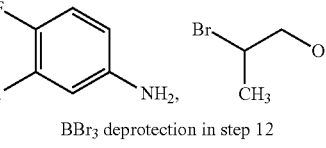 BBr₃ deprotection in step 12 | 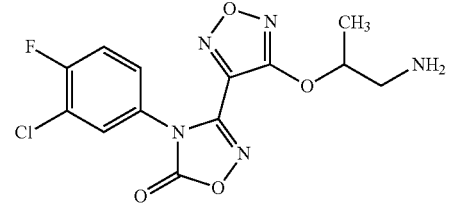 [SMILES: CC(CN)Oc1nonc1-c1noc(=O)n1-c1ccc(F)c(Cl)c1] |

Intermediate 2: 4-(Benzyloxy)-N-hydroxy-1,2,5-oxadiazole-3-carbimidoyl chloride (Int 2)

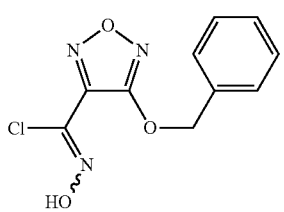 [SMILES: ON=C(Cl)c1nonc1OCc1ccccc1]

The title compound was prepared similar as described for Intermediate Int 1j using in step 3 benzylbromide in place of (2-bromoethoxy)(tert-butyl)dimethylsilane.

Intermediate 2/1: N-Hydroxy-4-(2,2,2-trifluoroethoxy)-1,2,5-oxadiazole-3-carbimidoyl chloride (Int 2/1)

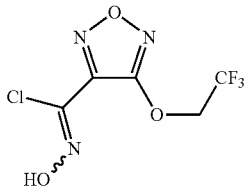 [SMILES: ON=C(Cl)c1nonc1OCC(F)(F)F]

The title compound was prepared similar as described for Intermediate Int 2 using 1,1,1-trifluoro-2-iodoethane in place of benzylbromide.

Intermediate 3: N-hydroxy-4-methoxy-1,2,5-oxadiazole-3-carbimidoyl chloride (Int 3)

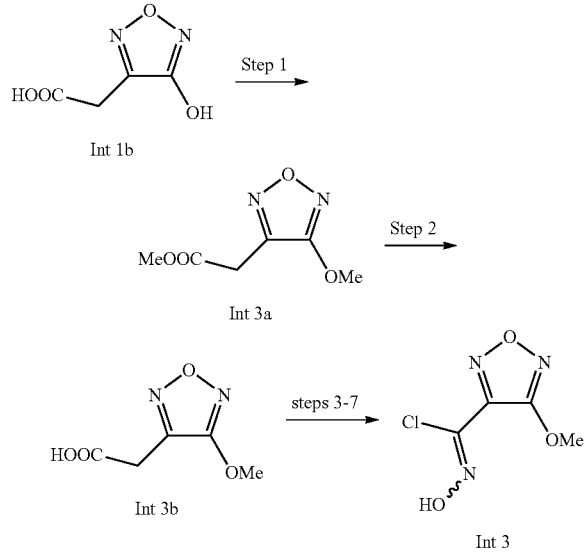

Step 1: Methyl 2-(4-methoxy-1,2,5-oxadiazol-3-yl)acetate (Int 3a)

2-(4-Hydroxy-1,2,5-oxadiazol-3-yl)acetic acid (Int 3b) (500 mg, 3.47 mmol) was dissolved in CH$_3$CN (25 mL). Trimethylsilyldiazomethane (2M solution in hexane, 4.3 mL, 8.6 mmol) was added. The mixture was stirred at rt for 4 h. Water was added (25 mL) and the mixture was extracted with EtOAc (3×25 mL). The combined organic layers were washed with brine (25 mL), dried over anhydrous MgSO$_4$, filtered, and concentrated to dryness to give the title compound as a yellow oil.

Step 2: 2-(4-Methoxy-1,2,5-oxadiazol-3-yl)acetic acid (Int 3b)

Methyl 2-(4-methoxy-1,2,5-oxadiazol-3-yl)acetate (Int 3a) (500 mg, 2.91 mmol) was dissolved in THF (20 mL). LiOH.H$_2$O (610 mg, 14.54 mmol) and water (1 mL) were added. The mixture was stirred at rt for 2 h. The pH was adjusted to pH=6 by adding 1M HCl. The mixture was extracted with DCM (3×25 mL). The combined organic layers were dried and concentrated to dryness to give the title compound as a yellow oil.

Steps 3-7: N-Hydroxy-4-methoxy-1,2,5-oxadiazole-3-carbimidoyl chloride (Int 3)

The title compound was prepared similar as described for Intermediate Int 1j steps 5-9 using in step 5 2-(4-methoxy-1,2,5-oxadiazol-3-yl)acetic acid (Int 3b) in place of 2-(4-(2-((tert-butyldimethylsilyl)oxy)ethoxy)-1,2,5-oxadiazol-3-yl) acetic acid Int 1e.

Intermediate 4: 2-((4-(4-(3-Chloro-4-fluorophenyl)-5-oxo-4,5-dihydro-1,2,4-oxadiazol-3-yl)-1,2,5-oxadiazol-3-yl)oxy)ethyl methanesulfonate (Int 4)

The title compound was prepared similar as described for Intermediate 1, steps 1-13, using in step 10 3-chloro-4-fluoroaniline in place of 3-bromo-4-fluoroaniline.

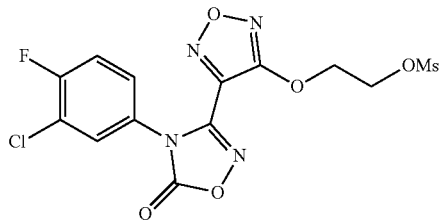 [SMILES: CS(=O)(=O)OCCOc1nonc1-c1noc(=O)n1-c1ccc(F)c(Cl)c1]

Intermediate 4/1: 3-((4-(4-(3-Chloro-4-fluorophenyl)-5-oxo-4,5-dihydro-1,2,4-oxadiazol-3-yl)-1,2,5-oxadiazol-3-yl)oxy)propyl methanesulfonate (Int 4/1)

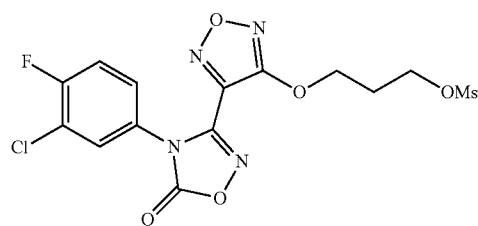 [SMILES: CS(=O)(=O)OCCCOc1nonc1-c1noc(=O)n1-c1ccc(F)c(Cl)c1]

The title compound was prepared similar as described for Intermediate 1, steps 1-13, using in step 3 (3-bromopropoxy)(tert-butyl)dimethylsilane in place of (2-bromoethoxy)(tert-butyl) dimethylsilane and in step 10 3-chloro-4-fluoroaniline in place of 3-bromo-4-fluoroaniline.

Intermediate 5: tert-Butyl 3-((4-(4-(3-chloro-4-fluorophenyl)-5-oxo-4,5-dihydro-1,2,4-oxadiazol-3-yl)-1,2,5-oxadiazol-3-yl)oxy)propanoate (Int 5)

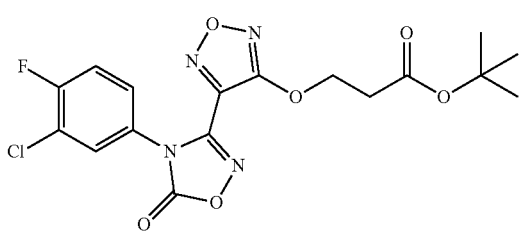 [SMILES: CC(C)(C)OC(=O)CCOc1nonc1-c1noc(=O)n1-c1ccc(F)c(Cl)c1]

The title compound was prepared similar as described for Intermediate 1, steps 1-11, using in step 3 tert-butyl 4-bromopropanoate in place of (2-bromoethoxy) (tert-butyl) dimethylsilane and in step 10 3-chloro-4-fluoroaniline in place of 3-bromo-4-fluoroaniline.

Intermediate 5/1: tert-Butyl 4-((4-(4-(3-chloro-4-fluorophenyl)-5-oxo-4,5-dihydro-1,2,4-oxadiazol-3-yl)-1,2,5-oxadiazol-3-yl)oxy)butanoate (Int 5/1)

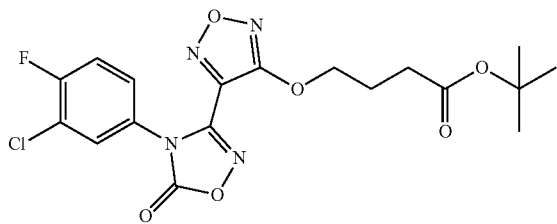 [SMILES: CC(C)(C)OC(=O)CCCOc1nonc1-c1noc(=O)n1-c1ccc(F)c(Cl)c1]

The title compound was prepared similar as described for Intermediate 5 using tert-butyl 4-bromobutanoate in place of tert-butyl 4-bromopropanoate.

Intermediate 6a and 6b: N-(2-((4-(4-(3-Chloro-4-fluorophenyl)-5-oxo-4,5-dihydro-1,2,4-oxadiazol-3-yl)-1,2,5-oxadiazol-3-yl)oxy)propyl)sulfamide (Int 6a, Int 6b)

Step 1: N-(2-((4-(4-(3-Chloro-4-fluorophenyl)-5-oxo-4,5-dihydro-1,2,4-oxadiazol-3-yl)-1,2,5-oxadiazol-3-yl)oxy)propyl)sulfamide (Int 6 racemate)

To a solution of 3-(4-((1-aminopropan-2-yl)oxy)-1,2,5-oxadiazol-3-yl)-4-(3-chloro-4-fluorophenyl)-1,2,4-oxadiazol-5(4H)-one (Int 1/7) (320 mg, 0.90 mmol) and triethylamine (227 mg, 2.25 mmol) in dichloromethane (10 mL) sulfamoyl chloride (124 mg, 1.08 mmol) was added at 0° C. The mixture was stirred at this temperature for 4 h, quenched by addition of water (20 mL) and extracted with EtOAc(3× 20 mL). The combined organic layers were dried over anhydrous $Na_2SO_4$, filtered and concentrated to dryness to give the title compound as a white solid.

Step 2: N-(2-((4-(4-(3-Chloro-4-fluorophenyl)-5-oxo-4,5-dihydro-1,2,4-oxadiazol-3-yl)-1,2,5-oxadiazol-3-yl)oxy)propyl)sulfamide (Int 6a and Int 6b)

Chiral HPLC separation (Chiralpak AD-H column, SFC, $CO_2$/MeOH=75:25) of N-(2-((4-(4-(3-chloro-4-fluorophenyl)-5-oxo-4,5-dihydro-1,2,4-oxadiazol-3-yl)-1,2,5-oxadiazol-3-yl)oxy)propyl)sulfamide (Int 6 racemate) afforded N-(2-((4-(4-(3-chloro-4-fluorophenyl)-5-oxo-4,5-dihydro-1,2,4-oxadiazol-3-yl)-1,2,5-oxadiazol-3-yl)oxy)propyl)sulfamide (Int 6a, first eluting enantiomer with a retention time

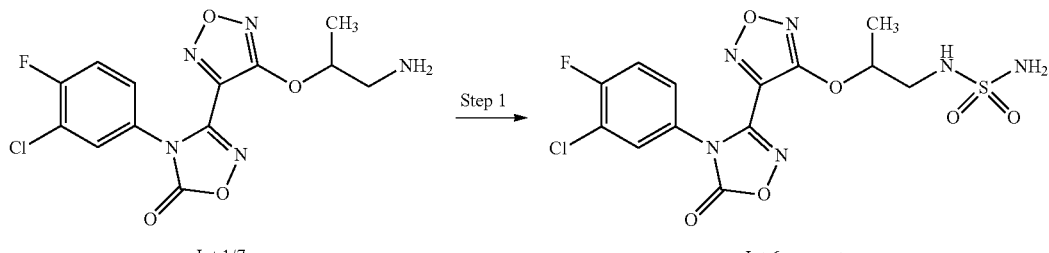

Int 1/7 → Step 1 → Int 6 racemate

Step 2 | chiral HPLC

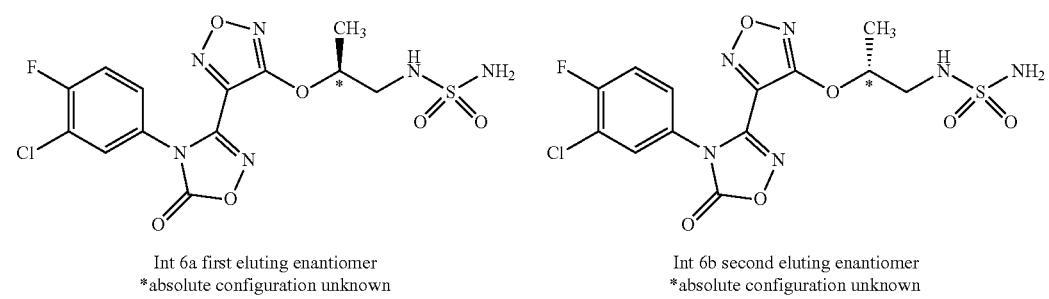

Int 6a first eluting enantiomer
*absolute configuration unknown

Int 6b second eluting enantiomer
*absolute configuration unknown of 1.11 min) and N-(2-((4-(4-(3-chloro-4-fluorophenyl)-5-oxo-4,5-dihydro-1,2,4-oxadiazol-3-yl)-1,2,5-oxadiazol-3-yl)oxy)propyl)sulfamide (Int 6b, second eluting enantiomer with a retention time of 1.29 min).

Intermediate 7: 4-(3-Chloro-4-fluorophenyl)-3-(4-(2-(methylamino)ethoxy)-1,2,5-oxadiazol-3-yl)-1,2,4-oxadiazol-5(4H)-one hydrochloride (Int 7)

cooling with an ice bath. Then 4-amino-N-(3-chloro-4-fluorophenyl)-N'-hydroxy-1,2,5-oxadiazole-3-carboximidamide (Int 7c) (360 mg, 1.2 mmol) was added in 3 portions with vigorous stirring, while the temperature of the mixture was maintained below 10° C. After the exothermic reaction ended, the mixture was stirred at 55° C. for 10 h, cooled to rt, and treated with $H_2O$ (40 mL). The product was extracted with EtOAc (3×40 mL). The organic layer was washed with water (40 mL) and brine (40 mL), dried over $Na_2SO_4$, and

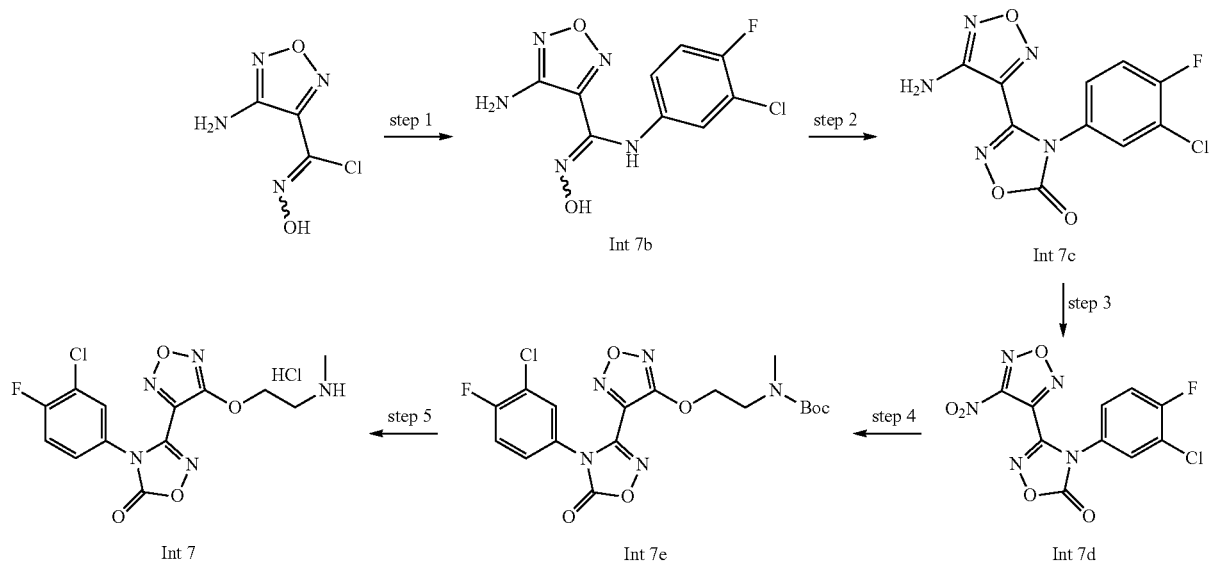

Step 1: 4-Amino-N-(3-chloro-4-fluorophenyl)-N'-hydroxy-1,2,5-oxadiazole-3-carboximidamide (Int 7b)

To a solution of 4-amino-N-hydroxy-1,2,5-oxadiazole-3-carbimidoyl chloride (500 mg, 3.08 mmol) and 3-chloro-4-fluoroaniline (446 mg, 3.08 mmol) in $H_2O$ and THF (24 mL, 1:1) was added $NaHCO_3$ (388 mg, 4.62 mmol). The mixture was stirred at 65° C. for 2 h. Then the mixture was diluted with EtOAc (50 mL). The organic layer was washed with water (30 mL) and brine (30 mL), dried over $Na_2SO_4$ and concentrated. The residue was purified by column chromatography (PE:EtOAc=5:1) to give the title compound as a white solid.

Step 2: 3-(4-Amino-1,2,5-oxadiazol-3-yl)-4-(3-chloro-4-fluorophenyl)-1,2,4-oxadiazol-5(4H)-one (Int 7c)

A mixture of 4-amino-N-(3-chloro-4-fluorophenyl)-N'-hydroxy-1,2,5-oxadiazole-3-carboximidamide (Int 7b) (400 mg, 1.4 mmol), CDI (324 mg, 2.0 mmol) in EtOAc (20 mL) was heated to 60° C., and stirred for 20 min. The reaction was cooled to rt, diluted with EtOAc (30 mL), washed with water (40 mL) and brine (40 mL), dried over $Na_2SO_4$, and concentrated. The residue was purified by column chromatography (PE:EA=8:1) to give the title compound as a white solid.

Step 3: 4-(3-Chloro-4-fluorophenyl)-3-(4-nitro-1,2,5-oxadiazol-3-yl)-1,2,4-oxadiazol-5(4H)-one (Int 7d)

To a 30% solution of $H_2O_2$ (12 mL) and $(NH_4)_2S_2O_8$ (274 mg, 1.2 mmol) was added slowly 98% $H_2SO_4$ (8 mL) under concentrated. The residue was purified by column chromatography on silica gel (PE:EA=5:1) to give the title compound as a white solid.

Step 4: tert-Butyl (2-((4-(4-(3-chloro-4-fluorophenyl)-5-oxo-4,5-dihydro-1,2,4-oxadiazol-3-yl)-1,2,5-oxadiazol-3-yl)oxy)ethyl)(methyl)carbamate (Int 7e)

To a stirred solution of 4-(3-chloro-4-fluorophenyl)-3-(4-nitro-1,2,5-oxadiazol-3-yl)-1,2,4-oxadiazol-5(4H)-one (Int 7d) (320 mg, 0.98 mmol) in THF (8 mL) was added tert-butyl (2-hydroxyethyl)(methyl)carbamate (342 mg, 1.96 mmol), and then 30% NaOH (0.28 mL, 2.94 mmol). The reaction mixture was stirred at rt for 10 min, water (80 mL) was added and the aqueous phase was extracted with EtOAc (3×80 mL). The combined organic layers were washed with brine (80 mL), dried over $Na_2SO_4$, and concentrated. The residue was purified by column chromatography on silica gel (PE:EA=8:1) to give the title compound as a white solid.

Step 5: 4-(3-Chloro-4-fluorophenyl)-3-(4-(2-(methylamino)ethoxy)-1,2,5-oxadiazol-3-yl)-1,2,4-oxadiazol-5(4H)-one hydrochloride (Int 7)

A solution of tert-butyl (2-((4-(4-(3-chloro-4-fluorophenyl)-5-oxo-4,5-dihydro-1,2,4-oxadiazol-3-yl)-1,2,5-oxadiazol-3-yl)oxy)ethyl)(methyl)carbamate (Int 7e) (400 mg, 0.88 mmol) in a mixture of dry dioxane (10 mL) and 6.5 N hydrogen chloride in dioxane (20 mL) was stirred at rt overnight, then diluted with $Et_2O$ and stirred at 0° C. for 1 h. The precipitated crystals were filtered off, washed with $Et_2O$ and dried to give the title compound as a white solid.

Intermediate 8: 3-(2-Chloroethyl)aniline (Int 8)

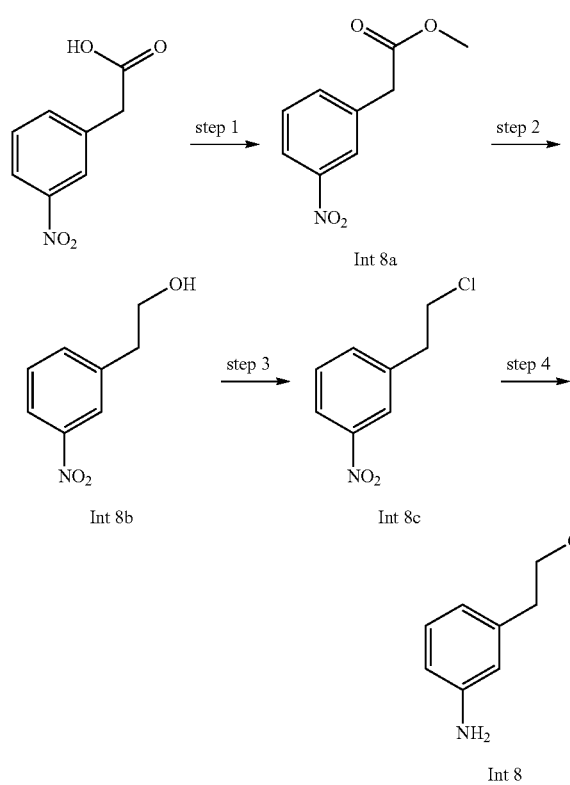

Step 1: Methyl 2-(3-nitrophenyl)acetate (Int 8a)

2-(3-Nitrophenyl)acetic acid (400 mg, 2.21 mmol) was dissolved in a mixture of MeOH: $Et_2O$ (10 mL, 1:1) and cooled to 0° C. To this solution was added a 2M solution of trimethylsilyldiazomethane (5.5 mL, 11.0 mmol). The reaction was quenched by the addition of glacial acetic acid (7 mL) and concentrated to give the title compound as a colorless oil which was used without further purification.

Step 2: 2-(3-Nitrophenyl)ethan-1-ol (Int 8b)

A solution of methyl 2-(3-nitrophenyl)acetate (Int 8a) (1.20 g, 6.20 mmol) and $NaBH_4$ (235 mg, 6.20 mmol) in THF (100 mL) was cooled to 0° C., then MeOH (10 mL) was added slowly, followed by stirring at rt overnight. Water was added to terminate the reaction. The aqueous layer was extracted with ethyl acetate 3 times, the combined organic phase was washed with brine, dried over sodium sulfate and concentrated to give the title compound as a yellow solid.

Step 3: 1-(2-Chloroethyl)-3-nitrobenzene (Int 8c)

Into a 100 mL round-bottom flask was added 2-(3-nitrophenyl)ethan-1-ol (Int 8b) (1.67 g, 10.00 mmol) and sulfurous dichloride (20 mL) was added, and the reaction was stirred at 70° C. for 3 h and concentrated onto silica gel. The residue was purified by flash chromatography on silica gel (EtOAc/hexanes) to give the title compound as a yellow oil.

Step 4: 3-(2-Chloroethyl)aniline (Int 8)

A mixture of palladium on charcoal (0.20 g, 10% w/w) and 1-(2-chloroethyl)-3-nitrobenzene (Int 8c) (370 mg, 2.00 mmol) in absolute ethanol (100 mL) was hydrogenated at atmospheric pressure with vigorous stirring for 8 h. Further palladium on charcoal (0.10 g, 10% w/w) was added and stirring under $H_2$ atmosphere was continued for another 16 h. The catalyst was filtered off, the filter was washed with ethanol and the solvent was removed under vacuum to give the title compound as a white solid.

Int 9: 4—(N-(tert-Butoxycarbonyl)-S-methylsulfonimidoyl)benzoic acid (Int 9)

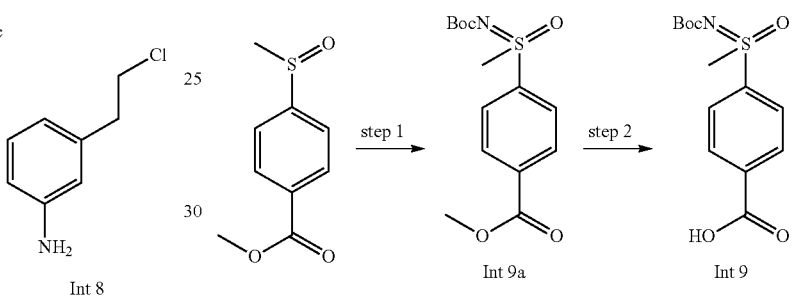

Step 1: Methyl 4-(N-(tert-butoxycarbonyl)-S-methylsulfonimidoyl)benzoate (Int 9a)

To a solution of methyl 4-(methylsulfinyl)benzoate (400 mg, 2.02 mmol), tert-butyl carbamate (472 mg, 4.04 mmol), [bis(acetoxy)iodo]benzene (976 mg, 3.03 mmol) and MgO (320 mg, 10.1 mmol) in of DCM (5 mL), was added $Rh_2(OAc)_4$ (40 mg, 0.09 mmol). The reaction mixture was stirred at 40° C. for 4 h and then concentrated under reduced pressure. The residue was purified by column chromatography (EtOAc: PE=1: 2) to give the title compound as a white solid.

Step 2: 4—(N-(tert-Butoxycarbonyl)-S-methylsulfonimidoyl)benzoic acid (Int 9)

To a solution of methyl 4-(N-(tert-butoxycarbonyl)-S-methylsulfonimidoyl)benzoate (Int 9a) (350 mg, 1.11 mmol) in MeOH (5 mL) was added $NaOH/H_2O$ (1N, 1 mL) and the reaction mixture was stirred at rt for 4 h. Then the mixture was concentrated under reduced pressure, the residue was diluted with water (30 mL), the pH was adjusted to ca. 5 by HCl (1N) and the mixture was extracted with EtOAc (3×20 mL). The combined organic layer was washed with brine (30 mL), dried over $Na_2SO_4$, filtered and concentrated under reduced pressure to give the title compound as a white solid.

Intermediate 100: 3-(4-((2-Aminoethyl)thio)-1,2,5-oxadiazol-3-yl)-4-(3-bromo-4-fluorophenyl)-1,2,4-oxadiazol-5(4H)-one (Int 100)

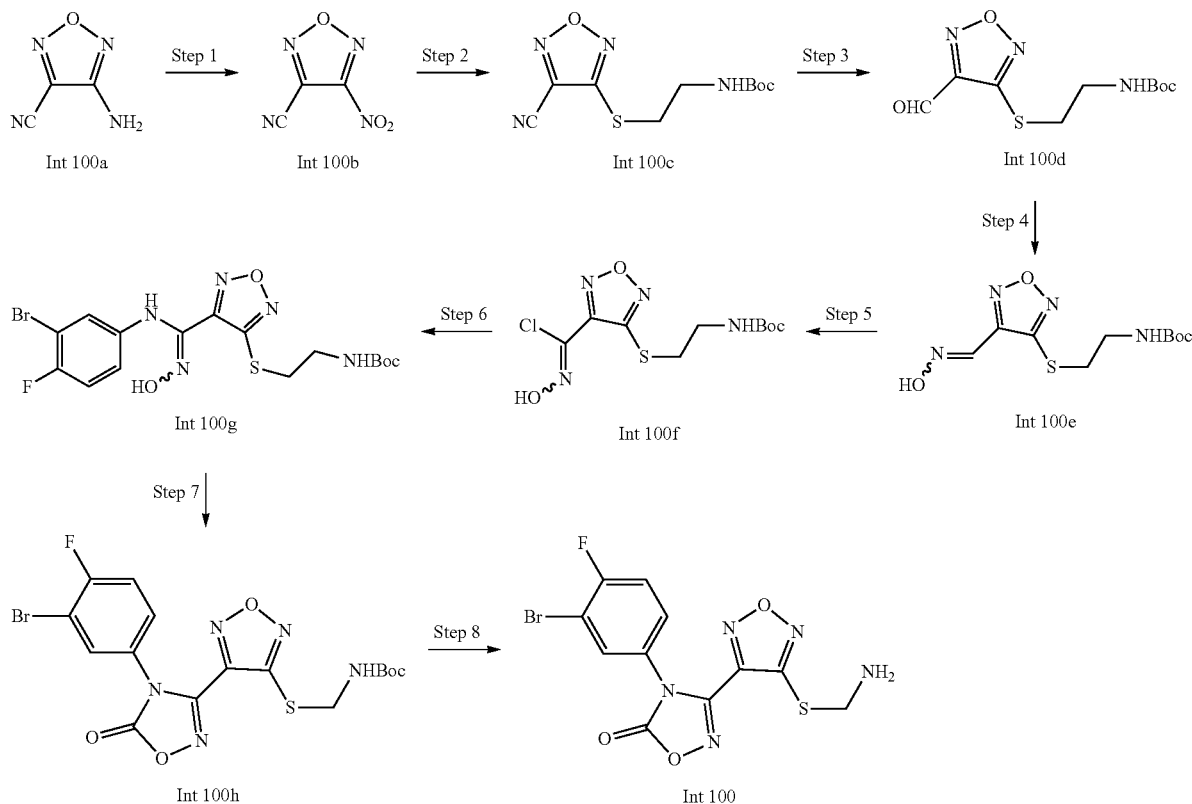

Step 1: 4-Nitro-1,2,5-oxadiazole-3-carbonitrile (Int 100)

To a mixture of $H_2O_2$ (30% aqueous solution, 30 mL) and $(NH_4)_2S_2O_8$ (6.22 g, 27.3 mmol) was added slowly concentrated $H_2SO_4$ (20 mL) under ice bath cooling. 4-Amino-1,2,5-oxadiazole-3-carbonitrile (Int 100a) (3.00 g, 27.3 mmol) was added in 3 portions under vigorous stirring, while the temperature of the mixture was kept below 10° C. The mixture was stirred at 55° C. for 5 h and cooled to rt. Water (50 mL) was added and the mixture was extracted by EtOAc (3×50 mL). The combined organic layers were washed with water (50 mL) and brine (50 mL), dried over anhydrous $Na_2SO_4$, filtered and concentrated to dryness. The residue was purified by column chromatography (PE/EtOAc=8:1) to give the title compound as a white solid.

Step 2: tert-Butyl (2-((4-cyano-1,2,5-oxadiazol-3-yl)thio)ethyl)carbamate (Int 100c)

To a stirred solution of 4-nitro-1,2,5-oxadiazole-3-carbonitrile (Int 100b) (570 mg, 4.07 mmol) in THF (15 mL) at 0° C. was added N-Boc-2-aminoethanethiol (1.08 g, 6.11 mmol). 50% aqueous NaOH (2 mL) was added and the mixture was stirred at rt for 10 min. Water (15 mL) was added and the aqueous layer was extracted with EtOAc (3×15 mL). The combined organic layers were washed with brine (15 mL), dried over anhydrous $Na_2SO_4$, filtered and concentrated to dryness. The residue was purified by column chromatography (PE:EtOAc=10:1) to give the title compound as a white solid.

Step 3: tert-Butyl (2-((4-formyl-1,2,5-oxadiazol-3-yl)thio)ethyl)carbamate (Int 100d)

To a solution of tert-butyl (2-((4-cyano-1,2,5-oxadiazol-3-yl)thio)ethyl)carbamate (Int 100c) (1.00 g, 3.70 mmol) in THF (15 mL) at −78° C. was added DIBAL-H (25% in toluene, 12.3 mL, 18.5 mmol) and the mixture was stirred at −78° C. for 30 min. The mixture was quenched with 2M HCl at −78° C., warmed to rt and extracted with EtOAc. The combined organic layers were washed with water and brine, dried over anhydrous $Na_2SO_4$, filtered and concentrated to dryness. The residue was purified by column chromatography to give the title compound as a white solid.

Step 4: tert-Butyl (2-((4-((hydroxyimino)methyl)-1,2,5-oxadiazol-3-yl)thio)ethyl)carbamate (Int 100e)

To a solution of tert-butyl (2-((4-formyl-1,2,5-oxadiazol-3-yl)thio)ethyl)carbamate (Int 100d) (700 mg, 2.56 mmol) in methanol (30 mL) and water (8 mL) was added $NH_2OH.HCl$ (230 mg, 3.33 mmol). $Na_2CO_3$ (163 mg, 1.54 mmol) in water (8 mL) was added and the mixture was stirred at rt for 30 min. Water (30 mL) was added and the formed precipitate was filtered off, washed with water to give the title compound as a white solid.

Step 5: tert-Butyl (2-((4-(chloro(hydroxyimino) methyl)-1,2,5-oxadiazol-3-yl)thio)ethyl)carbamate (Int 100f)

To a solution of tert-butyl (2-((4-((hydroxyimino) methyl)-1,2,5-oxadiazol-3-yl)thio)ethyl)carbamate (Int 100e) (700 mg, 2.43 mmol) in DMF (30 mL) was added NCS (388 mg, 2.92 mmol) at 0° C. The mixture was stirred at rt for 1 h. The mixture was poured into ice water (30 mL) and extracted with EtOAc (2×30 mL). The combined organic layers were washed with water and brine, dried over anhydrous Na$_2$SO$_4$, filtered and concentrated to dryness. The residue was purified by column chromatography (PE: EtOAc=15:1) to give the title compound as a white solid.

Step 6: tert-Butyl (2-((4-(N-(3-bromo-4-fluorophenyl)-N'-hydroxycarbamimidoyl)-1,2,5-oxadiazol-3-yl)thio)ethyl)carbamate (Int 100g)

To a solution of tert-butyl (2-((4-(chloro(hydroxyimino) methyl)-1,2,5-oxadiazol-3-yl)thio)ethyl)carbamate (Int 100f) (700 mg, 2.17 mmol) and 3-bromo-4-fluoroaniline (495 mg, 2.61 mmol) in H$_2$O/THF (1:1, 100 mL) was added NaHCO$_3$ (219 mg, 2.61 mmol). The mixture was stirred at 60° C. for 2 h. The mixture was diluted with EtOAc (50 mL). The organic layer was washed with water (30 mL) and brine (30 mL), dried over anhydrous Na$_2$SO$_4$, filtered and concentrated to dryness to give the title compound as a white solid.

Step 7: tert-Butyl (2-((4-(4-(3-bromo-4-fluorophenyl)-5-oxo-4,5-dihydro-1,2,4-oxadiazol-3-yl)-1,2,5-oxadiazol-3-yl)thio)ethyl)carbamate (Int 100h)

A mixture of tert-butyl (2-((4-(N-(3-bromo-4-fluorophenyl)-N'-hydroxycarbamimidoyl)-1,2,5-oxadiazol-3-yl)thio) ethyl)carbamate (Int 100g) (600 mg, 1.26 mmol), CDI (306 mg, 1.89 mmol) in EtOAc (25 mL) was stirred at 60° C. for 20 min. The mixture was cooled to rt and diluted with EtOAc (30 mL). The mixture was washed with water (20 mL) and brine (20 mL), dried over anhydrous Na$_2$SO$_4$, filtered and concentrated to dryness to give the title compound as a white solid.

Step 8: 3-(4-((2-Aminoethyl)thio)-1,2,5-oxadiazol-3-yl)-4-(3-bromo-4-fluorophenyl)-1,2,4-oxadiazol-5 (4H)-one (Int 100)

To a stirred solution of tert-butyl (2-((4-(4-(3-bromo-4-fluorophenyl)-5-oxo-4,5-dihydro-1,2,4-oxadiazol-3-yl)-1,2, 5-oxadiazol-3-yl)thio)ethyl)carbamate (Int 100h) (600 mg, 1.19 mmol) in DCM (25 mL) was added TFA (2.4 mL) at 0° C. and the mixture was stirred at rt for 3 h. Saturated NaHCO$_3$ (30 mL) was added and the aqueous layer was extracted with DCM. The combined organic layers were washed with saturated NaHCO$_3$ and brine, dried over anhydrous Na$_2$SO$_4$, filtered and concentrated to dryness to give the title compound as a colorless solid.

Intermediates 100/1 to 100/20

The following Intermediates were prepared similar as described for Intermediate 100 using the appropriate building blocks.

| Int. # | Building blocks | | Structure |
|---|---|---|---|
| Int 100/1 | 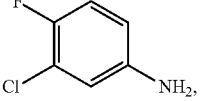 | 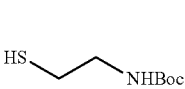 | 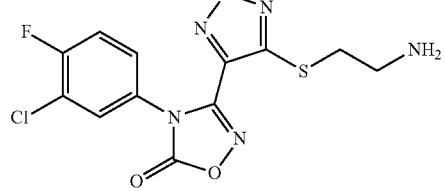 |
| Int 100/2 | 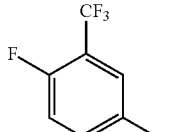 | 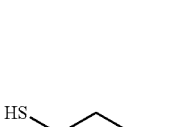 | 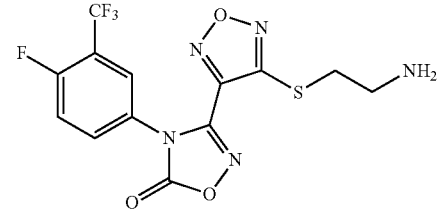 [SMILES: NCCSc1nonc1-c1noc(=O)n1-c1ccc(F)c(C(F)(F)F)c1] |
| Int 100/3 | 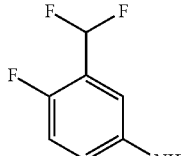 |  | 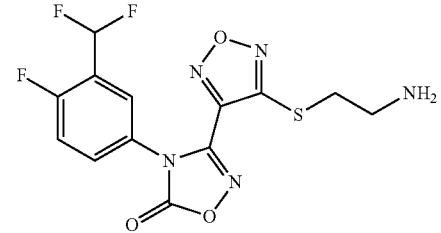 [SMILES: NCCSc1nonc1-c1noc(=O)n1-c1ccc(F)c(C(F)F)c1] |

| Int. # | Building blocks | Structure |
|---|---|---|
| Int 100/4 | 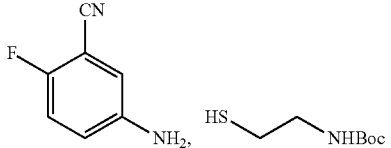 | 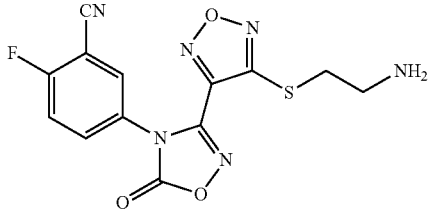 [SMILES: N#Cc1cc(-n2c(-c3nonc3SCCN)noc2=O)ccc1F] |
| Int 100/5 | 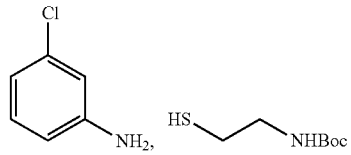 [SMILES: Nc1cccc(Cl)c1 ; CC(C)(C)OC(=O)NCCS] | 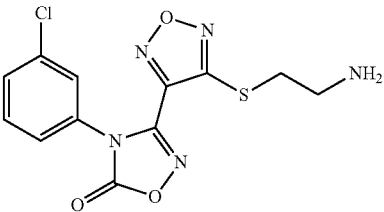 [SMILES: NCCSc1nonc1-c1noc(=O)n1-c1cccc(Cl)c1] |
| Int 100/6 | 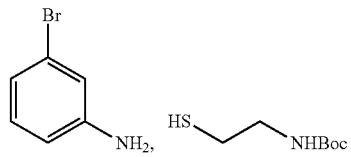 | 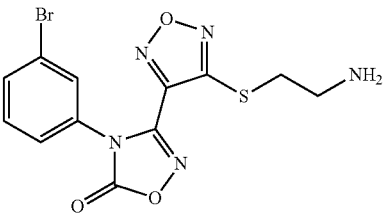 [SMILES: NCCSc1nonc1-c1noc(=O)n1-c1cccc(Br)c1] |
| Int 100/7 | 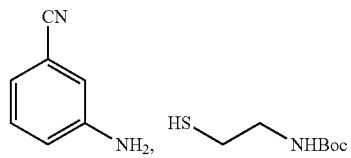 [SMILES: N#Cc1cccc(N)c1 ; CC(C)(C)OC(=O)NCCS] | 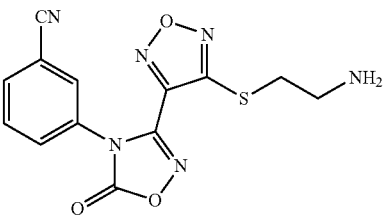 |
| Int 100/8 | 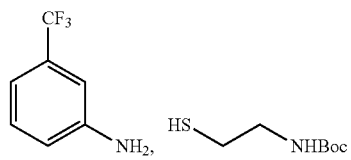 | 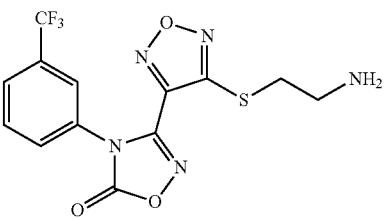 |
| Int 100/9 |  | 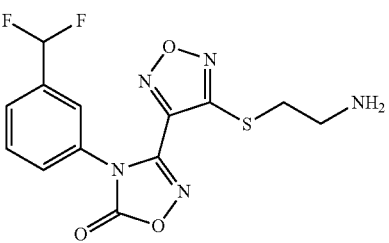 [SMILES: NCCSc1nonc1-c1noc(=O)n1-c1cccc(C(F)F)c1] |

-continued
| Int. # | Building blocks | Structure |
|---|---|---|
| Int 100/10 | 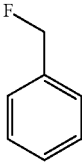, 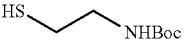 | 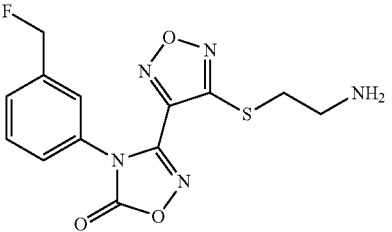 [SMILES: NCCSc1nonc1-c1noc(=O)n1-c1cccc(CF)c1] |
| Int 100/11 | 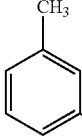,  | 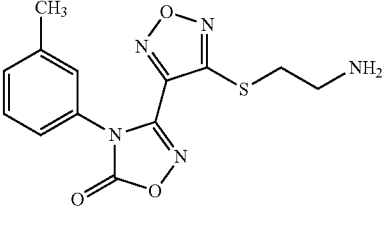 |
| Int 100/12 | 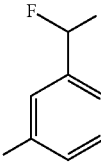,  | 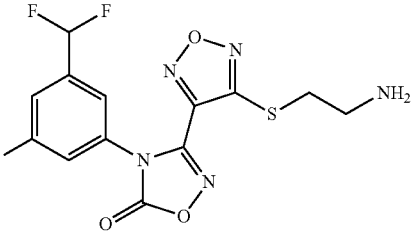 |
| Int 100/13 | 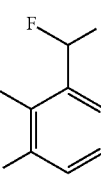,  | 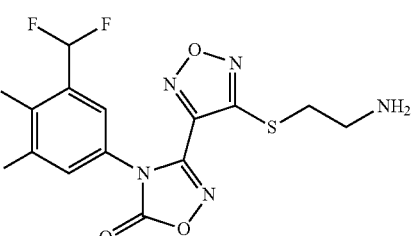 |
| Int 100/14 | 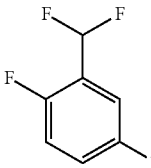, 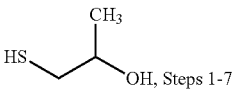, Steps 1-7 | 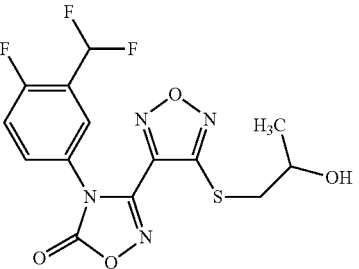 [SMILES: CC(O)CSc1nonc1-c1noc(=O)n1-c1ccc(F)c(C(F)F)c1] |
| Int 100/15 | 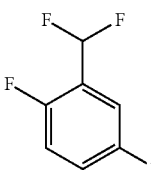, 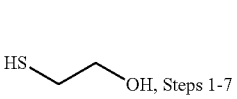, Steps 1-7 | 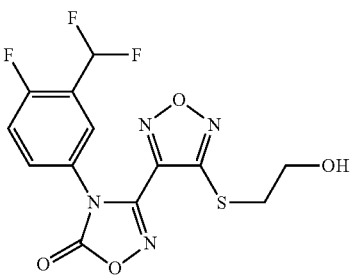 [SMILES: O=c1onc(-c2nonc2SCCO)n1-c1ccc(F)c(C(F)F)c1] |

-continued

| Int. # | Building blocks | Structure |
|---|---|---|
| Int 100/16 | (2-trifluoromethylpyridin-4-amine); HS-CH2CH2-NHBoc | product structure |
| Int 100/17 | (5-trifluoromethylpyridin-3-amine); HS-CH2CH2-NHBoc | product structure |
| Int 100/20 | (3-bromo-4-fluoroaniline); HS-CH2-CH(CH3)-OH, Steps 1-7 | product structure |

Intermediate 101: 4-(Benzylthio)-N-hydroxy-1,2,5-oxadiazole-3-carbimidoyl chloride (Int 101)

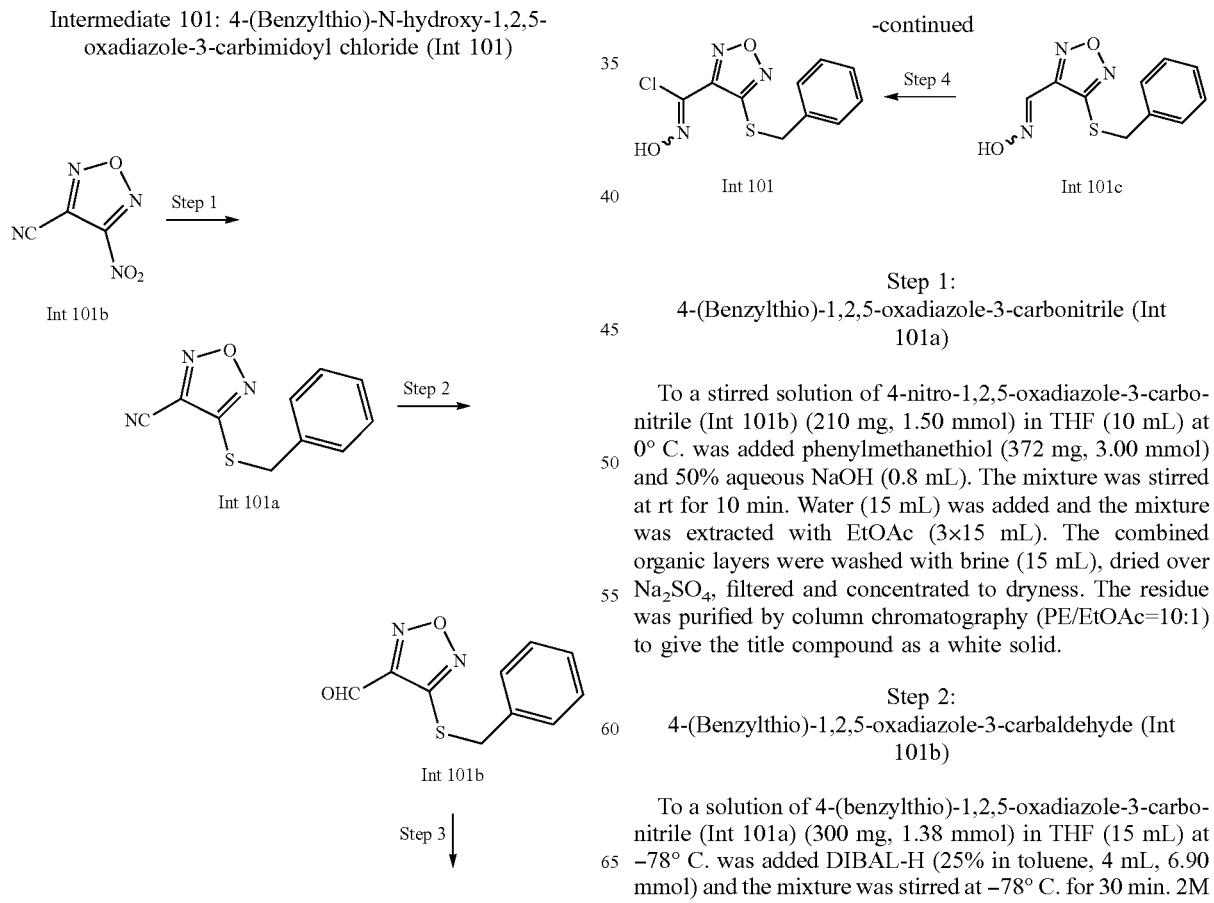

Step 1: 4-(Benzylthio)-1,2,5-oxadiazole-3-carbonitrile (Int 101a)

To a stirred solution of 4-nitro-1,2,5-oxadiazole-3-carbonitrile (Int 101b) (210 mg, 1.50 mmol) in THF (10 mL) at 0° C. was added phenylmethanethiol (372 mg, 3.00 mmol) and 50% aqueous NaOH (0.8 mL). The mixture was stirred at rt for 10 min. Water (15 mL) was added and the mixture was extracted with EtOAc (3×15 mL). The combined organic layers were washed with brine (15 mL), dried over $Na_2SO_4$, filtered and concentrated to dryness. The residue was purified by column chromatography (PE/EtOAc=10:1) to give the title compound as a white solid.

Step 2: 4-(Benzylthio)-1,2,5-oxadiazole-3-carbaldehyde (Int 101b)

To a solution of 4-(benzylthio)-1,2,5-oxadiazole-3-carbonitrile (Int 101a) (300 mg, 1.38 mmol) in THF (15 mL) at −78° C. was added DIBAL-H (25% in toluene, 4 mL, 6.90 mmol) and the mixture was stirred at −78° C. for 30 min. 2M aqueous HCl was added at −78° C. and the mixture was warmed to rt. The mixture was extracted with EtOAc. The combined organic layers were washed with water and brine, dried over anhydrous Na₂SO₄, filtered and concentrated to dryness. The residue was purified by column chromatography to give the title compound as a yellow solid.

Step 3:
4-(Benzylthio)-1,2,5-oxadiazole-3-carbaldehyde oxime (Int 101c)

To a solution of 4-(benzylthio)-1,2,5-oxadiazole-3-carbaldehyde (Int 101b) (200 mg, 0.90 mmol) in methanol (15 mL) and water (4 mL) was added NH₂OH HCl (81 mg, 1.17 mmol). Na₂CO₃ (57 mg, 0.54 mmol) in water (3 mL) was added and the mixture was stirred at rt for 30 min. Water (20 mL) was added and the formed precipitate was filtered off, washed with water and dried to give the title compound as a white solid which was used in the next step without further purification.

Step 4: 4-(Benzylthio)-N-hydroxy-1,2,5-oxadiazole-3-carbimidoyl chloride (Int 101)

To a solution of 4-(benzylthio)-1,2,5-oxadiazole-3-carbaldehyde oxime (Int 101c) (200 mg, 0.85 mmol) in DMF (20 mL) was added NCS (136 mg, 1.02 mmol) at 0° C. The mixture was stirred at rt for 1 h. The mixture was poured into ice water (20 mL) and extracted with EtOAc (2×30 mL). The combined organic layers were washed with water and brine, dried over anhydrous Na₂SO₄, filtered and concentrated to dryness. The residue was purified by column chromatography (PE/EtOAc=8:1) to give the title compound as a white solid.

Intermediates 101/1 to 101/3

The following Intermediates were prepared similar as described for Intermediate 101 using the appropriate thiol building blocks.

| Int. # | Thiol building block | Structure |
|---|---|---|
| Int 101/1 | MeSH | ![structure] |
| Int 101/2 | HS-CH₂CF₃ | ![structure] |
| Int 101/3 | HS-cyclopropyl | ![structure] |

Intermediate 102: 3-(4-((2-Aminopropyl)thio)-1,2,5-oxadiazol-3-yl)-4-(3-(difluoromethyl)-4-fluorophenyl)-1,2,4-oxadiazol-5(4H)-one hydroiodide (Int 102)

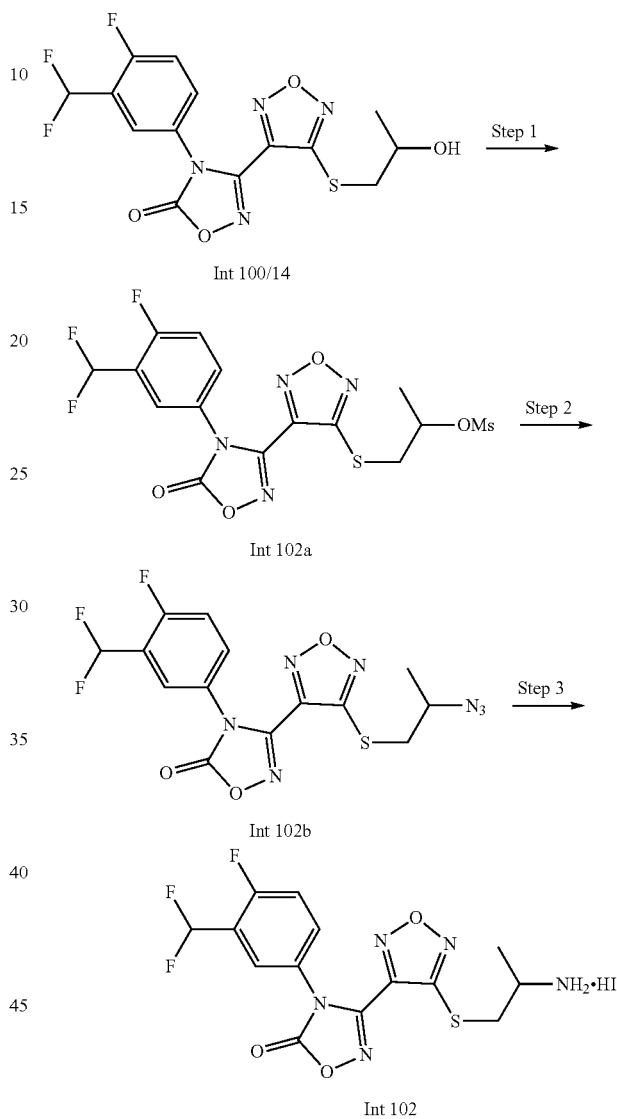

Step 1: 1-((4-(4-(3-(Difluoromethyl)-4-fluorophenyl)-5-oxo-4,5-dihydro-1,2,4-oxadiazol-3-yl)-1,2,5-oxadiazol-3-yl)thio)propan-2-yl methanesulfonate (Int 102a)

To a solution 4-(3-(difluoromethyl)-4-fluorophenyl)-3-(4-((2-hydroxypropyl)thio)-1,2,5-oxadiazol-3-yl)-1,2,4-oxadiazol-5(4H)-one (Int 100/14) (560 mg, 1.44 mmol) in dichloromethane (20 mL) was added methanesulfonyl chloride (0.18 mL, 1.73 mmol) in one portion. The mixture was stirred for 5 min at rt and triethylamine (218 mg, 2.16 mmol) was added in one portion. After stirring for additional 10 min, the reaction was quenched with water (20 mL). The aqueous layer was extracted with ethyl acetate (2 x 25 mL).

Step 2: 3-(4-((2-Azidopropyl)thio)-1,2,5-oxadiazol-3-yl)-4-(3-(difluoromethyl)-4-fluorophenyl)-1,2,4-oxadiazol-5(4H)-one (Int 102b)

1-((4-(4-(3-(Difluoromethyl)-4-fluorophenyl)-5-oxo-4,5-dihydro-1,2,4-oxadiazol-3-yl)-1,2,5-oxadiazol-3-yl)thio) propan-2-yl methanesulfonate (Int 102a) (536 mg, 1.15 mmol) was dissolved in DMF (10 mL). NaN₃ (98 mg, 1.50 mmol) was added and the mixture was heated at 80° C. for 2 h. Water (25 mL) was added and the mixture was extracted with EtOAc (3×20 mL). The combined organic layers were dried over anhydrous Na₂SO₄, filtered and concentrated to dryness to give the title compound as a white solid.

Step 3: 3-(4-((2-Aminopropyl)thio)-1,2,5-oxadiazol-3-yl)-4-(3-bromo-4-fluorophenyl)-1,2,4-oxadiazol-5(4H)-one hydroiodide (Int 102)

A solution of 3-(4-((2-azidopropyl)thio)-1,2,5-oxadiazol-3-yl)-4-(3-(difluoromethyl)-4-fluorophenyl)-1,2,4-oxadiazol-5(4H)-one (Int 102b) (435 mg, 1.05 mmol) in methanol (15 mL) was treated with sodium iodide (945 mg, 6.30 mmol) and the mixture was stirred at 25° C. for 5 min. A solution of chlortrimethylsilane (684 mg, 6.30 mmol) in methanol (5 mL) was added dropwise and the mixture was stirred at 25° C. for 40 min. The mixture was slowly poured into a solution of sodium thiosulfate (1.13 g, 7.14 mmol) in water (10 mL) that was cooled at 0° C. The solid that precipitated was filtered, washed with water, and dried to give the title compound as white solid.

Intermediate 102/1

The following Intermediate was prepared similar as described for Intermediate 102 using the appropriate Intermediates as starting material.

| Int. # | Starting material | Structure |
|---|---|---|
| Int 102/1 | Int 100/20 | 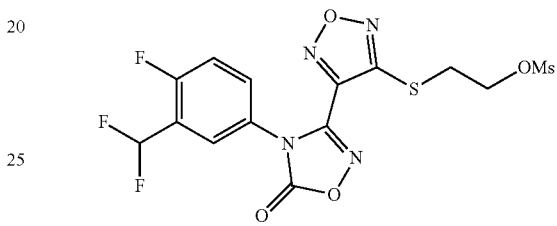 |

Intermediate 103: 2-((4-(4-(3-(Difluoromethyl)-4-fluorophenyl)-5-oxo-4,5-dihydro-1,2,4-oxadiazol-3-yl)-1,2,5-oxadiazol-3-yl)thio)ethyl methanesulfonate (Int 103)

To a solution of 4-(3-(difluoromethyl)-4-fluorophenyl)-3-(4-((2-hydroxyethyl)thio)-1,2,5-oxadiazol-3-yl)-1,2,4-oxadiazol-5(4H)-one (Int 100/15) (140 mg, 0.37 mmol) in DCM (8 mL) methanesulfonyl chloride (0.06 mL, 0.56 mmol) was added and the mixture was stirred for 5 min at rt. TEA (0.08 mL, 0.56 mmol) was added and the mixture was stirred for 10 min. Water (5 mL) was added and the mixture was extracted with EtOAc (2×5 mL). The combined organic layers were dried over anhydrous Na₂SO₄, filtered and concentrated to dryness to give the title compound as yellow solid.

Intermediate 104a and 104b: N-(1-((4-(4-(3-(Difluoromethyl)-4-fluorophenyl)-5-oxo-4,5-dihydro-1,2,4-oxadiazol-3-yl)-1,2,5-oxadiazol-3-yl)thio)propan-2-yl)-2-sulfamoylacetamide (Int 104a, Int 104b)

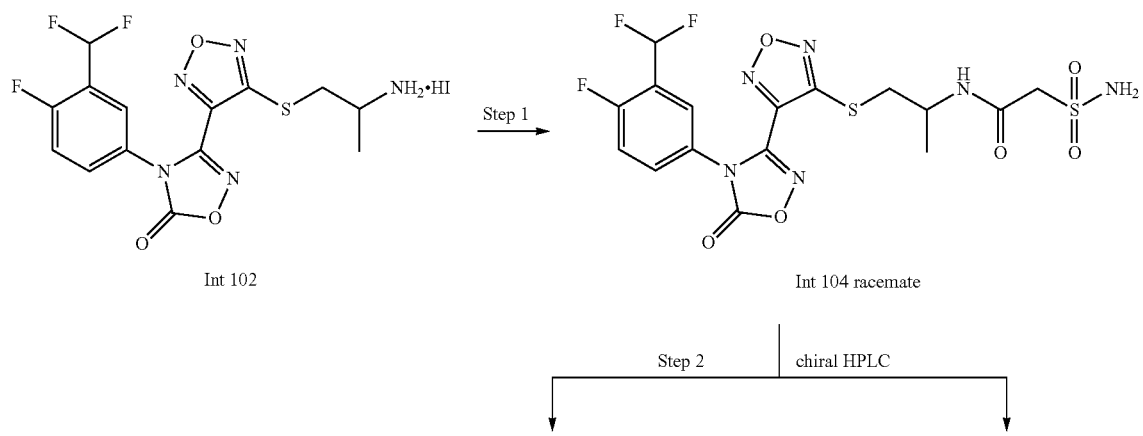

-continued

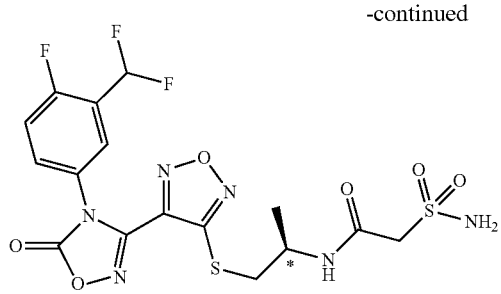

Int 104a first eluting enantiomer
*absolute configuration unknown

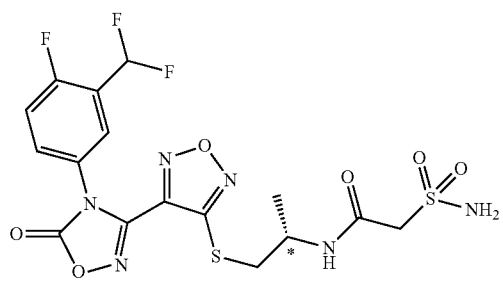

Int 104b second eluting enantiomer
*absolute configuration unknown

Step 1: N-(1-((4-(4-(3-(Difluoromethyl)-4-fluorophenyl)-5-oxo-4,5-dihydro-1,2,4-oxadiazol-3-yl)-1,2,5-oxadiazol-3-yl)thio)propan-2-yl)-2-sulfamoylacetamide (Int 104 racemate)

To a solution of 3-(4-((2-aminopropyl)thio)-1,2,5-oxadiazol-3-yl)-4-(3-(difluoromethyl)-4-fluorophenyl)-1,2,4-oxadiazol-5(4H)-one hydroiodide (Int 102) (416 mg, 0.81 mmol), HATU (462 mg, 1.22 mmol) and $Et_3N$ (245 mg, 2.43 mmol) in DMF (8 mL) 2-sulfamoylacetic acid (135 mg, 0.97 mmol) was added and the mixture was stirred at rt overnight. EtOAc (20 mL) was added and the mixture was extracted with water (2×20 mL). The combined organic layers were dried over anhydrous $Na_2SO_4$, filtered and concentrated to dryness. The residue was purified by column chromatography to give the title compound as a white solid.

Step 2: N-(1-((4-(4-(3-(Difluoromethyl)-4-fluorophenyl)-5-oxo-4,5-dihydro-1,2,4-oxadiazol-3-yl)-1,2,5-oxadiazol-3-yl)thio)propan-2-yl)-2-sulfamoylacetamide (Int 104a and Int 104b)

Chiral HPLC separation (Chiralcel OZ-H column, SFC, $CO_2$/0.03% $NH_3$ in MeOH (=30:70) of N-(1-((4-(4-(3-(difluoromethyl)-4-fluorophenyl)-5-oxo-4,5-dihydro-1,2,4-oxadiazol-3-yl)-1,2,5-oxadiazol-3-yl)thio)propan-2-yl)-2-sulfamoylacetamide (Int 104 racemate) afforded N-(1-((4-(4-(3-(difluoromethyl)-4-fluorophenyl)-5-oxo-4,5-dihydro-1,2,4-oxadiazol-3-yl)-1,2,5-oxadiazol-3-yl)thio)propan-2-yl)-2-sulfamoylacetamide (Int 104a, first eluting enantiomer with a retention time of 0.95 min) and N-(1-((4-(4-(3-(difluoromethyl)-4-fluorophenyl)-5-oxo-4,5-dihydro-1,2,4-oxadiazol-3-yl)-1,2,5-oxadiazol-3-yl)thio)propan-2-yl)-2-sulfamoylacetamide (Int 104b, second eluting enantiomer with a retention time of 2.45 min).

Intermediate 104/1a to 104/3b

The following Intermediates were prepared similar as described for Intermediate 104 using the appropriate Intermediates as starting material.

| Int. # | Starting material | Structure chiral-HPLC |
|---|---|---|
| Int 104/1a | Int 102 | ![structure] <br> * absolute configuration unknown <br> Chiralpak AD-H column, SFC, $CO_2$/0.03% $NH_3$ in MeOH (= 40:60) first eluting enantiomer with a retention time of 1.93 min) |

| Int. # | Starting material | Structure chiral-HPLC |
|---|---|---|
| Int 104/1b | Int 102 | *absolute configuration unknown*<br><br>Chiralpak AD-H column, SFC, CO$_2$/0.03% NH$_3$ in MeOH (= 40:60) second eluting enantiomer with a retention time of 3.13 min) |
| Int 104/2a | Int 102 | *absolute configuration unknown*<br><br>Chiralpak IC column, SFC, CO$_2$/0.03% NH$_3$ in MeOH (= 87:13) first eluting enantiomer with a retention time of 1.67 min) |
| Int 104/2b | Int 102 | *absolute configuration unknown*<br><br>Chiralpak IC column, SFC, CO$_2$/0.03% NH$_3$ in MeOH (= 87:13) second eluting enantiomer with a retention time of 2.14 min) |
| Int 104/3a | Int 102/1 | *absolute configuration unknown*<br><br>Chiralcel OZ-H column, SFC, CO$_2$/0.03% NH$_3$ in MeOH (= 30:70) first eluting enantiomer with a retention time of 1.11 min) |

-continued
| Int. # | Starting material | Structure chiral-HPLC |
|---|---|---|
| Int 104/3b | Int 102/1 | (structure shown below) |
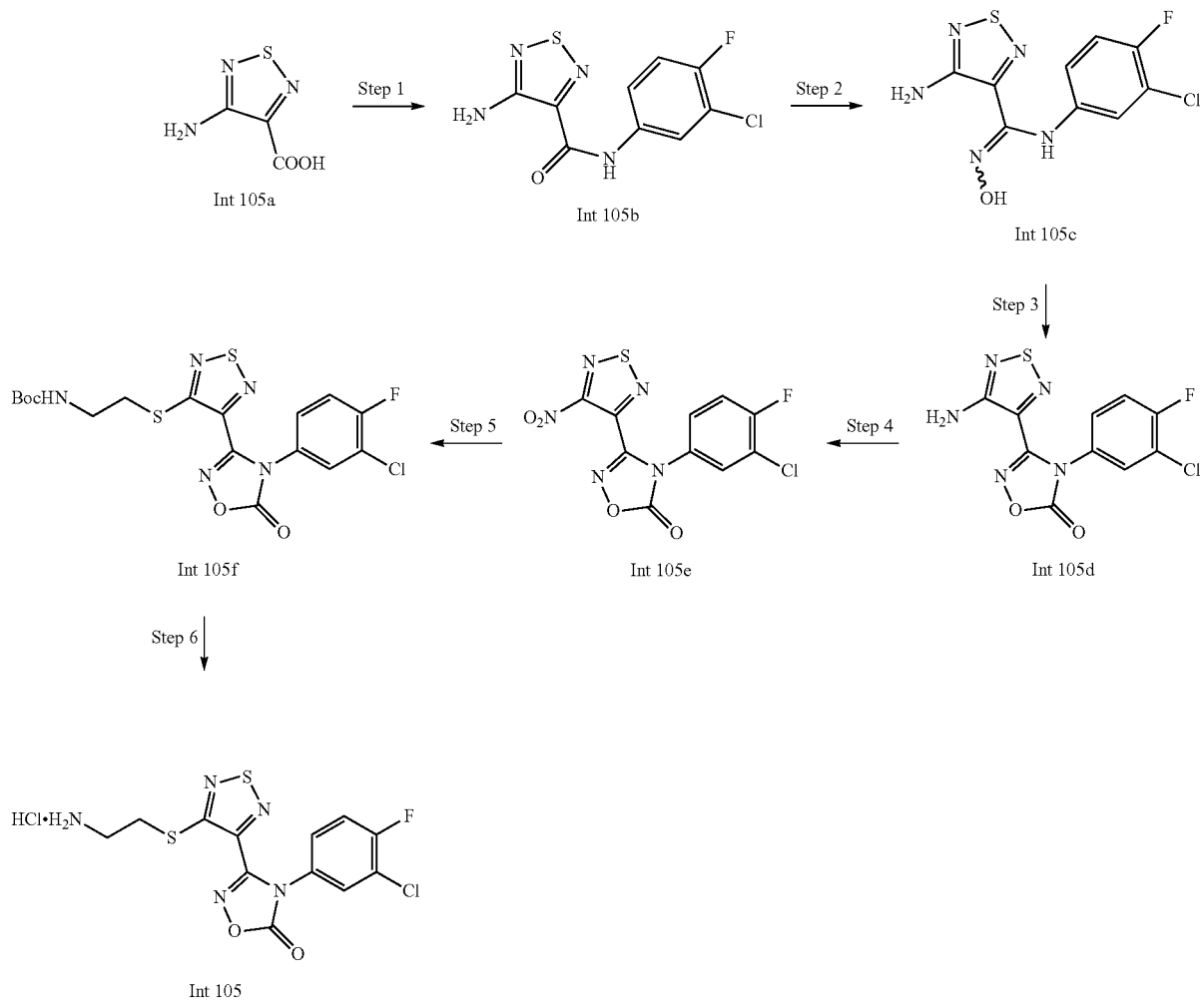
* absolute configuration unknown
Chiralcel OZ-H column, SFC, CO$_2$/0.03% NH$_3$ in MeOH
(= 30:70) second eluting enantiomer with a retention time of
4.68 min)
Intermediate 105: 3-(4-((2-Aminoethyl)thio)-1,2,5-thiadiazol-3-yl)-4-(3-chloro-4-fluorophenyl)-1,2,4-oxadiazol-5(4H)-one hydrochloride (Int 105)

Step 1: 4-Amino-N-(3-chloro-4-fluorophenyl)-1,2,5-thiadiazole-3-carboxamide (Int 105b)

A solution of 4-amino-1,2,5-thiadiazole-3-carboxylic acid (Int 105a) (443 mg, 3.00 mmol), 3-chloro-4-fluoroaniline (443 mg, 3.00 mmol), HATU (1.70 g, 4.50 mmol) and Et$_3$N (909 mg, 9.00 mmol) in DMF (20 mL) was stirred at rt overnight. EtOAc (50 mL) was added and the mixture was washed with water (2×50 mL). The combined organic layers were dried over anhydrous Na$_2$SO$_4$, filtered and concentrated to dryness. The residue was purified by column chromatography (PE: EtOAc=2:1) to give the title compound as white solid.

Step 2: 4-Amino-N-(3-chloro-4-fluorophenyl)-N'-hydroxy-1,2,5-thiadiazole-3-carboximidamide (Int 105c)

4-Amino-N-(3-chloro-4-fluorophenyl)-1,2,5-thiadiazole-3-carboxamide (Int 105b) (720 mg, 2.65 mmol) was suspended in benzene (15 mL) and phosphorus pentachloride (1.10 g, 5.29 mmol) was added. The mixture was heated at 120° C. for 2.5 h. The mixture was cooled to rt and concentrated to dryness. The residue was dissolved in THF (15 mL) and 50 wt. % hydroxylamine in water (2.6 mL) was added. The mixture was stirred at 60° C. for 2 h. The mixture was concentrated, diluted with EtOAc and the aqueous layer was extracted with EtOAc once. The combined organic layers were concentrated to dryness.

The residue was purified by column chromatography (PE: EtOAc=3: 1) to give the title compound as off-white solid.

Step 3: 3-(4-Amino-1,2,5-thiadiazol-3-yl)-4-(3-chloro-4-fluorophenyl)-1,2,4-oxadiazol-5(4H)-one (Int 105d)

A mixture of 4-amino-N-(3-chloro-4-fluorophenyl)-N'-hydroxy-1,2,5-thiadiazole-3-carboximidamide (Int 105c) (510 mg, 1.78 mmol), CDI (432 mg, 2.67 mmol) in EtOAc (20 mL) was stirred at 60° C. for 20 min. The mixture was cooled to rt and diluted with EtOAc (50 mL). The organic layer was washed with water (50 mL) and brine (50 mL), dried over anhydrous Na$_2$SO$_4$, filtered and concentrated to dryness. The residue was purified by column chromatography (PE: EtOAc=1: 3) to give the title compound as white solid.

Step 4: 4-(3-Chloro-4-fluorophenyl)-3-(4-nitro-1,2,5-thiadiazol-3-yl)-1,2,4-oxadiazol-5(4H)-one (Int 105e)

To a 30 wt. % solution of H$_2$O$_2$ in water (10 mL) 98% H$_2$SO$_4$ (10 mL) was added slowly under cooling with an ice bath. 3-(4-Amino-1,2,5-thiadiazol-3-yl)-4-(3-chloro-4-fluorophenyl)-1,2,4-oxadiazol-5(4H)-one (Int 105d) (500 mg, 1.60 mmol) was added in 3 portions with vigorous stirring, while the temperature of the mixture was kept below 10° C. The mixture was stirred at 55° C. for 5 h. The mixture was cooled to rt and water (200 mL) was added. The mixture was extracted with EtOAc (3×100 mL) and the combined organic layers were washed with water (100 mL) and brine (100 mL), dried over anhydrous Na$_2$SO$_4$, filtered and concentrated to dryness. The residue was purified by column chromatography (PE: EtOAc=5: 1) to give the title compound as white solid.

Step 5: tert-Butyl (2-((4-(4-(3-chloro-4-fluorophenyl)-5-oxo-4,5-dihydro-1,2,4-oxadiazol-3-yl)-1,2,5-thiadiazol-3-yl)thio)ethyl)carbamate (Int 105f)

To a stirred solution of 4-(3-chloro-4-fluorophenyl)-3-(4-nitro-1,2,5-thiadiazol-3-yl)-1,2,4-oxadiazol-5(4H)-one (Int 105e) (150 mg, 0.44 mmol) in THF (10 mL) tert-butyl 2-mercaptoethylcarbamate (92 mg, 0.52 mmol) was added. A saturated aqueous sodium bicarbonate solution (0.5 mL) was added and the mixture was stirred at rt for 1 h. Water (50 mL) was added and the mixture was extracted with EtOAc (3×50 mL). The combined organic layers were washed with brine (50 mL), dried over anhydrous Na$_2$SO$_4$, filtered and concentrated to dryness. The residue was purified by column chromatography (PE: EtOAc=5: 1) to give the title compound as white solid.

Step 6: 3-(4-((2-Aminoethyl)thio)-1,2,5-thiadiazol-3-yl)-4-(3-chloro-4-fluorophenyl)-1,2,4-oxadiazol-5(4H)-one hydrochloride (Int 105)

A mixture of tert-butyl (2-((4-(4-(3-chloro-4-fluorophenyl)-5-oxo-4,5-dihydro-1,2,4-oxadiazol-3-yl)-1,2,5-thiadiazol-3-yl)thio)ethyl)carbamate (Int 105f) (180 mg, 0.38 mmol), dioxane (4 mL) and 6.5M hydrogen chloride in dioxane (8 mL) was stirred at rt overnight. The mixture was diluted with diethyl ether and stirred at 0° C. for 1 h. The precipitated crystals were filtered off, washed with diethyl ether and dried to give the title compound as white solid.

Intermediate 106: 3-(4-((2-Aminoethyl)thio)-1,2,5-oxadiazol-3-yl)-4-(3-bromo-4,5-difluorophenyl)-1,2,4-oxadiazol-5(4H)-one hydrochloride (Int 106)

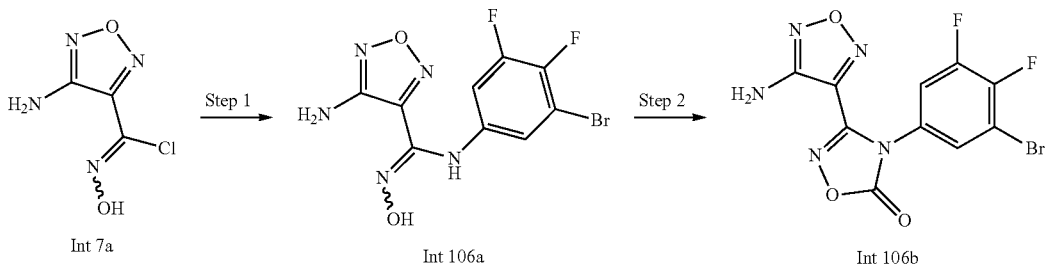

Int 7a → Step 1 → Int 106a → Step 2 → Int 106b

Step 3

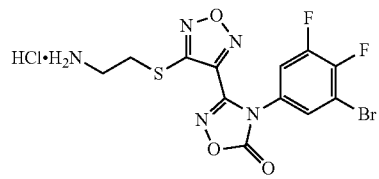 Int 106

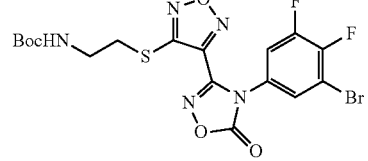 Int 106d

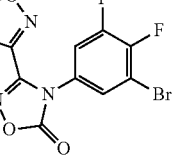 Int 106c

Step 1: 4-Amino-N-(3-bromo-4,5-difluorophenyl)-N'-hydroxy-1,2,5-oxadiazole-3-carboximidamide (Int 106a)

To a solution of 4-amino-N-hydroxy-1,2,5-oxadiazole-3-carbimidoyl chloride (Int 7a) (250 mg, 1.54 mmol) and 3-bromo-4,5-difluoroaniline (320 mg, 1.54 mmol) in H$_2$O and THF (12 mL,1:1) was added NaHCO$_3$ (194 mg, 2.31 mmol). The mixture was stirred at 65° C. for 2 hours. Then the mixture was diluted with EtOAc (50 mL). The organic layer was washed with water (30 mL) and brine (30 mL), dried over Na$_2$SO$_4$ and concentrated. The residue was purified by column chromatography on silica gel (PE: EtOAc=5:1) to give the title compound as a white solid.

Step 2: 3-(4-Amino-1,2,5-oxadiazol-3-yl)-4-(3-bromo-4,5-difluorophenyl)-1,2,4-oxadiazol-5(4H)-one (Int 106b)

A mixture of 4-amino-N-(3-bromo-4,5-difluorophenyl)-N'-hydroxy-1,2,5-oxadiazole-3-carboximidamide (Int 106a) (200 mg, 0.60 mmol), CDI (146 mg, 0.90 mmol) in EtOAc (10 mL) was stirred at 60° C. for 20 min. The mixture was cooled to rt, diluted with EtOAc (15 mL), washed with water (20 mL) and brine (20 mL). The organic phase was dried over Na$_2$SO$_4$, and concentrated to dryness. The residue was purified by column chromatography on silica gel (PE: EtOAc=8:1) to give the title compound as a white solid.

Step 3: 4-(3-Bromo-4,5-difluorophenyl)-3-(4-nitro-1,2,5-oxadiazol-3-yl)-1,2,4-oxadiazol-5(4H)-one (Int 106c)

To a 30% solution of H$_2$O$_2$ (6 mL) and (NH$_4$)$_2$S$_2$O$_8$ (114 mg, 0.50 mmol) was added slowly 98% H$_2$SO$_4$ (4 mL) under cooling with an ice bath. Then 3-(4-amino-1,2,5-oxadiazol-3-yl)-4-(3-bromo-4,5-difluorophenyl)-1,2,4-oxadiazol-5(4H)-one (Int 106b) (180 mg, 0.50 mmol) was added in 3 portions with vigorous stirring, while the temperature of the mixture was maintained below 10° C. After the exothermic reaction ended, the mixture was stirred at 55° C. for 10 hours, cooled to rt, and treated with H$_2$O (20 mL). The product was extracted with EtOAc (3×20 mL). The organic layer was washed with water (20 mL) and brine (20 mL), dried over Na$_2$SO$_4$, and concentrated. The residue was purified by column chromatography on silica gel (PE: EtOAc=5:1) to give the title compound as a white solid.

Step 4: tert-Butyl (2-((4-(4-(3-bromo-4,5-difluorophenyl)-5-oxo-4,5-dihydro-1,2,4-oxadiazol-3-yl)-1,2,5-oxadiazol-3-yl)thio)ethyl)carbamate (Int 106d)

To a stirred solution of 4-(3-bromo-4,5-difluorophenyl)-3-(4-nitro-1,2,5-oxadiazol-3-yl)-1,2,4-oxadiazol-5(4H)-one (Int 106c) (160 mg, 0.41 mmol) in THF (10 mL) was added tert-butyl (2-mercaptoethyl)carbamate (86 mg, 0.49 mmol), and then saturated aqueous NaHCO$_3$ (0.5 mL). The reaction mixture was stirred at rt for1 h. Water (50 mL) was added and the aqueous layer was extracted with EtOAc (3×50 mL). The combined organic layers were washed with brine (50 mL), dried over Na$_2$SO$_4$, and concentrated. The residue was purified by column chromatography on silica gel (PE: EtOAC=5:1) to give the title compound as a white solid.

Step 5: 3-(4-((2-Aminoethyl)thio)-1,2,5-oxadiazol-3-yl)-4-(3-bromo-4,5-difluorophenyl)-1,2,4-oxadiazol-5(4H)-one hydrochloride (Int 106)

A mixture of tert-butyl (2-((4-(4-(3-bromo-4,5-difluorophenyl)-5-oxo-4,5-dihydro-1,2,4-oxadiazol-3-yl)-1,2,5-oxadiazol-3-yl)thio)ethyl)carbamate (Int 106d) (200 mg, 0.38 mmol) in dry dioxane (5 mL) and 6.5 N hydrogen chloride in dioxane (10 mL) was stirred at rt overnight, then diluted with diethyl ether and stirred at 0° C. for 1 h. The precipitated crystals were filtered off, washed with diethyl ether and dried under vacuum to give the title compound as a white solid.

Intermediates 106/1 to 106/2

The following Intermediates were prepared similar as described for Intermediate 106 using the appropriate building blocks.

| Int. # | Building blocks | Structure |
|---|---|---|
| Int 106/1 | ![](F,F,Br,NH2 aniline) HS-CH2CH2-NHBoc | difluorobromophenyl oxadiazolone-oxadiazole-S-CH2CH2-NH2·HCl |

| Int. # | Building blocks | Structure |
|---|---|---|
| Int 106/2 | 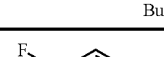 | 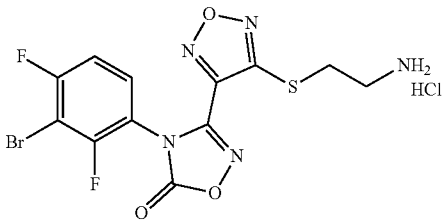 [SMILES: NCCSc1nonc1-c1noc(=O)n1-c1ccc(F)c(Br)c1F ; Cl] |

Intermediate 107: 2-(3-((((9H-Fluoren-9-yl)methoxy)carbonyl)amino)oxetan-3-yl)acetic acid (Int 107)

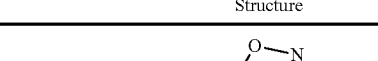

Step 1: 2-(3-((((9H-Fluoren-9-yl)methoxy)carbonyl)amino)oxetan-3-yl)acetic acid (Int 107)

To a solution of 2-(3-aminooxetan-3-yl)acetic acid (262 mg, 2.00 mmol) in DCM (20 mL) was added (9H-fluoren-9-yl)methyl(2,5-dioxopyrrolidin-1-yl) carbonate (675 mg, 2.00 mmol) and DIEA (6.00 mmol) and the mixture was stirred at rt for 18 h. The mixture was diluted with DCM (20 mL) and water (20 mL), the organic layer was washed with water (20 mL×2) and brine (20 mL). After removal of the solvent under vacuum the residue was purified by silica gel chromatography (gradient 0-15 percent MeOH in DCM) to give the title compound as a colorless oil.

EXAMPLES

Compounds of the present invention can be prepared by methods known to those who are skilled in the art. The following examples are only meant to represent examples of the invention and are in no way meant to be a limit of the invention.

Example 1

N-(3-Bromo-4-fluorophenyl)-N'-hydroxy-4-(2-(methylsulfonamido)ethoxy)-1,2,5-oxadiazole-3-carboximidamide (1)

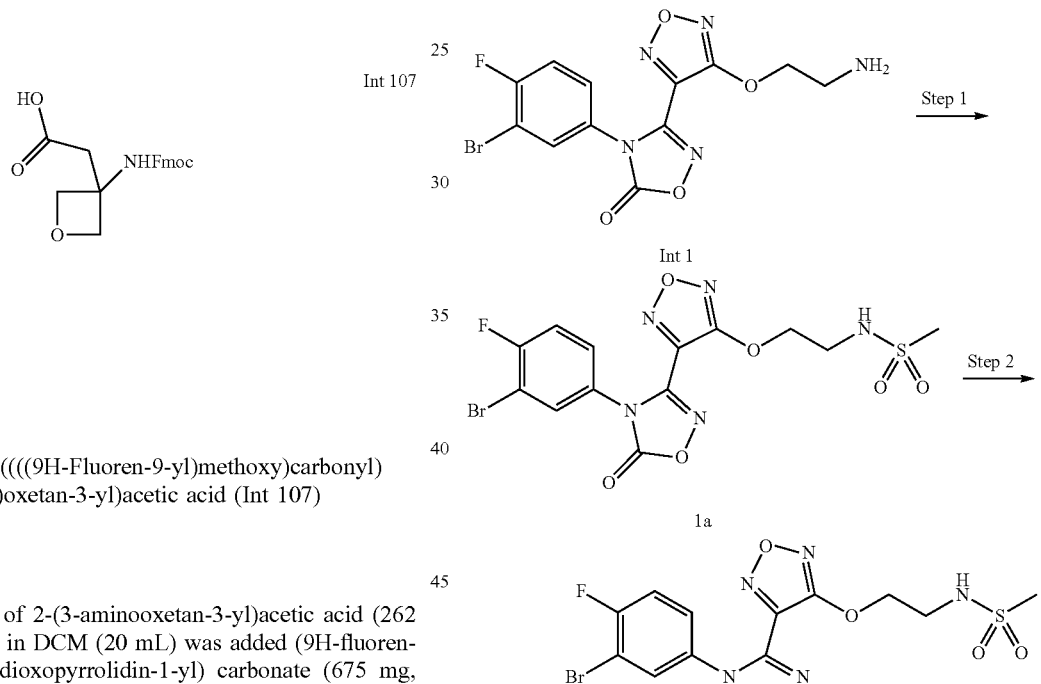

Example 1

Step 1: N-(2-((4-(4-(3-Bromo-4-fluorophenyl)-5-oxo-4,5-dihydro-1,2,4-oxadiazol-3-yl)-1,2,5-oxadiazol-3-yl)oxy)ethyl)methanesulfonamide (1a)

To a solution of 3-(4-(2-aminoethoxy)-1,2,5-oxadiazol-3-yl)-4-(3-bromo-4-fluorophenyl)-1,2,4-oxadiazol-5(4H)-one (Int 1) (134 mg, 0.35 mmol) in DCM (8 mL) was added methanesulfonyl chloride (0.06 mL, 0.52 mmol) in one portion at 0° C. The mixture was stirred for 5 min at 0° C. and TEA (0.08 mL, 0.52 mmol) was added in one portion. After stirring for additional 10 min at 0° C. water (10 mL) was added. The mixture was extracted with EtOAc (2×10 mL), dried over anhydrous Na₂SO₄, filtered and concentrated to dryness to give the title compound as a white solid.

Step 2: N-(3-Bromo-4-fluorophenyl)-N'-hydroxy-4-(2-(methylsulfonamido)ethoxy)-1,2,5-oxadiazole-3-carboximidamide (1)

To a solution of N-(2-((4-(4-(3-bromo-4-fluorophenyl)-5-oxo-4,5-dihydro-1,2,4-oxadiazol-3-yl)-1,2,5-oxadiazol-3-yl)oxy)ethyl)methanesulfonamide (1a) (108 mg, 0.23 mmol) in THF (8 mL) was added 2M NaOH (0.5 mL). The mixture was stirred at rt for 30 min. The mixture was extracted with EtOAc (3×20 mL). The combined organic layers were washed with brine (10 mL), dried over anhydrous Na₂SO₄, filtered and concentrated to dryness. The residue was purified by HPLC to give the title compound as a white solid. ¹H NMR (500 MHz, DMSO-d₆): δ ppm 11.43 (s, 0.9H), 10.37 (s, 0.1H), 9.13 (s, 0.1H), 9.01 (s, 0.9 H), 8.07-8.06 (m, 0.1H), 7.35-7.14 (m, 2.9H), 6.72-6.70 (m, 1H), 4.43-4.41 (m, 0.2H), 4.28-4.26 (m, 1.8H), 3.42-3.27 (m, 2H), 2.94 (s, 2.7H) 2.90 (s, 0.3H). MS (ESI): m/z 437.8 [M+H]⁺.

Example 1/1 to 1/4

The following Examples were prepared similar as described for Example 1 using the appropriate Intermediates and building blocks.

Example 2

4-(2-((2-Amino-3,4-dioxocyclobut-1-en-1-yl)amino)ethoxy)-N-(3-bromo-4-fluorophenyl)-N'-hydroxy-1,2,5-oxadiazole-3-carboximidamide (2)

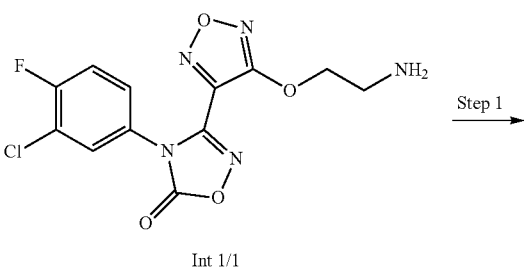

Int 1/1

Step 1

| # | Int. # | Structure | Analytical data |
|---|---|---|---|
| 1/1 | Int 1/1 | 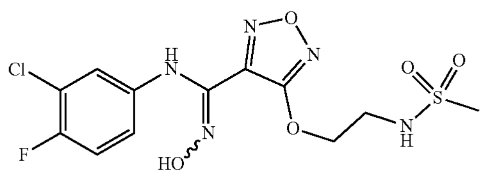 [SMILES: CS(=O)(=O)NCCOc1nonc1C(=NO)Nc1ccc(F)c(Cl)c1] | ¹H NMR (500 MHz, DMSO-d₆): δ ppm 11.44 (s, 0.9H), 10.37 (s, 0.1H), 9.15 (s, 0.1 H), 9.01 (s, 0.9H), 7.94-7.92 (m, 0.1H), 7.34-7.30 (m, 1.9H), 7.20 (dd, J₁ = J₂ = 9.0 Hz, 1H), 7.01 (dd, J₁ = 6.5 Hz, J₂ = 2.5 Hz, 1H), 4.42 (t, J = 5.0 Hz, 1.8H), 4.28 (t, J = 5.0 Hz, 0.2H) 3.40-3.26 (m, 2H), 2.93 (s, 2.7H), 2.89 (s, 0.3H). MS (ESI): m/z 393.9 [M + H]⁺. |
| 1/2 | Int 1/1 | 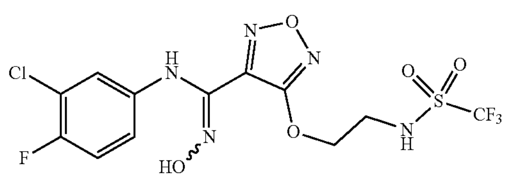 [SMILES: O=S(=O)(NCCOc1nonc1C(=NO)Nc1ccc(F)c(Cl)c1)C(F)(F)F] | ¹H NMR (500 MHz, DMSO-d₆) δ ppm 11.45 (s, 0.9H), 10.36 (s, 0.1H), 9.82-9.76 (m, 1H), 9.15 (s, 0.1H), 9.06 (s, 0.9H), 7-95-7.92 (m, 0.1H), 7.40-7.34 (m, 0.2H), 7.22-7.15 (m, 0.9H), 7.00-6.96 (m, 0.9H), 6.68-6.64 (m, 0.9H), 4.46-4.42 (m, 0.2H), 4.32-4.26 (m, 1.8H), 3.60-3.56 (m, 1.8H). MS (ESI): m/z 448.0 [M + H]⁺. |
| 1/3 | Int 1/1 | 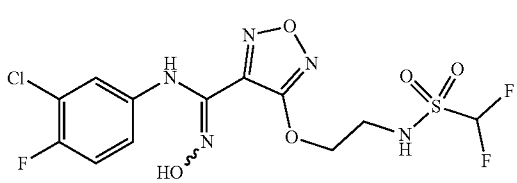 [SMILES: O=S(=O)(NCCOc1nonc1C(=NO)Nc1ccc(F)c(Cl)c1)C(F)F] | ¹H NMR (500 MHz, DMSO-d₆): δ ppm 11.46 (s, 0.9H), 10.35 (s, 0.1H), 9.15 (s, 0.1H), 9.04 (s, 0.9H), 8.80-8.76 (m, 1H), 7.96-7.93 (m, 0.1H), 7.35-7.31 (m, 0.2H), 7.22-7.15 (m, 0.9H), 7.01-6.97 (m, 0.9H), 6.96 (t, J = 52 Hz, 1H), 6.69-6.64 (m, 0.9H), 4.44-4.39 (m, 0.2H), 4.31-4.25 (m, 1.8H), 3.54-3.50 (m, 0.2H), 3.45-3.38 (m, 1.8H). MS (ESI): m/z 430.0 [M + H]⁺. |
| 1/4 | Int 1/1, step 1 | 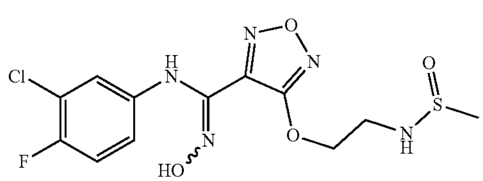 [SMILES: CS(=O)NCCOc1nonc1C(=NO)Nc1ccc(F)c(Cl)c1] | ¹H NMR (500 MHz, DMSO-d₆): δ ppm 11.43 (s, 0.9H), 10.36 (s, 0.1H), 9.16 (s, 0.1H), 9.03 (s, 0.9H), 7.95-7.92 (m, 0.1H), 7.36-7.32 (m, 0.2H), 7.22-7.17 (m, 0.9H), 7.03-6.98 (m, 0.9H), 6.30-6.25 (m, 1H), 4.46-4.42 (m, 0.2H), 4.29-4.24 (m, 1.8H), 3.45-3.22 (m, 2H), 2.54-2.50 (m, 3H). MS (ESI): m/z 378.0 [M + H]⁺. |

-continued

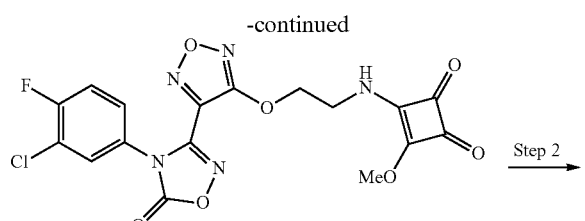

2a

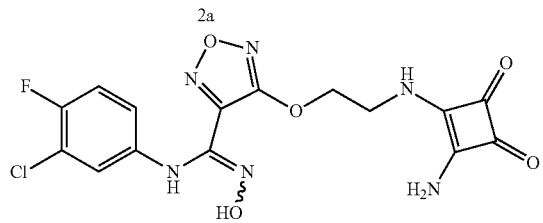

Example 2

Step 1: 3-((2-((4-(4-(3-Chloro-4-fluorophenyl)-5-oxo-4,5-dihydro-1,2,4-oxadiazol-3-yl)-1,2,5-oxadiazol-3-yl)oxy)ethyl)amino)-4-methoxycyclobut-3-ene-1,2-dione (2a)

To a solution of 3-(4-(2-aminoethoxy)-1,2,5-oxadiazol-3-yl)-4-(3-chloro-4-fluorophenyl)-1,2,4-oxadiazol-5(4H)-one (Int 1/1) (150 mg, 0.44 mmol) and 3,4-dimethoxycyclobut-3-ene-1,2-dione (125 mg, 0.88 mmol) in MeOH (50 mL) was added DIPEA (216 mg, 1.67 mmol) at rt. The mixture was stirred at rt overnight. The mixture was concentrated to give an oil, which was dissolved in EtOAc (100 mL). The organic layer was washed with water (2×100 mL), dried over anhydrous $Na_2SO_4$, filtered and concentrated to dryness to give the title compound as a white solid.

Step 2: 4-(2-((2-Amino-3,4-dioxocyclobut-1-en-1-yl)amino)ethoxy)-N-(3-chloro-4-fluorophenyl)-N'-hydroxy-1,2,5-oxadiazole-3-carboximidamide (2)

To a solution of 3-((2-((4-(4-(3-chloro-4-fluorophenyl)-5-oxo-4,5-dihydro-1,2,4-oxadiazol-3-yl)-1,2,5-oxadiazol-3-yl)oxy)ethyl)amino)-4-methoxycyclobut-3-ene-1,2-dione (2a) (121 mg, 0.27 mmol) in MeOH (30 mL) was added $NH_3$/MeOH (7M, 10 mL) at rt. The mixture was stirred at rt overnight. The mixture was concentrated to dryness and the residue was purified by HPLC to give the title compound as a white solid. $^1H$ NMR (500 MHz, DMSO-$d_6$) δ ppm 11.43 (s, 0.9H) 10.35 (s, 0.1H), 9.13 (s, 0.1H), 9.01 (s, 0.9H), 7.70-7.40 (m, 3H), 7.17 (dd, $J_1=J_2=9.0$ Hz, 1H), 6.99 (dd, $J_1=6.5$ Hz, $J_2=2.5$ Hz, 1H), 6.68-6.65 (m, 1H), 4.52-4.38 (m, 2H), 3.83-3.79 (m, 2H). MS (ESI): m/z 410.8 $[M+H]^+$.

Examples 2/1 to 2/7

The following Examples were prepared similar as described for Example 2 using the appropriate Intermediates and carboxylic acid building blocks.

| # | Int. # | Structure | Analytical data |
|---|--------|-----------|-----------------|
| 2/1 | Int 1 | 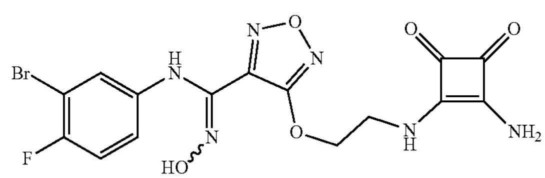 [SMILES: Nc1c(NCCOc2nonc2C(=NO)Nc2ccc(F)c(Br)c2)c(=O)c1=O] | $^1H$ NMR (500 MHz, DMSO-$d_6$): δ ppm 11.42 (s, 0.9H), 10.34 (s, 0.1H), 9.11 (s, 0.1H), 8.99 (s, 0.9H), 8.06-7.30 (m, 3H), 7.16-7.10 (m, 2H), 6.72-6.69 (m, 1H), 4.52-4.37 (m, 2H), 3.90-3.80 (m, 2H), MS (ESI): m/z 454.9 $[M+H]^+$. |
| 2/2 | Int 1 $NH_2Me$ instead of $NH_3$, Step 2 | 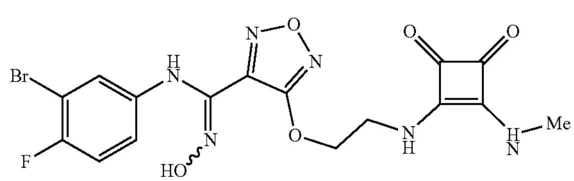 [SMILES: CNc1c(NCCOc2nonc2C(=NO)Nc2ccc(F)c(Br)c2)c(=O)c1=O] | $^1H$ NMR (500 MHz, DMSO-$d_6$): δ ppm 11.43 (s, 0.9H), 10.35 (s, 0.1H), 9.11 (s, 0.1H), 9.01 (s, 0.9H), 8.07-7.28 (m, 2H), 7.15-7.10 (m, 2H), 6.71-6.68 (m, 1H), 4.51-4.36 (m, 2H), 3.89-3.86 (m, 2H), 3.14-3.05 (m, 3H). MS (ESI): m/z 454.9 $[M+H]^+$. |
| 2/3 | Int 1/5 | 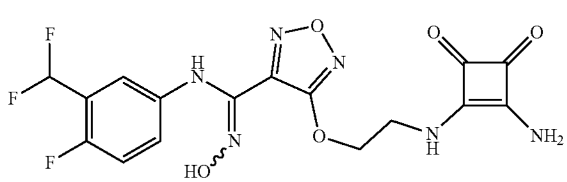 [SMILES: Nc1c(NCCOc2nonc2C(=NO)Nc2ccc(F)c(C(F)F)c2)c(=O)c1=O] | $^1H$ NMR (500 MHz, DMSO-$d_6$): δ ppm 11.40 (s, 1H), 10.31 (s, 0.1H), 9.15 (s, 0.1H), 9.06 (s, 0.9H), 7.93-7.29 (m, 2H), 7.21-7.09 (m, 1H), 6.99-6.89 (m, 2H), 4.54-4.50 (m, 0.2H), 4.37-4.33 (m, 1.8H). MS (ESI): m/z 427.0 $[M+H]^+$. |
| 2/4 | Int 1/1 | 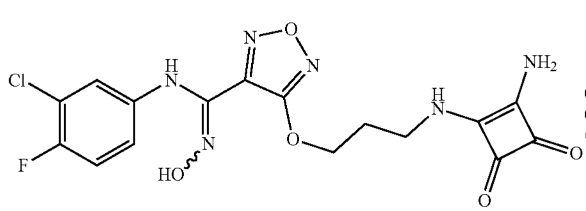 [SMILES: Nc1c(NCCCOc2nonc2C(=NO)Nc2ccc(F)c(Cl)c2)c(=O)c1=O] | $^1H$ NMR (500 MHz, DMSO-$d_6$): δ ppm 11.43 (s, 1H), 10.37 (s, 0.1H), 9.13 (s, 0.1H), 9.03 (s, 0.9H), 7.95-7.93 (m, 0.1H), 7.75-7.25 (m, 3.2H), 7.20-7.17 (m, 0.9H), 7.03-7.01 (m, 0.9H), 6.68-6.65 (m, 0.9H), 4.45 (t, J = 5.0 Hz, 0.2H), 4.27 (t, J = 5.0 Hz, 1.8H), 3.58-3.49 (m, 2H), 2.03-1.87 (m, 2H). MS (ESI): m/z 425.0 $[M+H]^+$. |

-continued

| # | Int. # | Structure | Analytical data |
|---|---|---|---|
| 2/5 | Int 1/2 | 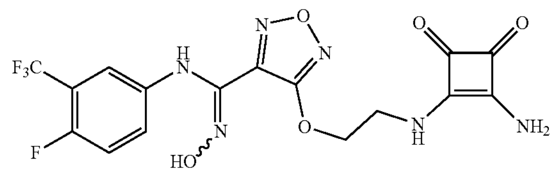 [SMILES: Nc1c(NCCOc2nonc2C(=NO)Nc2ccc(F)c(C(F)(F)F)c2)c(=O)c1=O] | $^1$H NMR (500 MHz, DMSO-d$_6$): δ ppm 11.55 (s, 0.9 H), 10.41 (s, 0.1H), 9.29 (s, 0.1H), 9.15 (s, 0.9H), 8.08-6.98 (m, 6H), 4.54-4.50 (m, 0.2H), 4.41-4.37 (m, 1.8H), 3.90-3.82 (m, 2H). MS (ESI): m/z 445.1 [M + H]$^+$. |
| 2/6 | Int 1/3 | 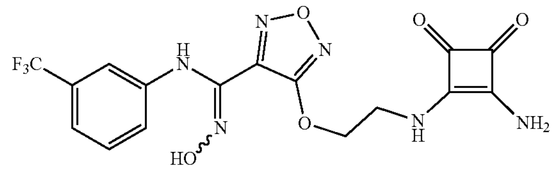 [SMILES: Nc1c(NCCOc2nonc2C(=NO)Nc2cccc(C(F)(F)F)c2)c(=O)c1=O] | $^1$H NMR (500 MHz, DMSO-d$_6$): δ ppm 11.58 (s, 0.9H), 10.46 (s, 0.1H), 9.31 (s, 0.1H), 9.21 (s, 0.9H), 8.10-6.94 (m, 7H), 4.56-4.52 (m, 0.2H), 4.39-4.35 (m, 1.8 H), 3.90-3.80 (m, 2H). MS (ESI): m/z 427.1 [M + H]$^+$. |
| 2/7 | Int 1/4 | 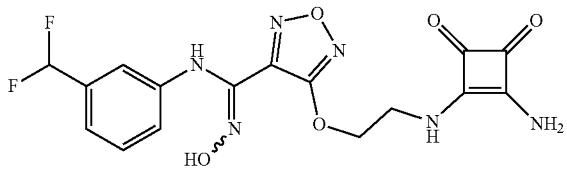 | $^1$H NMR (500 MHz, DMSO-d$_6$): δ ppm 11.42 (s, 0.9H), 10.34 (s, 0.1H), 9.14 (s, 0.1H), 9.10 (s, 0.9H), 7.89-6.79 (m, 8H), 4.54-4.50 (m, 0.2H), 4.34-4.30 (m, 1.8H), 3.90-3.78 (m, 2H). MS (ESI): m/z 409.1 [M + H]$^+$. |

Example 3

N-(2-((4-(N-(3-Chloro-4-fluorophenyl)-N'-hydroxy-carbamimidoyl)-1,2,5-oxadiazol-3-yl)oxy)ethyl)morpholine-3-carboxamide (3)

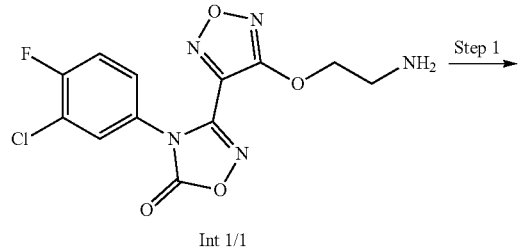

Int 1/1

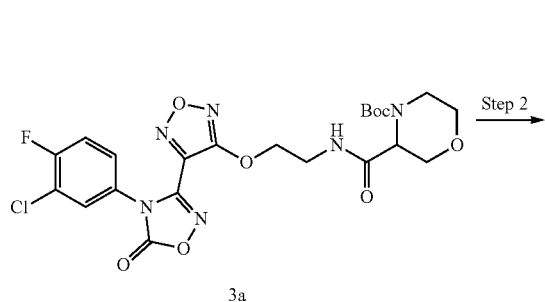

3a

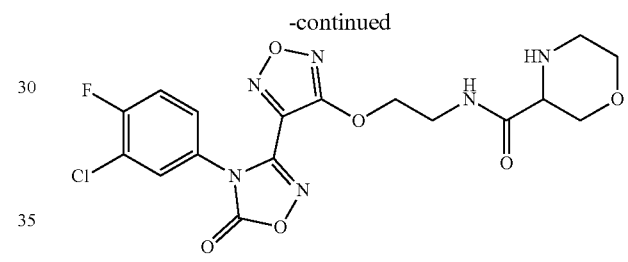

3b

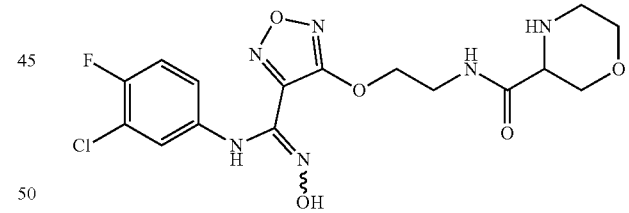

Example 3

Step 1: tert-Butyl 3-((2-((4-(4-(3-chloro-4-fluorophenyl)-5-oxo-4,5-dihydro-1,2,4-oxadiazol-3-yl)-1,2,5-oxadiazol-3-yl)oxy)ethyl)carbamoyl)morpholine-4-carboxylate (3a)

To a solution of 4-(tert-butoxycarbonyl)morpholine-3-carboxylic acid (180 mg, 0.78 mmol), Et$_3$N (105 mg, 1.04 mmol) and HATU (297 mg, 0.78 mmol) in DCM (20 mL) was added 3-(4-(2-aminoethoxy)-1,2,5-oxadiazol-3-yl)-4-(3-chloro-4-fluorophenyl)-1,2,4-oxadiazol-5(4H)-one (Int 1/1) (170 mg, 0.52 mmol) and the mixture was stirred at rt overnight. The mixture was concentrated to dryness and the residue was dissolved in DCM (50 mL). The organic layer was washed with water (2×50 mL), dried over anhydrous Na$_2$SO$_4$, filtered and concentrated to dryness. The residue was purified by column chromatography (EA:PE=1:2) to give the title compound as yellow solid.

Step 2: N-(2-((4-(4-(3-Chloro-4-fluorophenyl)-5-oxo-4,5-dihydro-1,2,4-oxadiazol-3-yl)-1,2,5-oxadiazol-3-yl)oxy)ethyl)morpholine-3-carboxamide (3b)

To a solution tert-butyl 3-((2-((4-(4-(3-chloro-4-fluorophenyl)-5-oxo-4,5-dihydro-1,2,4-oxadiazol-3-yl)-1,2,5-oxadiazol-3-yl)oxy)ethyl)carbamoyl)morpholine-4-carboxylate (3a) (175 mg, 0.31 mmol) in DCM (20 mL) was added TFA (1 mL) and the mixture was stirred at rt overnight. The mixture was concentrated to dryness to give the title compound.

Step 3: N-(2-((4-(N-(3-Chloro-4-fluorophenyl)-N-hydroxycarbamimidoyl)-1,2,5-oxadiazol-3-yl)oxy)ethyl)morpholine-3-carboxamide (3)

To a solution of N-(2-((4-(4-(3-Chloro-4-fluorophenyl)-5-oxo-4,5-dihydro-1,2,4-oxadiazol-3-yl)-1,2,5-oxadiazol-3-yl)oxy)ethyl)morpholine-3-carboxamide (3b) (140 mg, 0.31 mmol) in MeOH (3 mL) was added aqueous NaOH (1M, 0.5 mL) at rt and the mixture was stirred overnight. Water was added and the mixture was extracted with EtOAc (20 mL). The combined organic layers were washed with brine (20 mL), dried over anhydrous Na$_2$SO$_4$, filtered and concentrated to dryness. The residue was purified by HPLC to give the title compound as a white solid. $^1$H NMR (500 MHz, CD$_3$OD): δ ppm 7.09 (dd, J$_1$=J$_2$=9.0 Hz, 1H), 7.07-7.02 (m, 1H), 6.77-6.75 (m, 1H), 4.31-4.29 (m, 2H), 4.20-4.17 (m, 1H), 4.09-4.07 (m, 1H), 4.02-4.00 (m, 1H), 3.79-3.53 (m, 4H), 3.39-3.25 (m, 2H). MS (ESI): m/z 429.1 [M+H]$^+$.

Examples 3/1 to 3/4

The following Examples were prepared similar as described for Example 3 using the appropriate Intermediates.

| # | Int. # | Structure | Analytical data |
|---|---|---|---|
| 3/1 | Int 1/1, Step 1 | 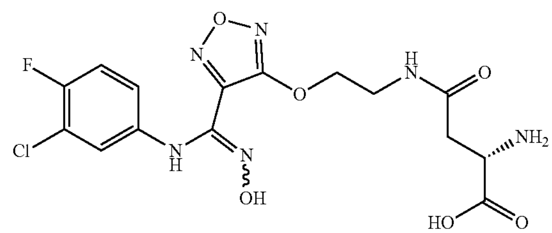 [SMILES: N[C@@H](CC(=O)NCCOc1nonc1C(=NO)Nc1ccc(F)c(Cl)c1)C(=O)O] | $^1$H-NMR (500 MHz, CD$_3$OD): δ: 7.12-7.07 (m, 1H), 7.03-7.00 (m, 1H), 6.79-6.75 (m, 1H), 4.33-4.29 (m, 2H), 3.88-3.83 (m, 1H), 3.62-3.45 (m, 2H), 2.98-2.94 (m, 1H), 2.70-2.65 (m, 1H). MS (ESI): m/z 429.0 [M − H]$^-$ |
| 3/2 | Int 1/1, Step 1 | 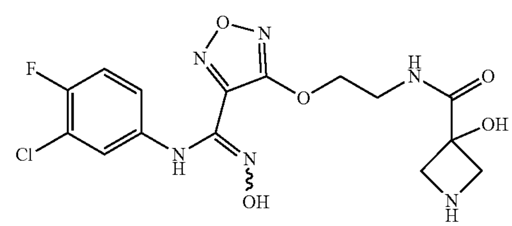 [SMILES: O=C(NCCOc1nonc1C(=NO)Nc1ccc(F)c(Cl)c1)C1(O)CNC1] | $^1$H NMR (500 MHz, CD$_3$OD): δ ppm 7.11 (dd, J1 = J2 = 9.0 Hz, 1H), 7.06-7.01 (m, 1H), 6.80-6.75 (m, 1H), 4.38-4.32 (m, 4H), 4.07-4.05 (m, 2H), 3.61-3.58 (m, 2H). MS (ESI): m/z 415.1 [M + H]$^+$. |
| 3/3 | Int 1/1, Step 1 | 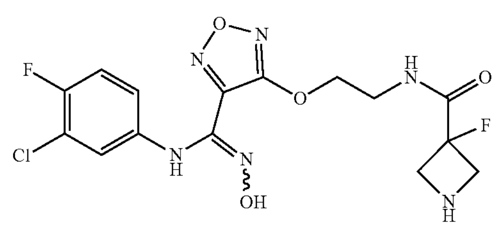 [SMILES: O=C(NCCOc1nonc1C(=NO)Nc1ccc(F)c(Cl)c1)C1(F)CNC1] | $^1$H NMR (500 MHz, DMSO-d$_6$): δ ppm 11.52 (s, 0.9H), 10.39 (s, 0.1H), 9.13 (s, 0.1H), 8.98 (s, 0.9H), 8.37-8.33 (m, 1H), 7.92-7.89 (m, 0.1H), 7.45-7.39 (m, 0.2H), 7.22-7.16 (m, 0.9H), 7.03-6.99 (m, 0.9H), 6.71-6.66 (m, 0.9H), 4.46-4.42 (m, 0.2H), 4.32-4.27 (m, 1.8H), 3.91-3.81 (m, 2H), 3.60-3.42 (m, 4H). MS (ESI): m/z 417.1 [M + H]$^+$. |
| 3/4 | Int 1/1, Step 1 | 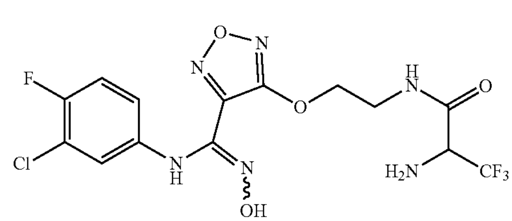 [SMILES: NC(C(=O)NCCOc1nonc1C(=NO)Nc1ccc(F)c(Cl)c1)C(F)(F)F] | $^1$H NMR (500 MHz, CD$_3$OD): δ ppm 7.09 (t, J = 8.5 Hz, 1H), 7.04-7.00 (m, 1H), 6.78-6.73 (m, 1H), 4.54-4.46 (m, 1H), 4.34-4.28 (m, 2H), 3.64-3.60 (m, 2H). MS (ESI): m/z 441.1 [M + H]$^+$ |

Example 4

N$^1$-(2-((4-(N-(3-Chloro-4-fluorophenyl)-N'-hydroxycarbamimidoyl)-1,2,5-oxadiazol-3-yl)oxy)ethyl)oxalamide (1/4)

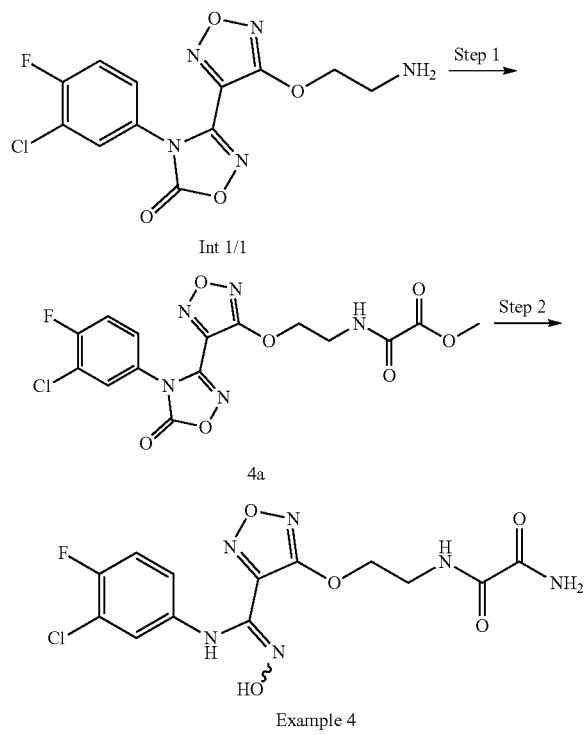

Example 4

Step 1: Methyl 2-((2-((4-(4-(3-Chloro-4-fluorophenyl)-5-oxo-4,5-dihydro-1,2,4-oxadiazol-3-yl)-1,2,5-oxadiazol-3-yl)oxy)ethyl)amino)-2-oxoacetate (4a)

To a solution of methyl 2-chloro-2-oxoacetate (94 mg, 0.78 mmol), Et$_3$N (105 mg, 1.04 mmol) in DCM (20 mL) 3-(4-(2-aminoethoxy)-1,2,5-oxadiazol-3-yl)-4-(3-chloro-4-fluorophenyl)-1,2,4-oxadiazol-5(4H)-one (Int 1/1) (170 mg, 0.52 mmol) was added and the mixture was stirred at rt overnight. The mixture was concentrated to dryness and the residue was dissolved in DCM (50 mL). The organic layer was washed with water (2×50 mL), dried over anhydrous Na$_2$SO$_4$, filtered and concentrated to dryness. The residue was purified by column chromatography (EA:PE=1:2) to give the title compound as a yellow solid.

Step 2: N$^1$-(2-((4-(N-(3-Chloro-4-fluorophenyl)-N'-hydroxycarbamimidoyl)-1,2,5-oxadiazol-3-yl)oxy)ethyl)oxalamide (4)

To a solution of methyl 2-((2-((4-(4-(3-chloro-4-fluorophenyl)-5-oxo-4,5-dihydro-1,2,4-oxadiazol-3-yl)-1,2,5-oxadiazol-3-yl)oxy)ethyl)amino)-2-oxoacetate (4a) (150 mg, 0.34 mmol) in MeOH (3 mL) was added NH$_3$/MeOH (7M, 1 mL) at rt and the mixture was stirred overnight. Water was added and the mixture was extracted with EtOAc (20 mL). The organic layer was washed with brine (20 mL), dried over anhydrous Na$_2$SO$_4$, filtered and concentrated to dryness. The residue was purified by HPLC to give the title compound as a white solid. $^1$H NMR (500 MHz, DMSO-d$_6$) δ ppm 11.44 (s, 0.9H), 10.34 (s, 0.1H), 9.11 (s, 0.1H), 9.00 (s, 0.9H), 8.87-8.85 (m, 1H), 8.07-7.81 (m, 2H), 7.33-6.42 (m, 3H), 4.47-4.46 (m, 0.2H), 4.33-4.31 (m, 1.8H), 3.56-3.44 (m, 2H). MS (ESI): m/z 387.0 [M+H]$^+$.

Examples 4/1 to 4/2

The following Examples were prepared similar as described for Example 4 using the appropriate Intermediates.

| # | Int. # | Structure | Analytical data |
|---|---|---|---|
| 4/1 | Int 1/2, Step 1 | (structure shown) | $^1$H NMR (500 MHz, DMSO-d$_6$): δ ppm 11.60 (s, 0.9H), 10.40 (s, 0.1H), 9.31 (s, 0.1H), 9.15 (s, 0.9H), 8.19-8.14 (m, 0.1H), 7.61-7.00 (m, 5.9H), 4.46-4.42 (m, 0.2H), 4.33-4.29 (m, 1.8H), 3.96-3.92 (m, 2H), 3.44-3.41 (m, 0.2H), 3.37-3.32 (m, 1.8H). MS (ESI): m/z 471.1 [M + H]$^+$. |
| 4/2 | Int 1/5, Step 1 | (structure shown) | $^1$H NMR (500 MHz, DMSO-d$_6$): δ ppm 11.44 (s, 0.9H), 10.32 (s, 0.1H), 9.20 (S, 0.1H), 9.06 (s, 0.9H), 7.95-7.90 (m, 0.1H), 7.63-7.59 (m, 1.1H), 7.50-7.48 (m, 1H), 7.40-7.30 (m, 1.1H), 7.21-6.91 (m, 3.7H), 4.45-4.40 (m, 0.2H), 4.29-4.25 (m, 1.8H), 3.93 (s, 2H), 3.42-3.39 (m, 0.2H), 3.33-3.27 (m, 1.8H). MS (ESI): m/z 453.1 [M + H]$^+$. |

Example 5

N-(3-Chloro-4-fluorophenyl)-N'-hydroxy-4-(2-ureidoethoxy)-1,2,5-oxadiazole-3-carboximidamide (5)

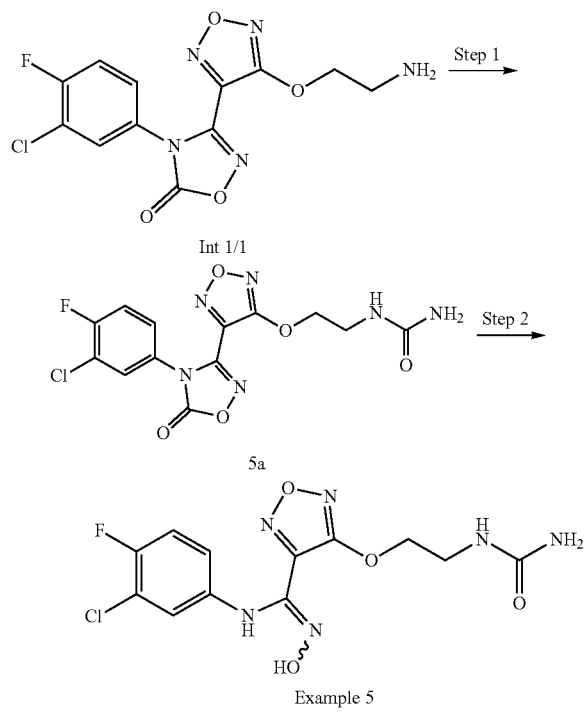

Example 5

Step 1: 1-(2-((4-(4-(3-Chloro-4-fluorophenyl)-5-oxo-4,5-dihydro-1,2,4-oxadiazol-3-yl)-1,2,5-oxadiazol-3-yl)oxy)ethyl)urea (5a)

To a solution of trimethylsilyl)isocyanate (90 mg, 0.78 mmol) and Et$_3$N (105 mg, 1.04 mmol) in DCM (20 mL) 3-(4-(2-aminoethoxy)-1,2,5-oxadiazol-3-yl)-4-(3-chloro-4-fluorophenyl)-1,2,4-oxadiazol-5(4H)-one (Int 1/1) (170 mg, 0.52 mmol) was added and the mixture was stirred at rt overnight. The mixture was concentrated to dryness and the residue was dissolved in DCM (50 mL). The organic layer was washed with water (2×50 mL), dried over anhydrous Na$_2$SO$_4$, filtered and concentrated to dryness. The residue was purified by column chromatography (EA:PE=1:2) to give the title compound as a yellow solid.

Step 2: N-(3-Chloro-4-fluorophenyl)-N'-hydroxy-4-(2-ureidoethoxy)-1,2,5-oxadiazole-3-carboximidamide (5)

To a solution of 1-(2-((4-(4-(3-Chloro-4-fluorophenyl)-5-oxo-4,5-dihydro-1,2,4-oxadiazol-3-yl)-1,2,5-oxadiazol-3-yl)oxy)ethyl)urea (5a) (150 mg, 0.39 mmol) in MeOH (3 mL) aqueous NaOH (1M, 0.5 mL) was added and the mixture was stirred at rt overnight. Water was added and the mixture was extracted with EtOAc (20 mL). The organic layer was washed with brine (20 mL), dried over anhydrous Na$_2$SO$_4$, filtered and concentrated to dryness. The residue was purified by HPLC to give the title compound as a white solid. $^1$H NMR (500 MHz, CD$_3$OD) δ ppm 7.10 (dd, J$_1$=J$_2$=9.0 Hz, 1H), 7.01 (dd, J$_1$=6.5 Hz, J$_2$=2.5 Hz, 1H), 6.79-6.76 (m, 1H), 4.24-4.22 (m, 2H), 3.43-3.41 (m, 2H). MS (ESI): m/z 359.1 [M+H]$^+$.

Example 6

N-(3-Bromo-4-fluorophenyl)-N'-hydroxy-4-(2-(sulfamoylamino)ethoxy)-1,2,5-oxadiazole-3-carboximidamide (6)

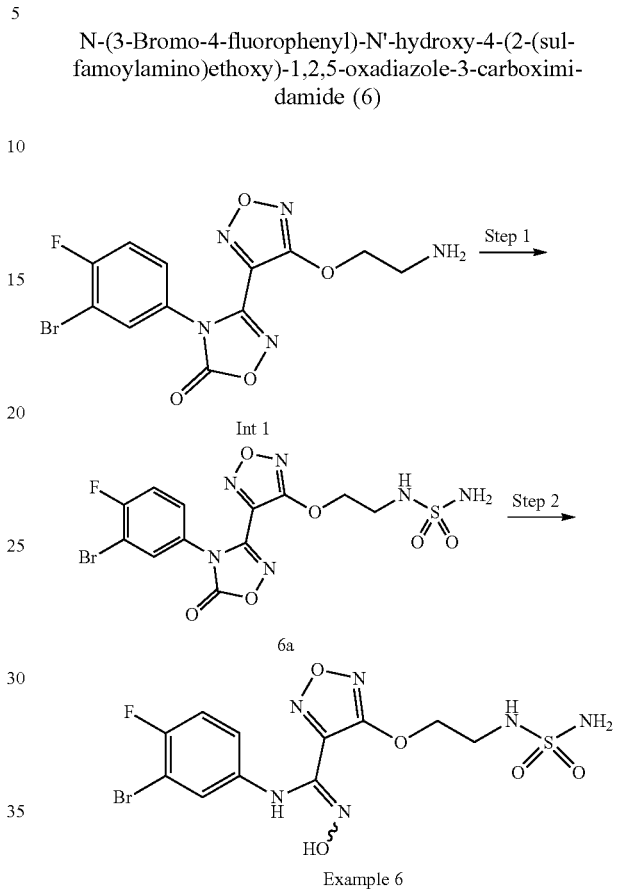

Example 6

Step 1: N-(2-((4-(4-(3-Bromo-4-fluorophenyl)-5-oxo-4,5-dihydro-1,2,4-oxadiazol-3-yl)-1,2,5-oxadiazol-3-yl)oxy)ethyl)sulfamide (6a)

To a solution of 3-(4-(2-aminoethoxy)-1,2,5-oxadiazol-3-yl)-4-(3-bromo-4-fluorophenyl)-1,2,4-oxadiazol-5(4H)-one (Int 1) (150 mg, 0.37 mmol) in DCM (5 mL) sulfamoyl chloride (63 mg, 0.55 mmol) and TEA (57 mg, 0.55 mmol) were added and the mixture was stirred at rt for 10 min. Water (10 mL) was added and the mixture was extracted with EtOAc (2×10 mL). The combined organic layers were dried over anhydrous Na$_2$SO$_4$, filtered and concentrated to dryness to give the title compound as a yellow solid.

Step 2: N-(3-bromo-4-fluorophenyl)-N'-hydroxy-4-(2-(sulfamoylamino)ethoxy)-1,2,5-oxadiazole-3-carboximidamide (6)

To a solution of N-(2-((4-(4-(3-bromo-4-fluorophenyl)-5-oxo-4,5-dihydro-1,2,4-oxadiazol-3-yl)-1,2,5-oxadiazol-3-yl)oxy)ethyl)sulfamide (6a) (130 mg, 0.27 mmol) in THF (8 mL) was added 2M aqueous NaOH (0.5 mL). The mixture was stirred at rt for 30 min. The mixture was extracted with EtOAc (3×20 mL). The combined organic layers were washed with brine (10 mL), dried over anhydrous Na$_2$SO$_4$ and concentrated to dryness. The residue was purified by reversed HPLC to give the title compound as a white solid.

¹H NMR (500 MHz, DMSO-d₆): δ ppm 11.46 (s, 0.9 H), 10.36 (s, 0.1 H), 9.14 (s, 0.1H), 9.01 (s, 0.9H), 8.10-8.08 (m, 0.1H), 7.31-7.12 (m, 2H), 6.83-6.65 (m, 3.9H), 4.46 (t, J=6.0 Hz, 0.2H), 4.30 (t, J=6.0 Hz, 1.8H), 3.31-3.29 (m, 0.2H), 3.22-3.18 (m, 1.8H). MS (ESI): m/z 341.0 [M+H]⁺.

Examples 6/1 to 6/6

The following Examples were prepared similar as described for Example 6 using the appropriate Intermediates.

| # | Int. # | Structure | Analytical data |
|---|---|---|---|
| 6/1 | Int 1/1 | 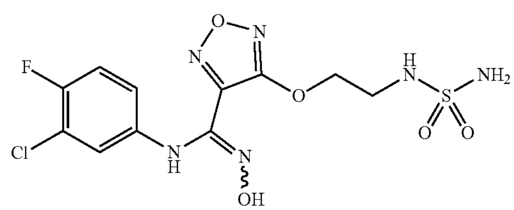 [SMILES: NS(=O)(=O)NCCOc1nonc1C(=NO)Nc1ccc(F)c(Cl)c1] | ¹H NMR (500 MHz, DMSO-d₆): δ ppm 11.45 (s, 0.9H), 10.35 (s, 0.1H), 9.15 (s, 0.1H), 9.00 (s, 0.9H), 7.95-7.93 (m, 0.1H), 7.34-7.32 (m, 0.2H), 7.20 (dd, J₁ = J₂ = 9.0 Hz, 0.9H), 7.01-7.00 (m, 0.9H), 6.80-6-78 (m, 0.9H), 6.70-6.63 (m, 3H), 4.47-4.45 (m, 0.2H), 4.32-4.40 (m, 1.8H), 3.29-3.27 (m, 0.2H), 3.22-3.19 (m, 1.8H). MS (ESI) m/z 395.1 [M + H]⁺. |
| 6/2 | Int 1/5 | 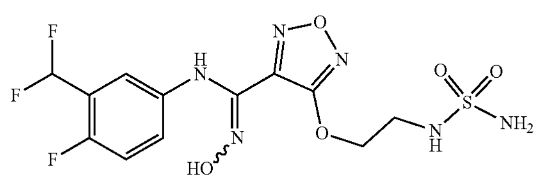 [SMILES: NS(=O)(=O)NCCOc1nonc1C(=NO)Nc1ccc(F)c(C(F)F)c1] | ¹H NMR (500 MHz, DMSO-d₆): δ ppm 11.40 (s, 0.9H), 10.30 (s, 0.1H), 9.15 (s, 0.1H), 9.04 (s, 0.9H), 7.30-6.63 (m, 7H), 4.47-4.45 (m, 0.2H), 4.29-4.26 (m, 2H), 3.30-3.29 (m, 0.2H), 3.20-3.16 (m, 2H). MS (ESI): m/z 411.1 [M + H]⁺. |
| 6/3 | Int 1/4 | 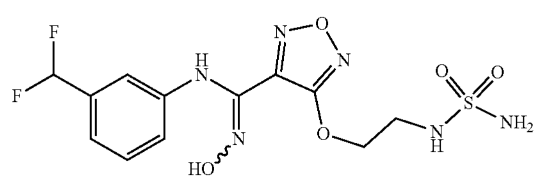 [SMILES: NS(=O)(=O)NCCOc1nonc1C(=NO)Nc1cccc(C(F)F)c1] | ¹H NMR (500 MHz, DMSO-d₆): δ ppm 11.43 (s, 0.9H), 10.33 (s, 0.1H), 9.15 (s, 0.1H), 9.09 (s, 0.9H), 7.89-6.63 (m, 8H), 4.47-4.45 (m, 0.2H), 4.26-4.24 (m, 1.8H), 3.30-3.29 (m, 0.2H), 3.16-3.13 (m, 1.8H). MS (ESI): m/z 393.1 [M+H]⁺. |
| 6/4 | Int 7 | 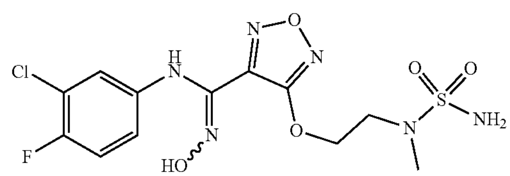 [SMILES: CN(CCOc1nonc1C(=NO)Nc1ccc(F)c(Cl)c1)S(N)(=O)=O] | ¹H NMR (500 MHz, DMSO-d₆): δ ppm 11.41 (br s, 0.9H), 10.40 (s, 0.1H), 9.14 (br s, 0.1H), 9.03 (br s, 0.9H), 7.94-7.91 (m, 0.1H), 7.35-7.30 (m, 0.2H), 7.21-7.16 (m, 0.2H), 7.01-6.98 (m, 0.9H), 6.79 (br s, 1H), 6.70-6.64 (m, 0.9H), 4.55-4.52 (m, 0.2H), 4.41-4.36 (m, 1.8H), 3.39-3.36 (m, 0.2H), 3.29-3.25 (m, 1.8H), 2.70 (s, 0.3H), 2.68 (s, 2.7H). MS (ESI): m/z 409.0 [M + H]⁺. |
| 6/5 | Int 7, Step 1 | 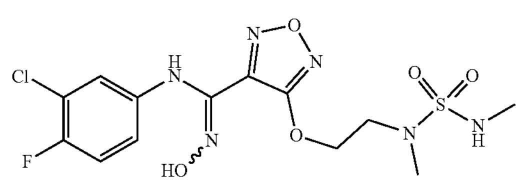 [SMILES: CNS(=O)(=O)N(C)CCOc1nonc1C(=NO)Nc1ccc(F)c(Cl)c1] | ¹H NMR (500 MHz, DMSO-d₆): δ ppm 11.37 (br s, 0.9H), 10.39 (s, 0.1H), 9.14 (s, 0.1H), 9.04 (br s, 0.9H), 7.94-7.91 (m, 0.1H), 7.36-7.31 (m, 0.2H), 7.22-7.15 (m, 0.9H), 7.02-6.97 (m, 0.9H), 6.68-6.63 (m, 0.9H), 4.54-4.50 (m, 0.2H), 4.39-4.35 (m, 1.8H), 3.51-3.46 (m, 0.2H), 3.40-3.36 (m, 1.8H), 2.75 (s, 0.3H), 2.73 (s, 2.7H), 2.45 (s, 2.7H), 2.40 (s, 0.3H). LCMS (ESI): m/z 423.0 [M + H]⁺. |
| 6/6 | Int 1/1, Step 1 | 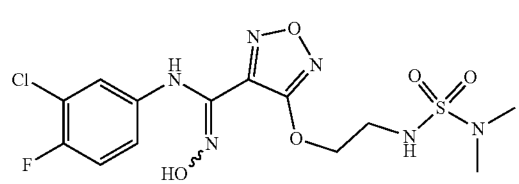 [SMILES: CN(C)S(=O)(=O)NCCOc1nonc1C(=NO)Nc1ccc(F)c(Cl)c1] | ¹H NMR (500 MHz, DMSO-d₆): δ ppm 11.42 (s, 0.9H), 10.36 (s, 0.1H), 9.15 (s, 0.1H), 9.04 (s, 0.9H), 7.95-7.93 (m, 0.1H), 7.46-7.92 (m, 1H), 7.36-7.31 (m, 0.2H), 7.22-7.17 (m, 0.9H), 6.69-6.64 (m, 0.9H), 4.43-4.39 (m, 0.2H), 4.26-4.22 (m, 1.8H), 3.35-3.30 (m, 0.2H), 3.21-3.15 (m, 1.8H), 2.66 (s, 5.4H), 2.62 (s, 0.6H). MS (ESI): m/z 423.1 [M + H]⁺. |

Example 7

N-(2-((4-(N-(3-chloro-4-fluorophenyl)-N'-hydroxycarbamimidoyl)-1,2,5-oxadiazol-3-yl)oxy)ethyl)cyclopropane-1,1-dicarboxamide (7)

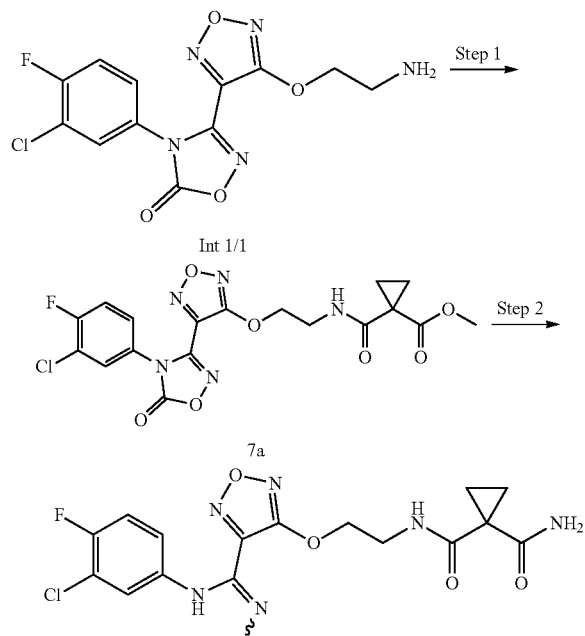

Example 7

Step 1: Methyl 1-((2-((4-(4-(3-chloro-4-fluorophenyl)-5-oxo-4,5-dihydro-1,2,4-oxadiazol-3-yl)-1,2,5-oxadiazol-3-yl)oxy)ethyl)carbamoyl)cyclopropane-1-carboxylate (7a)

To a solution of 1-(methoxycarbonyl) cyclopropanecarboxylic acid (112 mg, 0.78 mmol), HATU (296 mg, 0.78 mmol) and TEA (105 mg, 1.04 mmol) in DCM (20 mL) was added Int 1/1 (170 mg, 0.52 mmol) at rt. After stirring overnight the mixture was concentrated and redissolved in DCM (50 mL). The organic phase was washed with water (2×50 mL), dried over Na₂SO₄, and concentrated under vacuum. The residue was purified by column chromatography (EA: PE=1:2) to give the title compound as a yellow solid.

Step 2: N-(2-((4-(N-(3-chloro-4-fluorophenyl)-N'-hydroxycarbamimidoyl)-1,2,5-oxadiazol-3-yl)oxy)ethyl)cyclopropane-1,1-dicarboxamide (7)

To a solution of compound 7a (150 mg, 0.32 mmol) in MeOH (3 mL) was added NH₃/MeOH (7N, 1 mL) at rt and the mixture was stirred overnight. Then water was added, extracted with EtOAc (20 mL), washed with brine (20 mL), the organic layer was dried over Na₂SO₄, filtered and concentrated, purified by HPLC to give the title compound as a white solid. $^1$H NMR (500 MHz, CD3OD): δ ppm 7.11-7.06 (m, 1H), 7.04-7.01 (m, 1H), 6.80-6.76 (m, 1H), 4.32-4.30 (m, 2H), 3.56-3.54 (m, 2H),1.41 (s, 4H). MS (ESI): m/z 427.1 [M+H]⁺.

Example 7/1

N¹-(2-((4-(N-(3-chloro-4-fluorophenyl)-N'-hydroxycarbamimidoyl)-1,2,5-oxadiazol-3-yl)oxy)ethyl)malonamide (7/1)

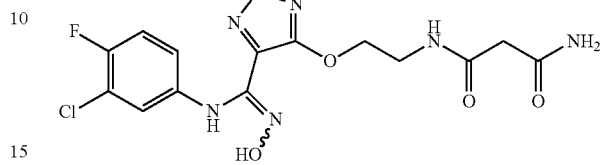

The title compound was prepared similar as described for Example 7 using 3-methoxy-3-oxopropanoic acid in place of 1-(methoxycarbonyl) cyclopropanecarboxylic acid. $^1$H-NMR (500 MHz, DMSO-d₆): δ ppm 11.45 (s, 0.9H), 10.39 (s, 0.1H), 9.13 (s, 0.1H), 9.01 (s, 0.9H), 8.26-8.22 (m, 1H), 7.94-7.92 (m, 0.1H), 7.44 (s, 1H), 7.45-7.43 (m, 0.2H), 7.23-7.18 (m, 0.9H), 7.05 (s, 1H), 7.03-7.00 (m, 0.9H), 6.69-6.65 (m, 0.9H), 4.42-4.37 (m, 0.2H), 2.26-4.21 (m, 1.8H), 3.50-3.47 (m, 0.2H), 3.40-3.35 (m, 1.8H), 3.00 (s, 2H). MS (ESI): m/z 401.0 [M+H]⁺.

Example 8

4-(Benzyloxy)-N-(3-bromo-4-fluorophenyl)-N'-hydroxy-1,2,5-oxadiazole-3-carboximidamide (8)

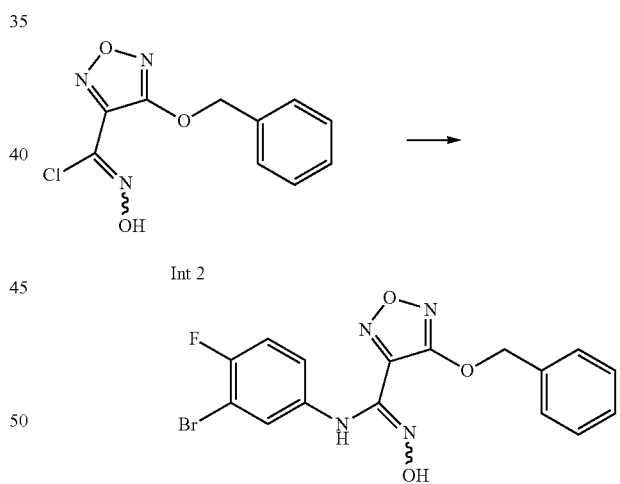

Example 8

To a solution of 4-(benzyloxy)-N-hydroxy-1,2,5-oxadiazole-3-carbimidoyl chloride (Int 2) (60 mg, 0.24 mmol) and 3-bromo-4-fluoroaniline (54 mg, 0.28 mmol) in H₂O (8 mL) was added NaHCO₃ (25 mg, 0.28 mmol). The mixture was stirred at 60° C. for 2 h. The mixture was diluted with EtOAc (10 mL). The organic layer was washed with water (10 mL) and brine (10 mL), dried over anhydrous Na₂SO₄, filtered and concentrated to dryness. The residue was purified by HPLC to give the title compound as a white solid. $^1$H NMR (500 MHz, DMSO-d₆): δ ppm 11.41 (s, 0.9H),10.40 (s, 0.1H), 9.16 (s, 0.1H), 9.04 (s, 0.9H), 8.06-8.04 (m, 0.1H), 7.49-7.08 (m, 7H) 6.64-6.61 (m, 0.9H), 5.45 (s, 0.3H), 5.26 (s, 1.7H). MS (ESI): m/z 406.8 [M+H]⁺.

Example 8/1

N-(3-Bromo-4-fluorophenyl)-N-hydroxy-4-methoxy-1,2,5-oxadiazole-3-carboximidamide (8/1)

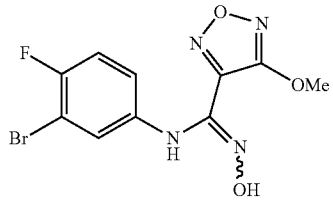

The title compound was prepared similar as described for Example 8 using N-hydroxy-4-methoxy-1,2,5-oxadiazole-3-carbimidoyl chloride (Int 3) in place of 4-(benzyloxy)-N-hydroxy-1,2,5-oxadiazole-3-carbimidoyl chloride (Int 2). $^1$H NMR (500 MHz, DMSO-d$_6$): δ ppm 11.48 (s, 0.9H), 10.36 (s, 0.1H), 9.13 (s, 0.1H) 8.99 (s, 0.9 H), 8.06-6.68 (m, 3H), 4.10 (s, 0.3H), 3.97 (s, 2.7H). MS (ESI): m/z 330.8 [M+H]⁺.

Example 8/2: N-(3-Bromo-4-fluorophenyl)-N-hydroxy-4-methoxy-1,2,5-oxadiazole-3-carboximidamide (8/2)

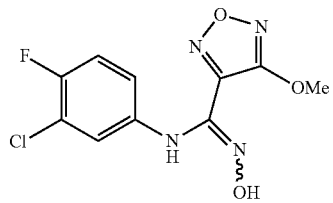 [SMILES: COc1nonc1C(=NO)Nc1ccc(F)c(Cl)c1]

The title compound was prepared similar as described for Example 8 using N-hydroxy-4-methoxy-1,2,5-oxadiazole-3-carbimidoyl chloride (Int 3) in place of 4-(benzyloxy)-N-hydroxy-1,2,5-oxadiazole-3-carbimidoyl chloride (Int 2) and 3-chloro-4-fluoroaniline in place of 3-bromo-4-fluoroaniline. $^1$H NMR (500 MHz, DMSO-d$_6$): δ ppm 11.49 (s, 0.9H), 10.36 (s, 0.1H), 9.14 (s, 0.1H), 8.99 (s, 0.9H), 7.93-7.91 (m, 0,1H), 7.34-7.31 (m, 0.2H), 7.20 (dd, J$_1$=J$_2$=9.0 Hz, 0.9H), 6.99-6.97 (m, 0.9H), 6.68-6.65 (m, 0.9H), 4.10 (s, 0.3H), 3.97 (s, 2.7H). MS (ESI): m/z 287.0 [M+H]⁺.

Example 8/3

N-(3-Bromo-4-fluorophenyl)-N'-hydroxy-4-(2,2,2-trifluoroethoxy)-1,2,5-oxadiazole-3-carboximidamide (8/3)

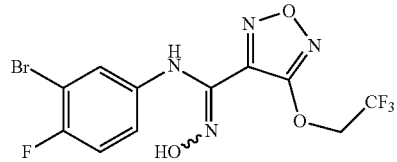 [SMILES: ON=C(Nc1ccc(F)c(Br)c1)c1nonc1OCC(F)(F)F]

The title compound was prepared similar as described for Example 8 using N-hydroxy-4-(2,2,2-trifluoroethoxy)-1,2,5-oxadiazole-3-carbimidoyl chloride (Int 2/1) in place of 4-(benzyloxy)-N-hydroxy-1,2,5-oxadiazole-3-carbimidoyl chloride (Int 2). $^1$H NMR (500 MHz, DMSO-d$_6$): δ ppm 11.55 (s, 0.9H), 10.48 (s, 0.1H), 9.18 (s, 0.1H), 9.18 (s, 0.1H), 9.05 (s, 0.9H), 7.33-6.67 (m, 3H), 5.23-5.02 (m, 2H). MS (ESI): m/z 398.9 [M+H]⁺.

Example 9

N-(2-((4-(N-(3-chloro-4-fluorophenyl)-N'-hydroxycarbamimidoyl)-1,2,5-oxadiazol-3-yl)oxy)ethyl)-1H-tetrazole-5-carboxamide (9)

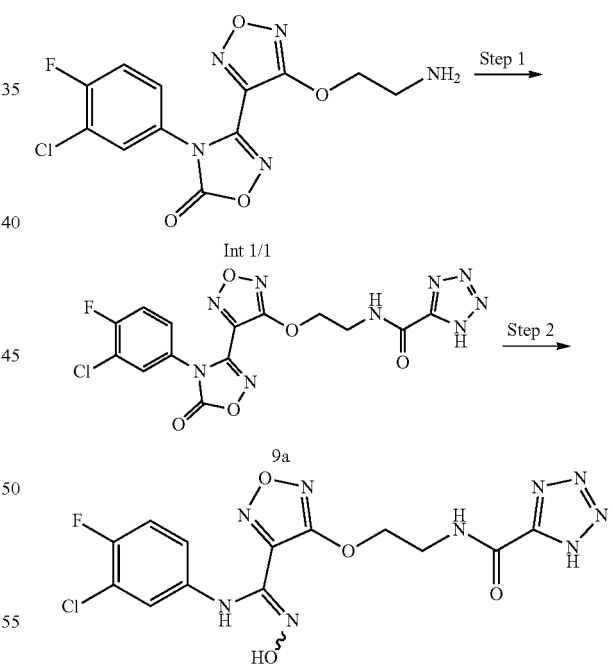

Example 9

Step 1: N-(2-((4-(4-(3-Chloro-4-fluorophenyl)-5-oxo-4,5-dihydro-1,2,4-oxadiazol-3-yl)-1,2,5-oxadiazol-3-yl)oxy)ethyl)-1H-tetrazole-5-carboxamide (9a)

To a solution of 1 H-tetrazole-5-carboxylic acid (89 mg, 0.78 mmol), HATU (297 mg, 0.78 mmol) and Et₃N (105 mg, 1.04 mmol) in DCM (20 mL) 3-(4-(2-aminoethoxy)-1,2,5-oxadiazol-3-yl)-4-(3-chloro-4-fluorophenyl)-1,2,4-oxadiazol-5(4H)-one (Int 1/1) (170 mg, 0.52 mmol) was added and the mixture was stirred at rt overnight. The mixture was concentrated to dryness and the residue was dissolved in DCM (50 mL). The organic layer was washed with water (2×50 mL), dried over anhydrous $Na_2SO_4$, filtered and concentrated to dryness. The residue was purified by column chromatography (EA:PE=1:2) to give the title compound as a yellow solid.

Step 2: N-(2-((4-(N-(3-chloro-4-fluorophenyl)-N'-hydroxycarbamimidoyl)-1,2,5-oxadiazol-3-yl)oxy)ethyl)-1H-tetrazole-5-carboxamide (9)

To a solution of N-(2-((4-(4-(3-chloro-4-fluorophenyl)-5-oxo-4,5-dihydro-1,2,4-oxadiazol-3-yl)-1,2,5-oxadiazol-3-yl)oxy)ethyl)-1H-tetrazole-5-carboxamide (9a) (150 mg, 0.34 mmol) in MeOH (3 mL) aqueous NaOH (1N, 0.5 mL) was added and the mixture was stirred at rt overnight. Water was added and the mixture was extracted with EtOAc (20 mL). The organic layer was washed with brine (20 mL), dried over anhydrous $Na_2SO_4$, filtered and concentrated to dryness. The residue was purified by HPLC to give the title compound as a white solid. $^1$H NMR (500 MHz, DMSO-$d_6$): δ ppm 11.44 (s, 0.9 H), 10.30 (s, 0.1H), 9.41-9.39 (m, 0.9H), 9.15 (s, 0.1H), 9.02 (s, 0.9H), 7.93-7.91 (m, 0.1H), 7.30-7.26 (m, 0.2H), 7.14-7.09 (m, 0.9H), 6.98-6.96 (m, 0.9H), 6.66-6.62 (m, 0.9H), 4.59-4.55 (m, 0.2H) 4.41-4.38 (m, 1.8H), 3.76-3.72 (m, 0.2H), 3.65-3.61 (m, 1.8H). MS (ESI): m/z 412 [M+H]$^+$.

Examples 9/1 to 9/22

The following Examples were prepared similar as described for Example 9 using the appropriate Intermediates and carboxylic acid building blocks.

| # | Int. # | Structure | Analytical data |
|---|---|---|---|
| 9/1 | Int 1/1 | 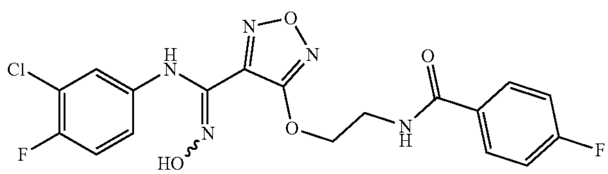 [SMILES: O=C(NCCOc1nonc1C(=NO)Nc1ccc(F)c(Cl)c1)c1ccc(F)cc1] | $^1$H NMR (500 MHz, DMSO-$d_6$): δ ppm 11.40 (s, 0.9H), 10.34 (s, 0.1H), 9.09 (s, 0.1H), 8.99 (s, 0.9H), 7.91-6.61 (m, 7H), 4.54-4.50 (m, 0.2H), 4.39-4.36 (m, 1.8H), 3.69-3.65 (m, 0.2H), 3.60-3.56 (m, 1.8H). MS (ESI): m/z 436.13 [M − H]$^−$. |
| 9/2 | Int 1/1 | 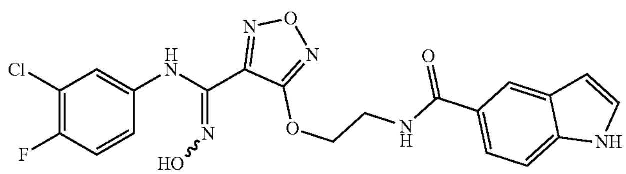 [SMILES: O=C(NCCOc1nonc1C(=NO)Nc1ccc(F)c(Cl)c1)c1ccc2[nH]ccc2c1] | $^1$H NMR (500 MHz, DMSO-$d_6$): δ ppm 11.41, 11.32 (s, 0.9H), 10.77 (s, 0.1H), 10.34 (s, 0.1H), 9.25-6.49 (m, 10H), 4.57-4.54 (m, 0.2H), 4.42-4.39 (m, 1.8H), 3.73-3.70 (m, 0.2H), 3.64-3.61 (m, 1.8H). MS (ESI): m/z 457.1 [M − H]$^−$. |
| 9/3 | Int 1/1 | 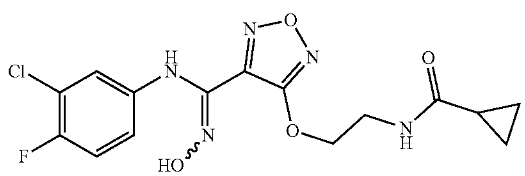 [SMILES: O=C(NCCOc1nonc1C(=NO)Nc1ccc(F)c(Cl)c1)C1CC1] | $^1$H NMR (500 MHz, DMSO-$d_6$): δ ppm 11.44 (s, 0.9 H), 10.34 (s, 0.1H), 9.13 (s, 0.1H), 8.99 (s, 0.9H), 8.27-8.25 (m, 0.9H), 7.95-7.93 (m, 0.1H), 7.32-6.68 (m, 3H), 4.40-4.37 (m, 0.2H), 4.25-4.22 (m, 1.8H), 3.49-3.45 (m, 0.2H), 3.40-3.35 (m, 1.8H), 1.54-1.50 (m, 1H), 0.68-0.63 (m, 4H). MS (ESI): m/z 382.1 [M − H]$^−$. |
| 9/4 | Int 1/1 | 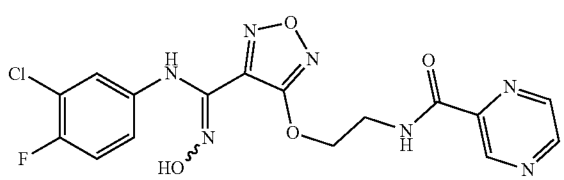 [SMILES: O=C(NCCOc1nonc1C(=NO)Nc1ccc(F)c(Cl)c1)c1cnccn1] | $^1$H NMR (500 MHz, CD$_3$OD-$d_4$): δ ppm 9.27-9.26 (m, 1H), 8.82-8.81 (m, 1H), 8.72-8.71 (m, 1H), 7.00-6.97 (m, 2H) 6.76-6.73 (m, 1H), 4.43 (t, J = 5.5 Hz, 2H), 3.78 (t, J = 5.5 Hz, 2H). MS (ESI): m/z 422.1 [M + H]$^+$. |
| 9/5 | Int 1/1 | 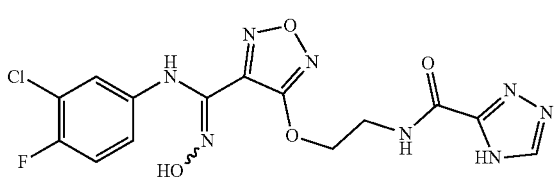 [SMILES: O=C(NCCOc1nonc1C(=NO)Nc1ccc(F)c(Cl)c1)c1nnc[nH]1] | $^1$H NMR (500 MHz, DMSO-$d_6$): δ ppm 14.65 (s, 1H), 11.43 (s, 1H), 9.15 (s, 0.1H), 8.99 (s, 0.9H), 8.90-8.30 (m, 2H), 7.90-6.65 (m, 3H), 4.52-4.50, 4.39-4.37 (m, 0.9H) 3.70-3.57 (m, 2H). MS (ESI): m/z 411.1 [M + H]$^+$. |
| 9/6 | Int 1/1 | 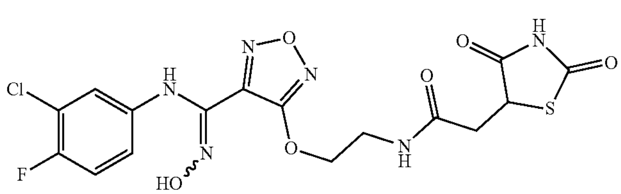 [SMILES: O=C(CC1SC(=O)NC1=O)NCCOc1nonc1C(=NO)Nc1ccc(F)c(Cl)c1] | $^1$H NMR (500 MHz, DMSO-$d_6$): δ ppm 11.96 (s, 0.9H), 11.44 (s, 0.9H), 10.40 (s, 0.1H), 9.15 (s, 0.1H), 9.02 (s, 0.9H), 8.36-8.34 (m, 0.9H), 7.95-7.94 (m, 0.1H), 7.32-7.00 (m, 3H), 4.62-4.21 (m, 3H), 3.48-3.35 (m, 2H), 3.00-2.83 (m, 2H). MS (ESI): m/z 473.0 [M + H]$^+$. |

-continued

| # | Int. # | Structure | Analytical data |
|---|---|---|---|
| 9/7 | Int 1/6 | 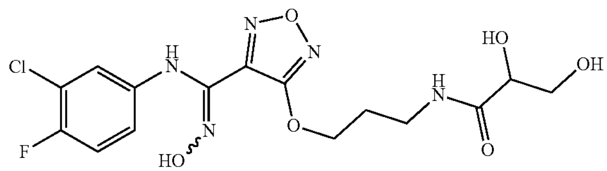 [SMILES: O=C(NCCCOc1nonc1C(=NO)Nc1ccc(F)c(Cl)c1)C(O)CO] | ¹H NMR (500 MHz, CD₃OD): δ ppm 7.11-7.07 (m, 1H), 7.03-7.01 (m, 1H), 6.77-6.74 (m, 1H), 4.24 (t, J = 7.5 Hz, 2H), 4.08-4.06 (m, 1H), 3.79-3.69 (m, 2H), 3.22-3.28 (m, 2H), 1.92-1.86 (m, 2H). MS (ESI): m/z 418.0 [M + H]⁺. |
| 9/8 | Int 1/6 | 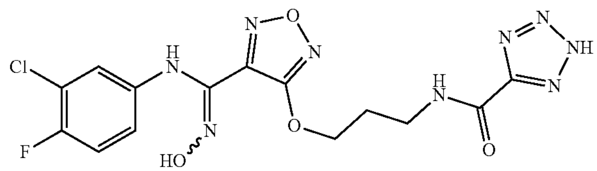 [SMILES: O=C(NCCCOc1nonc1C(=NO)Nc1ccc(F)c(Cl)c1)c1nn[nH]n1] | ¹H NMR (500 MHz, DMSO-d₆): δ ppm 11.43 (s, 0.9H), 10.37 (s, 0.1H), 9.40-9.36 (m, 1H), 9.14 (s, 0.1H), 9.05 (s, 0.9H), 7.96-7.94 (m, 0.1H), 7.34-7.31 (m, 0.2H), 7.22-7.18 (m, 0.9H), 7.02-7.00 (m, 0.9H), 6.68-6.65 (m, 0.9H), 4.46-4.42 (m, 0.2H), 4.28-4.24 (m, 1.8H), 3.45-3.41 (m, 0.2H), 2.08-2.04 (m, 0.2H), 1.94-1.86 (m, 1.8H). MS (ESI): m/z 426.1 [M + H]⁺. |
| 9/9 | Int 1/1, CO₂H / CO₂Me step 1 | 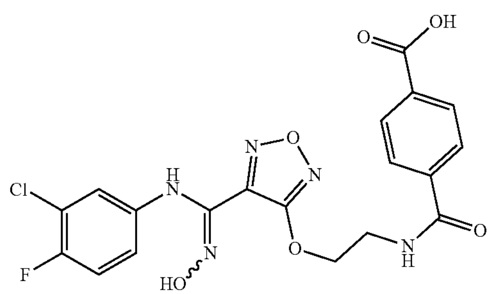 [SMILES: O=C(O)c1ccc(C(=O)NCCOc2nonc2C(=NO)Nc2ccc(F)c(Cl)c2)cc1] | ¹H-NMR (500 MHz, DMSO-d₆): δ: 13.2 (br s, 1H), 11.43 (s, 0.9H), 10.35 (s, 0.1H), 9.11 (s, 0.1H), 9.01 (s, 0.9H), 8.86-8.80 (m, 1H), 8.04-7.86 (m, 4H), 7.31-6.65 (m, 3H), 4.56-4.50 (m, 0.2H), 4.41-4.37 (m, 1.8H), 3.72-3.70 (m, 0.2H), 3.63-3.59 (m, 1.8H). MS (ESI): m/z 464.0 [M + H]⁺. |
| 9/10 | Int 1/1 | 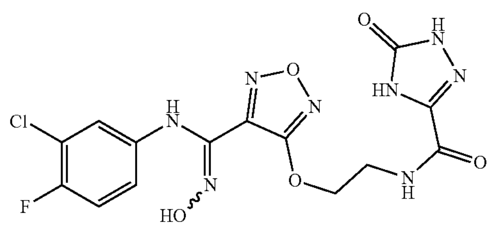 [SMILES: O=C(NCCOc1nonc1C(=NO)Nc1ccc(F)c(Cl)c1)c1n[nH]c(=O)[nH]1] | ¹H NMR (500 MHz, DMSO-d₆): δ ppm 12.10-11.80 (m, 2H), 11.42 (s, 0.9H), 10.34 (s, 0.1H), 9.10 (s, 0.1H), 9.00 (s, 0.9H), 8.74-8.71 (m, 1H), 8.7.95-7.90 (m, 0.1H), 7.32-7.24 (m, 0.2H), 7.20-7.10 (m, 0.9H), 6.99-6.96 (m, 0.9H), 6.67-6.63 (m, 0.9H), 4.50-4.48 (m, 0.2H), 4.38-4.30 (m, 1.8H), 3.54-3.50 (m, 2H). MS (ESI): m/z 427.1 [M + H]⁺. |
| 9/11 | Int 1/1, step 1 | 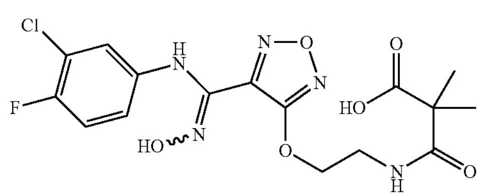 [SMILES: CC(C)(C(=O)O)C(=O)NCCOc1nonc1C(=NO)Nc1ccc(F)c(Cl)c1] | 1H NMR (500 MHz, CD₃OD): δ ppm 7.11-7.08 (m, 1H), 7.04-7.01 (m, 1H), 6.79-6.74 (m, 1H), 4.31-4.28 (m, 2H), 3.54-3.52 (m, 2H), 1.41 (s, 6H). MS (ESI): m/z 430.1 [M + H]⁺. |
| 9/12 | Int 1/1 | 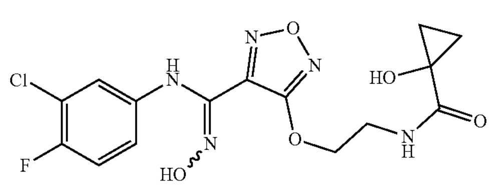 [SMILES: O=C(NCCOc1nonc1C(=NO)Nc1ccc(F)c(Cl)c1)C1(O)CC1] | 1H NMR (500 MHz, DMSO-d6): δ ppm 11.43 (s, 1H), 9.11 (s, 1H), 8.12-8.09 (m, 1H) 7.33-6.69 (m, 3H), 6.23 (s, 1H), 4.41-4.26 (m, 2H), 3.54-3.42 (m, 2H), 1.04-0.80 (m, 4H). MS (ESI): m/z 400.1 [M + H]⁺. |

| # | Int. # | Structure | Analytical data |
|---|---|---|---|
| 9/13 | Int 1/1, step 1 | (structure shown) | $^1$H-NMR (500 MHz, CD$_3$OD): δ ppm 8.51 (s, 1H), 8.22-8.19 (m, 1H), 8.07-8.04 (m, 1H), 7.62-7.57 (m, 1H), 6.98-6.94 (m, 2H), 6.77-6.72 (m, 1H), 4.46-4.41 (m, 2H), 3.77-3.73 (m, 2H). MS (ESI): m/z 464.1 [M + H]$^+$. |
| 9/14 | Int 1/1 | (structure shown) | $^1$H-NMR (500 MHz, DMSO-d$_6$): δ ppm 11.44 (s, 0.9H),10.40 (s, 0.1H), 9.15 (s, 0.1H), 9.02 (s, 0.9H), 8.44-8.40 (m, 1H), 7.32-6.65 (m, 5H), 4.42-4.40 (m, 0.2H), 4.27-4.23 (m, 1.8H), 3.89 (s, 2H), 3.43-3.39 (m, 2H). MS (ESI): m/z 437.1 [M + H]$^+$. |
| 9/15 | Int 1/1 | (structure shown) | $^1$H-NMR (500 MHz, DMSO-d$_6$): δ ppm 11.44 (s, 0.9H), 10.34 (s, 0.1H), 9.15 (s, 0.1H), 9.02 (s, 0.9H), 8.64-8.62 (m, 1H), 7.95-7.93 (m, 0.1H), 7.30-7.28 (m, 0.2H), 7.22-7.16 (m, 0.9), 7.02-6.99 (m, 0.9H), 6.69-6.65 (m, 0.9H), 4.34-4.32 (m, 0.2H), 4.25-4.23 (m, 1.8H), 4.07-4.06 (m, 2H), 3.44-3.40 (m, 2H), 3.09 (s, 3H). MS (ESI): m/z 436.0 [M + H]$^+$. |
| 9/16 | Int 1/1 | (structure shown) | $^1$H NMR (500 MHz, DMSO-d$_6$): δ ppm 11.44-11.39 (m, 0.9H), 10.31 (s, 0.1H), 9.11 (s, 0.1H), 8.98 (s, 0.9H), 8.03-7.89 (m, 2H), 7.61 (s, 0.1H), 7.35-7.30 (m, 0.2H), 7.24-7.16 (m, 0.9H), 7.06-7.01 (m, 0.9H), 6.71-6.67 (m, 0.9H), 4.75-4.68 (m, 2H), 4.44-4.37 (m, 2.2H), 4.22-4.17 (m, 1.8H), 3.60-3.38 (m, 2H), 1.39-1.24 (m, 9H). MS (ESI): m/z 515.2 [M + H]$^+$. |
| 9/17 | Int 1/1 | (structure shown) | $^1$H NMR (500 MHz, DMSO-d$_6$): δ ppm 11.44 (s, 0.9H), 10.34 (.01H), 9.18 (s, 0.1H), 9.01 (s, 0.9H), 8.92-8.86 (m, 1H), 8.73 (s, 1H), 7.95-7.91 (m, 0.1H), 7.45-7.40 (m, 0.2H), 7.20-7.15 (m, 0.9H), 7.00-6.97 (m, 0.9H), 6.68-6.64 (m, 0.9H), 4.52-4.48 (m, 0.2H), 4.35-4.30 (m, 1.8H), 3.59-3.55 (m, 0.2H), 3.49-3.44 (m, 1.8H), 2.67-2.63 (m, 3H). MS (ESI): m/z 401.1 [M + H]$^+$. |
| 9/18 | Int 1/1 | (structure shown) | $^1$H NMR (500 MHz, DMSO-d$_6$): δ ppm 11.47-11.39 (m, 0.9H), 10.34 (s, 0.1H), 9.13 (s, 0.1H), 9.00 (s, 0.9H), 8.26-8.20 (m, 0.2H), 8.12-8.06 (m, 0.8H), 7.95-7.91 (m, 0.1H), 7.79-7.75 (m, 0.8H), 7.39-7.36 (m, 0.2H), 7.35-7.32 (m, 0.2H), 7.22-7.16 (m, 0.9H), 7.02-6.98 (m, 0.9H), 6.69-6.65 (m, 0.9H), 4.37-4.32 (m, 0.2H), 4.22-4.15 (m, 1.8H), 3.70-3.40 (m, 2H), 2.48-2.40 (m, 1H), 1.80-1.75 (m, 1H), 1.40-1.30 (m, 9H). MS (ESI): m/z 535.0 [M + H]$^+$. |

| # | Int. # | Structure | Analytical data |
|---|---|---|---|
| 9/19 | Int 1/1 | 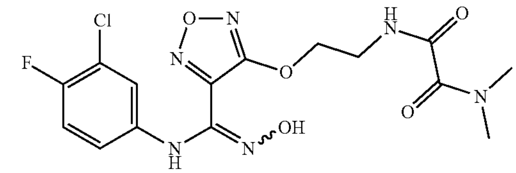 [SMILES: CN(C)C(=O)C(=O)NCCOc1nonc1C(=NO)Nc1ccc(F)c(Cl)c1] | $^1$H NMR (500 MHz, DMSO-d$_6$): δ ppm 11.44 (s, 0.9H), 10.34 (s, 0.1H), 9.14 (s, 0.1H), 9.00 (m. 0.9H), 8.87-8.83 (m, 1H), 7.95-7.91 (m, 0.1H), 7.45-7.40 (m, 0.2H), 7.22-7.17 (m, 0.9H), 7.05-7.00 (m, 0.9H), 6.711-6.67 (m, 0.9H), 4.50-4.47 (m, 0.2H), 4.34-4.29 (m, 1.8H), 3.61-3.57 (m, 0.2H), 3.50-3.46 (m, 1.8H), 2.97 (s, 2.7H), 2.89 (s, 0.3H), 2.85 (s, 2.7H), 2.82 (s, 0.3H). MS (ESI): m/z 415.1 [M + H]$^+$. |
| 9/20 | Int 1/3 | 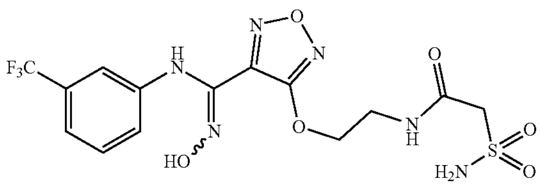 [SMILES: NS(=O)(=O)CC(=O)NCCOc1nonc1C(=NO)Nc1cccc(C(F)(F)F)c1] | $^1$H NMR (500 MHz, DMSO-d$_6$): δ ppm 11.57 (s, 0.9H), 10.43 (s, 0.1H), 9.30 (s, 0.1H), 9.21 (s, 0.9H), 8.42-8.37 (m, 1H), 8.12-8.09 (m, 0.1H), 7.62-7.50 (m, 0.2H), 7.41-7.35 (m, 0.9H), 7.26-7.22 (m, 1H), 7.10 (s, 0.9H), 6.96-6.92 (m, 2.9H), 4,42-4.39 (m, 0.2H), 4.24-4.19 (m, 1.8H), 3.88 (s, 2H), 3.55-3.51 (m, 0.2H), 3.40-3.34 (m, 1.8H). MS (ESI): m/z 453.1 [M + H]$^+$. |
| 9/21 | Int 1/2 | 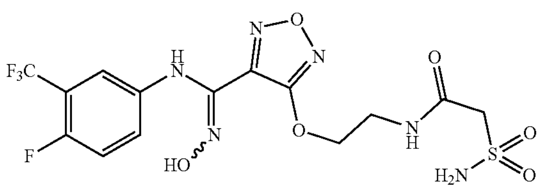 [SMILES: NS(=O)(=O)CC(=O)NCCOc1nonc1C(=NO)Nc1ccc(F)c(C(F)(F)F)c1] | $^1$H NMR (500 MHz, DMSO-d$_6$): δ ppm 11.56 (s, 0.9H), 10.41 (s, 0.1H), 9.30 (s, 0.1H), 9.16 (s, 0.9H), 8.18-8.14 (m, 0.1H), 7.68-7.64 (m, 0.1H), 7.45-7.41 (m, 0.1H), 7.34-7.27 (m, 0.9H), 7.18-7.13 (m, 0.9H), 7.02-6.97 (m, 0.9H), 6.94 (s br, 2H), 4.42-4.39 (m, 0.2H), 4.28-4.22 (m, 1.8H), 3.88 (s, 2H), 3.57-3.72 (m, 0.2H), 3.44-3.38 (m, 1.8H). MS (ESI): m/z 471.0 [M + H]$^+$. |
| 9/22 | Int 7 | 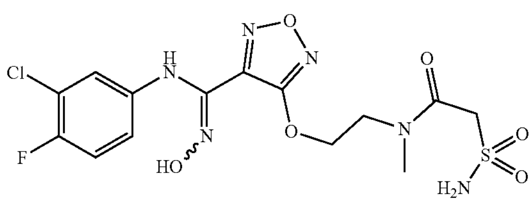 [SMILES: CN(CCOc1nonc1C(=NO)Nc1ccc(F)c(Cl)c1)C(=O)CS(N)(=O)=O] | $^1$H NMR (500 MHz, DMSO-d$_6$): δ ppm 11.46-10.39 (m, 0.9H), 10.41-10.38 (m, 0.1H), 9.25-9.20 (m, 0.1H), 9.04-9.02 (m, 0.9H), 7.95-7.90 (m, 0.2H), 7.38-7.33 (m, 0.1H), 7.23-7.16 (m, 0.9H), 7.03-6.94 (m, 2.9H), 6.68-6.63 (m, 0.9H), 4.60-4.30 (m, 2H), 4.25 (s, 0.8H), 4.18 s, 1.2H), 3.85-3.65 (m, 2H), 3.09 (s, 1.8H), 2.88 (s, 1.2H). MS (ESI): m/z 451.0 [M + H]$^+$. |

Example 10 N-(3-Chloro-4-fluorophenyl)-N'-hydroxy-4-(2-morpholinoethoxy)-1,2,5-oxadiazole-3-carboximidamide (10)

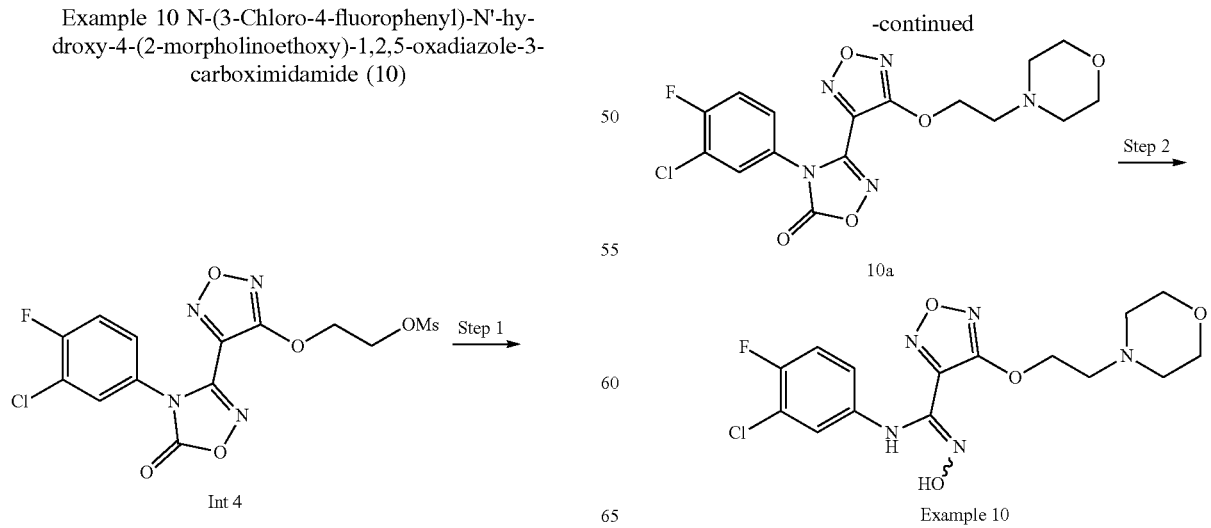

Step 1: 4-(3-Chloro-4-fluorophenyl)-3-(4-(2-morpholinoethoxy)-1,2,5-oxadiazol-3-yl)-1,2,4-oxadiazol-5(4H)-one (10a)

To a solution 2-((4-(4-(3-chloro-4-fluorophenyl)-5-oxo-4,5-dihydro-1,2,4-oxadiazol-3-yl)-1,2,5-oxadiazol-3-yl)oxy) ethyl methanesulfonate (Int 4) (169 mg, 0.41 mmol) in DMF (5 mL) $K_2O0_3$ (141 mg, 1.03 mmol) and morpholine (54 mg, 0.62 mmol) were added and the mixture was stirred at rt overnight. Water (20 mL) was added and the mixture was extracted with EtOAc (3×20 mL). The combined organic layers were washed with brine, dried over anhydrous $Na_2SO_4$, filtered and concentrated to dryness to give the title compound as a brown solid.

Step 2: N-(3-Chloro-4-fluorophenyl)-N'-hydroxy-4-(2-morpholinoethoxy)-1,2,5-oxadiazole-3-carboximidamide (10)

To a solution of 4-(3-chloro-4-fluorophenyl)-3-(4-(2-morpholinoethoxy)-1,2,5-oxadiazol-3-yl)-1,2,4-oxadiazol-5(4H)-one (10a) (118 mg, 0.29 mmol) in MeOH (5 mL) 2M aqueous NaOH (1 mL) was added and the mixture was stirred at rt for 30 min. The mixture was extracted with EtOAc (3×20 mL). The combined organic layers were washed with brine (1×10 mL), dried over anhydrous $Na_2SO_4$, filtered and concentrated to dryness. The residue was purified by reversed HPLC to give the title compound as a white solid. $^1$H NMR (500 MHz, $CD_3OD$): δ ppm 7.10 (dd, $J_1=J_2=8.5$ Hz, 1H), 7.02-7.00 (m, 1H), 6.79-6.76 (m, 1H), 4.76-4.74 (m, 2H), 4.10-3.80 (m, 4H), 3.69-3.67 (m, 2H), 3.60-3.40 (m, 4H). MS (ESI): m/z 386.1 [M+H]$^+$.

Example 10/1

N-(3-Chloro-4-fluorophenyl)-N'-hydroxy-4-(2-(4-methylpiperazin-1-yl)ethoxy)-1,2,5-oxadiazole-3-carboximidamide (10)

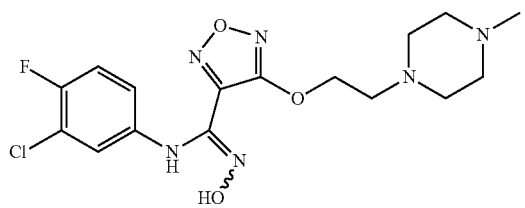

Example 10/1

The title compound was prepared similar as described for example 10 using in step 1 1-methylpiperazine in place of morpholine. $^1$H NMR (500 MHz, $CD_3OD$): δ ppm 7.10 (dd, $J_1=J_2=9.0$ Hz, 1H), 7.01-6.99 (m, 1H), 6.76-6.73 (m, 1H), 4.43-4.41 (m, 2H), 3.40-3.30 (m, 4H), 2.96-2.90 (m, 9H). MS (ESI): m/z 399.1 [M+H]$^+$.

Example 11

4-((4-(N-(3-Chloro-4-fluorophenyl)-N'-hydroxycarbamimidoyl)-1,2,5-oxadiazol-3-yl)oxy)butanamide (11)

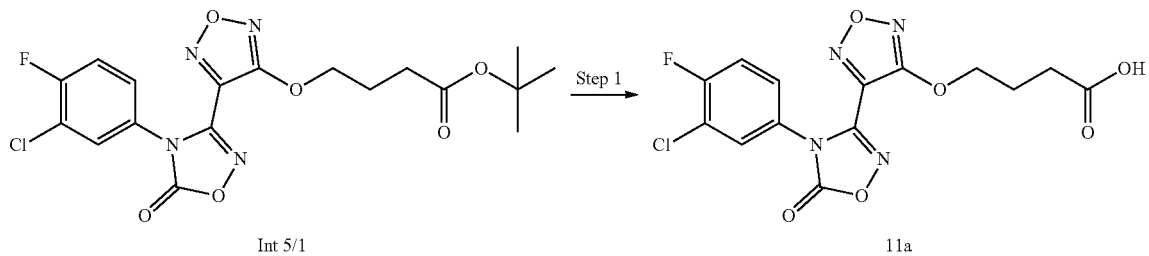

Int 5/1    Step 1    11a

Step 2

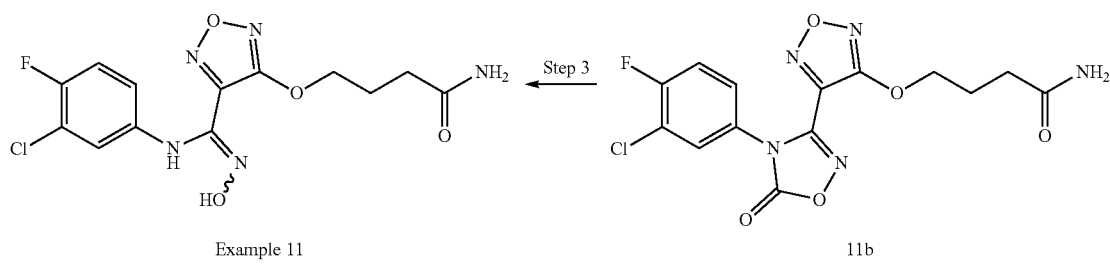

Example 11    Step 3    11b

Step 1: 4-((4-(4-(3-Chloro-4-fluorophenyl)-5-oxo-4,5-dihydro-1,2,4-oxadiazol-3-yl)-1,2,5-oxadiazol-3-yl)oxy)butanoic acid (11a)

To a solution of tert-butyl 4-((4-(4-(3-chloro-4-fluorophenyl)-5-oxo-4,5-dihydro-1,2,4-oxadiazol-3-yl)-1,2,5-oxadiazol-3-yl)oxy)butanoate (Int 5/1) (685 mg, 1.55 mmol) in 1,4-dioxane (5 mL) a 4M hydrogen chloride solution in dioxane (6 mL, 24 mmol) and 10 drops of water were added and the mixture was stirred at rt for 12 h. The mixture was concentrated to dryness. The residue was suspended in acetonitrile and the mixture was concentrated to dryness. The residue was dissolved in DCM. The organic layer was dried over anhydrous $Na_2SO_4$, filtered and concentrated to dryness to give the title compound as a white solid.

Step 2: 4-((4-(4-(3-Chloro-4-fluorophenyl)-5-oxo-4,5-dihydro-1,2,4-oxadiazol-3-yl)-1,2,5-oxadiazol-3-yl)oxy)butanamide (11b)

To a solution of 4-((4-(4-(3-chloro-4-fluorophenyl)-5-oxo-4,5-dihydro-1,2,4-oxadiazol-3-yl)-1,2,5-oxadiazol-3-yl)oxy)butanoic acid (11a) (590 mg, 1.54 mmol), HATU (878 mg, 2.31 mmol) and $Et_3N$ (233 mg, 2.31 mmol) in DCM (20 mL) $NH_4Cl$ (98 mg, 1.85 mmol) was added and the mixture was stirred at rt overnight. The mixture was concentrated to dryness and the residue was dissolved in DCM (50 mL). The organic layer was washed with water (2×50 mL). The combined organic layers were dried over anhydrous $Na_2SO_4$, filtered and concentrated to dryness. The residue was purified by column chromatography (PE: EA=1:1) to give the title compound as a white solid.

Step 3: 4-((4-(N-(3-Chloro-4-fluorophenyl)-N'-hydroxycarbamimidoyl)-1,2,5-oxadiazol-3-yl)oxy)butanamide (11)

To a solution of 4-((4-(4-(3-chloro-4-fluorophenyl)-5-oxo-4,5-dihydro-1,2,4-oxadiazol-3-yl)-1,2,5-oxadiazol-3-yl)oxy)butanamide (11b) (150 mg, 0.39 mmol) in THF (8 mL) 2M aqueous NaOH (0.5 mL) was added and the mixture was stirred at rt for 30 min. The mixture was extracted with EtOAc (3×20 mL) and the combined organic layers were washed with brine (10 mL), dried over anhydrous $Na_2SO_4$, filtered and concentrated to dryness. The residue was purified by reversed HPLC to give the title compound as a white solid. $^1$H NMR (500 MHz, $d_6$-DMSO): δ ppm 11.44 (s, 0.9H), 10.40 (br s, 0.1H), 9.17 (s, 0.1H), 9.04 (s, 0.9H), 7.94-6.64 (m, 5H), 4.20-4.37 (m, 2H), 4.22-4.19 (m, 1.8H), 2.21-2.08 (m, 2H), 1.98-1.79 (m, 2H). MS (ESI): m/z 358.1 [M+H]$^+$.

Example 12

N-(3-Chloro-4-fluorophenyl)-N'-hydroxy-4-(3-(5-methyl-4H-1,2,4-triazol-3-yl)propoxy)-1,2,5-oxadiazole-3-carboximidamide (12)

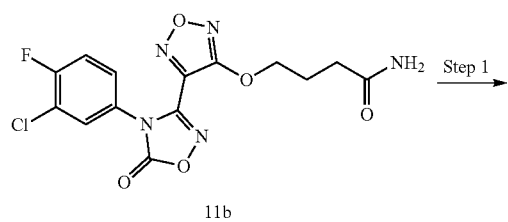

11b

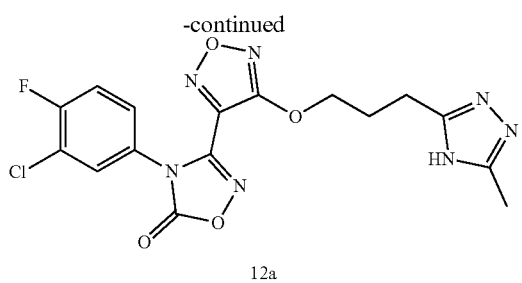

12a

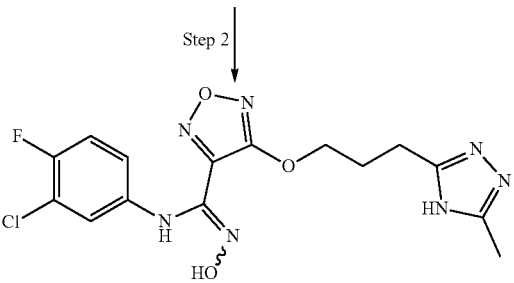

Example 12

Step 1: 4-(3-Chloro-4-fluorophenyl)-3-(4-(3-(5-methyl-4H-1,2,4-triazol-3-yl)propoxy)-1,2,5-oxadiazol-3-yl)-1,2,4-oxadiazol-5(4H)-one (12a)

To a solution of compound 4-((4-(4-(3-chloro-4-fluorophenyl)-5-oxo-4,5-dihydro-1,2,4-oxadiazol-3-yl)-1,2,5-oxadiazol-3-yl)oxy)butanamide (11 b) (200 mg, 0.52 mmol) in 1,4-dioxane (10 mL) N,N-dimethylacetamide dimethyl acetal (0.84 mL, 5.74 mmol) was added. The mixture was heated to reflux for 5 h, cooled to rt and concentrated to dryness. The residue was dissolved in acetic acid (10 mL) and hydrazine monohydrate (0.82 mL, 1.66 mmol) was added. The mixture was heated for 3 h at 90° C., cooled to rt and concentrated to dryness. Saturated aqueous sodium bicarbonate (10 mL) was added and the mixture was extracted with chloroform. The combined organic layers were washed with water and brine, dried over anhydrous $Na_2SO_4$, filtered and concentrated to dryness. The residue was triturated with ethyl acetate to afford the title compound as a white solid.

Step 2: N-(3-Chloro-4-fluorophenyl)-N'-hydroxy-4-(3-(5-methyl-4H-1,2,4-triazol-3-yl)propoxy)-1,2,5-oxadiazole-3-carboximidamide (12)

To a solution of 4-(3-chloro-4-fluorophenyl)-3-(4-(3-(5-methyl-4H-1,2,4-triazol-3-yl)propoxy)-1,2,5-oxadiazol-3-yl)-1,2,4-oxadiazol-5(4H)-one (12a) (140 mg, 0.33 mmol) in THF (8 mL) 2M aqueous NaOH (0.5 mL) was added and the mixture was stirred at rt for 30 min. The mixture was extracted with EtOAc (3×20 mL). The combined organic layers were washed with brine (10 mL), dried over anhydrous $Na_2SO_4$ and concentrated to dryness. The residue was purified by reversed HPLC to give the title compound as a white solid. $^1$H NMR (500 MHz, $d_6$-DMSO): δ ppm 11.44 (s, 0.9H), 10.40 (s, 0.1H), 9.17 (s, 0.1H), 9.06 (s, 0.9H), 7.94-7.93 (m, 0.1H), 7.34-7.32 (m, 0.2H), 7.21-7.17 (m, 0.9H), 7.00-6.98 (m, 0.9H), 6.66-6.63 (m, 0.9H), 4.48-4.46 (m, 0.2H), 4.29-4.26 (m, 1.8H), 2.82-2.68 (m, 2H), 2.38 (s, 3H), 2.18-1.98 (m, 2H). MS (ESI): m/z 396.1 [M+H]$^+$.

Example 13

3-((4-(N-(3-Chloro-4-fluorophenyl)-N'-hydroxycarbamimidoyl)-1,2,5-oxadiazol-3-yl)oxy)propanoic acid (13)

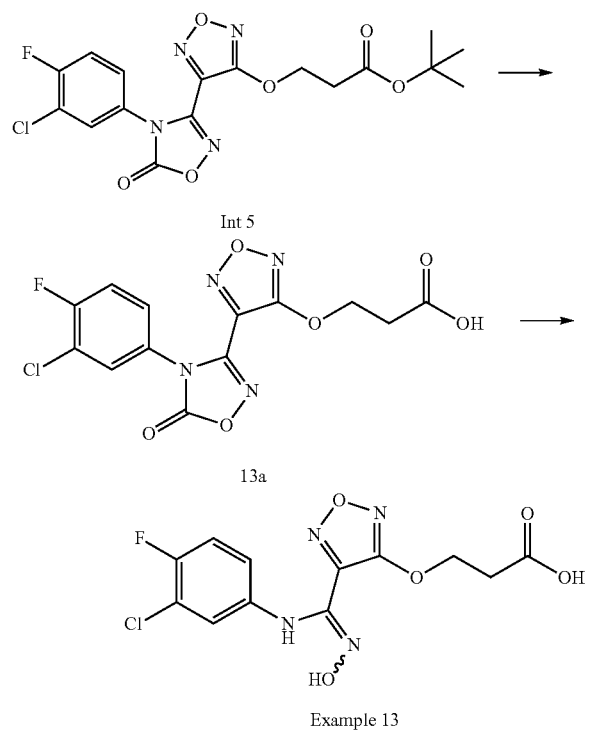

Example 13

Step 1: 3-((4-(4-(3-Chloro-4-fluorophenyl)-5-oxo-4,5-dihydro-1,2,4-oxadiazol-3-yl)-1,2,5-oxadiazol-3-yl)oxy)propanoic acid (13a)

The title compound was prepared similar as described for Example 11a, step 1, using tert-butyl 3-((4-(4-(3-chloro-4-fluorophenyl)-5-oxo-4,5-dihydro-1,2,4-oxadiazol-3-yl)-1,2,5-oxadiazol-3-yl)oxy)propanoate (Int 5) in place of tert-butyl 4-((4-(4-(3-chloro-4-fluorophenyl)-5-oxo-4,5-dihydro-1,2,4-oxadiazol-3-yl)-1,2,5-oxadiazol-3-yl)oxy)butanoate (Int 5/1).

Step 2: 3-((4-(N-(3-Chloro-4-fluorophenyl)-N'-hydroxycarbamimidoyl)-1,2,5-oxadiazol-3-yl)oxy)propanoic acid (13)

To a solution of 3-((4-(4-(3-chloro-4-fluorophenyl)-5-oxo-4,5-dihydro-1,2,4-oxadiazol-3-yl)-1,2,5-oxadiazol-3-yl)oxy)propanoic acid (13a) (150 mg, 0.41 mmol) in a mixture of THF (8 mL) and MeOH (10 mL) 2M aqueous NaOH (0.5 mL) was added and the mixture was stirred at rt for 30 min. The mixture was extracted with EtOAc (3×20 mL) and the combined organic layers were washed with brine (10 mL), dried over anhydrous Na$_2$SO$_4$ and concentrated to dryness. The residue was purified by reversed HPLC to give the title compound as a white solid. $^1$H NMR (500 MHz, d$_6$-DMSO): δ ppm 12.52 (br s, 0.9H), 11.45 (s, 0.1H), 10.35 (s, 0.1H), 9.16 (s, 0.1H), 9.03 (s, 0.9H), 7.93-7.92 (m, 0.1H), 7.36-7.31 (m, 0.2H), 7.19 (dd, J$_1$=J$_2$=9.5 Hz, 0.9H), 6.98-6.96 (m, 0.9H), 6.65-6.62 (m, 0.9H), 4.57-4.55 (m, 0.2H), 4.41-4.39 (m, 1.8H), 2.79-2.77 (m, 0.2H), 2.65-2.63 (m, 1.8H). MS (ESI): m/z 345.0 [M+H]$^+$.

Example 14

N-(3-Chloro-4-fluorophenyl)-N'-hydroxy-4-(2-((5-methyl-1,3,4-oxadiazol-2-yl)amino)ethoxy)-1,2,5-oxadiazole-3-carboximidamide (14)

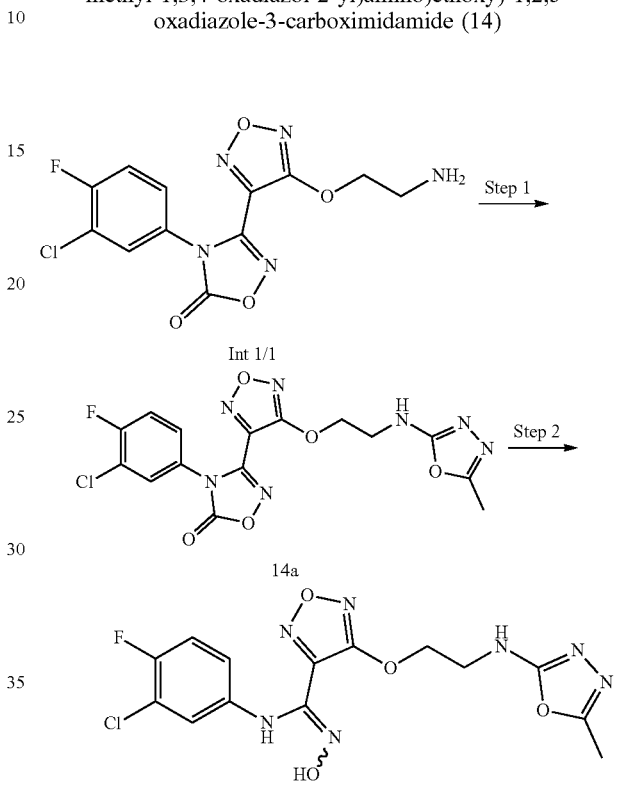

Example 14

Step 1: 4-(3-Chloro-4-fluorophenyl)-3-(4-(2-((5-methyl-1,3,4-oxadiazol-2-yl)amino)ethoxy)-1,2,5-oxadiazol-3-yl)-1,2,4-oxadiazol-5(4H)-one (14a)

To a solution of 3-(4-(2-aminoethoxy)-1,2,5-oxadiazol-3-yl)-4-(3-chloro-4-fluorophenyl)-1,2,4-oxadiazol-5(4H)-one (Int 1/1) (150 mg, 0.44 mmol) in DMF (5 mL) 2-bromo-5-methyl-1,3,4-oxadiazole (86 mg, 0.53 mmol) and Cs$_2$CO$_3$ (286 mg, 0.88 mmol) were added and the mixture was stirred at 65° C. overnight. Water (20 mL) was added and the mixture was extracted with EtOAc (20 mL). The combined organic layers were washed with brine (20 mL), dried over anhydrous Na$_2$SO$_4$, filtered and concentrated to dryness. The residue was purified by column chromatography (EA:PE=1:2) to give the title compound as a yellow solid.

Step 2: N-(3-Chloro-4-fluorophenyl)-N'-hydroxy-4-(2-((5-methyl-1,3,4-oxadiazol-2-yl)amino)ethoxy)-1,2,5-oxadiazole-3-carboximidamide (14)

To a solution of 4-(3-chloro-4-fluorophenyl)-3-(4-(2-((5-methyl-1,3,4-oxadiazol-2-yl)amino)ethoxy)-1,2,5-oxadiazol-3-yl)-1,2,4-oxadiazol-5(4H)-one (14a) (99 mg, 0.23 mmol) in MeOH (3 mL) aqueous NaOH (1M, 0.5 mL) was added and the mixture was stirred at rt overnight. Water was added and the mixture was extracted with EtOAc (20 mL). The combined organic layers were washed with brine (20 mL), dried over anhydrous Na$_2$SO$_4$, filtered and concentrated to dryness. The residue was purified by HPLC to give the title compound as a white solid. $^1$H NMR (500 MHz, DMSO-d$_6$): δ ppm 11.43 (s, 0.9H), 10.34 (s, 0.1H), 9.13 (s, 0.1H), 9.02 (s, 0.9H), 7.61-6.63 (m, 4H), 4.53-4.51 (m, 0.2H), 4.37-4.35 (m, 1.8H), 3.57-3.56 (m, 0.2H), 3.47-3.44 (m, 1.8H), 2.29 (s, 3H). MS (ESI): m/z 398.1 [M+H]$^+$.

Example 15

4-(2-((5-Amino-4H-1,2,4-triazol-3-yl)amino) ethoxy)-N-(3-chloro-4-fluorophenyl)-N'-hydroxy-1, 2,5-oxadiazole-3-carboximidamide (15)

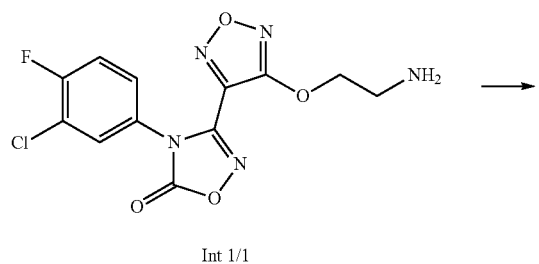

Int 1/1

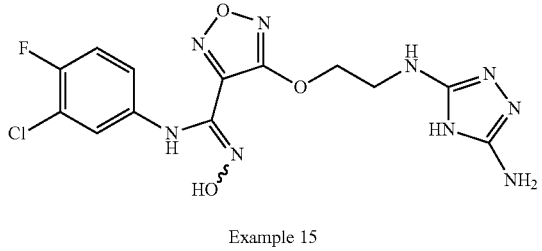

Example 15

To a solution of 3-(4-(2-aminoethoxy)-1,2,5-oxadiazol-3-yl)-4-(3-chloro-4-fluorophenyl)-1,2,4-oxadiazol-5(4H)-one (Int 1/1) (170 mg, 0.52 mmol) in MeCN (3 mL) dimethyl cyanocarbonimidodithioate (114 mg, 0.78 mmol) was added and the mixture was stirred at 45° C. for 30 min. A solution of hydrazine hydrate (25 mg, 0.78 mmol) in EtOH (2 mL) was added and the mixture was stirred at 90° C. for 1 h. Water was added and the mixture was extracted with EtOAc (20 mL). The organic layer was washed with brine (20 mL), dried over anhydrous Na$_2$SO$_4$, filtered and concentrated to dryness. The residue was purified by HPLC to give the title compound as a white solid. $^1$H NMR (500 MHz, CD3OD): δ ppm 7.07 (dd, J$_1$=J$_2$=8.5 Hz, 1H), 6.99-6.97 (m, 1H), 6.76-6.73 (m, 1H), 4.40-4.37 (m, 2H), 3.55-3.54 (m, 2H). MS (ESI): m/z 398.1 [M+H]$^+$.

Example 16

N-(3-Chloro-4-fluorophenyl)-N'-hydroxy-4-((1-(sulfamoylamino)propan-2-yl)oxy)-1,2,5-oxadiazole-3-carboximidamide (16)

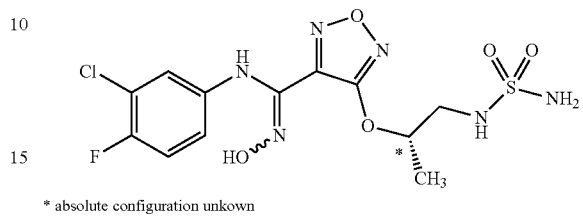

* absolute configuration unkown

To a solution of N-(2-((4-(4-(3-chloro-4-fluorophenyl)-5-oxo-4,5-dihydro-1,2,4-oxadiazol-3-yl)-1,2,5-oxadiazol-3-yl)oxy)propyl)sulfamide (Int 6a, first eluting enantiomer) (53 mg, 0.12 mmol) in MeOH (3 mL) aqueous 2M NaOH (1 mL) was added and the mixture was stirred at rt for 30 min. Water was added and the mixture was extracted with EtOAc (3×20 mL). The combined organic layers were washed with brine (10 mL), dried over anhydrous Na$_2$SO$_4$ and concentrated to dryness. The residue was purified by HPLC to give the title compound as a white solid. $^1$H NMR (500 MHz, DMSO-d$_6$): δ ppm 11.37 (s, 1H), 10.32 (s, 0.1H), 9.15 (s, 0.1H), 9.04 (s, 0.9H), 7.95-6.59 (m, 6H), 4.75-4.74 (m, 1H), 3.04-3.02 (m, 2H), 1.36 (d, J=6.0 Hz, 0.3H), 1.05 (d, J=6.0 Hz, 2.7H). MS (ESI): m/z 409.0 [M+H]$^+$.

Example 16/1

N-(3-Chloro-4-fluorophenyl)-N'-hydroxy-4-((1-(sulfamoylamino)propan-2-yl)oxy)-1,2,5-oxadiazole-3-carboximidamide (16/1)

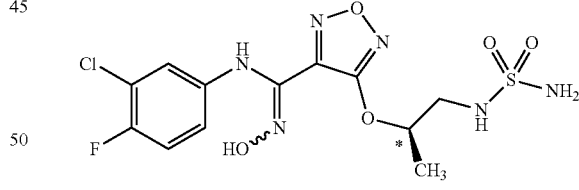

* absolute configuration unkown

The title compound was prepared similar as described for Example 16 using N-(2-((4-(4-(3-chloro-4-fluorophenyl)-5-oxo-4,5-dihydro-1,2,4-oxadiazol-3-yl)-1,2,5-oxadiazol-3-yl)oxy)propyl)sulfamide (Int 6b, second eluting enantiomer) in place of N-(2-((4-(4-(3-chloro-4-fluorophenyl)-5-oxo-4,5-dihydro-1,2,4-oxadiazol-3-yl)-1,2,5-oxadiazol-3-yl)oxy) propyl)sulfamide (Int 6a, first eluting enantiomer). $^1$H NMR (500 MHz, DMSO-d$_6$): δ ppm 11.36 (s, 1H), 10.32 (s, 0.1 H), 9.14 (s, 0.1H), 9.04 (s, 0.9H), 7.93-6.59 (m, 6H), 4.76-4.73 (m, 1H), 3.04-3.02 (m, 2H), 1.37 (d, J=6.0 Hz, 0.3H), 1.05 (d, J=6.0 Hz, 2.7H). MS (ESI): m/z 408.9 [M+H]$^+$.

Example 17

4-((1-Aminopropan-2-yl)oxy)-N-(3-chloro-4-fluorophenyl)-N'-hydroxy-1,2,5-oxadiazole-3-carboximidamide (17)

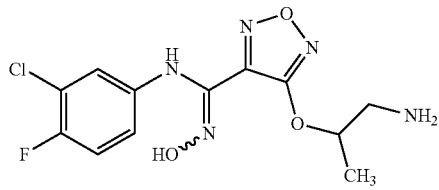 [SMILES: CC(CN)Oc1nonc1C(=NO)Nc1ccc(F)c(Cl)c1]

To a solution of 3-(4-((1-aminopropan-2-yl)oxy)-1,2,5-oxadiazol-3-yl)-4-(3-chloro-4-fluorophenyl)-1,2,4-oxadiazol-5(4H)-one (Int 1/7) (80 mg, 0.23 mmol) in MeOH (3 mL) 2M aqueous NaOH (1 mL) was added and the mixture was stirred at rt for 30 min. Water was added and the mixture was extracted with EtOAc (3×20 mL). The combined organic layers were washed with brine (10 mL), dried over anhydrous $Na_2SO_4$, concentrated and purified by HPLC to give the title compound as white solid. $^1$H NMR (500 MHz, $CD_3OD$) δ ppm 7.13-6.73 (m, 3H), 4.68-4.01 (m, 1H), 3.16-2.71 (m, 2H), 1.45-1.07 (m, 3H). MS (ESI): m/z 330.1 [M+H]$^+$.

Example 18

(3S,4R)—N-(2-((4-(N-(3-Chloro-4-fluorophenyl)-N'-hydroxycarbamimidoyl)-1,2,5-oxadiazol-3-yl)oxy)ethyl)-3,4-dihydroxypyrrolidine-1-carboxamide (18)

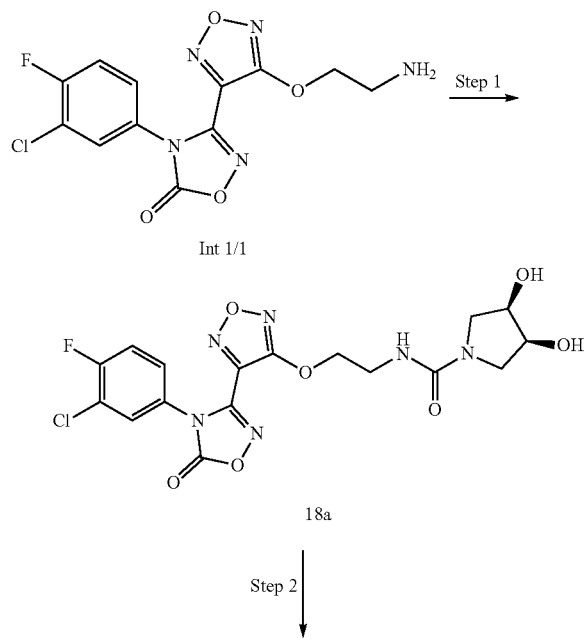

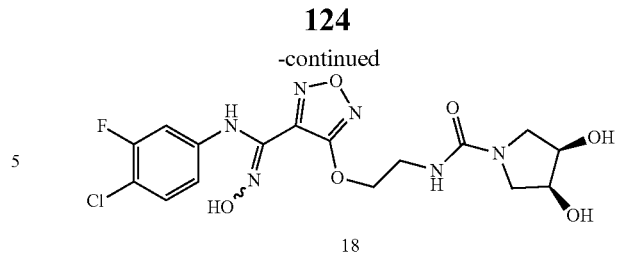

Step 1: (3S,4R)—N-(2-((4-(4-(3-Chloro-4-fluorophenyl)-5-oxo-4,5-dihydro-1,2,4-oxadiazol-3-yl)-1,2,5-oxadiazol-3-yl)oxy)ethyl)-3,4-dihydroxypyrrolidine-1-carboxamide (18a)

To a stirred solution of 3-(4-(2-aminoethoxy)-1,2,5-oxadiazol-3-yl)-4-(3-chloro-4-fluorophenyl)-1,2,4-oxadiazol-5(4H)-one (Int 1/1) (0.40 g, 1.17 mmol) in THF (10.0 mL) DIPEA (0.60 mL, 3.52 mmol) and CDI (285 mg, 1.76 mmol) were added at 0° C. The mixture was stirred for 10 min at rt. (3R,4S)-Pyrrolidine-3,4-diol (163 mg, 1.17 mmol) was added and the mixture was stirred at rt for 1 h. The mixture was poured in ice cold water.

The aqueous layer was extracted with EtOAc (2×50 mL). The combined organic layers were washed with cold water, dried over anhydrous $Na_2SO_4$, filtered and concentrated to dryness to give the title compound as off white solid.

Step 2: (3S,4R)—N-(2-((4-(N-(3-Chloro-4-fluorophenyl)-N'-hydroxycarbamimidoyl)-1,2,5-oxadiazol-3-yl)oxy)ethyl)-3,4-dihydroxypyrrolidine-1-carboxamide (18)

To a stirred solution of (3S,4R)—N-(2-((4-(4-(3-chloro-4-fluorophenyl)-5-oxo-4,5-dihydro-1,2,4-oxadiazol-3-yl)-1,2,5-oxadiazol-3-yl)oxy)ethyl)-3,4-dihydroxypyrrolidine-1-carboxamide (17a) (0.30 g, 0.64 mmol) in EtOH (10.0 mL) 2M aqueous NaOH (3.0 mL) was added at 0° C. The mixture was allowed to warm to rt and stirred for 2 h. The mixture was concentrated to dryness and the residue was suspended with ice cold water. The aqueous layer was extracted with EtOAc (2×50 mL). The combined organic layers were washed with cold water, dried over anhydrous $Na_2SO_4$, filtered and concentrated to dryness. The residue was purified by column chromatography (DCM/MeOH 95:5) to give the title compound as off white solid. $^1$H NMR (400 MHz, DMSO-$d_6$): δ ppm 11.44 (s, 0.8H), 10.22 (s, 0.2H), 7.95-7.93 (m, 0.2H), 7.34-7.32 (m, 0.4H), 7.20 (dd, $J_1$=$J_2$=9.2 Hz, 0.8 Hz), 7.02-7.00 (m, 0.8H), 6.29-6.26 (m, 0.8H), 5.76 (s, 0.2H), 4.90-3.00 (m, 10H), 2.03-1.24 (m, 2H). MS (ESI): m/z 445.2 [M+H]$^+$.

Example 19

N-(2-((4-(N-(3-Chloro-4-fluorophenyl)-N'-hydroxycarbamimidoyl)-1,2,5-oxadiazol-3-yl)oxy)ethyl)-2,3-dihydroxypropanamide (19)

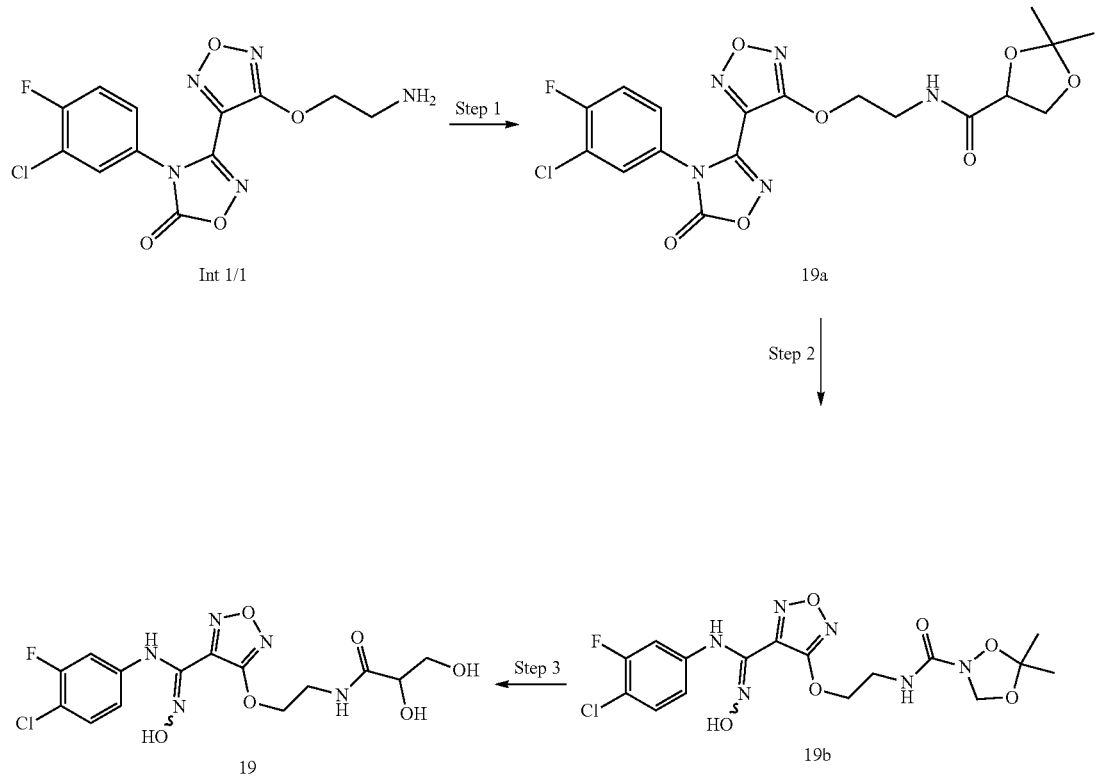

Step 1: N-(2-((4-(4-(3-Chloro-4-fluorophenyl)-5-oxo-4,5-dihydro-1,2,4-oxadiazol-3-yl)-1,2,5-oxadiazol-3-yl)oxy)ethyl)-2,2-dimethyl-1,3-dioxolane-4-carboxamide (19a)

To a stirred solution of 2,2-dimethyl-1,3-dioxolane-4-carboxylic acid (0.40 mL, 2.93 mmol) in DCM (15.0 mL) DIPEA (1.5 mL, 8.79 mmol), DCC (0.603 g, 2.93 mmol) and HOBt (0.4 g, 2.93 mmol) were added and the mixture was stirred for 20 min at rt. Then 3-(4-(2-aminoethoxy)-1,2,5-oxadiazol-3-yl)-4-(3-chloro-4-fluorophenyl)-1,2,4-oxadiazol-5(4H)-one (Int 1/1) was added (1.0 g, 2.93 mmol) and the mixture was stirred for 16 h at rt. The mixture was poured in ice cold water. Aqueous layer was extracted with DCM (2×100 mL). The combined organic layers were washed with water, dried over anhydrous $Na_2SO_4$, filtered and concentrated to dryness. The residue was purified by column chromatography (DCM/MeOH 95:5) to give the title compound as off white solid.

Step 2: N-(2-((4-(N-(3-Chloro-4-fluorophenyl)-N-hydroxycarbamimidoyl)-1,2,5-oxadiazol-3-yl)oxy)ethyl)-2,2-dimethyl-1,3-dioxolane-4-carboxamide (19b)

To a stirred solution of N-(2-((4-(4-(3-chloro-4-fluorophenyl)-5-oxo-4,5-dihydro-1,2,4-oxadiazol-3-yl)-1,2,5-oxadiazol-3-yl)oxy)ethyl)-2,2-dimethyl-1,3-dioxolane-4-carboxamide (19a) (0.50 g, 1.07 mmol) in EtOH (10.0 mL) 2M aqueous NaOH (5.0 mL) was added at 0° C. The mixture was allowed to warm to rt and stirred for 2 h. The mixture was concentrated to dryness and the residue was suspended in water. The aqueous layer was extracted with EtOAc (2×50 mL). The combined organic layers were washed with water, dried over anhydrous $Na_2SO_4$, filtered and concentrated to dryness to give the title compound as a yellow solid.

Step 3: N-(2-((4-(N-(3-Chloro-4-fluorophenyl)-N'-hydroxycarbamimidoyl)-1,2,5-oxadiazol-3-yl)oxy)ethyl)-2,3-dihydroxypropanamide (19)

To a stirred solution of N-(2-((4-(N-(3-chloro-4-fluorophenyl)-N'-hydroxycarbamimidoyl)-1,2,5-oxadiazol-3-yl)oxy)ethyl)-2,2-dimethyl-1,3-dioxolane-4-carboxamide (19b) (0.40 g, 0.90 mmol) in 1,4-dioxane (5.0 mL) 4M HCl in dioxane (5.0 mL) was added at 0° C. The mixture was allowed to warm to rt and stirred for 1h. The mixture was concentrated to dryness and the residue was suspended with water. The aqueous layer was extracted with EtOAc (2×50 mL). The combined organic layers were dried over anhydrous $Na_2SO_4$, filtered and concentrated to dryness. The residue was purified by column chromatography (DCM/MeOH 95:5) to give the title compound as an off white solid.
$^1$H NMR (400 MHz, DMSO-$d_6$): δ ppm 11.44 (s, 0.9H), 10.30 (s, 0.1H), 9.11 (s, 0.1H), 8.98 (s, 0.9H), 7.95-7.92 (m, 1.1H), 7.34-7.30 (m, 0.2H), 7.20 (dd, $J_1=J_2=9.2$ Hz, 0.9H), 7.03-7.00 (m, 0.9H), 6.70-6.63 (m, 0.9H), 5.58-5.57 (m, 1H), 4.67-3.354 (m, 8H). MS (ESI): m/z 445.2 [M−H].

Example 20

N-(3-Chloro-4-fluorophenyl)-N'-hydroxy-4-(2-(methylsulfonyl)ethoxy)-1,2,5-oxadiazole-3-carboximidamide (20)

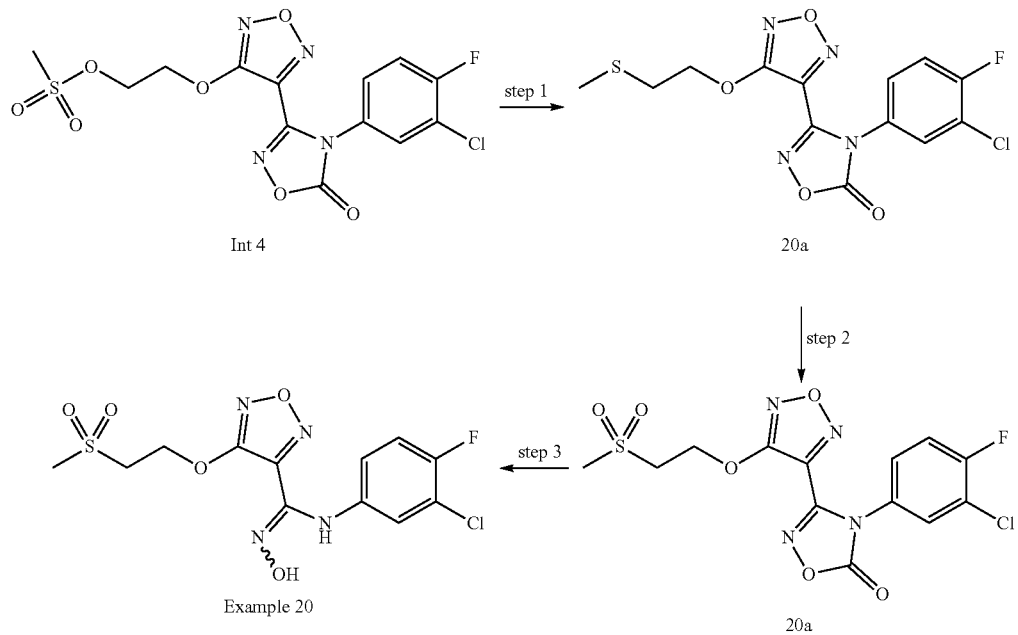

Step 1: 4-(3-Chloro-4-fluorophenyl)-3-(4-(2-(methylthio)ethoxy)-1,2,5-oxadiazol-3-yl)-1,2,4-oxadiazol-5(4H)-one (20a)

To a solution of 2-((4-(4-(3-chloro-4-fluorophenyl)-5-oxo-4,5-dihydro-1,2,4-oxadiazol-3-yl)-1,2,5-oxadiazol-3-yl)oxy)ethyl methanesulfonate (Int 4) (185 mg, 0.44 mmol) in DMF (5 mL) was added MeSNa (46 mg, 0.66 mmol) and the reaction mixture was stirred and heated at 80° C. overnight. Then water (25 mL) was added and the mixture was extracted with EtOAc (3×20 mL). The combined organic phase was dried over Na$_2$SO$_4$ and concentrated to dryness to give the crude title compound as a yellow solid.

Step 2: 4-(3-Chloro-4-fluorophenyl)-3-(4-(2-(methylsulfonyl)ethoxy)-1,2,5-oxadiazol-3-yl)-1,2,4-oxadiazol-5(4H)-one (20b)

To a solution of 4-(3-chloro-4-fluorophenyl)-3-(4-(2-(methylthio)ethoxy)-1,2,5-oxadiazol-3-yl)-1,2,4-oxadiazol-5(4H)-one (20a) (98 mg, 0.26 mmol) in DCM (4 mL) was added MCPBA (85%, 132 mg, 0.65 mmol) at rt, and the mixture was stirred for 3 h. Water (20 mL) was added, and the mixture was extracted with DCM (3×20 mL). The combined organic phase was dried over Na$_2$SO$_4$ and concentrated to dryness to give the crude title compound as a yellow solid.

Step 3: N-(3-Chloro-4-fluorophenyl)-N'-hydroxy-4-(2-(methylsulfonyl)ethoxy)-1,2,5-oxadiazole-3-carboximidamide (20)

To a solution of 4-(3-chloro-4-fluorophenyl)-3-(4-(2-(methylsulfonyl)ethoxy)-1,2,5-oxadiazol-3-yl)-1,2,4-oxadiazol-5(4H)-one (20b) (94 mg, 0.23 mmol) in MeOH (3 mL) was added 2 N NaOH (1 mL), and the mixture was stirred at rt for 30 min. EtOAc was added (3×20 mL) and the combined organic layer was washed with brine (10 mL), dried over Na$_2$SO$_4$ and concentrated. The residue was purified by HPLC to give the title compound as white solid. $^1$H NMR (500 MHz, DMSO-d$_6$): δ ppm 11.48 (s, 0.9H), 10.45 (s, 0.1H), 9.25 (s, 0.1H), 9.00 (s, 0.9H), 7.95-7.91 (m, 0.1H), 7.40-7.35 (m, 0.2H), 7.22-7.17 (m, 0.9H), 7.01 (m, 0.9H), 6.70-6.65 (m, 0.9H), 4.76-4.74 (m, 0.2H), 4.67-4.62 (m, 1.8H), 3.72-3.68 (m, 0.2H), 3.67-3.63 (m, 1.8H), 3.09 (s, 2.7H), 3.01 (s, 0.3H). MS (ESI): m/z 378.9 [M+H]$^+$.

Example 20/1

N-(3-Chloro-4-fluorophenyl)-N'-hydroxy-4-(3-(methylsulfonyl)propoxy)-1,2,5-oxadiazole-3-carboximidamide (20/1)

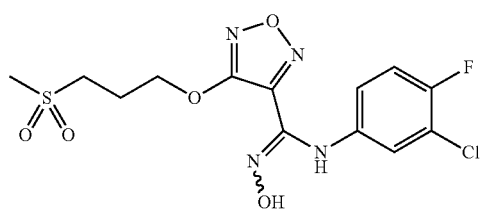 [SMILES: CS(=O)(=O)CCCOc1nonc1C(=NO)Nc1ccc(F)c(Cl)c1]

The title compound was prepared similar as described for example 17, using compound Int 4/1 instead of Int 4 as starting material. $^1$H NMR (500 MHz, DMSO-d$_6$): δ ppm 11.46 (s, 0.9H), 10.41 (s, 0.1H), 9.17 (s, 0.1H), 9.04 (s, 0.9H), 9.05-9.03 (m, 0.1H), 7.35-7.31 (m, 0.2H), 7.22-7.18 (m, 0.9H), 7.01-6.97 (m, 0.9H), 6.69-6.65 (m, 0.9H), 4.54-4.49 (m, 0.2H), 4.36-4.31 (m, 1.8H), 3.26-3.21 (m, 0.2H), 3.15-3.10 (m, 1.8H), 3.00 (s, 3H), 2.21-2.18 (m, 0.2H), 2.10-2.03 (m, 1.8H). MS (ESI): m/z 393.0 [M+H]$^+$.

Example 21

N-(3-Chloro-4-fluorophenyl)-N-hydroxy-4-(2-(methylsulfonoamidimidamido) ethoxy)-1,2,5-oxadiazole-3-carboximidamide (21)

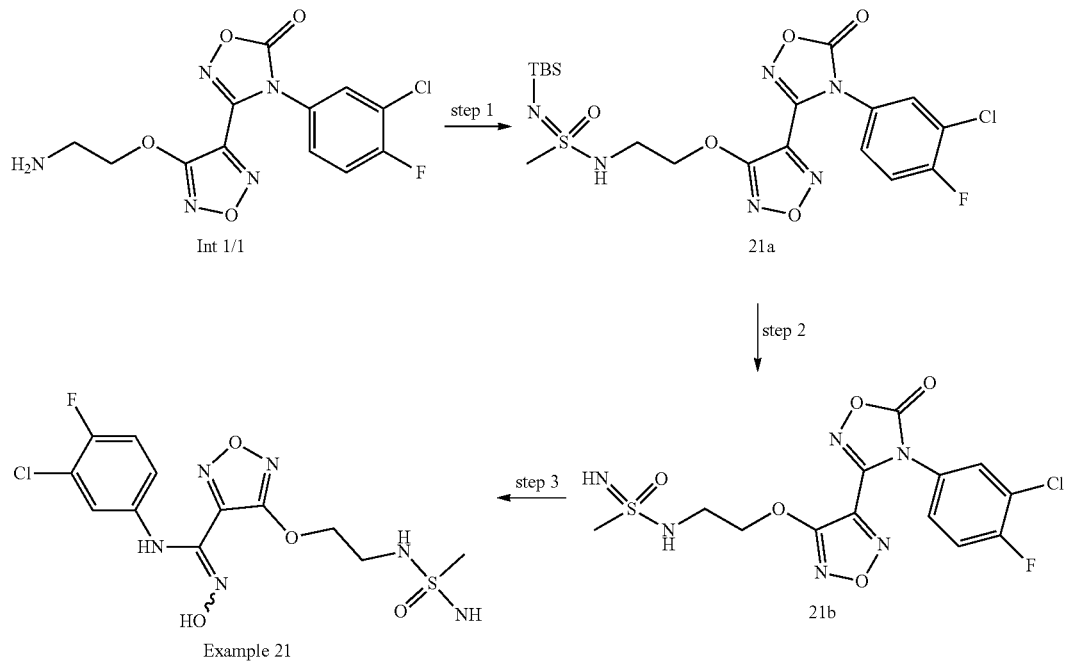

Step 1: N'-(tert-Butyldimethylsilyl)-N-(2-((4-(4-(3-chloro-4-fluorophenyl)-5-oxo-4,5-dihydro-1,2,4-oxadiazol-3-yl)-1,2,5-oxadiazol-3-yl)oxy)ethyl)methanesulfonimidamide (21a)

To a stirred suspension of dichlorotriphenyl-□⁵-phosphane (667 mg, 2.00 mmol) in dry CHCl₃ (3 mL) under a N₂ atmosphere was added TEA (0.70 mL, 5.00 mmol). The mixture was stirred for 10 min at rt, a yellow suspension immediately formed. The reaction mixture was cooled to 0° C. and a solution of N-(tert-butyldimethylsilyl)-methanesulfonamide (418 mg, 2.00 mmol, RSC Advances, 5(6), 4171-4174; 2015) in dry CHCl₃ (2 mL) was added. The reaction mixture was stirred for 20 min at 0° C., after 5 min a clear solution formed. No attempt was made to isolate the sulfonimidoyl chloride intermediate. To the reaction mixture was added a solution of 3-(4-(2-aminoethoxy)-1,2,5-oxadiazol-3-yl)-4-(3-chloro-4-fluorophenyl)-1,2,4-oxadiazol-5 (4H)-one (Int 1/1) (200 mg, 0.59 mmol) in dry CHCl₃ (4 mL) in one portion. The mixture was stirred at 0° C. for 30 min then warmed to rt overnight. The solvent was removed under reduced pressure to give a crude residue which was purified by preparative TLC (EA:PE=1:1) to give the title compound as a light yellow oil.

Step 2: N-(2-((4-(4-(3-Chloro-4-fluorophenyl)-5-oxo-4,5-dihydro-1,2,4-oxadiazol-3-yl)-1,2,5-oxadiazol-3-yl)oxy)ethyl)methanesulfonimidamide (21b)

A solution of N'-(tert-butyldimethylsilyl)-N-(2-((4-(4-(3-chloro-4-fluorophenyl)-5-oxo-4,5-dihydro-1,2,4-oxadiazol-3-yl)-1,2,5-oxadiazol-3-yl)oxy)ethyl)methanesulfon-imid-amide (21a) (160 mg, 0.30 mmol) in HCl in dioxane (10 mL) was stirred at rt for 30 min. The solvent was removed under reduced pressure to give the crude title compound as a yellow solid, which was used directly for further transformations.

Step 3: N-(3-Chloro-4-fluorophenyl)-W-hydroxy-4-(2-(methylsulfonoamidimidamido)ethoxy)-1,2,5-oxadiazole-3-carboximidamide (21)

To a stirred suspension of N-(2-((4-(4-(3-chloro-4-fluorophenyl)-5-oxo-4,5-dihydro-1,2,4-oxadiazol-3-yl)-1,2,5-oxadiazol-3-yl)oxy)ethyl)methanesulfonimidamide (21b) (113 mg, 0.27 mmol) in MeOH (8 mL) was added NaOH (4N, 2 mL), and the mixture was stirred at rt for 40 min. The solvent was removed under reduced pressure and water (5 mL) was added. The pH was adjusted to 5 and the mixture was extracted with EtOAc (2×50 mL).

The organic phase was concentrated and the residue was purified by HPLC to give the title compound as a white solid. $^1$H NMR (500 MHz, CD₃OD): δ ppm 7.09 (t, J=9.0 Hz, 1H), 7.04-7.01 (m, 1H), 6.79-6.75 (m, 1H), 4.43-4.40 (m, 2H), 3.64-3.60 (m, 2H), 3.50 (s, 3H). MS (ESI): m/z 393.0 [M+H]+

Example 22

N-(3-(2-Chloroethyl)phenyl)-N'-hydroxy-4-methoxy-1,2,5-oxadiazole-3-carboximidamide (22)

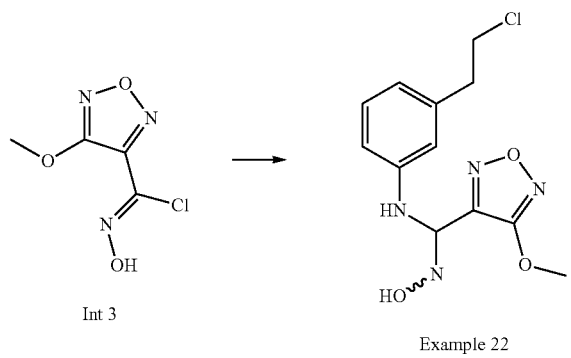 [SMILES: COc1nonc1/C(Cl)=N/O ; COc1nonc1C(NO)Nc1cccc(CCCl)c1]

To a solution of N-hydroxy-4-methoxy-1,2,5-oxadiazole-3-carbimidoyl chloride (Int 3) (170 mg, 1.00 mmol) and 3-(2-chloroethyl)aniline (Int 8) (310 mg, 2.00 mmol) in H$_2$O (50 mL) was added NaHCO$_3$ (340 mg, 4.10 mmol). The mixture was stirred at 60° C. for 2 h. Then the reaction solution was diluted with EtOAc (100 mL), the organic layer was washed with water (100 mL) and brine (100 mL), dried over Na$_2$SO$_4$ and concentrated. The residue was purified by HPLC to give the title compound as a white solid. $^1$H NMR (400 MHz, DMSO-d$_6$): δ ppm 11.23 (s, 1 H), 8.86 (s, 1 H), 7.13-7.09 (m, 1H), 6.85-6.81 (m, 1H), 6.66-6.62 (m, 1H), 6.60 (s, 1H), 3.88 (s, 3H), 3.70 (t, J=6.9 Hz, 2H), 2.88 (t, J=6.9 Hz, 2H). MS (ESI): m/z 297.1 [M+H]$^+$.

Example 100

N-(3-Bromo-4-fluorophenyl)-N'-hydroxy-4-((2-(methylsulfonamido)ethyl)thio)-1,2,5-oxadiazole-3-carboximidamide (100)

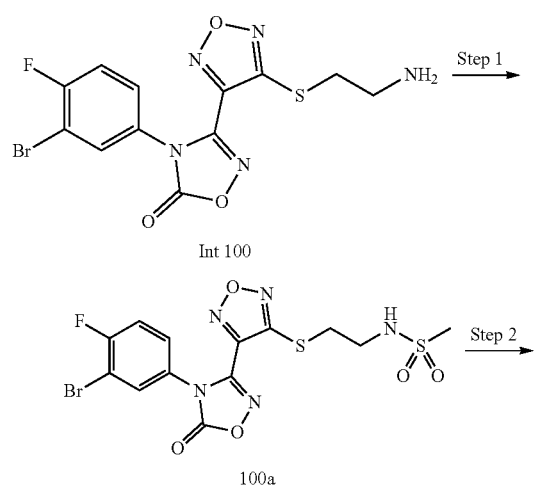

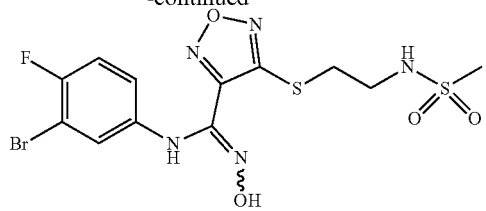

Example 100

Step 1: N-(2-((4-(4-(3-Bromo-4-fluorophenyl)-5-oxo-4,5-dihydro-1,2,4-oxadiazol-3-yl)-1,2,5-oxadiazol-3-yl)thio)ethyl)methanesulfonamide (100a)

To a solution of 3-(4-((2-aminoethyl)thio)-1,2,5-oxadiazol-3-yl)-4-(3-bromo-4-fluorophenyl)-1,2,4-oxadiazol-5 (4H)-one (Int 100) (140 mg, 0.35 mmol) in DCM (8 mL) was added MsCl (0.06 mL, 0.52 mmol) in one portion. The mixture was stirred for 5 min at rt and TEA (0.08 mL, 0.52 mmol) was added. After stirring for additional 10 min water (5 mL) was added. The mixture was extracted with EtOAc (2×5 mL). The combined organic layers were dried over anhydrous Na$_2$SO$_4$, filtered and concentrated to dryness to give the title compound as a yellow solid.

Step 2: N-(3-Bromo-4-fluorophenyl)-N'-hydroxy-4-((2-(methylsulfonamido)ethyl)thio)-1,2,5-oxadiazole-3-carboximidamide (100)

To a solution of N-(2-((4-(4-(3-bromo-4-fluorophenyl)-5-oxo-4,5-dihydro-1,2,4-oxadiazol-3-yl)-1,2,5-oxadiazol-3-yl)oxy)ethyl)methanesulfonamide (100a) (120 mg, 0.25 mmol) in THF (8 mL) was added 2M NaOH (0.5 mL). The mixture was stirred at rt for 30 min. The mixture was extracted with EtOAc (3×20 mL) and the combined organic layers were washed with brine (10 mL), dried over anhydrous Na$_2$SO$_4$, filtered and concentrated to dryness. The residue was purified by HPLC to give to the title compound as a white solid. $^1$H NMR (500 MHz, DMSO-d$_6$): δ ppm 11.78 (s, 1H), 8.99 (s, 1H), 7.38 (t, J=5.7 Hz, 1H), 7.17 (dd, J$_1$=J$_2$=9.0 Hz, 1H), 7.11-7.10 (m, 1H), 6.72-6.69 (m, 1H), 3.36-3.28 (m, 4H), 2.93 (s, 3H). MS (ESI): m/z 453.6 [M+H]$^+$.

Example 100/1

N-(3-(Difluoromethyl)-4-fluorophenyl)-N'-hydroxy-4-((2-((2-(methylsulfonyl)ethyl)sulfonamido)ethyl)thio)-1,2,5-oxadiazole-3-carboximidamide (100/1)

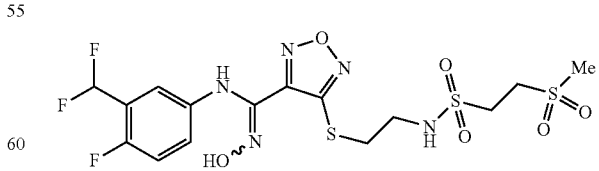

The title compound was prepared similar to procedure described for Example 100, using 3-(4-((2-aminoethyl)thio)-1,2,5-oxadiazol-3-yl)-4-(3-(difluoromethyl)-4-fluorophenyl)-1,2,4-oxadiazol-5(4H)-one (Int 100/3) in place of 3-(4-((2-aminoethyl)thio)-1,2,5-oxadiazol-3-yl)-4-(3- bromo-4-fluorophenyl)-1,2,4-oxadiazol-5(4H)-one (Int 100) and 2-(methylsulfonyl)ethane-1-sulfonyl chloride in place of MsCl.

$^1$H NMR (300 MHz, CD$_3$OD): δ ppm 7.09-6.72 (m, 4H), 3.57-3.54 (m, 4H), 3.53-3.47 (m, 2H), 3.36-3.33 (m, 2H), 3.09-3.06 (s, 3H). MS (ESI): m/z 518.0 [M+1]$^+$.

Example 101

N-(3-Bromo-4-fluorophenyl)-N'-hydroxy-4-((2-(sulfamoylamino)ethyl)thio)-1,2,5-oxadiazole-3-carboximidamide (101)

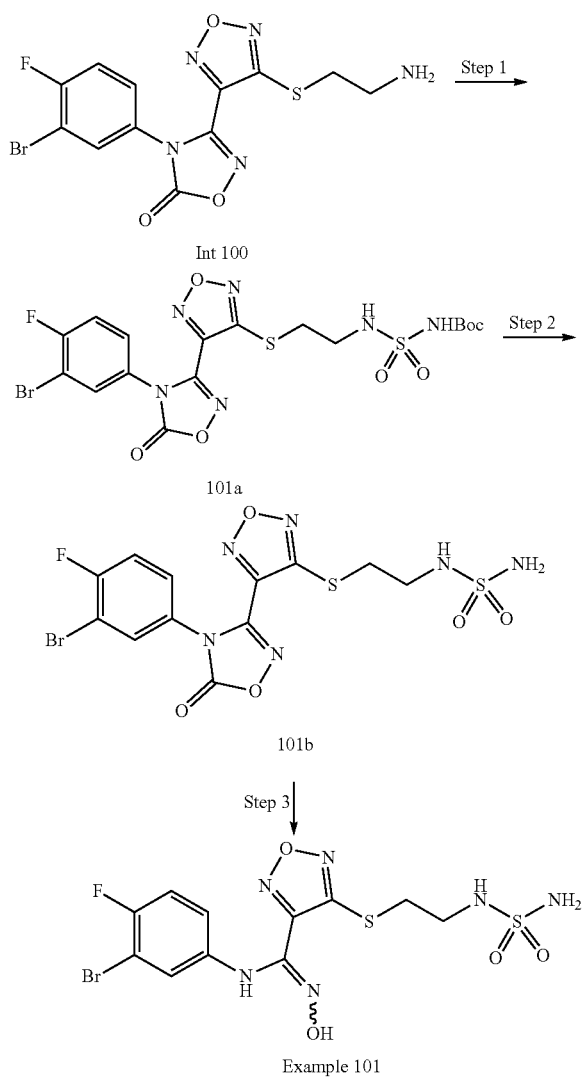

Example 101

Step 1: tert-Butyl N-(2-((4-(4-(3-Bromo-4-fluorophenyl)-5-oxo-4,5-dihydro-1,2,4-oxadiazol-3-yl)-1,2,5-oxadiazol-3-yl)thio)ethyl)sulfamoylcarbamate (101a)

To a solution of 3-(4-((2-aminoethyl)thio)-1,2,5-oxadiazol-3-yl)-4-(3-bromo-4-fluorophenyl)-1,2,4-oxadiazol-5(4H)-one (Int 100) (150 mg, 0.37 mmol) in DCM (5 mL) was added tert-butyl chlorosulfonylcarbamate (119 mg, 0.55 mmol) and TEA (57 mg, 0.55 mmol). The mixture was stirred at rt for 10 min and water (5 mL) was added. The mixture was extracted with EtOAc (2×5 mL), dried over anhydrous Na$_2$SO$_4$, filtered and concentrated to dryness to give the title compound as a yellow solid.

Step 2: N-(2-((4-(4-(3-Bromo-4-fluorophenyl)-5-oxo-4,5-dihydro-1,2,4-oxadiazol-3-yl)-1,2,5-oxadiazol-3-yl)thio)ethyl)sulfamide (101b) tert-Butyl N-(2-((4-(4-(3-bromo-4-fluorophenyl)-5-oxo-4,5-dihydro-1,2,4-oxadiazol-3-yl)-1,2,5-oxadiazol-3-yl)thio)ethyl)sulfamoylcarbamate (101a) (174 mg, 0.30 mmol) was added to a stirred solution of TFA (1 mL) in DCM (4 mL) at rt and stirring was continued for 3 h. The mixture was concentrated and the residue was dissolved in DCM. The organic layer was washed with saturated NaHCO$_3$ and brine, dried over anhydrous Na$_2$SO$_4$, filtered and concentrated to dryness to give the title compound as a yellow solid Step 3: N-(3-Bromo-4-fluorophenyl)-N-hydroxy-4-((2-(sulfamoylamino)ethyl)thio)-1,2,5-oxadiazole-3-carboximidamide (101)

To a solution of N-(2-((4-(4-(3-bromo-4-fluorophenyl)-5-oxo-4,5-dihydro-1,2,4-oxadiazol-3-yl)-1,2,5-oxadiazol-3-yl)thio)ethyl)sulfamide (101b) (131 mg, 0.27 mmol) in THF (8 mL) was added 2M NaOH (0.5 mL) and the mixture was stirred at rt for 30 min. The mixture was extracted with EtOAc (3×20 mL) and the combined organic layers were washed with brine (10 mL), dried over anhydrous Na$_2$SO$_4$, filtered and concentrated to dryness. The residue was purified by HPLC to give the title compound as a white solid. $^1$H NMR (500 MHz, DMSO-d$_6$): δ ppm 11.77 (s, 1H), 8.99 (s, 1H), 7.18 (dd, J$_1$=J$_2$=9.0 Hz, 1H), 7.11-7.09 (m, 1H), 6.88-6.86 (m, 1H), 6.71-6.65 (m, 3H), 3.31-3.27 (m, 4H). MS (ESI): m/z 455.0 [M+H]$^+$.

Example 101/1

N-(3-Chloro-4-fluorophenyl)-N'-hydroxy-4-((2-(sulfamoylamino)ethyl)thio)-1,2,5-oxadiazole-3-carboximidamide (101/1)

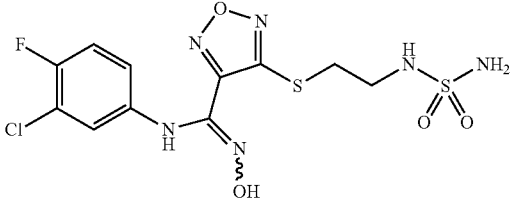 [SMILES: NS(=O)(=O)NCCSc1nonc1C(=NO)Nc1ccc(F)c(Cl)c1]

The title compound was prepared similar as described for Example 101 using in step 1 3-(4-((2-aminoethylthio)-1,2,5-oxadiazol-3-yl)-4-(3-chloro-4-fluorophenyl)-1,2,4-oxadiazol-5(4H)-one (Int 100/1) in place of 3-(4-((2-aminoethypthio)-1,2,5-oxadiazol-3-yl)-4-(3-bromo-4-fluorophenyl)-1,2,4-oxadiazol-5(4H)-one (Int 100). $^1$H NMR (500 MHz, DMSO-d$_6$): δ ppm 11.77 (s, 1 H), 8.99 (s, 1 H), 7.21 (dd, J$_1$=J$_2$=9.0 Hz, 1 H), 6.99-6.97 (m, 1H), 6.87-6.85 (m, 1 H), 6.68-6.64 (m, 3H), 3.32-3.26 (m, 4H). MS (ESI): m/z 411.1 [M+H]$^+$.

Example 102

4-((2-((2-Amino-3,4-dioxocyclobut-1-en-1-yl)amino)ethyl)thio)—N-(3-chloro-4-fluorophenyl)-N'-hydroxy-1,2,5-oxadiazole-3-carboximidamide (102)

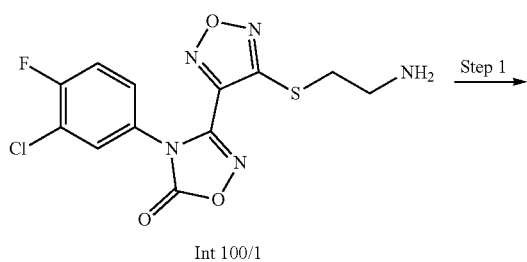

Int 100/1

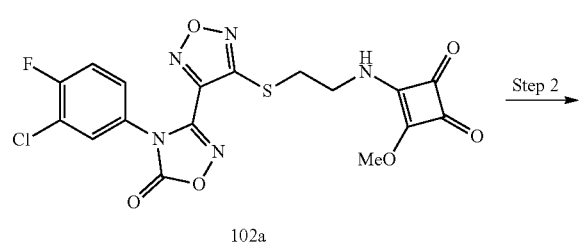

102a

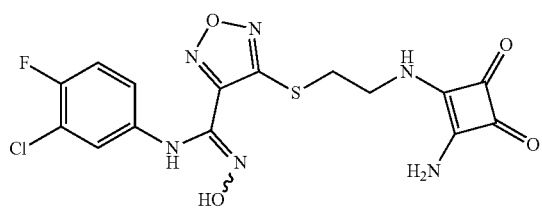

Example 102

Step 1: 3-((2-((4-(4-(3-Chloro-4-fluorophenyl)-5-oxo-4,5-dihydro-1,2,4-oxadiazol-3-yl)-1,2,5-oxadiazol-3-yl)thio)ethyl)amino)-4-methoxycyclobut-3-ene-1,2-dione (102a)

To a solution of 3-(4-((2-aminoethyl)thio)-1,2,5-oxadiazol-3-yl)-4-(3-chloro-4-fluorophenyl)-1,2,4-oxadiazol-5(4H)-one (Int 100/1) (150 mg, 0.42 mmol) and 3,4-dimethoxycyclobut-3-ene-1, 2-dione (119 mg, 0.84 mmol) in MeOH (50 mL) DIPEA (216 mg, 1.67 mmol) was added and the mixture was stirred at rt overnight. The mixture was concentrated to dryness and the residue was dissolved in EtOAc (100 mL). The organic layer was washed with water (2×100 mL), dried over anhydrous $Na_2SO_4$, filtered and concentrated to dryness to give the title compound as a white solid.

Step 2: 4-((2-((2-Amino-3,4-dioxocyclobut-1-en-1-yl)amino)ethyl)thio)—N-(3-chloro-4-fluorophenyl)-N'-hydroxy-1,2,5-oxadiazole-3-carboximidamide (102)

To a solution of 3-((2-((4-(4-(3-chloro-4-fluorophenyl)-5-oxo-4,5-dihydro-1,2,4-oxadiazol-3-yl)-1,2,5-oxadiazol-3-yl)thio)ethyl)amino)-4-methoxycyclobut-3-ene-1,2-dione (102a) (125 mg, 0.27 mmol) in MeOH (30 mL) $NH_3$/MeOH (7M, 10 mL) was added and the mixture was stirred at rt overnight. The mixture was concentrated to dryness and the residue was purified by HPLC to give the title compound as white solid. $^1H$ NMR (500 MHz, DMSO-$d_6$): δ ppm 11.73 (s, 0.95H), 10.56 (s, 0.05H), 9.10 (s, 0.05H), 8.92 (s, 0.95H), 7.80-7.40 (m, 3H), 7.20 (dd, $J_1=J_2=9.0$ Hz, 1 H), 7.01 (dd, $J_1=7.0$ Hz, $J_2=3.0$ Hz, 1H), 6.67-6.64 (m, 1H), 3.95-3.80 (m, 2H), 3.41-3.38 (m, 2H). MS (ESI): m/z 427.0 $[M+H]^+$.

Examples 102/1 to 102/2

The following Examples were prepared similar as described for Example 102 using the appropriate Intermediates

| # | Int. # | Structure | Analytical data |
|---|---|---|---|
| 102/1 | Int 100/9 | 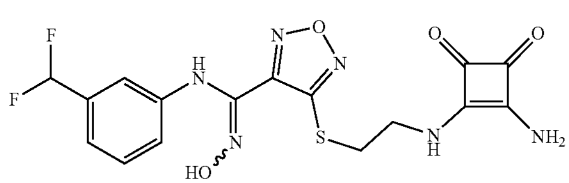 [SMILES: Nc1c(NCCSc2nonc2C(=NO)Nc2cccc(C(F)F)c2)c(=O)c1=O] | $^1H$ NMR (500 MHz, DMSO-$d_6$): δ ppm 11.75 (s, 1H), 9.06 (s, 1H), 7.75-7.28 (m, 4H), 7.09-7.05 (m, 1H), 6.96-6.94 (m, 1H), 6.82-6.80 (m, 1H), 3.94-3.84 (m, 2H), 3.42-3.38 (m, 2H). MS (ESI): m/z 425.1 $[M + H]^+$. |
| 102/2 | Int 105 | 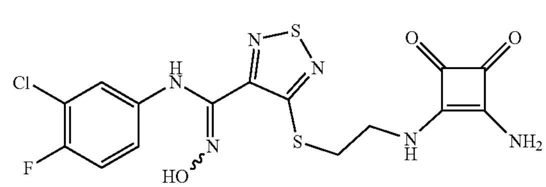 [SMILES: Nc1c(NCCSc2nsnc2C(=NO)Nc2ccc(F)c(Cl)c2)c(=O)c1=O] | $^1H$ NMR (500 MHz, DMSO-$d_6$): δ ppm 11.37 (s, 1H), 8.88 (s, 1H), 7.64-7.11 (m, 4H), 6.90-6.88 (m, 1H), 6.41-6.38 (m, 1H), 3.87 (m, 2H), 3.44 (m, 2H). MS (ESI): m/z 442.9 $[M + H]^+$. |

Example 103

4-(Benzylthio)—N-(3-chloro-4-fluorophenyl)-N'-hydroxy-1,2,5-oxadiazole-3-carboximidamide (103)

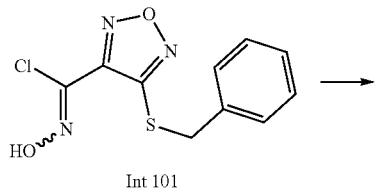

Int 101 → was purified by HPLC to give the title compound as a white solid. ¹H NMR (500 MHz, DMSO-d₆): δ ppm 11.70 (s, 1H), 9.00 (s, 1H), 7.44 (d, J=7.5 Hz, 2H), 7.37-7.28 (m, 3H), 7.18 (dd, J₁=J₂=9.0 Hz, 1H), 6.96-6.93 (m, 1H), 6.65-6.62 (m, 1H), 4.42 (s, 2H). MS (ESI): m/z 378.8 [M+H]⁺.

Example 103/1 to 103/3

The following Examples were prepared similar as described for Example 103 using the appropriate Intermediates and aniline building blocks.

| # | Int. # | Structure | Analytical data |
|---|--------|-----------|-----------------|
| 103/1 | Int 101/1 | 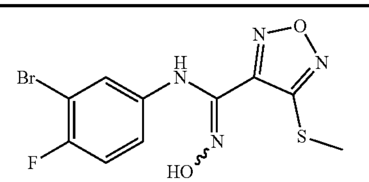 | ¹H NMR (500 MHz, DMSO-d₆): δ ppm 11.74 (s, 1H), 8.98 (s, 1H), 7.18 (dd, J1 = J2 = 9.0 Hz, 1H), 7.11-7.09 (m, 1H), 6.72-6.69 (m, 1H), 2.62 (m, 3H). MS (ESI): m/z 346.7 [M + H]⁺. |
| 103/2 | Int 101/2 | 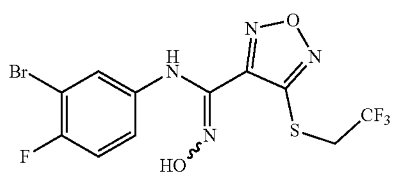 [SMILES: ON=C(Nc1ccc(F)c(Br)c1)c1nonc1SCC(F)(F)F] | ¹H NMR (500 MHz, DMSO-d₆): δ ppm 11.82 (s, 1H), 9.02 (s, 1H), 7.21-7.18 (m, 1H), 7.12-7.10 (m, 1H), 6.79-6.76 (m, 1H), 4.26 (q, J = 10.5 Hz, 2H). MS (ESI): m/z 414.9 [M + H]⁺. |
| 103/3 | Int 101/3 | 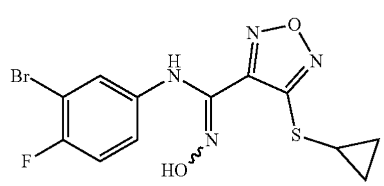 [SMILES: ON=C(Nc1ccc(F)c(Br)c1)c1nonc1SC1CC1] | ¹H NMR (500 MHz, DMSO-d₆): δ ppm 11.69 (s, 1H), 8.97 (s, 1H), 7.20-7.17 (m, 1H), 7.08-7.06 (m, 1H), 6.72-6.69 (m, 1H), 2.44-2.41 (m, 1H), 1.13-1.09 (m, 2H), 0.69-0.66 (m, 2H) MS (ESI): m/z 373.0 [M + H]⁺. |

-continued

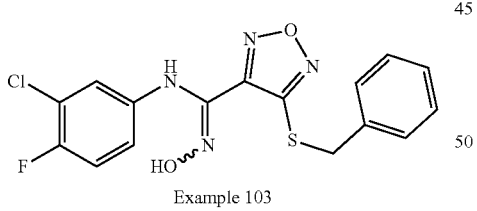

Example 103

To a solution of 4-(benzylthio)—N-hydroxy-1,2,5-oxadiazole-3-carbimidoyl chloride (Int 101) (200 mg, 0.74 mmol) and 3-chloro-4-fluoroaniline (128 mg, 0.88 mmol) in H₂O/THF (1:1, 40 mL) was added NaHCO₃ (74 mg, 0.88 mmol). The mixture was stirred at 60° C. for 2 h. The mixture was diluted with EtOAc (50 mL). The organic layer was washed with water (30 mL) and brine (30 mL), dried over anhydrous Na₂SO₄, filtered and concentrated to dryness. The residue

Example 104

4-(Benzylsulfonyl)-N-(3-chloro-4-fluorophenyl)-N'-hydroxy-1,2,5-oxadiazole-3-carboximidamide (104)

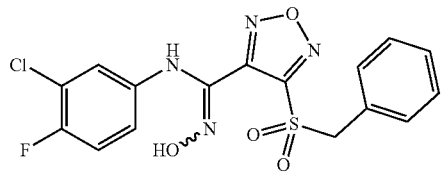 [SMILES: O=S(=O)(Cc1ccccc1)c1nonc1C(=NO)Nc1ccc(F)c(Cl)c1]

To a solution of 4-(benzylthio)—N-(3-chloro-4-fluorophenyl)-N'-hydroxy-1,2,5-oxadiazole-3-carboximidamide (Example 103) (100 mg, 0.26 mmol) in DCM (10 mL) at 0° C. was added MCPBA (180 mg, 1.04 mmol). The mixture was stirred at rt for 2 h. Water (100 mL) was added and the mixture was extracted with EtOAc (3×50 mL). The combined organic layers were washed with brine (50 mL), dried over anhydrous Na₂SO₄, filtered and concentrated to dryness. The residue was purified by HPLC to give the title compound as a white solid. ¹H NMR (500 MHz, CD₃OD):

δ ppm 7.42-7.33 (m, 5H), 7.08-7.00 (m, 2H), 6.74-6.70 (m, 1H), 5.15 (s, 2H). MS (ESI): m/z 410.8 [M+H]$^+$.

Example 105

N-(3-Bromo-4-fluorophenyl)-N'-hydroxy-4-(methylsulfinyl)-1,2,5-oxadiazole-3-carboximidamide (105)

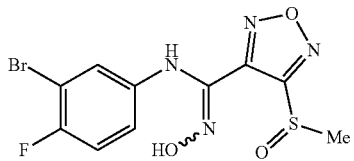 [SMILES: CS(=O)c1nonc1C(=NO)Nc1ccc(F)c(Br)c1]

To a solution of N-(3-bromo-4-fluorophenyl)-N'-hydroxy-4-(methylthio)-1,2,5-oxadiazole-3-carboximidamide (Example 103/1) (236 mg, 0.68 mmol) in DCM (8 mL) was added m-CPBA (85%, 138 mg, 0.68 mmol). The mixture was stirred at rt for 2 h. The mixture was diluted with DCM (20 mL) and aqueous Na$_2$SO$_3$ (10 mL). The organic layer was washed with aqueous NaHCO$_3$ (10 mL), water (20 mL) and brine (20 mL), dried over anhydrous Na$_2$SO$_4$, filtered and concentrated to dryness. The residue was purified by HPLC to give the title compound as a white solid. $^1$H NMR (500 MHz, CD$_3$OD): δ ppm 11.84 (s, 1H), 9.01 (s, 1H), 7.26-7.24 (m, 1H), 7.20 (dd, J$_1$=J$_2$=10.5 Hz, 1H), 6.93-6.90 (m, 1H), 3.17 (s, 3H). MS (ESI): m/z 362.8 [M+H]$^+$.

Example 106

N-(3-Bromo-4-fluorophenyl)-N'-hydroxy-4-(S-methylsulfonimidoyl)-1,2,5-oxadiazole-3-carboximidamide (106)

Step 1: N-((4-(N-(3-bromo-4-fluorophenyl)-N'-hydroxycarbamimidoyl)-1,2,5-oxadiazol-3-yl)(methyl)(oxo)-16-sulfaneylidene)-2,2,2-trifluoroacetamide (106a)

To a solution of N-(3-Bromo-4-fluorophenyl)-N'-hydroxy-4-(methylsulfinyl)-1,2,5-oxadiazole-3-carboximidamide (Example 105) (213 mg, 0.59 mmol), 2,2,2-trifluoroacetamide (133 mg, 1.18 mmol), MgO (95 mg, 2.36 mmol), (diacetoxyiodo)benzene (475 mg, 1.48 mmol) in DCM (8 mL) was added Rh$_2$(AcO)$_4$ (5 mg) under Ar. The mixture was stirred at 40° C. overnight. The mixture was diluted with DCM (20 mL). The organic layer was washed with water (20 mL) and brine (20 mL), dried over anhydrous Na$_2$SO$_4$, filtered and concentrated to dryness. The residue was purified by column chromatography (PE/EtOAc=3:1) to give the title compound as a white solid.

Step 2: N-(3-Bromo-4-fluorophenyl)-N'-hydroxy-4-(S-methylsulfonimidoyl)-1,2,5-oxadiazole-3-carboximidamide (106)

To a solution of N-((4-(N-(3-bromo-4-fluorophenyl)-N'-hydroxycarbamimidoyl)-1,2,5-oxadiazol-3-yl)(methyl)(oxo)-16-sulfaneylidene)-2,2,2-trifluoroacetamide (106a) (97 mg, 0.20 mmol) in MeOH (3 mL) was added K$_2$O0$_3$ (69 mg, 0.50 mmol). The mixture was stirred at rt for 1 h. The mixture was diluted with EtOAc (20 mL). The organic layer was washed with water (20 mL) and brine (20 mL), dried over anhydrous Na$_2$SO$_4$, filtered and concentrated to dryness. The residue was purified by HPLC to give the title compound as a white solid. $^1$H NMR (500 MHz, DMSO-d$_6$): δ ppm 11.96 (s, 1H), 9.22 (s, 1H), 7.18-7.12 (m, 2H), 6.69-6.60 (m, 1 H), 3.53 (s, 3H). MS (ESI): m/z 380.0 [M+H]$^+$.

Example 107

N-(2-((4-(N-(3-(Difluoromethyl)-4-fluorophenyl)-N'-hydroxycarbamimidoyl)-1,2,5-oxadiazol-3-yl)thio)ethyl)-2,3-dihydroxypropanamide (107)

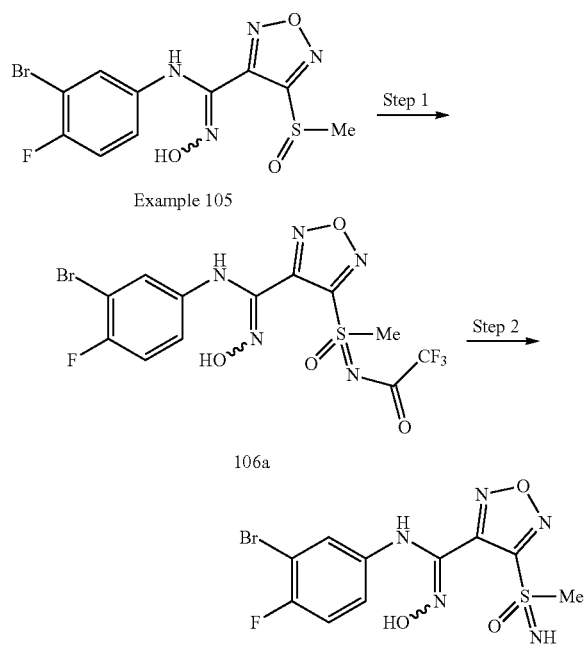

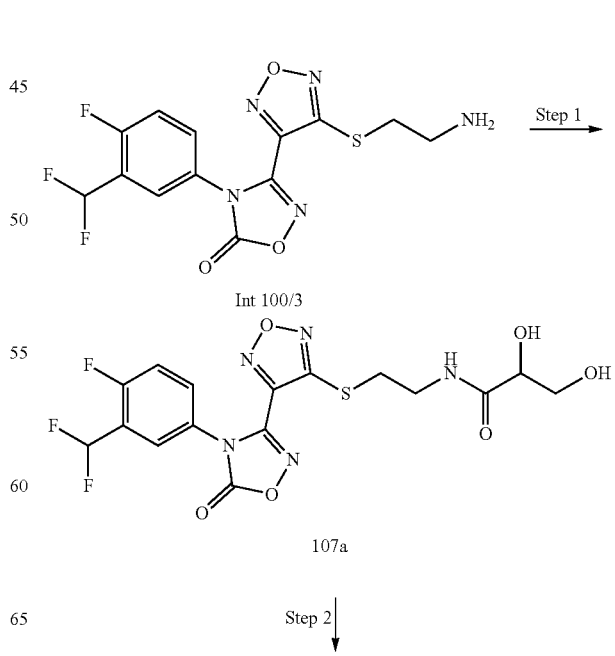

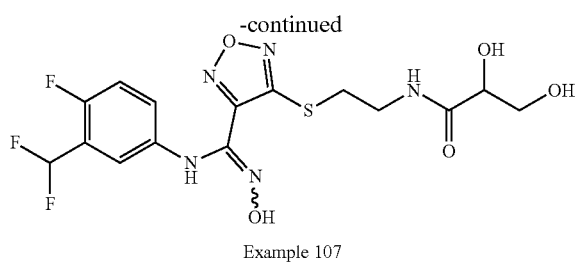

Example 107

Step 1: N-(2-((4-(4-(3-(Difluoromethyl)-4-fluorophenyl)-5-oxo-4,5-dihydro-1,2,4-oxadiazol-3-yl)-1,2,5-oxadiazol-3-yl)thio)ethyl)-2,3-dihydroxypropanamide (107a)

To a mixture of 2,3-dihydroxypropanoic acid (83 mg, 0.78 mmol), HATU (296 mg, 0.78 mmol) and Et₃N (105 mg, 1.04 mmol) in DCM (20 mL) 3-(4-((2-aminoethyl)thio)-1,2,5-oxadiazol-3-yl)-4-(3-(difluoromethyl)-4-fluorophenyl)-1,2,4-oxadiazol-5(4H)-one (Int 100/3) (170 mg, 0.52 mmol) was added and the mixture was stirred at rt overnight. The mixture was concentrated to dryness and the residue was dissolved in DCM (50 mL). The organic layer was washed with water (2×50 mL), dried over anhydrous Na₂SO₄, filtered and concentrated to dryness. The residue was purified by column chromatography (EA: PE=1: 2) to give the title compound as a yellow solid.

Step 2: N-(2-((4-(N-(3-(Difluoromethyl)-4-fluorophenyl)-N'-hydroxycarbamimidoyl)-1,2,5-oxadiazol-3-yl)thio)ethyl)-2,3-dihydroxypropanamide (107)

To a solution of N-(2-((4-(4-(3-(difluoromethyl)-4-fluorophenyl)-5-oxo-4,5-dihydro-1,2,4-oxadiazol-3-yl)-1,2,5-oxadiazol-3-yl)thio)ethyl)-2,3-dihydroxypropanamide (107a) (152 mg, 0.33 mmol) in MeOH (3 mL) aqueous NaOH solution was added (1M, 0.5 mL) at rt and the mixture was stirred at rt overnight. Water was added and the mixture was extracted with EtOAc (20 mL). The combined organic layers were washed with brine (20 mL), dried over anhydrous Na₂SO₄, filtered and concentrated to dryness. The residue was purified by HPLC to give the title compound as a white solid. $^1$H NMR (500 MHz, CD₃OD): δ ppm 7.10-6.80 (m, 4H), 4.09-4.07 (m, 1H), 3.79-3.76 (m, 1H), 3.71-3.68 (m, 1H), 3.65-3.61 (m, 2H), 3.34-3.32 (m, 2H). MS (ESI): m/z 436.0 [M+H]⁺.

Examples 107/1 to 107/41

The following Examples were prepared similar as described for Example 107 using the appropriate Intermediates and carboxylic acid building blocks.

| # | Int. # | Structure | Analytical data |
|---|---|---|---|
| 107/1 | Int 100/3 | 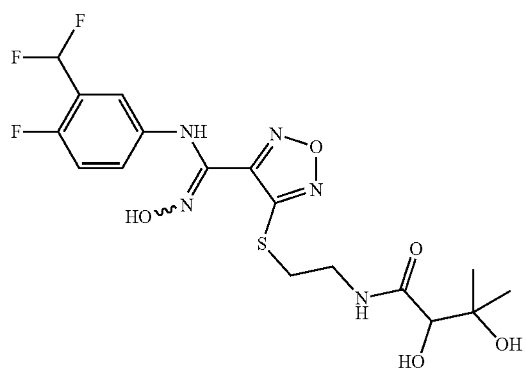 [SMILES: CC(C)(O)C(O)C(=O)NCCSc1nonc1C(=NO)Nc1ccc(F)c(C(F)F)c1] | $^1$H NMR (500 MHz, DMSO-d₆): δ ppm 11.70 (br s, 1H), 9.02 (s, 1H), 8.16-8.14 (m, 1H), 7.22-6.87 (m, 3H), 5.66 (d, 1H, J = 6.0 Hz), 4.69 (s, 1H), 3.63 (d, J = 5.5 Hz, 1H), 3.53-3.46 (m, 2H), 3.30-3.27 (m, 2H), 1.08 (s, 3H), 1.05 (s, 3H). MS (ESI): m/z 464.0 [M + H]⁺. |
| 107/2 | Int 100/12 | 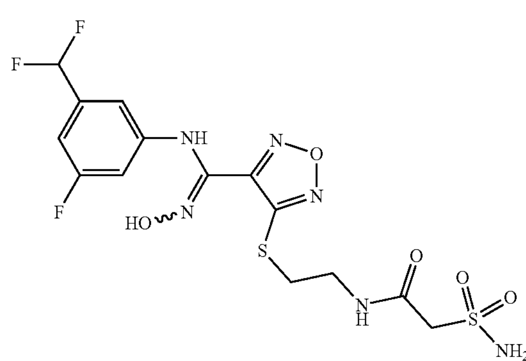 [SMILES: NS(=O)(=O)CC(=O)NCCSc1nonc1C(=NO)Nc1cc(F)cc(C(F)F)c1] | $^1$H NMR (500 MHz, DMSO-d₆): δ ppm 12.02 (s, 1H), 9.27 (s, 1H), 8.49 (t, J = 5.5 Hz, 1H), 7.05-6.66 (m, 6H), 3.89 (s, 2H), 3.52-3.48 (m, 2H), 3.28 (t, J = 6.5 Hz, 2H). MS (ESI): m/z 469.0 [M + H]⁺. |

| # | Int. # | Structure | Analytical data |
|---|---|---|---|
| 107/3 | Int 100/4 | 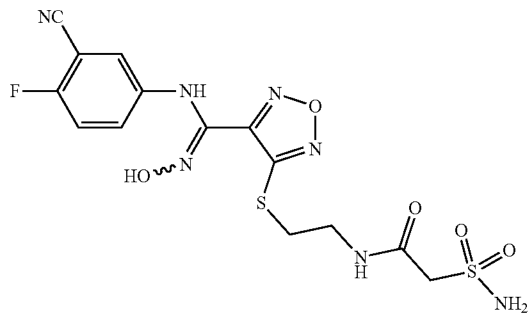 [SMILES: N#Cc1cc(NC(=NO)c2nonc2SCCNC(=O)CS(N)(=O)=O)ccc1F] | ¹H NMR (500 MHz, DMSO-d₆): δ ppm 11.91 (s, 1H), 9.14 (s, 1H), 8.49 (t, J = 5.5 Hz, 1H), 7.37-7.33 (m, 1H), 7.25-7.23 (m, 1H), 7.13-7.10 (m, 1H), 6.95 (s, 2H), 3.88 (s, 2H), 3.52-3.49 (m, 2H), 3.27 (t, J = 6.5 Hz, 2H). MS (ESI): m/z 444.0 [M + H]⁺. |
| 107/4 | Int 100/6 | 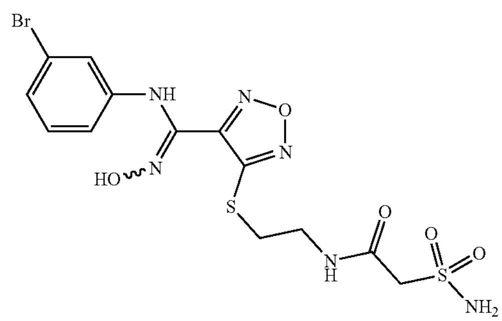 [SMILES: NS(=O)(=O)CC(=O)NCCSc1nonc1C(=NO)Nc1cccc(Br)c1] | ¹H NMR (500 MHz, DMSO-d₆): δ ppm 11.83 (s, 1H), 9.04 (s, 1H), 8.51-8.48 (m, 1H), 7.13-7.05 (m, 2H), 6.98-6.95 (m, 2H), 6.64-6.61 (m, 1H), 3.88 (s, 2H), 3.51-3.47 (m, 2H), 3.27 (t, J = 8.0 Hz, 2H). MS (ESI): m/z 481.0 [M + H]⁺. |
| 107/5 | Int 100/5 | 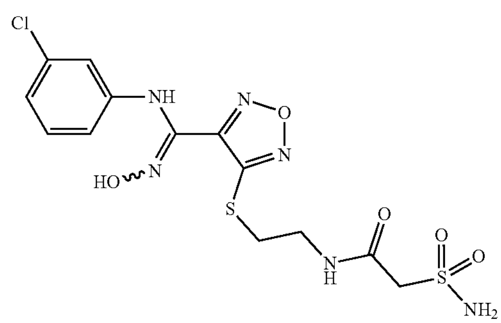 [SMILES: NS(=O)(=O)CC(=O)NCCSc1nonc1C(=NO)Nc1cccc(Cl)c1] | ¹H NMR (500 MHz, DMSO-d₆): δ ppm 11.81 (s, 1H), 9.04 (s, 1H), 8.48 (t, J = 5.5 Hz, 1H), 7.19-7.15 (m, 1H), 6.95-6.93 (m, 1H), 6.83-6.82 (m, 1H), 6.60-6.58 (m, 2H), 3.88 (s, 2H), 3.51-3.47 (m, 2H), 3.27 (t, J = 6.5 Hz, 2H). MS (ESI): m/z 435.0 [M + H]⁺. |
| 107/6 | Int 100/3 | 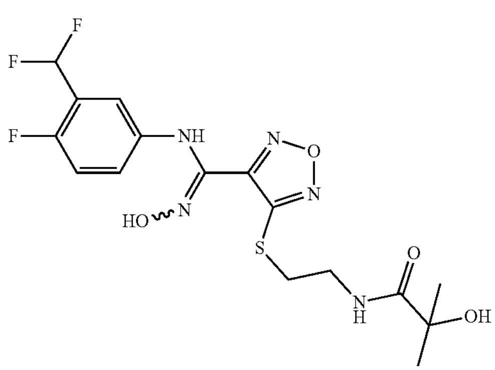 [SMILES: CC(C)(O)C(=O)NCCSc1nonc1C(=NO)Nc1ccc(F)c(C(F)F)c1] | ¹H NMR (500 MHz, DMSO-d₆): δ ppm 11.70 (s, 1H), 9.03 (s, 1H), 7.99-7.97 (m, 1H) 7.23-6.90 (m, 4H), 5.34 (br s, 1H) 3.48-3.44 (m, 2H), 3.29-3.26 (m, 2H), 1.22 (s, 6H). MS (ESI): m/z 434.0 [M + H]⁺. |

| # | Int. # | Structure | Analytical data |
|---|---|---|---|
| 107/7 | Int 100/3 | 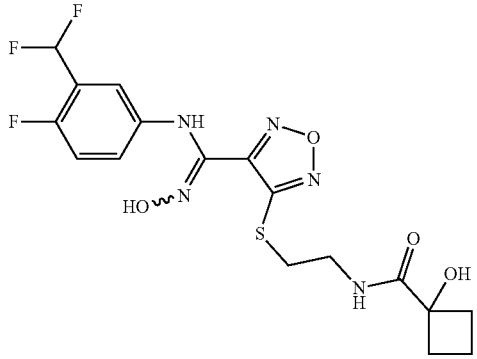 [SMILES: O=C(NCCSc1nonc1C(=NO)Nc1ccc(F)c(C(F)F)c1)C1(O)CCC1] | $^1$H NMR (500 MHz, DMSO-d$_6$): δ ppm 11.68 (s, 1H), 9.01 (s, 1H), 7.86-7.84 (m, 1H) 7.23-6.91 (m, 4H), 6.00 (s, 1H), 3.49-3.46 (m, 2H), 3.32-3.26 (m, 2H), 2.38-2.33 (m, 2H), 2.04-1.98 (m, 2H), 1.75-1.70 (m, 2H). MS (ESI): m/z 446.1 [M + H]$^+$. |
| 107/8 | Int 100/3 | 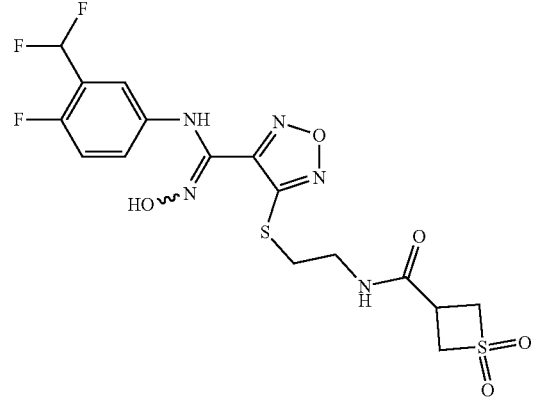 [SMILES: O=C(NCCSc1nonc1C(=NO)Nc1ccc(F)c(C(F)F)c1)C1CS(=O)(=O)C1] | $^1$H NMR (500 MHz, DMSO-d$_6$): δ ppm 11.71 (s, 1H), 9.03 (s, 1H), 8.57-8.55 (m, 1H) 7.23-6.89 (m, 4H), 4.31-4.23 (m, 4H), 3.50-3.47 (m, 2H), 3.30-3.24 (m, 3H). MS (ESI): m/z 480.0 [M + H]$^+$. |
| 107/9 | Int 100/3 | 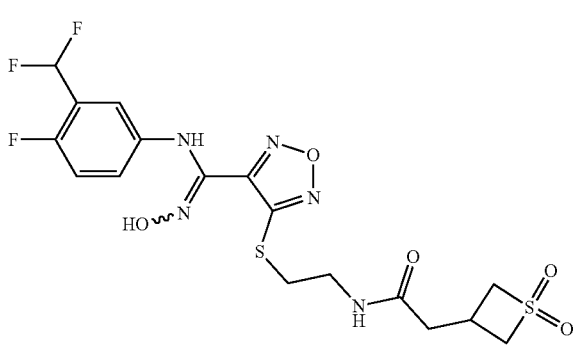 [SMILES: O=C(CC1CS(=O)(=O)C1)NCCSc1nonc1C(=NO)Nc1ccc(F)c(C(F)F)c1] | $^1$H NMR (500 MHz, DMSO-d$_6$): δ ppm 11.71 (s, 1H), 9.03 (s, 1H), 8.31-8.29 (m, 1H) 7.22-6.90 (m, 4H), 4.28-4.22 (m, 2H), 3.86-3.83 (m, 2H), 3.45-3.41 (m, 2H), 3.24-3.21 (m, 2H), 2.77-2.73 (m, 1H), 2.51-2.50 (m, 2H). MS (ESI): m/z 480.0 [M + H]$^+$. |
| 107/10 | Int 100/11 | 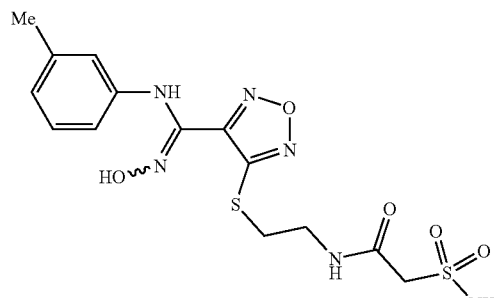 | $^1$H NMR (500 MHz, DMSO-d$_6$): δ ppm 11.15 (s, 1H), 8.74 (s, 1H), 8.49 (t, J = 5.5Hz, 1H), 7.05-7.02 (m, 1H), 6.94 (br s, 2H), 6.74-6.73 (m, 1H), 6.59 (s, 1H), 6.47-6.45 (m, 1H), 3.88 (s, 2H), 3.49-3.45 (m, 2H), 3.27-3.24 (m, 2H), 2.19 (s, 3H). MS (ESI): m/z 414.9 [M + H]$^+$. |

| # | Int. # | Structure | Analytical data |
|---|---|---|---|
| 107/11 | Int 100/10 | 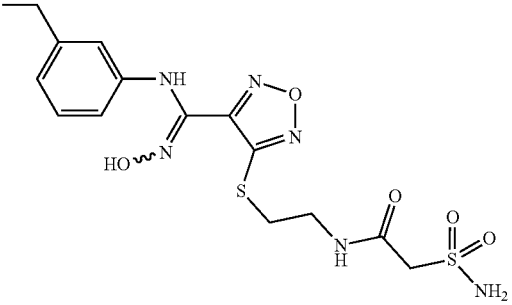 | $^1$H NMR (500 MHz, DMSO-d$_6$): δ ppm 11.64 (s, 1H), 8.93 (s, 1H), 8.49 (t, J = 5.5 Hz, 1H), 7.22-7.19 (m, 1H), 7.98-7.92 (m, 3H), 6.80 (s, 1H), 6.69-6.68 (m, 1H), 5.31 (d, J = 47.5 Hz, 2H), 3.88 (s, 2H), 3.49-3.46 (m, 2H), 3.37-3.25 (m, 2H). MS (ESI): m/z 433.0 [M + H]$^+$. |
| 107/12 | Int 100/7 | 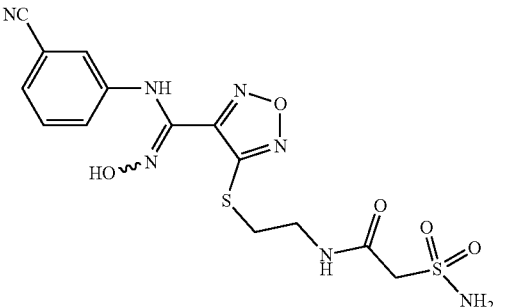 | $^1$H NMR (500 MHz, DMSO-d$_6$): δ ppm 11.96 (s, 1H), 9.20 (s, 1H), 8.50-8.48 (m, 1H), 7.39-7.33 (m, 2H), 7.16 (s, 1H), 7.01-6.95 (m, 3H), 3.88 (s, 2H), 3.52-3.48 (m, 2H), 3.28-3.26 (m, 2H). MS (ESI): m/z 426.0 [M + H]$^+$. |
| 107/13 | Int 100/7 | 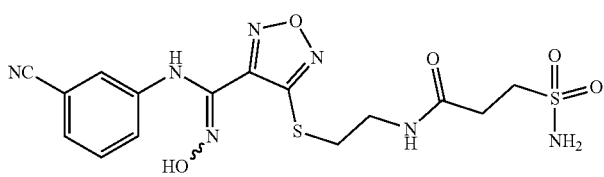 [SMILES: N#Cc1cccc(NC(=NO)c2nonc2SCCNC(=O)CCS(N)(=O)=O)c1] | $^1$H NMR (500 MHz, DMSO-d$_6$): δ ppm 11.94 (s, 1H), 9.20 (s, 1H), 8.37-8.35 (m, 1H), 7.39-7.32 (m, 2H), 7.16 (s, 1H), 7.01-6.99 (m, 1H), 6.86 (br s, 2H), 3.47-3.43 (m, 2H), 3.26-3.23 (m, 2H), 3.19-3.16 (m, 2H), 2.55-2.51 (m, 2H). MS (ESI): m/z 440.0 [M + H]$^+$. |
| 107/14 | Int 100 | 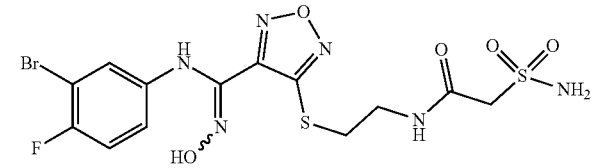 [SMILES: NS(=O)(=O)CC(=O)NCCSc1nonc1C(=NO)Nc1ccc(F)c(Br)c1] | $^1$H NMR (500 MHz, DMSO-d$_6$): δ ppm 11.75 (s, 1H), 8.98 (s, 1H), 8.49-8.47 (m, 1H), 7.20-7.16 (m, 1H), 7.11-7.09 (m, 1H), 6.94 (br s, 2H), 6.71-6.68 (m, 1H), 3.87 (s, 2H), 3.50-3.48 (m, 2H), 3.28-3.25 (m, 2H). MS (ESI): m/z 496.9 [M + H]$^+$. |
| 107/15 | Int 100/5 | 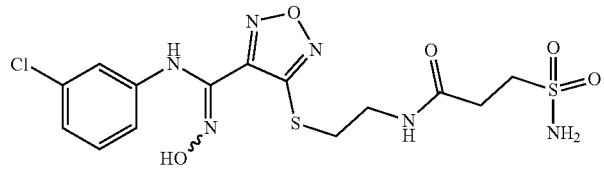 [SMILES: NS(=O)(=O)CCC(=O)NCCSc1nonc1C(=NO)Nc1cccc(Cl)c1] | $^1$H NMR (500 MHz, DMSO-d$_6$): δ ppm 11.81 (s, 1H), 9.05 (s, 1H), 8.37-8.35 (m, 1H), 7.19-7.16 (m, 1H), 6.95-6.93 (m, 1H), 6.87-6.83 (m, 3H), 6.60-6.58 (m, 1H), 3.46-3.43 (m, 2H), 3.26-3.24 (m, 2H), 3.19-3.17 (m, 2H), 2.55-2.52 (m, 2H). MS (ESI): m/z 448.9 [M + H]$^+$. |
| 107/16 | Int 100/3 | 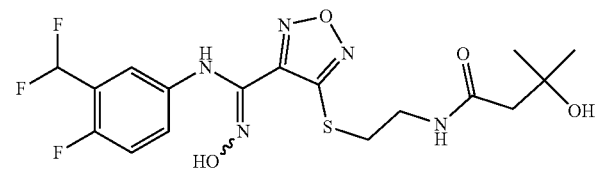 [SMILES: CC(C)(O)CC(=O)NCCSc1nonc1C(=NO)Nc1ccc(F)c(C(F)F)c1] | $^1$H NMR (500 MHz, DMSO-d$_6$): δ ppm 11.17 (s, 1H), 9.02 (s, 1H), 8.15-8.13 (m, 1H), 7.23-6.88 (m, 4H), 4.74 (s, 1H), 3.47-3.43 (m, 2H), 3.25-3.23 (m, 2H), 2.19 (s, 2H), 1.14 (s, 6H). MS (ESI): m/z 448.1 [M + H]$^+$. |
| 107/17 | Int 100/3 | 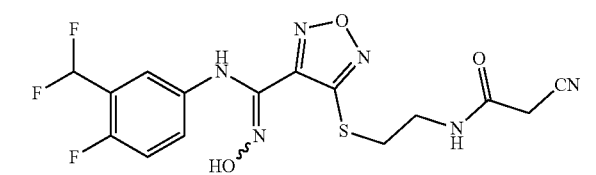 [SMILES: N#CCC(=O)NCCSc1nonc1C(=NO)Nc1ccc(F)c(C(F)F)c1] | $^1$H NMR (500 MHz, DMSO-d$_6$): δ ppm 11.71 (s, 1H), 9.02 (s, 1H), 8.55-8.53 (m, 1H), 7.23-6.88 (m, 4H), 3.64 (s, 2H), 3.49-3.45 (m, 2H), 3.27-3.24 (m, 2H). MS (ESI): m/z 415.1 [M + H]$^+$. |

-continued

| # | Int. # | Structure | Analytical data |
|---|---|---|---|
| 107/18 | Int 100/1 | 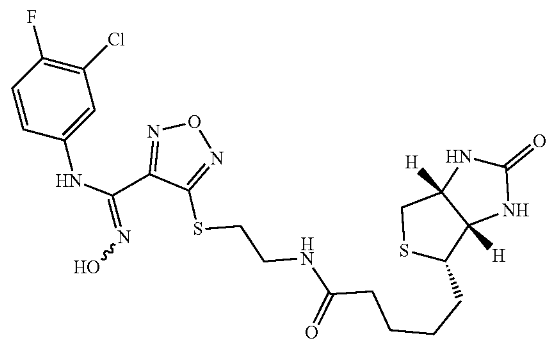 [SMILES: O=C(CCCC[C@@H]1SC[C@@H]2NC(=O)N[C@@H]21)NCCSc1nonc1C(=NO)Nc1ccc(F)c(Cl)c1] | $^1$H NMR (500 MHz, DMSO-d$_6$): δ ppm 11.75 (s, 1H), 9.00 (s, 1H), 8.11-8.07 (m, 1H), 7.23-7.17 (m, 1H), 7.00-6.97 (m, 1H), 6.69-6.65 (m, 1H), 6.41 (s, 1H), 6.36 (s, 1H), 4.31-4.27 (m, 1H), 4.13-4.09 (m, 1H), 3.44-3.40 (m, 2H), 3.24-3.21 (m, 2H), 3.09-3.05 (m, 1H), 2.81-2.78 (m, 1H), 2.57-2.54 (m, 1H), 2.08-2.05 (m, 2H), 1.57-1.44 (m, 4H), 1.30-1.29 (m, 2H). MS (ESI): m/z 558.1 [M + H]$^+$. |
| 107/19 | Int 100/2 | 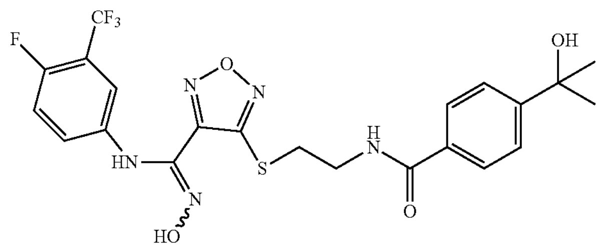 [SMILES: CC(C)(O)c1ccc(C(=O)NCCSc2nonc2C(=NO)Nc2ccc(F)c(C(F)(F)F)c2)cc1] | $^1$H NMR (500 MHz, DMSO-d$_6$): δ ppm 11.79 (s br, 1H), 9.13 (s, 1H), 8.70-8.68 (m,1H) 7.78 (d, J = 8.5 Hz, 2H), 7.54 (d, J = 8.5 Hz, 2H), 7.31-7.26 (m, 1H), 7.17-7.15 (m, 1H), 7.01-6.96 (m, 1H), 5.12 (s, 1H), 3.68-3.66 (m, 2H), 3.39-3.37 (m, 2H), 1.42 (s, 6H). MS (ESI): m/z 528.0 [M + H]$^+$. |
| 107/20 | Int 100/3 | 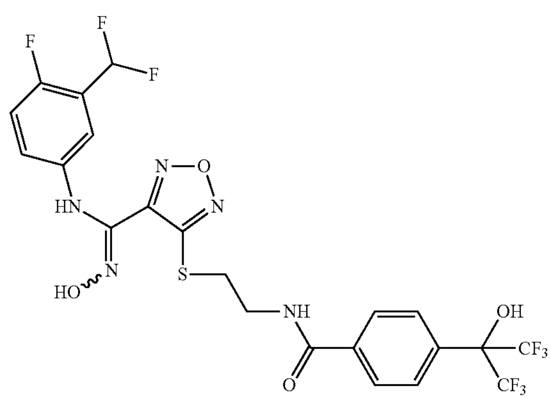 [SMILES: O=C(NCCSc1nonc1C(=NO)Nc1ccc(F)c(C(F)F)c1)c1ccc(C(O)(C(F)(F)F)C(F)(F)F)cc1] | $^1$H NMR (500 MHz, DMSO-d$_6$): δ ppm 11.68 (s br, 1H), 9.04 (s, 1H), 8.92-8.88 (m, 2H), 7.96-7.92 (m, 2H), 7.78 (d, J = 8.5 Hz, 2H), 7.22-6.87 (m, 4H), 3.70-3.66 (m, 2H), 3.40-3.37 (m, 2H). MS (ESI): m/z 618.0 [M + H]$^+$. |
| 107/21 | Int 100/2 | 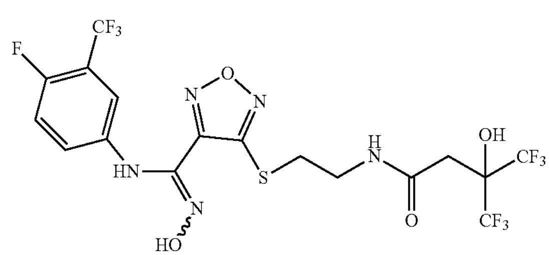 [SMILES: O=C(CC(O)(C(F)(F)F)C(F)(F)F)NCCSc1nonc1C(=NO)Nc1ccc(F)c(C(F)(F)F)c1] | $^1$H NMR (500 MHz, CD$_3$OD): δ ppm 7.19-7.11 (m, 2H), 7.05-7.00 (m, 1H), 3.64-3.61 (m, 2H), 3.32-3.30 (m, 2H), 2.81 (s, 2H). MS (ESI): m/z 574.0 [M + H]$^+$. |

| # | Int. # | Structure | Analytical data |
|---|---|---|---|
| 107/22 | Int 100/2, | 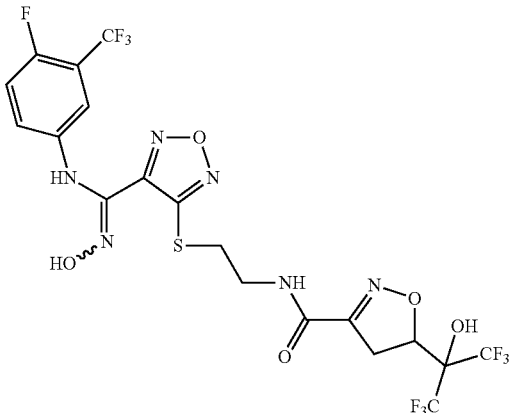 [SMILES: O=C(NCCSc1nonc1C(=NO)Nc1ccc(F)c(C(F)(F)F)c1)C1=NOC(C(O)(C(F)(F)F)C(F)(F)F)C1] | ¹H NMR (500 MHz, DMSO-d$_6$): δ ppm 11.84 (s, 1H), 9.14 (s, 1H), 8.85-8.82 (m, 1H), 8.71 (s, 1H), 7.32-7.28 (m, 1H), 7.17-7.14 (m, 1H), 7.00-6.98 (m, 1H), 5.28-5.24 (m, 1H), 3.48-3.33 (m, 6H). MS (ESI): m/z 629.0 [M + H]⁺. |
| 107/23 | Int 100/3 | 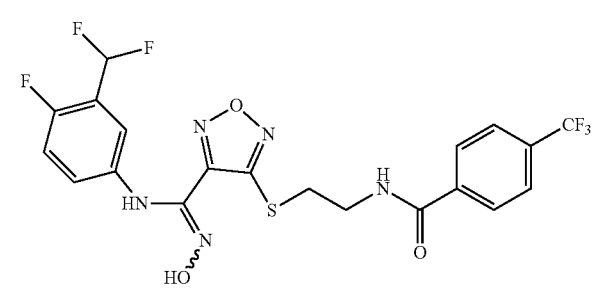 [SMILES: O=C(NCCSc1nonc1C(=NO)Nc1ccc(F)c(C(F)F)c1)c1ccc(C(F)(F)F)cc1] | ¹H NMR (500 MHz, DMSO-d$_6$): δ ppm 11.70 (s, 1H), 9.05-9.01 (m, 2H), 8.04 (d, J = 8 Hz, 2H), 7.88 (d, J = 8 Hz, 2H), 7.23-7.00 (m, 3H), 6.90-6.84 (m, 1H), 3.71-3.68 (m, 2H), 3.41-3.39 (m, 2H). MS (ESI): m/z 520.1 [M + H]⁺. |
| 107/24 | Int 100/3 | 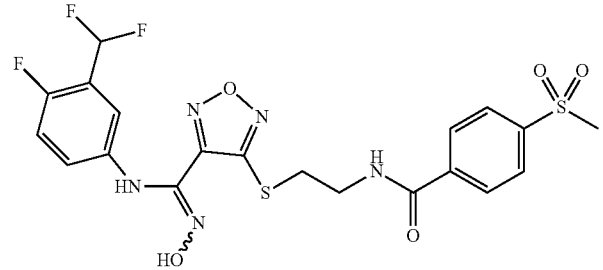 [SMILES: CS(=O)(=O)c1ccc(C(=O)NCCSc2nonc2C(=NO)Nc2ccc(F)c(C(F)F)c2)cc1] | ¹H NMR (500 MHz, DMSO-d$_6$): δ ppm 11.71 (s, 1H), 9.06-9.04 (m, 2H), 8.08-8.03 (m, 4H), 7.23-7.00 (m, 3H), 6.90-6.87 (m, 1H), 3.72-3.68 (m, 2H), 3.41-3.39 (m, 2H), 3.27 (s, 3H). MS (ESI): m/z 530.1 [M + H]⁺. |
| 107/25 | Int 100/3 | 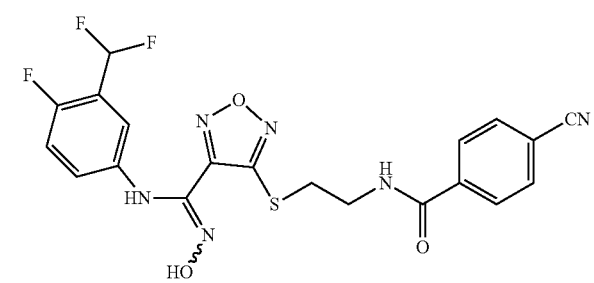 [SMILES: N#Cc1ccc(C(=O)NCCSc2nonc2C(=NO)Nc2ccc(F)c(C(F)F)c2)cc1] | ¹H NMR (500 MHz, DMSO-d$_6$): δ ppm 11.70 (s, 1H), 9.04-9.02 (m, 2H), 8.00-7.96 (m, 4H), 7.23-6.88 (m, 4H), 3.71-3.67 (m, 2H), 3.40-3.38 (m, 2H). MS (ESI): m/z 477.1 [M + H]⁺. |
| 107/26 | Int 100/3 | 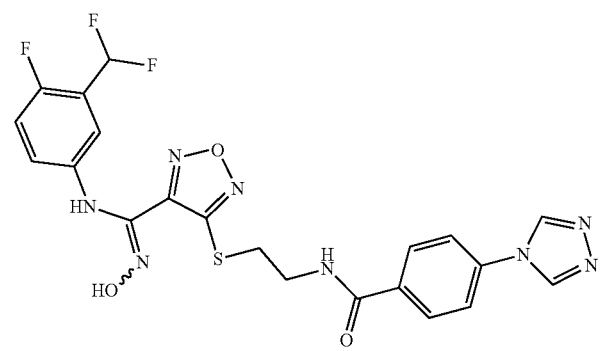 [SMILES: O=C(NCCSc1nonc1C(=NO)Nc1ccc(F)c(C(F)F)c1)c1ccc(-n2cnnc2)cc1] | ¹H NMR (500 MHz, DMSO-d$_6$): δ ppm 11.70 (s, 1H), 9.23 (s, 2H), 9.04 (s, 1H), 8.92-8.90 (m, 1H), 8.02 (d, J = 9 Hz, 2H), 7.86 (d, J = 9 Hz, 2H), 7.23-7.00 (m, 3H), 6.91-6.87 (m, 1H), 3.71-3.67 (m, 2H), 3.40-3.38 (m, 2H). MS (ESI): m/z 519.2 [M + H]⁺. |

| # | Int. # | Structure | Analytical data |
|---|---|---|---|
| 107/27 | Int 100/3 | 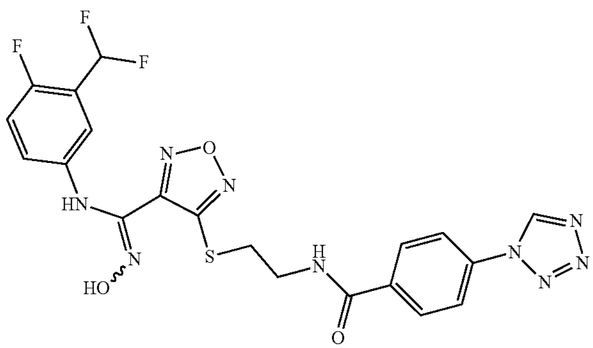 [SMILES: O=C(NCCSc1nonc1C(=NO)Nc1ccc(F)c(C(F)F)c1)c1ccc(-n2cnnn2)cc1] | ¹H NMR (500 MHz, DMSO-d₆): δ ppm 11.71 (s, 1H), 10.19 (s, 1H), 9.05 (s, 1H), 9.01-8.97 (m, 1H), 8.11-8.05 (m, 4H), 7.23-7.00 (m, 3H), 6.91-6.88 (m, 1H), 3.73-3.69 (m, 2H), 3.43-3.40 (m, 2H). MS (ESI): m/z 520.1 [M + H]⁺. |
| 107/28 | Int 100/3 | 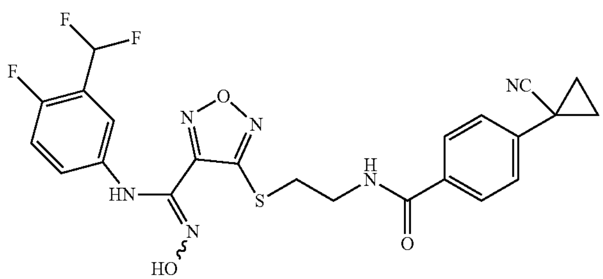 [SMILES: N#CC1(c2ccc(C(=O)NCCSc3nonc3C(=NO)Nc3ccc(F)c(C(F)F)c3)cc2)CC1] | ¹H NMR (500 MHz, DMSO-d₆): δ ppm 11.71 (s, 1H), 9.05 (s, 1H), 8.83-8.80 (m, 1H), 7.86 (d, J = 10.5 Hz, 2H), 7.42 (d, J = 10.5 Hz, 2H), 7.23-6.99 (m, 3H), 6.89-6.87 (m, 1H), 3.69-3.65 (m, 2H), 3.39-3.36 (m, 2H), 1.84-1.81 (m, 2H), 1.60-1.57 (m, 2H). MS (ESI): m/z 517.1 [M + H]⁺. |
| 107/29 | Int 100/3 | 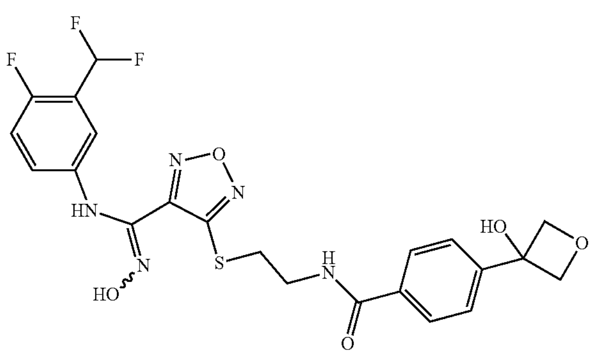 [SMILES: O=C(NCCSc1nonc1C(=NO)Nc1ccc(F)c(C(F)F)c1)c1ccc(C2(O)COC2)cc1] | ¹H NMR (500 MHz, DMSO-d₆): δ ppm 11.70 (s, 1H), 9.05 (s, 1H), 8.80-8.77 (m, 1H), 7.89-7.87 (m, 2H), 7.71-7.67 (m, 2H), 7.26-6.88 (m, 4H), 6.49 (s, 1H), 4.79 (d, J = 8.5 Hz, 2H), 4.68 (d, J = 8.5 Hz, 2H), 3.70-3.65 (m, 2H), 3.40-3.37 (m, 2H). MS (ESI): m/z 524.2 [M + H]⁺. |
| 107/30 | Int 100/3 | 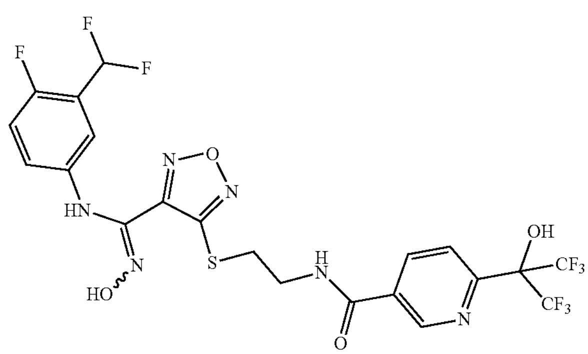 [SMILES: O=C(NCCSc1nonc1C(=NO)Nc1ccc(F)c(C(F)F)c1)c1ccc(C(O)(C(F)(F)F)C(F)(F)F)nc1] | ¹H NMR (500 MHz, DMSO-d₆): δ ppm 11.69 (s, 1H), 9.12-9.03 (m, 3H), 8.87 (s br, 1H), 8.38-8.36 (m, 1H), 7.99-7.98 (m, 1H), 7.23-6.88 (m, 4H), 3.72-3.69 (m, 2H), 3.41-3.38 (m, 2H). MS (ESI): m/z 619.1 [M + H]⁺. |
| 107/31 | Int 100/2 | 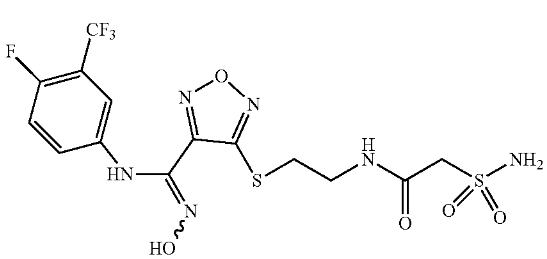 [SMILES: NS(=O)(=O)CC(=O)NCCSc1nonc1C(=NO)Nc1ccc(F)c(C(F)(F)F)c1] | ¹H NMR (500 MHz, DMSO-d₆): δ ppm 11.86 (s, 1H), 9.14 (s, 1H), 8.49-8.47 (m, 1H) 7.33-7.29 (m, 1H), 7.15-7.13 (m, 1H), 7.00-6.93 (m, 3H), 3.89 (s, 2H), 3.51-3.47 (m, 2H), 3.30-3.25 (m, 2H). MS (ESI): m/z 487.0 [M + H]⁺. |

| # | Int. # | Structure | Analytical data |
|---|---|---|---|
| 107/32 | Int 100/3 | 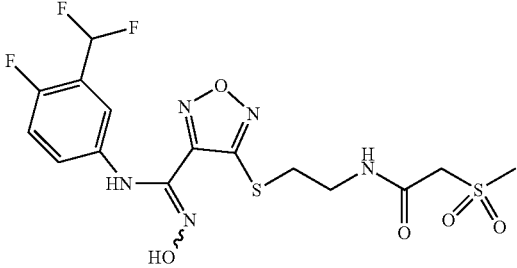 [SMILES: CS(=O)(=O)CC(=O)NCCSc1nonc1C(=NO)Nc1ccc(F)c(C(F)F)c1] | $^1$H NMR (500 MHz, DMSO-d$_6$): δ ppm 11.72 (s, 1H), 9.03 (s, 1H), 8.69-8.67 (m, 1H) 7.23-6.88 (m, 4H), 4.07 (s, 2H), 3.52-3.48 (m, 2H), 3.27-3.26 (m, 2H), 3.11 (s, 3H). MS (ESI): m/z 468.1 [M + H]$^+$. |
| 107/33 | Int 100/13 | 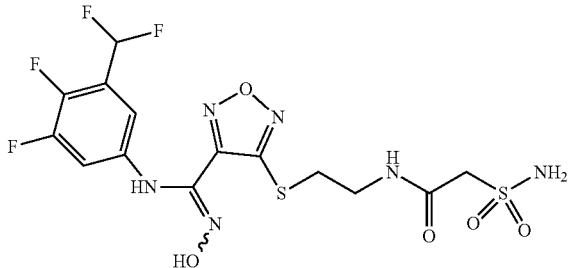 [SMILES: NS(=O)(=O)CC(=O)NCCSc1nonc1C(=NO)Nc1cc(F)c(F)c(C(F)F)c1] | $^1$H NMR (500 MHz, DMSO-d$_6$): δ ppm 11.98 (s, 1H), 9.20 (s, 1H), 8.49 (t, J = 5.5 Hz, 1H), 7.18 (t, J = 54 Hz, 1H), 6.99-6.94 (m, 3H), 6.79 (s, 1H), 3.88 (s, 2H), 3.52-3.48 (m, 2H), 3.28-3.25 (m, 2H). MS (ESI): m/z 486.9 [M + H]$^+$. |
| 107/34 | Int 100/17 | 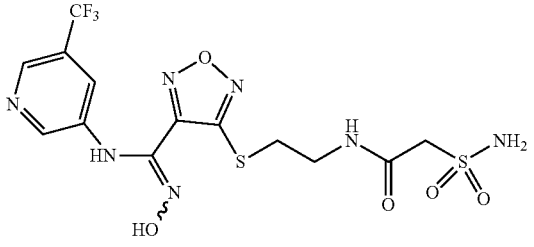 [SMILES: NS(=O)(=O)CC(=O)NCCSc1nonc1C(=NO)Nc1cncc(C(F)(F)F)c1] | $^1$H NMR (500 MHz, DMSO-d$_6$): δ ppm 12.14 (s br, 1H), 9.43 (s br, 1H), 8.51-8.46 (m, 2H), 8.33 (s, 1H), 7.42 (s, 1H), 6.95 (s br, 2H), 3.87 (2, 2H ), 3.53-3.49 (m, 2H), 3.30-3.26 (m, 2H). MS (ESI): m/z 469.9 [M + H]$^+$. |
| 107/35 | Int 100/2 | 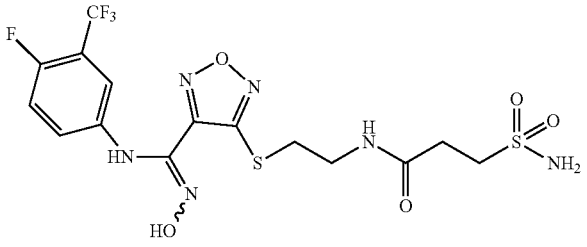 [SMILES: NS(=O)(=O)CCC(=O)NCCSc1nonc1C(=NO)Nc1ccc(F)c(C(F)(F)F)c1] | $^1$H NMR (500 MHz, DMSO-d$_6$): δ ppm 11.86 (s, 1H), 9.15 (s, 1H), 8.38-8.36 (m, 1H) 7.33-7.29 (m, 1H), 7.16-7.14 (m, 1H), 7.01-6.97 (m, 1H), 6.87 (s, 2H), 3.46-3.43 (m, 2H), 3.26-3.17 (m, 4H), 2.55-2.51 (m, 2H). MS (ESI): m/z 500.9 [M + H]$^+$. |
| 107/36 | Int 100/3 | 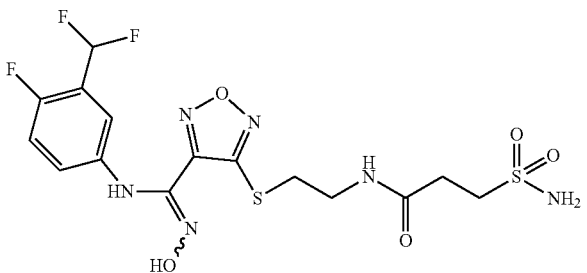 [SMILES: NS(=O)(=O)CCC(=O)NCCSc1nonc1C(=NO)Nc1ccc(F)c(C(F)F)c1] | $^1$H NMR (500 MHz, DMSO-d$_6$): δ ppm 11.71 (s, 1H), 9.03 (s, 1H), 8.36-8.34 (m, 1H), 7.20-7.16 (m, 1H), 7.12 (t, J = 54 Hz, 1H), 7.01-6.98 (m, 1H), 6.90-6.86 (m, 3H), 3.46-3.42 (m, 2H), 3.24-3.16 (m, 4H), 2.55-2.52 (m, 2H). MS (ESI): m/z 483.1 [M + H]$^+$. |

| # | Int. # | Structure | Analytical data |
|---|---|---|---|
| 107/37 | Int 100/3 | 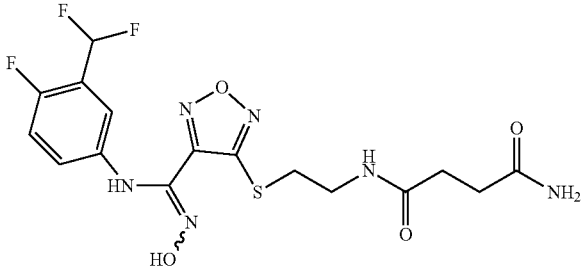 [SMILES: NC(=O)CCC(=O)NCCSc1nonc1C(=NO)Nc1ccc(F)c(C(F)F)c1] | ¹H NMR (400 MHz, CD₃OD): δ ppm 7.06-6.75 (m, 4H), 3.55-3.52 (m, 2H), 3.28-3.25 (m, 2H), 2.51-2.44 (m, 4H). MS (ESI): m/z 447.0 [M + 1]⁺. |
| 107/38 | Int 100/3 | 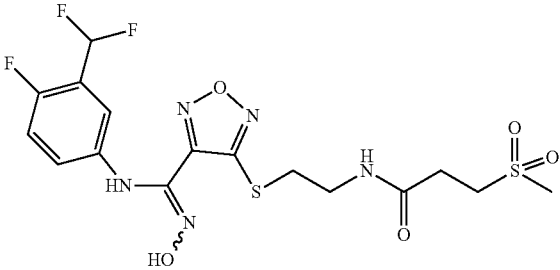 [SMILES: CS(=O)(=O)CCC(=O)NCCSc1nonc1C(=NO)Nc1ccc(F)c(C(F)F)c1] | ¹H NMR (300 MHz, CD₃OD): δ ppm 7.11-6.73 (m, 4H), 3.61-3.58 (m, 2H), 3.44-3.39 (m, 2H), 3.32-3.28 (m, 2H), 2.99 (s, 3H), 2.74-2.69 (m, 2H). MS (ESI): m/z 482.0 [M + 1]⁺. |
| 107/39 | Int 100/5 | 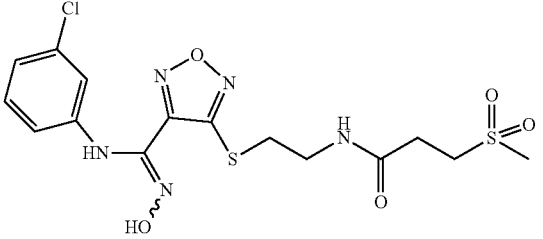 [SMILES: CS(=O)(=O)CCC(=O)NCCSc1nonc1C(=NO)Nc1cccc(Cl)c1] | ¹H NMR (500 MHz, DMSO-d₆): δ ppm 11.80 (s, 1H), 9.05 (s, 1H), 8.41-8.37 (m, 1H), 7.19-7.14 (m, 1H), 6.95-6.92 (m, 1H), 6.83 (s, 1H), 6.60-6.57 (m, 1H), 3.47-3.41 (m, 2H), 3.34-3.28 (m, 2H), 3.26-3.23 (m, 2H), 2.97 (s, 3H), 2.57-2.53 (m, 2H). MS (ESI): m/z 448.0 [M + 1]⁺. |
| 107/40 | Int 100/6 | 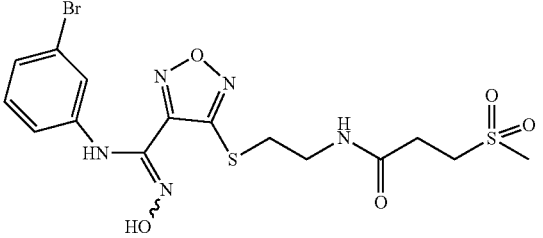 | ¹H NMR (500 MHz, DMSO-d₆): δ ppm 11.80 (s, 1H), 9.04 (s, 1H), 8.41-8.38 (m, 1H), 7.13-7.05 (m, 2H), 6.98 (s, 1H), 6.63-6.61 (m, 1H), 3.47-3.42 (m, 2H), 3.34-3.29 (m, 2H), 3.26-3.23 (m, 2H), 2.97 (s, 3H), 2.57-2.53 (m, 2H). MS (ESI): m/z 492.0 [M + 1]⁺. |
| 107/41 | Int 100 | 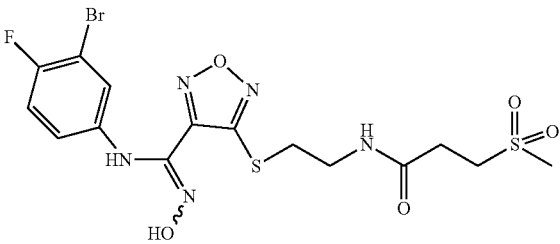 [SMILES: CS(=O)(=O)CCC(=O)NCCSc1nonc1C(=NO)Nc1ccc(F)c(Br)c1] | ¹H NMR (500 MHz, DMSO-d₆): δ ppm 11.73 (s, 1H), 8.98 (s, 1H), 8.40-8.37 (m, 1H), 7.19-7.15 (m, 1H), 7.11-7.08 (m, 1H), 6.72-6.69 (m, 1H), 3.47-3.23 (m, 6H), 2.98 (s, 3H), 2.57-2.53 (m, 2H). MS (ESI): m/z 509.9 [M + 1]⁺. |

Example 108

N-(3-(Difluoromethyl)-4-fluorophenyl)-N-hydroxy-4-((2-(3-hydroxy-3-methylazetidin-1-yl)ethyl)thio)-1,2,5-oxadiazole-3-carboximidamide (108)

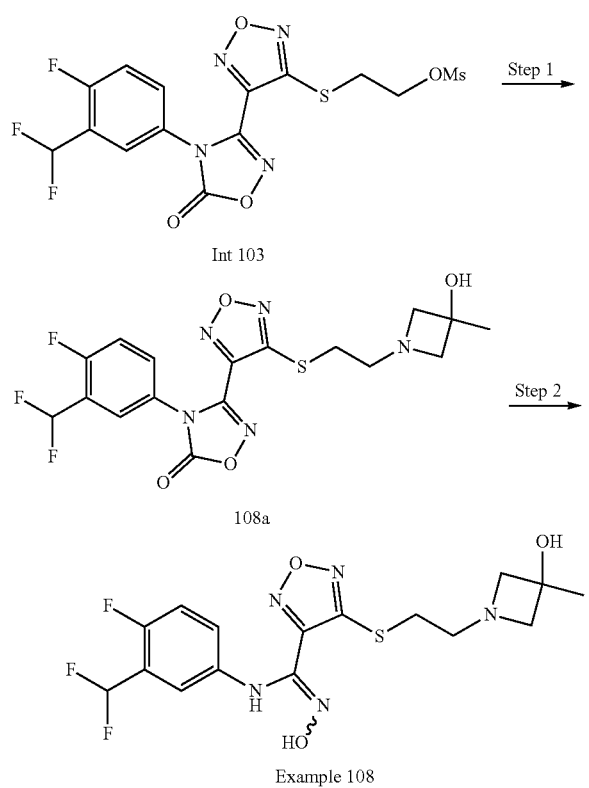

Step 1: 4-(3-(Difluoromethyl)-4-fluorophenyl)-3-(4-((2-(3-hydroxy-3-methylazetidin-1-yl)ethyl)thio)-1,2,5-oxadiazol-3-yl)-1,2,4-oxadiazol-5(4H)-one (108a)

To a suspension of 2-((4-(4-(3-(difluoromethyl)-4-fluorophenyl)-5-oxo-4,5-dihydro-1,2,4-oxadiazol-3-yl)-1,2,5-oxadiazol-3-yl)thio)ethyl methanesulfonate (Int 103) (140 mg, 0.31 mmol) in MeCN (2 mL) 3-methylazetidin-3-ol hydrochloride (45 mg, 0.37 mmol) and DIPEA (0.5 mL) were added and the mixture was heated to 60° C. for 24 h. The mixture was concentrated to dryness and the residue was purified by column chromatography (PE: EtOAc=5:1) to give the title compound as yellow solid.

Step 2: N-(3-(Difluoromethyl)-4-fluorophenyl)-N'-hydroxy-4-((2-(3-hydroxy-3-methylazetidin-1-yl)ethyl)thio)-1,2,5-oxadiazole-3-carboximidamide (108)

To a solution of 4-(3-(difluoromethyl)-4-fluorophenyl)-3-(4-((2-(3-hydroxy-3-methylazetidin-1-yl)ethyl)thio)-1,2,5-oxadiazol-3-yl)-1,2,4-oxadiazol-5(4H)-one (108a) (121 mg, 0.27 mmol) in THF (8 mL) 2M aqueous NaOH (0.5 mL) was added and the mixture was stirred at rt for 30 min. The mixture was extracted with EtOAc (3×20 mL). The combined organic layers were washed with brine (10 mL), dried over anhydrous Na₂SO₄, filtered and concentrated to dryness. The residue was purified by reversed HPLC to give the tilte compound as a white solid. ¹H NMR (500 MHz, CD₃OD): δ ppm 7.12-6.82 (m, 4H), 4.24-4.08 (m, 4H), 3.73-3.63 (m, 2H), 3.42 (t, J=7.0 Hz, 2H), 1.54 (s, 3H). MS (ESI): m/z 418.0 [M+H]⁺.

Examples 108/1 to 108/2

The following Examples were prepared similar as described for Example 108 using the appropriate Intermediates and amine building blocks.

| # | Int. # Amine | Structure | Analytical data |
|---|---|---|---|
| 108/1 | Int 103 ; azetidine-CO₂Me | azetidine-COOH product | ¹H NMR (500 MHz, CD₃OD): δ ppm 7.12-6.82 (m, 4H), 4.47-4.38 (m, 4H), 3.70 (t, J = 7.5 Hz, 3H), 3.44-3.41 (m, 2H). MS (ESI): m/z 432.0 [M + H]⁺. |

| # | Int. # Amine | Structure | Analytical data |
|---|---|---|---|
| 108/2 | Int 103 | 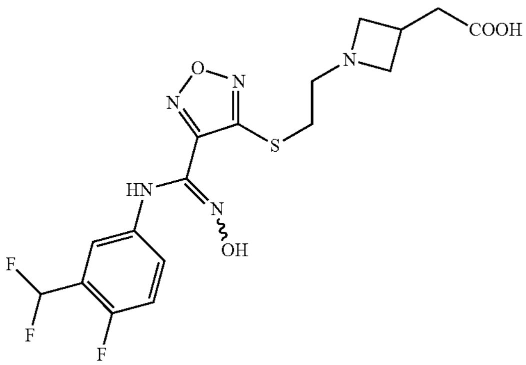 [SMILES: O=C(O)CC1CN(CCSc2nonc2C(=NO)Nc2ccc(F)c(C(F)F)c2)C1] | ¹H NMR (500 MHz, DMSO-d₆): δ ppm 11.77 (s, 1H), 9.06 (s, 1H), 7.24-6.90 (m, 4H), 4.20-4.12 (m, 2H), 3.89-3.81 (m, 2H), 3.55-3.51 (m, 2H), 3.37-3.33 (m, 2H), 3.02-2.97 (m, 2H), 2.68-2.65 (m, 2H). MS (ESI): m/z 446.2 [M + H]⁺. |

Example 109

4-((2-((2-Amino-3,4-dioxocyclobut-1-en-1-yl)amino)ethyl)sulfinyl)-N-(3-chloro-4-fluorophenyl)-N'-hydroxy-1,2,5-oxadiazole-3-carboximidamide (109)

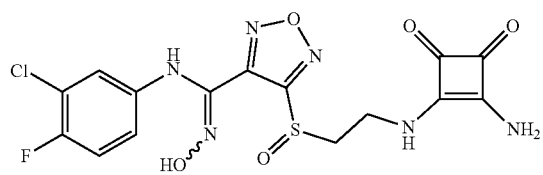 [SMILES: Nc1c(NCCS(=O)c2nonc2C(=NO)Nc2ccc(F)c(Cl)c2)c(=O)c1=O]

To a solution of 4-((2-((2-amino-3,4-dioxocyclobut-1-en-1-yl)amino)ethyl)thio)—N-(3-chloro-4-fluorophenyl)-N'-hydroxy-1,2,5-oxadiazole-3-carboximidamide (Example 102) (100 mg, 0.21 mmol) in DCM (3 mL) MCPBA (85%, 43 mg, 0.21 mmol) was added and the mixture was stirred at rt overnight. Aqueous Na₂SO₃ was added and the mixture was extracted with EtOAc (20 mL). The organic layer was washed with aqueous NaHCO₃ (20 mL) and brine (20 mL), dried over anhydrous Na₂SO₄, filtered and concentrated to dryness. The residue was purified by HPLC to give the title compound as a white solid. ¹H NMR (500 MHz, DMSO-d₆): δ ppm 11.82 (s, 1H), 9.07 (s, 1H), 7.24-7.21 (m, 1H), 7.15-7.13 (m, 1H), 6.91-6.88 (m, 1H), 6.72-6.68 (m, 2H), 3.63-3.27 (m, 4H). MS (ESI): m/z 442.9 [M+H]⁺.

Examples 109/1 to 109/3

The following Examples were prepared similar as described for Example 109 using the appropriate thioether starting materials.

| # | Starting material | Structure | Analytical data |
|---|---|---|---|
| 109/1 | Example 101/1 | 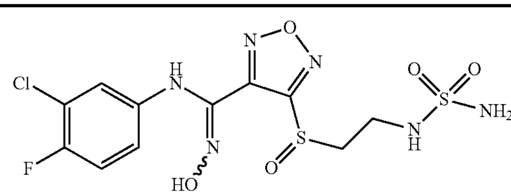 | ¹H NMR (500 MHz, DMSO-d₆): δ ppm 11.79 (s, 1H), 9.04 (s, 1H), 7.65-7.45 (m, 3H), 7.25-7.21 (m, 1H), 7.16-7.14 (m, 1H), 6.91-6.87 (m, 1H), 4.02-3.96 (m, 2H), 3.78-3.62 (m, 2H). MS (ESI): m/z 426.9 [M + H]⁺. |
| 109/2 | Example 103/3 | 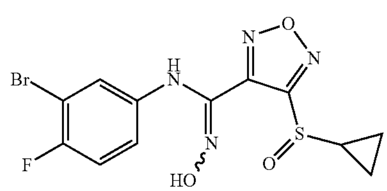 [SMILES: O=S(c1nonc1C(=NO)Nc1ccc(F)c(Br)c1)C1CC1] | ¹H NMR (500 MHz, DMSO-d₆): δ ppm 11.88 (s, 1H), 9.10 (s, 1H), 7.26-7.19 (m, 2H), 6.94-6.91 (m, 1H), 3.09-3.06 (m, 1H), 1.08-1.01 (m, 2H), 0.99-0.87 (m, 2H). MS (ESI): m/z 389.0 [M + H]⁺. |
| 109/3 | Example 103/2 | 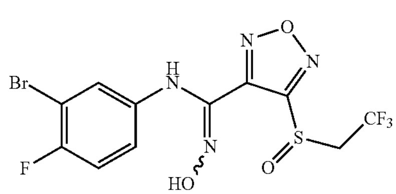 [SMILES: O=S(CC(F)(F)F)c1nonc1C(=NO)Nc1ccc(F)c(Br)c1] | ¹H NMR (500 MHz, DMSO-d₆): δ ppm 11.78 (s, 1H), 9.10 (s, 1H), 7.30-7.28 (m, 1H), 7.24-7.20 (m, 1H), 7.01-6.98 (m, 1H), 4.59-4.45 (m, 2H). MS (ESI): m/z 431.0 [M + H]⁺. |

Example 110

4-((2-((5-Amino-4H-1,2,4-triazol-3-yl)amino)ethyl)thio)—N-(3-(difluoromethyl)-4-fluorophenyl)-N'-hydroxy-1,2,5-oxadiazole-3-carboximidamide (110)

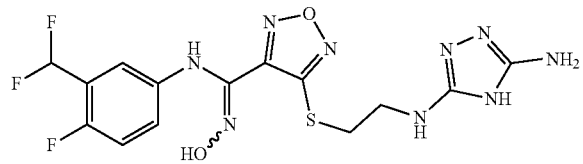 [SMILES: Nc1nnc(NCCSc2nonc2C(=NO)Nc2ccc(F)c(C(F)F)c2)[nH]1]

To a solution of 3-(4-((2-aminoethyl)thio)-1,2,5-oxadiazol-3-yl)-4-(3-(difluoromethyl)-4-fluorophenyl)-1,2,4-oxadiazol-5(4H)-one (Int 100/3) (194 mg, 0.52 mmol) in MeCN (3 mL) dimethyl cyanocarbonimidodithioate (114 mg, 0.78 mmol) was added at rt and the mixture was stirred at 45° C. for 30 min. A solution of hydrazine hydrate (25 mg, 0.50 mmol) in EtOH (2 mL) was added and the mixture was stirred at 90° C. for 1 h. Water was added and the mixture was extracted with EtOAc (20 mL). The organic layer was washed with brine (20 mL), dried over anhydrous $Na_2SO_4$, filtered and concentrated to dryness.

The residue was purified by HPLC to give the title compound as a white solid. $^1$H NMR (500 MHz, DMSO-$d_6$): δ ppm 11.71 (s, 1H), 9.04 (s, 1H), 7.47-6.87 (m, 7H), 3.52-3.48 (m, 2H), 3.39-3.36 (m, 2H). MS (ESI): m/z 430.1 [M+H]$^+$.

Example 111

N-(3-(Difluoromethyl)-4-fluorophenyl)-N'-hydroxy-4-((2-((5-methyl-1,3,4-oxadiazol-2-yl)amino)ethyl)thio)-1,2,5-oxadiazole-3-carboximidamide (111)

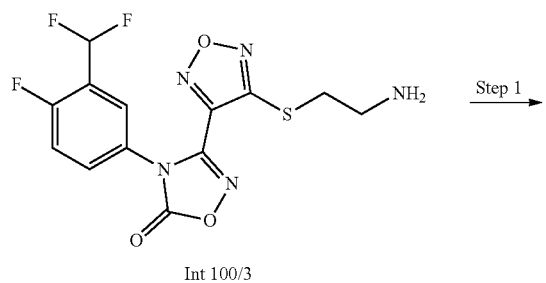

Int 100/3

Step 1 →

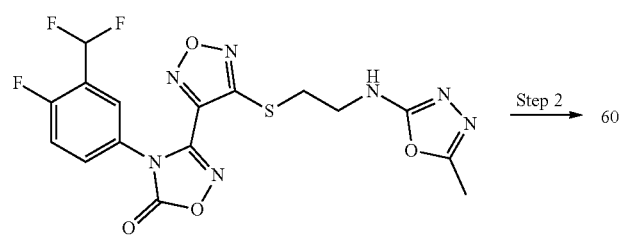

111a

Step 2 →

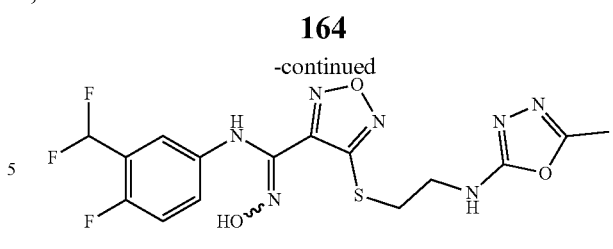

111

Step 1: 4-(3-(Difluoromethyl)-4-fluorophenyl)-3-(4-((2-((5-methyl-1,3,4-oxadiazol-2-yl)amino)ethyl)thio)-1,2,5-oxadiazol-3-yl)-1,2,4-oxadiazol-5(4H)-one (111a)

To a solution of 3-(4-((2-aminoethypthio)-1,2,5-oxadiazol-3-yl)-4-(3-(difluoromethyl)-4-fluorophenyl)-1,2,4-oxadiazol-5(4H)-one (Int 100/3) (164 mg, 0.44 mmol) in DMF (5 mL) 2-bromo-5-methyl-1,3,4-oxadiazole (86 mg, 0.53 mmol) and $Cs_2CO_3$ (286 mg, 0.88 mmol) were added and the mixture was stirred at 65° C. overnight. Water (20 mL) was added and the mixture was extracted with EtOAc (20 mL). The organic layer was washed with brine (20 mL), dried over anhydrous $Na_2SO_4$, filtered and concentrated to dryness. The residue was purified by column chromatography (EA: PE=1: 2) to give the title compound as a yellow solid.

Step 2: N-(3-(Difluoromethyl)-4-fluorophenyl)-N'-hydroxy-4-((2-((5-methyl-1,3,4-oxadiazol-2-yl)amino)ethyl)thio)-1,2,5-oxadiazole-3-carboximidamide (111)

To a solution of 4-(3-(difluoromethyl)-4-fluorophenyl)-3-(4-((2-((5-methyl-1,3,4-oxadiazol-2-yl)amino)ethyl)thio)-1,2,5-oxadiazol-3-yl)-1,2,4-oxadiazol-5(4H)-one (111a) (104 mg, 0.23 mmol) in MeOH (3 mL) aqueous NaOH (1M, 0.5 mL) was added and the mixture was stirred at rt overnight. Water was added and the mixture was extracted with EtOAc (20 mL). The organic layer was washed with brine (20 mL), dried over anhydrous $Na_2SO_4$, filtered and concentrated to dryness. The residue was purified by HPLC to give the title compound as a white solid. $^1$H NMR (500 MHz, DMSO-$d_6$): δ ppm 11.73 (s, 1H), 9.04 (s, 1H), 7.80-7.78 (m, 1H), 7.23-6.87 (m, 4H), 3.56-3.52 (m, 2H), 3.39-3.37 (m, 2H), 3.40-3.37 (m, 2H), 2.29 (s, 3H). MS (ESI): m/z 430.1 [M+H]$^+$.

Example 112

N-(3-(Difluoromethyl)phenyl)-N'-hydroxy-4-((2-(sulfamoylamino)ethyl)thio)-1,2,5-oxadiazole-3-carboximidamide (112)

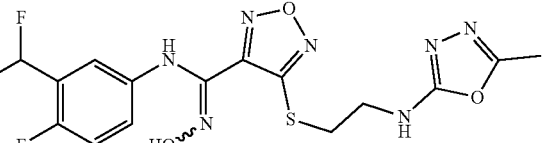

The title compound was prepared similar as described for Example 6 using in step 1 3-(4-((2-aminoethyl)thio)-1,2,5- oxadiazol-3-yl)-4-(3-(difluoromethyl)-4-fluorophenyl)-1,2,4-oxadiazol-5(4H)-one (Int 100/3) in place of 3-(4-(2-aminoethoxy)-1,2,5-oxadiazol-3-yl)-4-(3-bromo-4-fluorophenyl)-1,2,4-oxadiazol-5(4H)-one (Int 1). ¹H NMR (500 MHz, DMSO-d₆): δ ppm 11.79 (s, 1H), 9.08 (s, 1H), 7.31-7.28 (m, 1H), 7.09-6.80 (m, 3H), 6.65 (s, 2H), 3.32-3.25 (m, 4H). MS (ESI): m/z 409.1 [M+H]⁺.

Example 112/1

N'—Hydroxy-4-((2-(sulfamoylamino)ethyl)thio)—N-(2-(trifluoromethyl)pyridin-4-yl)-1,2,5-oxadiazole-3-carboximidamide (112/1)

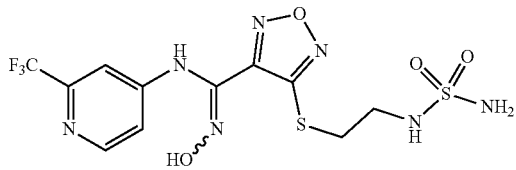 [SMILES: NS(=O)(=O)NCCSc1nonc1C(=NO)Nc1ccnc(C(F)(F)F)c1]

The title compound was prepared similar as described for Example 6 using in Step 1 3-(4-((2-aminoethyl)thio)-1,2,5-oxadiazol-3-yl)-4-(2-(trifluoromethyl)pyridin-4-yl)-1,2,4-oxadiazol-5(4H)-one (Int 100/16) in place of 3-(4-(2-aminoethoxy)-1,2,5-oxadiazol-3-yl)-4-(3-bromo-4-fluorophenyl)-1,2,4-oxadiazol-5(4H)-one (Int 1). ¹H NMR (500 MHz, DMSO-d₆): δ ppm 12.58 (s, 1H), 9.79 (s, 1H), 8.37 (d, J=5.0 Hz, 1H), 7.13-7.12 (m, 1H), 6.90-6.88 (m, 1H), 6.81-6.79 (m, 1H), 6.64 (br s, 2H), 3.64-3.29 (m, 4H). MS (ESI): m/z 427.9 [M+H]⁺.

Example 113

N-(4-(Difluoromethyl)-3-fluorophenyl)-N'-hydroxy-4-((2-ureidoethyl)thio)-1,2,5-oxadiazole-3-carboximidamide (113)

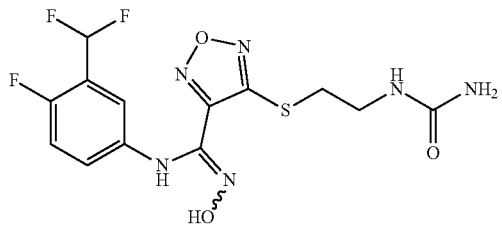 [SMILES: NC(=O)NCCSc1nonc1C(=NO)Nc1ccc(F)c(C(F)F)c1]

The title compound was prepared similar as described for Example 5 using in step 1 3-(4-((2-aminoethypthio)-1,2,5-oxadiazol-3-yl)-4-(3-(difluoromethyl)-4-fluorophenyl)-1,2,4-oxadiazol-5(4H)-one (Int 100/3) in place of 3-(4-(2-aminoethoxy)-1,2,5-oxadiazol-3-yl)-4-(3-chloro-4-fluorophenyl)-1,2,4-oxadiazol-5(4H)-one (Int 1/1). ¹H NMR (500 MHz, DMSO-d₆): δ ppm 11.73 (s, 1H), 9.04 (s, 1H), 7.23-6.87 (m, 4H), 6.26 (br s, 1H), 5.60 (5.60, br s, 2H), 3.37-3.33 (m, 2H), 3.23-3.20 (m, 2H). MS (ESI): m/z 391.1 [M+H]⁺.

Example 113/1

N-(4-(Difluoromethyl)phenyl)-N'-hydroxy-4-((2-ureidoethyl)thio)-1,2,5-oxadiazole-3-carboximidamide (113/1)

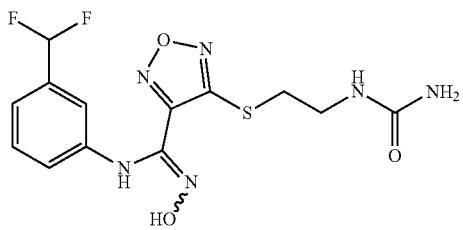 [SMILES: NC(=O)NCCSc1nonc1C(=NO)Nc1cccc(C(F)F)c1]

The title compound was prepared similar as described for Example 5 using in step 1 3-(4-((2-aminoethypthio)-1,2,5-oxadiazol-3-yl)-4-(3-(difluoromethyl)phenyl)-1,2,4-oxadiazol-5(4H)-one (Int 100/9) in place of 3-(4-(2-aminoethoxy)-1,2,5-oxadiazol-3-yl)-4-(3-chloro-4-fluorophenyl)-1,2,4-oxadiazol-5(4H)-one (Int 1/1). ¹H NMR (500 MHz, DMSO-d₆): δ ppm 11.74 (s, 1H), 9.05 (s, 1H), 7.31-7.28 (m, 1H), 7.09-6.81 (m, 4H), 6.25-6.22 (m, 1H), 5.53 (br s, 2H), 3.36-3.33 (m, 2H), 3.23,3.20 (m, 2H). MS (ESI): m/z 373.1 [M+H]⁺.

Example 114

N-(1-((4-(N-(3-(difluoromethyl)-4-fluorophenyl)-N'-hydroxycarbamimidoyl)-1,2,5-oxadiazol-3-yl)thio)propan-2-yl)-2-sulfamoylacetamide (114)

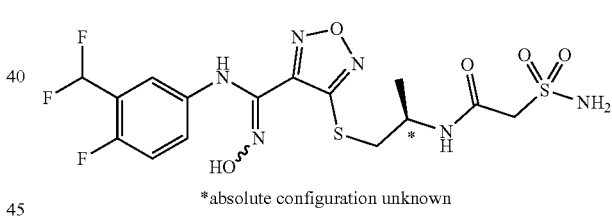

*absolute configuration unknown

To a solution of compound N-(1-((4-(4-(4-(difluoromethyl)-3-fluorophenyl)-5-oxo-4,5-dihydro-1,2,4-oxadiazol-3-yl)-1,2,5-oxadiazol-3-yl)thio)propan-2-yl)-2-sulfamoylacetamide (Int 104a, first eluting enantiomer) (111 mg, 0.22 mmol) in THF (8 mL) 2M aqueous NaOH (0.5 mL) was added and the mixture was stirred at rt for 30 min. The mixture was extracted with EtOAc (3×20 mL). The combined organic layers were washed with brine (10 mL), dried over anhydrous Na₂SO₄ and concentrated to dryness. The residue was purified by reversed HPLC to give the title compound as a white solid. ¹H NMR (500 MHz, DMSO-d₆): δ ppm 11.73 (s, 1H), 9.05 (s, 1H), 8.34 (d, J=8.0 Hz, 1H), 7.23-6.88 (m, 6H), 4.19-4.15 (m, 1H), 3.89-3.82 (m, 2H), 3.35-3.32 (m, 1H), 3.26-3.22 (m, 1H), 1.20 (d, J=6.5 Hz, 3H). MS (ESI): m/z 483.0 [M+H]⁺.

Examples 114/1 to 114/5

The following Examples were prepared similar as described for Example 114 using the appropriate Intermediates.

| # | Int. # | Structure | Analytical data |
|---|---|---|---|
| 114/1 | Int 104b | 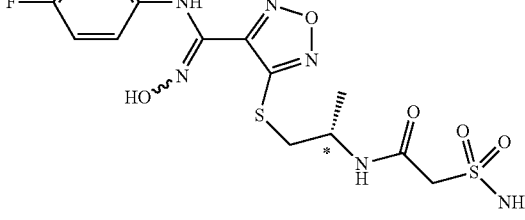 *absolute configuration unknown | ¹H NMR (500 MHz, DMSO-d₆): δ ppm 11.73 (s, 1H), 9.05 (s, 1H), 8.34 (d, J = 8.0 Hz, 1H), 7.23-6.88 (m, 6H), 4.21-4.15 (m, 1H), 3.89-3.83 (m, 2H), 3.35-3.31 (m, 1H), 3.26-3.22 (m, 1H), 1.20 (d, J = 6.5 Hz, 3H). MS (ESI): m/z 483.0 [M + H]⁺. |
| 114/2 | Int 104/1a | 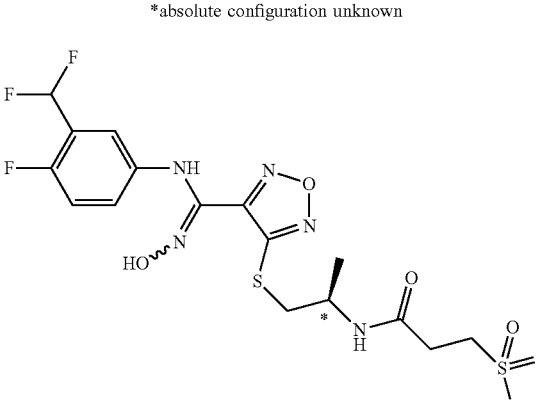 *absolute configuration unknown | ¹H NMR (500 MHz, CD₃OD): δ ppm 7.11-6.81 (m, 4H), 4.32-4.28 (m, 1H), 3.44-3.40 (m, 1H), 3.37-3.34 (m, 2H), 3.20-3.16 (m, 1H), 2.70-2.67 (m, 2H), 1.27 (d, J = 6.5 Hz, 3H). MS (ESI): m/z 497.0 [M + H]⁺. |
| 114/3 | Int 104/1b | 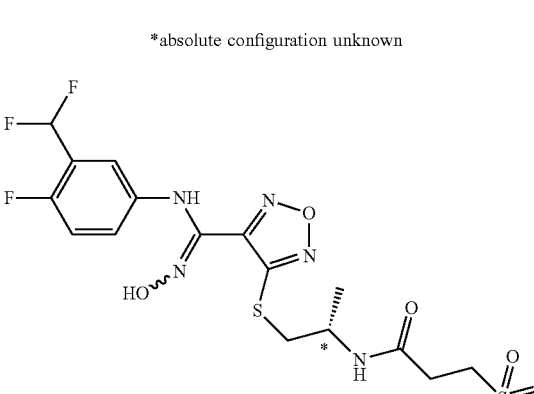 *absolute configuration unknown | ¹H NMR (500 MHz, CD₃OD): δ ppm 7.11-6.81 (m, 4H), 4.32-4.28 (m, 1H), 3.44-3.40 (m, 1H), 3.37-3.35 (m, 2H), 3.20-3.16 (m, 1H), 2.70-2.67 (m, 2H), 1.27 (d, J = 6.5 Hz, 3H). MS (ESI): m/z 497.0 [M + H]⁺. |
| 114/4 | Int 104/3a | 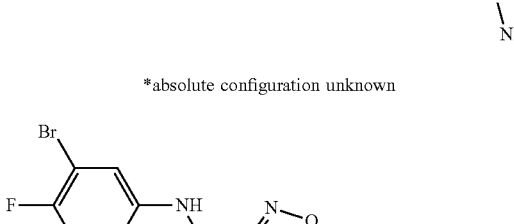 *absolute configuration unknown | ¹H NMR (500 MHz, CD₃OD): δ ppm 7.13-7.11 (m, 1H), 7.05 (dd, J₁ = J₂ = 10.5 Hz, 1H), 6.80-6.76 (m, 1H), 4.36-4.31 (m, 1H), 3.45-3.21 (m, 4H), 1.30 (d, J = 8.5 Hz, 3H). MS (ESI): m/z 511.0 [M + H]⁺. |

| # | Int. # | Structure | Analytical data |
|---|---|---|---|
| 114/5 | Int 104/3b | 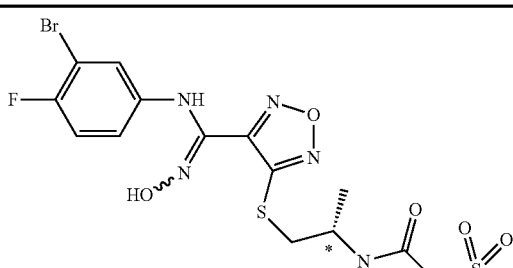 | $^1$H NMR (500 MHz, CD$_3$OD): δ ppm 7.13-7.11 (m, 1H), 7.05 (dd, J$_1$ = J$_2$ = 10.5 Hz, 1H), 4.36-4.31 (m, 1H), 3.45-3.21 (m, 4H), 1.30 (d, J = 8.5 Hz, 3H). MS (ESI): m/z 511.0 [M + H]$^+$. |

*absolute configuration unknown

Example 115

N$^1$-(1-((4-(N-(3-(Difluoromethyl)-4-fluorophenyl)-N'-hydroxycarbamimidoyl)-1,2,5-oxadiazol-3-yl)thio)propan-2-yl)malonamide (115)

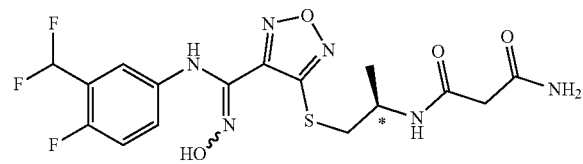

*absolute configuration unknown

To a solution of methyl 3-((1-((4-(4-(3-(difluoromethyl)-4-fluorophenyl)-5-oxo-4,5-dihydro-1,2,4-oxadiazol-3-yl)-1,2,5-oxadiazol-3-yl)thio)propan-2-yl)amino)-3-oxopropanoate (Int 104/2a, first eluting enantiomer) (83 mg, 0.17 mmol) in MeOH (1 mL) was added NH$_3$/MeOH (7M, 2 mL). The mixture was stirred at rt overnight. The mixture was concentrated to dryness and the residue was purified by HPLC to give the title compound as white solid. $^1$H NMR (500 MHz, DMSO-d$_6$): δ ppm 11.73 (br s, 1H), 9.03 (br s, 1H), 8.16-8.14 (m, 1H), 7.42-7.38 (m, 1H), 7.22-6.87 (m, 5H), 4.18-4.12 (m, 1H), 3.35-3.31 (m, 1H), 3.23-3.19 (m, 1H), 3-01-2.95 (m, 2H), 1.17 (d, J=6.5 Hz). MS (ESI): m/z 447.0 [M+H]$^+$.

Example 115/1

N$^1$-(1-((4-(N-(3-(difluoromethyl)-4-fluorophenyl)-N'-hydroxycarbamimidoyl)-1,2,5-oxadiazol-3-yl)thio)propan-2-yl)malonamide (115/1)

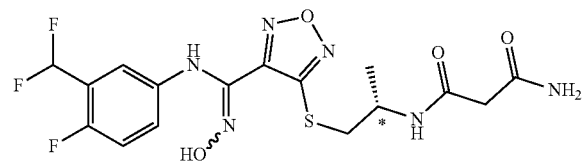

*absolute configuration unknown

The title compound was prepared as described for Example 115 using methyl 3-((1-((4-(4-(3-(difluoromethyl)-4-fluorophenyl)-5-oxo-4,5-dihydro-1,2,4-oxadiazol-3-yl)-1,2,5-oxadiazol-3-yl)thio)propan-2-yl)amino)-3-oxopropanoate (Int 104/2b, second eluting enantiomer) in place of methyl 3-((1-((4-(4-(3-(difluoromethyl)-4-fluorophenyl)-5-oxo-4,5-dihydro-1,2,4-oxadiazol-3-yl)-1,2,5-oxadiazol-3-yl)thio)propan-2-yl)amino)-3-oxopropanoate (Int 104/2a, first eluting enantiomer). $^1$H NMR (500 MHz, DMSO-d$_6$): δ ppm 11.73 (br s, 1H), 9.03 (br s, 1H), 8.16-8.15 (m, 1H), 7.42-7.38 (m, 1H), 7.23-6.87 (m, 5H), 4.18-4.11 (m, 1H), 3.35-3.32 (m, 1H), 3.23-3.19 (m, 1H), 3.01-2.95 (m, 2H), 1.16 (d, J=6.5 Hz, 3H). MS (ESI): m/z 447.1 [M+H]$^+$.

Example 116

N$^1$-(2-((4-(N-(3-Chloro-4-fluorophenyl)-N'-hydroxycarbamimidoyl)-1,2,5-oxadiazol-3-yl)thio)ethyl)oxalamide (116)

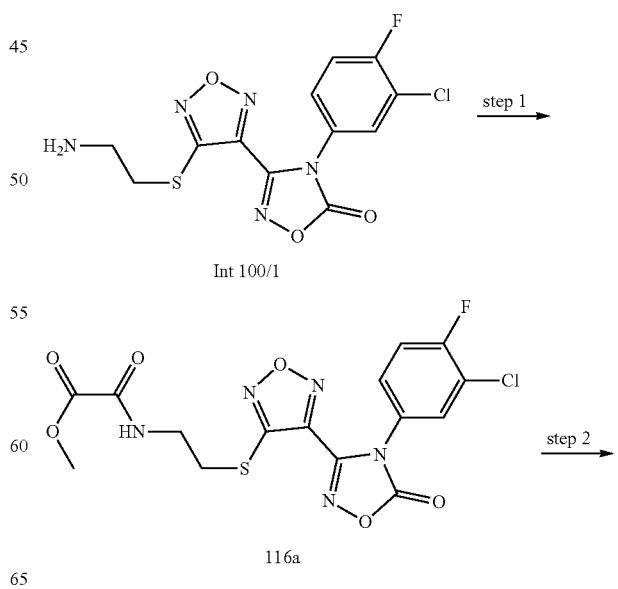

-continued

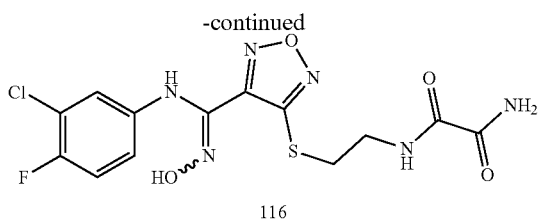

116

Step 1: Methyl 2-((2-((4-(4-(3-chloro-4-fluorophenyl)-5-oxo-4,5-dihydro-1,2,4-oxadiazol-3-yl)-1,2,5-oxadiazol-3-yl)thio)ethyl)amino)-2-oxoacetate (116a)

To a solution of 3-(4-((2-aminoethyl)thio)-1,2,5-oxadiazol-3-yl)-4-(3-chloro-4-fluorophenyl)-1,2,4-oxadiazol-5(4H)-one (Int 100/1) (149 mg, 0.42 mmol) in DCM (3 mL) was added TEA (85 mg, 0.84 mmol). Methyl 2-chloro-2-oxoacetate (62 mg, 0.51 mmol) was added drop-wise under ice/water cooling and stirring was continued at rt for 1 h. Water was added and the mixture was extracted with DCM (3×5 mL). The combined organic layer was concentrated under vacuum and the residue was purified by column chromatography on silica gel (EA: PE=1:4) to give the title compound as a white solid.

Step 2: N1-(2-((4-(N-(3-Chloro-4-fluorophenyl)-N'-hydroxycarbamimidoyl)-1,2,5-oxadiazol-3-yl)thio)ethyl)oxalamide (116)

To a solution of methyl 2-((2-((4-(4-(3-chloro-4-fluorophenyl)-5-oxo-4,5-dihydro-1,2,4-oxadiazol-3-yl)-1,2,5-oxadiazol-3-yl)thio)ethyl)amino)-2-oxoacetate (116a) (128 mg, 0.29 mmol) in MeOH (2 mL) was added NH$_3$/MeOH (2 mL, 7N) and the mixture was stirred at reflux overnight. The solvent was removed under vacuum, the residue was dissolved in MeOH (2 mL), NaOH (1 mL, 1N) was added and the mixture was stirred at rt for 1 h. Water was added and the mixture was extracted with EtOAc (3×5 mL). The combined organic layer was washed with brine and concentrated under vacuum. The residue was purified by HPLC to give the title compound as a white solid. $^1$H NMR (500 MHz, DMSO-d$_6$): δ ppm 11.75 (s, 1H), 8.98 (s, 1H), 8.94 (t, 1H, J=6 Hz), 8.06 (s, 1H), 7.81 (s, 1H), 7.22 (dd, J$_1$=J$_2$=8.5 Hz, 1H), 7.00-6.96 (m, 1H), 6.67-6.62 (m, 1H), 3.56-3.52 (m, 2H), 3.35-3.33 (m, 2H). MS (ESI): m/z 403.0 [M+H]$^+$.

Example 117

N-(2-((4-(N-(3-Chloro-4-fluorophenyl)-N'-hydroxycarbamimidoyl)-1,2,5-oxadiazol-3-yl)thio)ethyl)-1H-tetrazole-5-carboxamide (117)

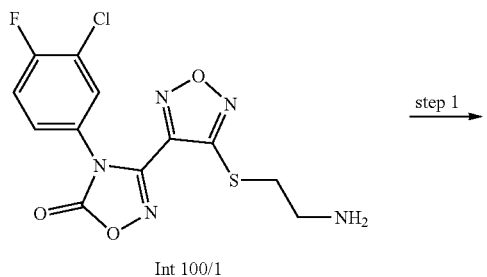

Int 100/1

-continued

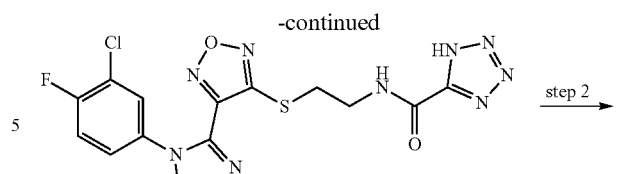

117a

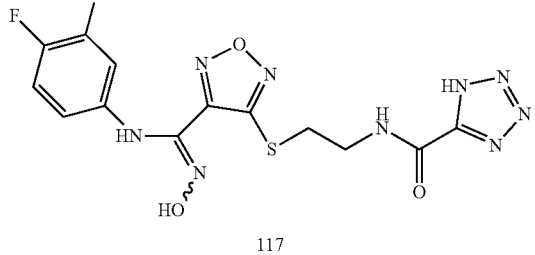

117

Step 1: N-(2-((4-(4-(3-Chloro-4-fluorophenyl)-5-oxo-4,5-dihydro-1,2,4-oxadiazol-3-yl)-1,2,5-oxadiazol-3-yl)thio)ethyl)-1H-tetrazole-5-carboxamide (117a)

To a solution of 3-(4-((2-aminoethyl)thio)-1,2,5-oxadiazol-3-yl)-4-(3-chloro-4-fluorophenyl)-1,2,4-oxadiazol-5(4H)-one (Int 100/1) (100 mg, 0.25 mmol), EDCI (72 mg, 0.38 mmol), HOBt (51 mg, 0.38 mmol) and DIPEA (132 mg, 1.02 mmol) in DMF (1.5 mL) was added 1 H-tetrazole-5-carboxylic acid (31 mg, 0.28 mmol) at rt. Then the mixture was stirred at rt for 18 h. H$_2$O (20 mL) was added and the mixture was extracted with EtOAc (20 mL). The organic layer was washed with brine (10 mL), dried over Na$_2$SO$_4$, and concentrated to give the title compound as a yellow solid.

Step 2: N-(2-((4-(N-(3-Chloro-4-fluorophenyl)-N'-hydroxycarbamimidoyl)-1,2,5-oxadiazol-3-yl)thio)ethyl)-1H-tetrazole-5-carboxamide (117)

To a solution of N-(2-((4-(4-(3-chloro-4-fluorophenyl)-5-oxo-4,5-dihydro-1,2,4-oxadiazol-3-yl)-1,2,5-oxadiazol-3-yl)thio)ethyl)-1H-tetrazole-5-carboxamide (117a) (100 mg, 0.20 mmol) in MeOH (5 mL) was added 1N NaOH (0.6 mL), and the mixture was stirred at rt for 30 min. The solvent was removed under vacuum and the residue was diluted with H$_2$O (15 mL) and extracted with EtOAc (3×20 mL). The combined organic layer was washed with brine (10 mL), dried over anhydrous Na$_2$SO$_4$, concentrated and the residue was purified by HPLC to give the title compound as a white solid. $^1$H NMR (500 MHz, DMSO-d$_6$): δ ppm 11.75 (s, 1H), 9.51-9.47 (m, 1H), 9.01 (s, 1H), 7.23-7.17 (m, 1H), 7.00-6.96 (m, 1H), 6.67-6.62 (m, 1H), 3.74-3.68 (m, 2H), 3.44-3.39 (m, 2H). MS (ESI): m/z 428.1 [M+H]$^+$.

Examples 117/1 to 117/24

The following Examples were prepared similar as described for Example 117 using the appropriate Intermediates and carboxylic acid building blocks.

| # | Int. # | Structure | Analytical data |
|---|---|---|---|
| 117/1 | Int 100/1 | 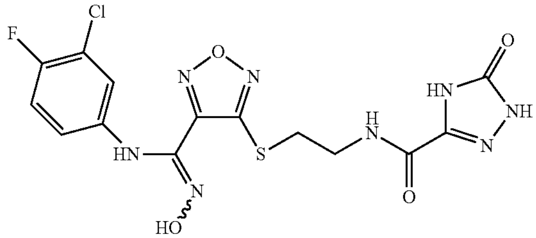 [SMILES: O=C(NCCSc1nonc1C(=NO)Nc1ccc(F)c(Cl)c1)c1n[nH]c(=O)[nH]1] | ¹H NMR (500 MHz, DMSO-d₆): δ ppm 12.09 (s, 1H), 11.98 (s, 1H), 11.75 (s, 1H), 8.99 (s, 1H), 8.82 (t, J = 6 Hz, 1H), 7.24-7.18 (m, 1H), 7.01-6.98 (m, 1H), 6.67-6.61 (m, 1H), 3.63-3.59 (m, 2H), 3.37-3.34 (m, 2H). MS (ESI): m/z 443.1 [M + H]⁺. |
| 117/2 | Int 100/1 | 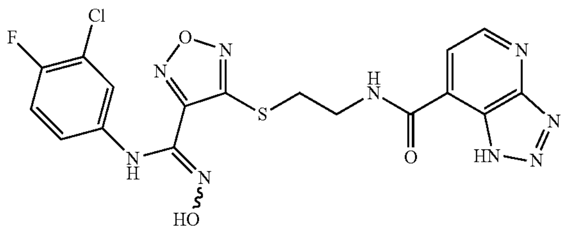 [SMILES: O=C(NCCSc1nonc1C(=NO)Nc1ccc(F)c(Cl)c1)c1ccnc2nn[nH]c12] | ¹H NMR (500 MHz, CD₃OD): δ ppm 8.58 (d, J = 4.5 Hz, 1H), 7.73 (d, J = 4.5 Hz, 1H), 7.04-7.00 (m, 1H), 6.98-6.95 (m, 1H), 6.72-6.67 (m, 1H), 4.02-3.98 (m, 2H), 3.57-3.53 (m, 2H). MS (ESI): m/z 478.0 [M + H]⁺. |
| 117/3 | Int 100/1 | 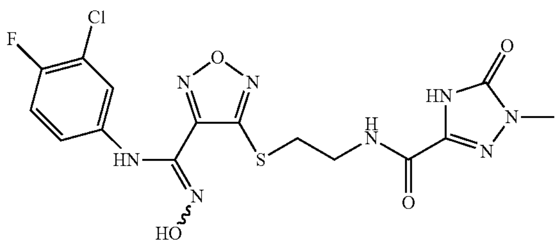 [SMILES: Cn1nc(C(=O)NCCSc2nonc2C(=NO)Nc2ccc(F)c(Cl)c2)[nH]c1=O] | ¹H NMR (500 MHz, DMSO-d₆): δ ppm 12.32 (s, 1H), 11.76 (s, 1H), 9.01 (s, 1H), 8.89-8.85 (m, 1H), 7.24-7.18 (m, 1H), 6.99-6.96 (m, 1H), 6.66-6.61 (m, 1H), 3.83-3.59 (m, 2H), 3.36-3.34 (m, 5H). MS (ESI): m/z 457.1 [M + H]⁺. |
| 117/4 | Int 100/1 | 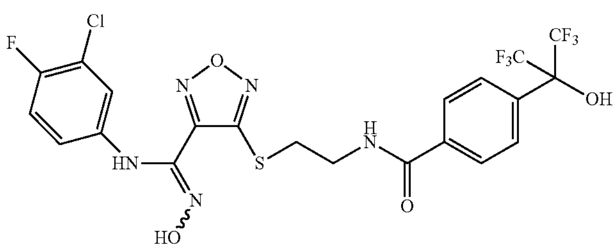 [SMILES: O=C(NCCSc1nonc1C(=NO)Nc1ccc(F)c(Cl)c1)c1ccc(C(O)(C(F)(F)F)C(F)(F)F)cc1] | ¹H NMR (500 MHz, DMSO-d₆): δ ppm 11.73 (s, 1H), 9.01 (s, 1H), 8.93-8.89 (m, 2H), 7.98-7.94 (m, 2H), 7.81-7.78 (m, 2H), 7.22-7.16 (m, 1H), 7.02-6.98 (m, 1H), 6.70-6.64 (m, 1H), 3.72-3.65 (m, 2H), 3.42-3.37 (m, 2H). MS (ESI): m/z 602.1 [M + H]⁺. |
| 117/5 | Int 100/1 | 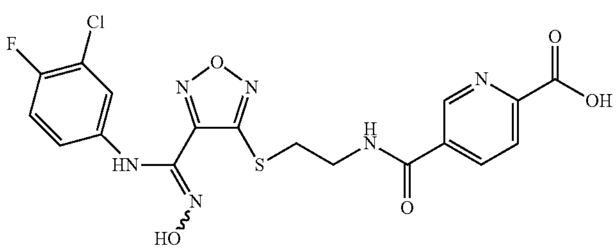 [SMILES: O=C(NCCSc1nonc1C(=NO)Nc1ccc(F)c(Cl)c1)c1ccc(C(=O)O)nc1] | ¹H NMR (500 MHz, DMSO-d₆): δ ppm 13.45 (s br, 1H), 11.73 (s, 1H), 9.14-9.12 (m, 1H), 9.07 (s, 1H), 9.00 (s, 1H), 8.35-8.31 (m, 1H), 8.16-8.11 (m, 1H), 7.23-7.17 (m, 1H), 7.00-6.97 (m, 1H), 6.69-6.65 (m, 1H), 3.73-3.69 (m, 2H), 3.42-3.39 (m, 2H). MS (ESI): m/z 481.1 [M + H]⁺. |
| 117/6 | Int 100/1 | 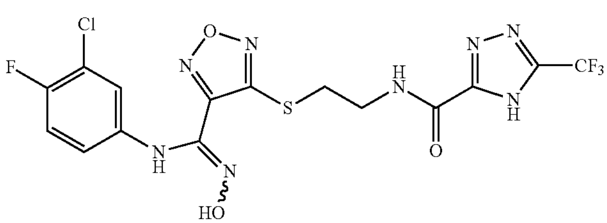 [SMILES: O=C(NCCSc1nonc1C(=NO)Nc1ccc(F)c(Cl)c1)c1nnc(C(F)(F)F)[nH]1] | ¹H NMR (500 MHz, DMSO-d₆): δ ppm 11.73 (s, 1H), 9.25 (s br, 1H), 8.98 (s, 1H), 7.22-7.17 (m, 1H), 6.99-6.95 (m, 1H), 6.66-6.62 (m, 1H), 3.71-3.65 (m, 2H), 3.43-3.38 (m, 2H). MS (ESI): m/z 495.0 [M + H]⁺. |

-continued

| # | Int. # | Structure | Analytical data |
|---|---|---|---|
| 117/7 | Int 100/1 | 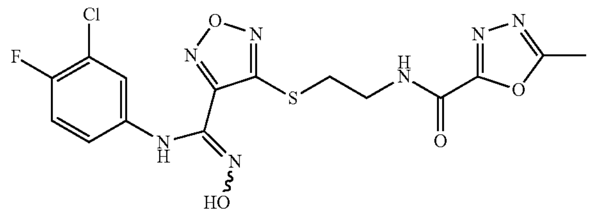 [SMILES: Cc1nnc(C(=O)NCCSc2nonc2C(=NO)Nc2ccc(F)c(Cl)c2)o1] | $^1$H NMR (500 MHz, DMSO-d$_6$): δ ppm 11.75 (s, 1H), 9.48-9.46 (m, 1H), 9.00 (s, 1H), 7.22-7.18 (m, 1H), 7.00-6.97 (m, 1H), 6.67-6.64 (m, 1H), 3.70-3.66 (m, 2H), 3.40-3.37 (m, 2H), 2.58 (s, 3H). MS (ESI): m/z 442.0 [M + H]$^+$. |
| 117/8 | Int 100/1 | 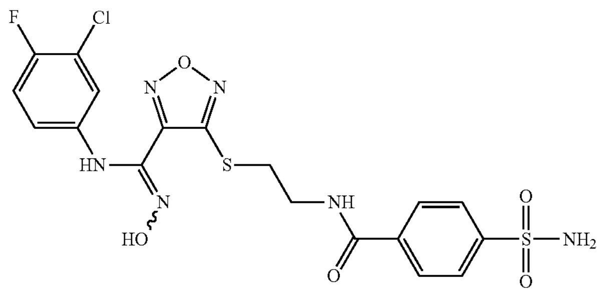 [SMILES: NS(=O)(=O)c1ccc(C(=O)NCCSc2nonc2C(=NO)Nc2ccc(F)c(Cl)c2)cc1] | $^1$H NMR (500 MHz, DMSO-d$_6$): δ ppm 11.73 (s, 1H), 9.00 (s, 1H), 8.98-8.94 (m, 1H), 8.00-7.97 (m, 2H), 7.92-7.89 (m, 2H), 7.49 (s, 2H), 7.23-7.17 (m, 1H), 7.00-6.97 (m, 1H), 6.69-6.65 (m, 1H), 3.71-3.66 (m, 2H), 3.42-3.37 (m, 2H). MS (ESI): m/z 515.0 [M + H]$^+$. |
| 117/9 | Int 100/1 | 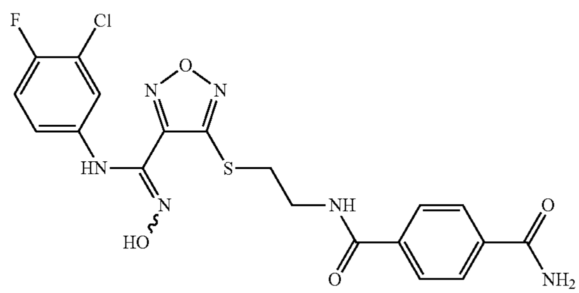 [SMILES: NC(=O)c1ccc(C(=O)NCCSc2nonc2C(=NO)Nc2ccc(F)c(Cl)c2)cc1] | $^1$H NMR (500 MHz, DMSO-d$_6$): δ ppm 11.73 (s, 1H), 9.00 (s, 1H), 8.89-8.85 (m, 1H), 8.08 (s, 1H), 7.96-7.86 (m, 4H), 7.51 (s, 1H), 7.22-7.16 (m, 1H), 7.00-6.87 (m, 1H), 6.69-6.64 (m, 1H), 3.71-3.66 (m, 2H), 3.41-3.37 (m, 2H). MS (ESI): m/z 479.0 [M + H]$^+$. |
| 117/10 | Int 100/3 | 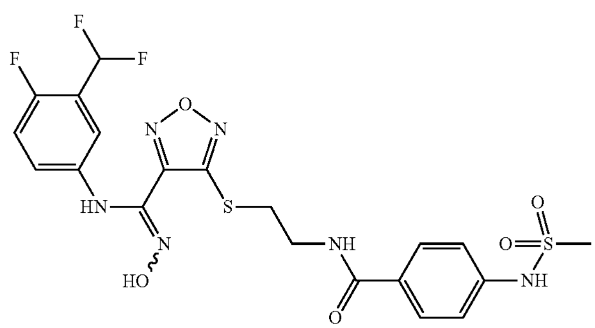 [SMILES: CS(=O)(=O)Nc1ccc(C(=O)NCCSc2nonc2C(=NO)Nc2ccc(F)c(C(F)F)c2)cc1] | $^1$H NMR (500 MHz, CD$_3$OD): δ ppm 7.83-7.81 (m, 2H), 7.33-7.31 (m, 2H), 7.07-6.79 (m, 4H), 3.79-3.76 (m, 2H), 3.44-3.41 (m, 2H), 3.04 (s, 3H). MS (ESI): m/z 544.9 [M + H]$^+$. |
| 117/11 | Int 100/1 | 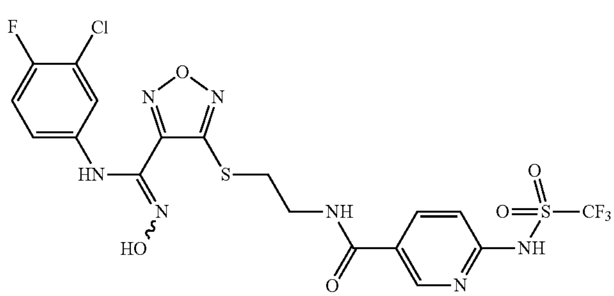 [SMILES: O=C(NCCSc1nonc1C(=NO)Nc1ccc(F)c(Cl)c1)c1ccc(NS(=O)(=O)C(F)(F)F)nc1] | $^1$H NMR (500 MHz, DMSO-d$_6$): δ ppm 14.56 (s, 1H), 11.73 (s, 1H), 9.01 (s, 1H), 8.96-8.94 (m, 1H), 8.52 (s, 1H), 8.43-8.40 (m, 1H), 7.65-7.63 (m, 1H), 7.22-7.18 (m, 1H), 6.99-6.97 (m, 1H), 6.68-6.65 (m, 1H), 3.68-3.64 (m, 2H), 3.37-3.34 (m, 2H). MS (ESI): m/z 583.9 [M + H]$^+$. |

-continued

| # | Int. # | Structure | Analytical data |
|---|---|---|---|
| 117/12 | Int 100/3 | 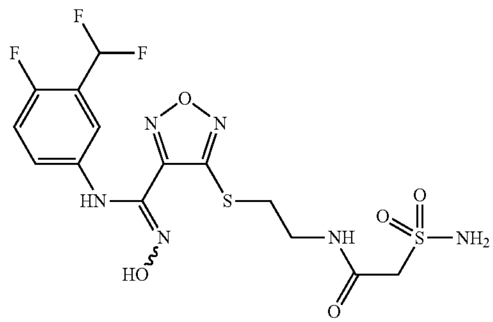 [SMILES: NS(=O)(=O)CC(=O)NCCSc1nonc1C(=NO)Nc1ccc(F)c(C(F)F)c1] | $^1$H NMR (500 MHz, DMSO-d$_6$): δ ppm 11.72 (s, 1H), 9.02 (s, 1H), 8.48 (t, J = 6.0 Hz, 1H), 7.21-7.16 (m, 1H), 7.12 (t, J = 54 Hz, 1H), 7.01-6.87 (m, 4H), 3.88 (s, 2H), 3.51-3.47 (m, 2H), 3.28-3.25 (m, 2H). MS (ESI): m/z 469.0 [M + H]$^+$. |
| 117/13 | Int 100/8 | 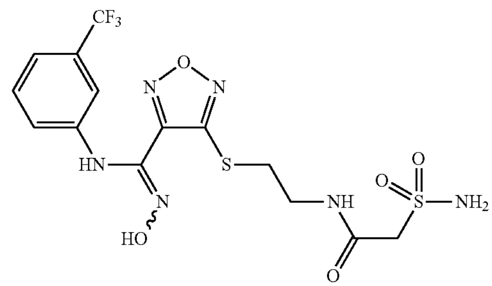 [SMILES: NS(=O)(=O)CC(=O)NCCSc1nonc1C(=NO)Nc1cccc(C(F)(F)F)c1] | $^1$H NMR (500 MHz, DMSO-d$_6$): δ ppm 11.91 (s, 1H), 9.20 (s, 1H), 8.51-8.49 (m, 1H), 7.41-7.36 (m, 1H), 7.24-7.20 (m, 1H), 7.08 (s, 1H), 6.96-6.90 (m, 3H), 3.88 (s, 2H), 3.51-3.47 (m, 2H), 3.29-3.26 (m, 2H). MS (ESI): m/z 468.9 [M + H]$^+$. |
| 117/14 | Int 100/3 | 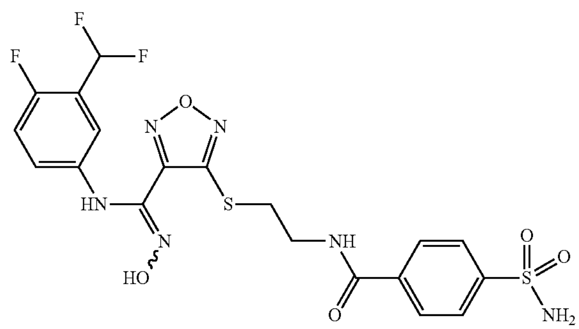 [SMILES: NS(=O)(=O)c1ccc(C(=O)NCCSc2nonc2C(=NO)Nc2ccc(F)c(C(F)F)c2)cc1] | $^1$H NMR (500 MHz, DMSO-d$_6$): δ ppm 11.70 (s, 1H), 9.04 (s, 1H), 8.98-8.95 (m, 1H), 7.99 (d, J = 8.5 Hz, 2H), 7.91 (d, J = 8.5 Hz, 2H), 7.49 (s, 2H), 7.23-7.00 (m, 3H), 6.91-6.87 (m, 1H), 3.71-3.67 (m, 2H), 3.41-3.38 (m, 2H). MS (ESI): m/z 531.1 [M + H]$^+$. |
| 117/15 | Int 100/9 | 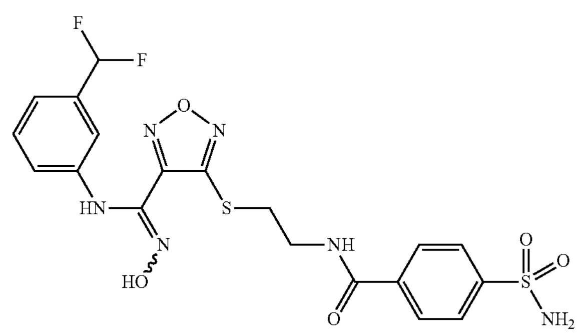 [SMILES: NS(=O)(=O)c1ccc(C(=O)NCCSc2nonc2C(=NO)Nc2cccc(C(F)F)c2)cc1] | $^1$H NMR (500 MHz, DMSO-d$_6$): δ ppm 11.73 (s, 1H), 9.07 (s, 1H), 8.98-8.96 (m, 1H), 7.99 (d, J = 8.5 Hz, 2H), 7.91 (d, J = 8.5 Hz, 2H), 7.49 (s, 2H), 7.31-7.26 (m, 1H), 7.09-6.80 (m, 4H), 3.71-3.67 (m, 2H), 3.41-3.39 (m, 2H). MS (ESI): m/z 513.1 [M + H]$^+$. |
| 117/16 | Int 100/2 | 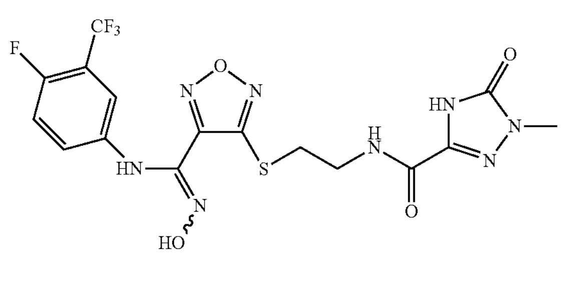 [SMILES: Cn1nc(C(=O)NCCSc2nonc2C(=NO)Nc2ccc(F)c(C(F)(F)F)c2)[nH]c1=O] | $^1$H NMR (500 MHz, DMSO-d$_6$): δ ppm 12.0-11.80 (m br, 2H), 9.32 (s, 1H), 8.86-8.83 (m, 1H), 7.34-7.28 (m, 1H), 7.16-7.13 (m, 1H), 6.98-6.94 (m, 1H), 3.63-3.59 (m, 2H), 3.38-3.32 (m, 5H). MS (ESI): m/z 491.1 [M + H]$^+$. |

-continued

| # | Int. # | Structure | Analytical data |
|---|---|---|---|
| 117/17 | Int 100/3 | 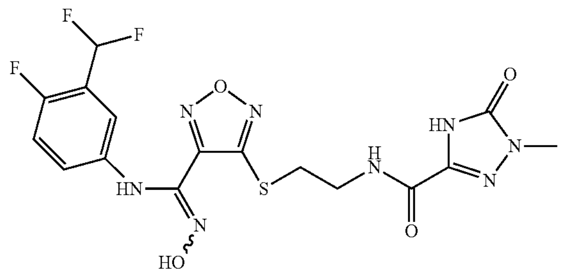 [SMILES: Cn1nc(C(=O)NCCSc2nonc2C(=NO)Nc2ccc(F)c(C(F)F)c2)[nH]c1=O] | $^1$H NMR (500 MHz, CD$_3$OD): δ ppm 7.10-7.02 (m, 2H), 6.96-6.80 (m, 2H), 3.73 (t, J = 6.5 Hz, 2H), 3.48 (s, 3H), 3.38 (t, J = 6.5 Hz, 2H). MS (ESI): m/z 473.0 [M + H]$^+$. |
| 117/18 | Int 100/8 | 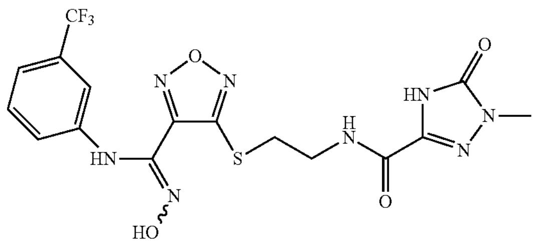 [SMILES: Cn1nc(C(=O)NCCSc2nonc2C(=NO)Nc2cccc(C(F)(F)F)c2)[nH]c1=O] | $^1$H NMR (500 MHz, CD$_3$OD): δ ppm 7.39-7.35 (m, 1H), 7.26-7.23 (m, 1H), 7.08 (s, 1H), 6.98-6.95 (m, 1H), 3.73 (t, J = 6.5 Hz, 2H), 3.47 (s, 3H), 3.39 (t, J = 6.5 Hz, 2H). MS (ESI): m/z 473.1 [M + H]$^+$. |
| 117/19 | Int 100/9 | 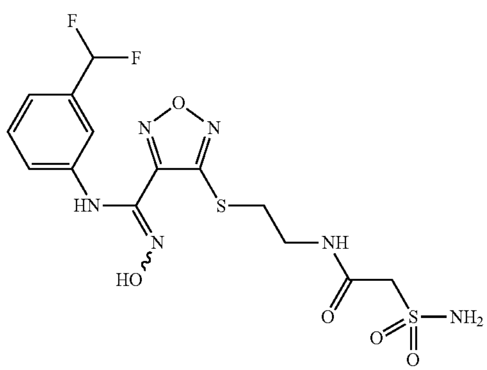 [SMILES: NS(=O)(=O)CC(=O)NCCSc1nonc1C(=NO)Nc1cccc(C(F)F)c1] | $^1$H NMR (500 MHz, DMSO-d$_6$): δ ppm 11.75 (s br, 1H), 9.07 (s br, 1H), 8.49-8.47 (m, 1H), 7.32-7.28 (m, 1H), 7.11-6.82 (m, 6H), 3.88 (s, 2H), 3.51-3.47 (m, 2H), 3.28-3.25 (m, 2H). MS (ESI): m/z 451.1 [M + H]$^+$. |
| 117/20 | Int 100/3 | 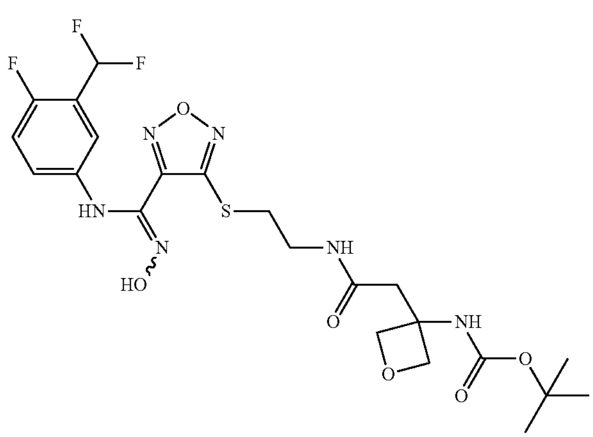 [SMILES: CC(C)(C)OC(=O)NC1(CC(=O)NCCSc2nonc2C(=NO)Nc2ccc(F)c(C(F)F)c2)COC1] | $^1$H NMR (500 MHz, DMSO-d$_6$): δ ppm 11.72 (s, 1H), 9.04 (s, 1H), 8.26-8.24 (m, 1H), 7.38 (s, 1H), 7.23-6.88 (m, 4H), 4.49 (s, 4H), 3.41-3.39 (m, 2H), 3.22-3.20 (m, 2H), 2.78 (s, 2H), 1.37 (s, 9H). MS (ESI): m/z 505.1 [M − 55]$^+$, 583.2 [M + Na]$^+$. |

-continued
| # | Int. # | Structure | Analytical data |
|---|---|---|---|
| 117/21 | Int 100/3 | 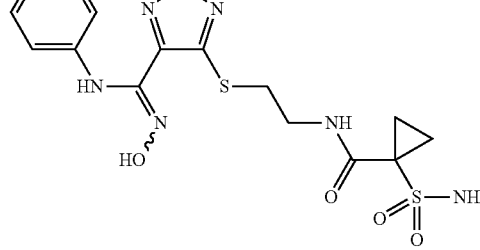 | $^1$H NMR (500 MHz, DMSO-d$_6$): δ ppm 11.72 (s, 1H), 9.03 (s, 1H), 8.05 (t, J = 6.0 Hz, 1H), 7.22-6.87 (m, 6H), 3.88 (s, 2H), 3.57-3.53 (m, 2H), 3.30-3.28 (m, 2H), 1.41-1.32 (m, 4H). MS (ESI): m/z 495.0 [M + H]$^+$. |
| 117/22 | Int 106/1 | 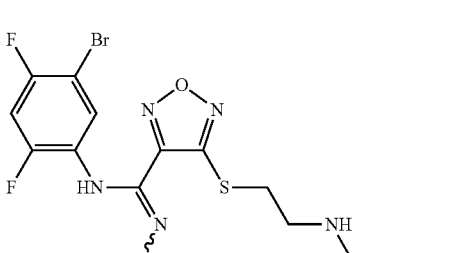 | $^1$H NMR (500 MHz, DMSO-d$_6$): δ ppm 11.62 (s, 1H), 8.82 (s, 1H), 8.51-8.47 (m, 1H), 7.50-7.41 (m, 2H), 6.94 (s, 2H), 3.89 (s, 2H), 3.51-3.47 (m, 2H), 3.27-3.24 (m, 2H). MS (ESI): m/z 515.0 [M + H]$^+$. |
| 117/23 | Int 106/2 | 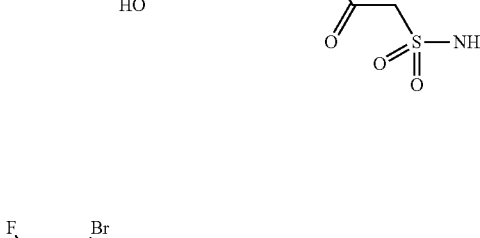 | $^1$H NMR (500 MHz, DMSO-d$_6$): δ ppm 11.59 (s, 1H), 8.83 (s, 1H), 8.50-8.46 (m, 1H), 7.18-7.13 (m, 2H), 6.96-6.92 (m, 2H), 3.89 (s, 2H), 3.50-3.47 (m, 2H), 3.27-3.24 (m, 2H). MS (ESI): m/z 515.0 [M + H]$^+$. |
| 117/24 | Int 106 | 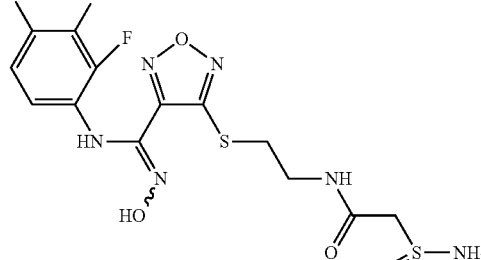 | $^1$H NMR (500 MHz, DMSO-d$_6$): δ ppm 11.99 (s, 1H), 9.12 (s, 1H), 8.51-8.47 (m, 1H), 6.94-6.77 (m, 2H), 3.88 (s, 2H), 3.52-3.47 (m, 2H), 3.29-3.26 (m, 2H). MS (ESI): m/z 515.0 [M + H]$^+$. |

Example 118

The following Example was prepared similar as described for Example 7 using the appropriate Intermediates and carboxylic acid building blocks.

| # | Int. # | Structure | Analytical data |
|---|---|---|---|
| 118 | Int 100/3, step 1 | 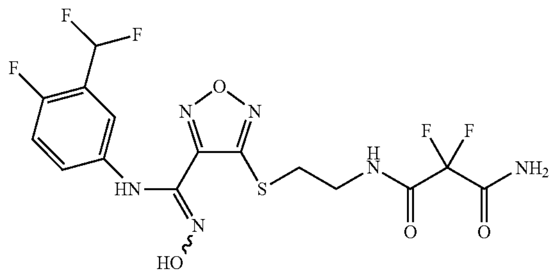 [SMILES: NC(=O)C(F)(F)C(=O)NCCSc1nonc1C(=NO)Nc1ccc(F)c(C(F)F)c1] | $^1$H NMR (500 MHz, CD$_3$OD): δ ppm 7.10-6.77 (m, 4H), 3.70-3.67 (m, 2H), 3.37-3.33 (m, 2H). MS (ESI): m/z 469.1 [M + H]$^+$. |

Examples 119 to 119/6

The following Examples were prepared similar as described for Example 4 using the appropriate Intermediates and building blocks.

| # | Int. # | Structure | Analytical data |
|---|---|---|---|
| 119 | Int 100/3, step 1 | 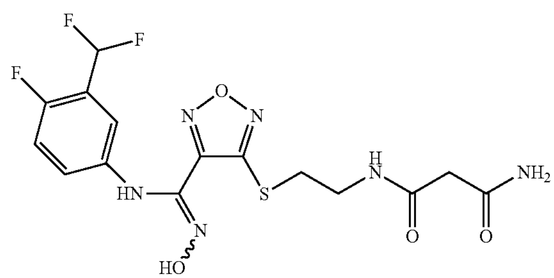 [SMILES: NC(=O)CC(=O)NCCSc1nonc1C(=NO)Nc1ccc(F)c(C(F)F)c1] | $^1$H NMR (500 MHz, DMSO-d$_6$): δ ppm 11.75 (s, 1H), 9.04 (s, 1H), 8.33-8.31 (m, 1H), 7.44 (s, 1H), 7.24-6.88 (m, 5H), 3.48-3.44 (m, 2H), 3.26-3.24 (m, 2H), 3.00 (s, 2H). MS (ESI): m/z 433.1 [M + H]$^+$. |
| 119/1 | Int 100/8, step 1 | 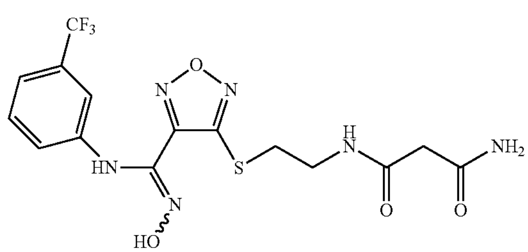 [SMILES: NC(=O)CC(=O)NCCSc1nonc1C(=NO)Nc1cccc(C(F)(F)F)c1] | $^1$H NMR (500 MHz, DMSO-d$_6$): δ ppm 11.91 (s, 1H), 9.19 (s, 1H), 8.33-8.31 (m, 1H), 7.44 (s, 1H), 7.40-7.36 (m, 1H), 7.23-7.20 (m, 1H), 7.09-7.04 (m, 2H), 6.93-6.89 (m, 1H), 3.48-3.44 (m, 2H), 3.26-3.24 (m, 2H), 3.00 (s, 2H). MS (ESI): m/z 433.1 [M + H]$^+$. |
| 119/2 | Int 100/9, step 1 | 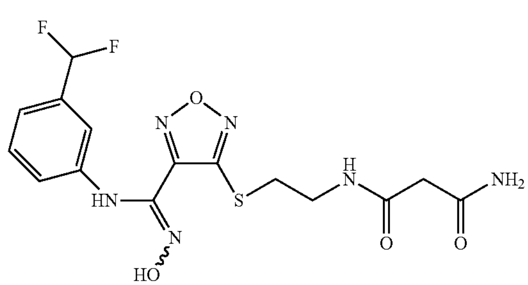 [SMILES: NC(=O)CC(=O)NCCSc1nonc1C(=NO)Nc1cccc(C(F)F)c1] | $^1$H NMR (500 MHz, DMSO-d$_6$): δ ppm 11.77 (s, 1H), 9.06 (s, 1H), 8.33-8.31 (m, 1H), 7.44 (s, 1H), 7.32-7.27 (m, 1H), 7.09-6.81 (m, 5H), 3.48-3.44 (m, 2H), 3.26-3.24 (m, 2H), 3.00 (s, 2H). MS (ESI): m/z 415.1 [M + H]+. |

-continued

| # | Int. # | Structure | Analytical data |
|---|---|---|---|
| 119/3 | Int 100/3, step 1 | (structure) | ¹H NMR (500 MHz, DMSO-d₆): δ ppm 11.76 (s, 1H), 9.04 (s, 1H), 7.61 (s, 1H), 7.56-7.53 (m, 1H), 7.37 (s, 1H), 7.19-7.15 (m, 1H), 7.12 (t, J = 54 Hz, 1H), 7.03-7.00 (m, 1H), 6.89-6.87 (m, 1H), 3.93 (s, 2H), 3.40-3.36 (m, 2H), 3.31-3.28 (m, 2H). MS (ESI): m/z 469.1 [M + H]⁺. |
| 119/4 | Int 100/9, step 1 | (structure) | ¹H NMR (500 MHz, DMSO-d₆): δ ppm 11.79 (s, 1H), 9.06 (s, 1H), 7.61 (s, 1H), 7.56-7.52 (m, 1H), 7.36 (s, 1H), 7.32-7.27 (m, 1H), 7.10-6.80 (m, 4H), 3.93 (s, 2H), 3.40-3.36 (m, 2H), 3.31-3.28 (m, 2H). MS (ESI): m/z 451.1 [M + H]⁺. |
| 119/5 | Int 100/3, step 1 | (structure) | ¹H NMR (300 MHz, CD₃OD): δ ppm 7.09-6.73 (m, 4H), 3.48-3.43 (m, 2H), 3.38-3.32 (m, 4H), 2.72-2.67 (m, 2H). MS (ESI): m/z 483.0 [M + H]⁺. |
| 119/6 | Int 100/3, step 1 | (structure) | ¹H NMR (500 MHz, DMSO-d₆): δ ppm 11.75 (s, 1H), 9.03 (s, 1H), 7.28-6.87 (m, 8H), 3.42 (s, 2H), 3.28-3.26 (m, 4H). MS (ESI): m/z 484.0 [M + H]⁺. |

Examples 120 to 120/1

The following Examples were prepared similar as described for Example 18 using the appropriate Intermediates and building blocks.

| # | Int. # | Structure | Analytical data |
|---|--------|-----------|-----------------|
| 120 | Int 100/1 | 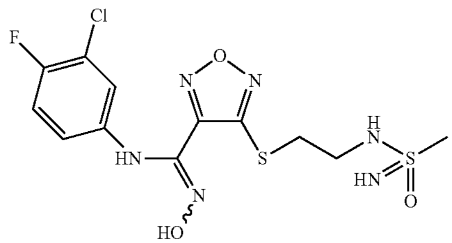 [SMILES: CS(=N)(=O)NCCSc1nonc1C(=NO)Nc1ccc(F)c(Cl)c1] | $^1$H NMR (500 MHz, CD$_3$OD): δ ppm 7.08 (dd, J$_1$ = J$_2$ = 8.5 Hz, 1H), 6.97-6.95 (m, 1H), 6.76-6.73 (m, 1H), 3.68-3.63 (m, 2H), 3.52 (s, 3H), 3.42-3.38 (m, 2H). MS (ESI): m/z 409.1 [M + H]$^+$. |
| 120/1 | Int 100/3 | 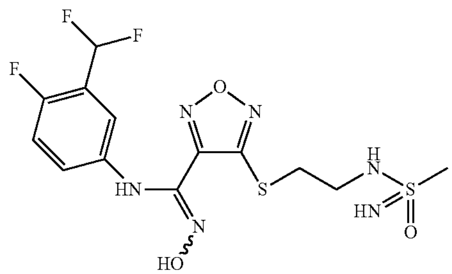 [SMILES: CS(=N)(=O)NCCSc1nonc1C(=NO)Nc1ccc(F)c(C(F)F)c1] | $^1$H NMR (500 MHz, CD$_3$OD): δ ppm 7.11-6.81 (m, 4H), 3.65 (t, J = 6.5 Hz, 2H), 3.50 (s, 3H), 3.40 (t, J = 6.5 Hz, 2H). MS (ESI): m/z 425.1 [M + H]$^+$. |

Example 121

N-(2-((4-(N-(3-Chloro-4-fluorophenyl)-N'-hydroxy-carbamimidoyl)-1,2,5-oxadiazol-3-yl)thio)ethyl)-6-(methylsulfonamido)nicotinamide (121)

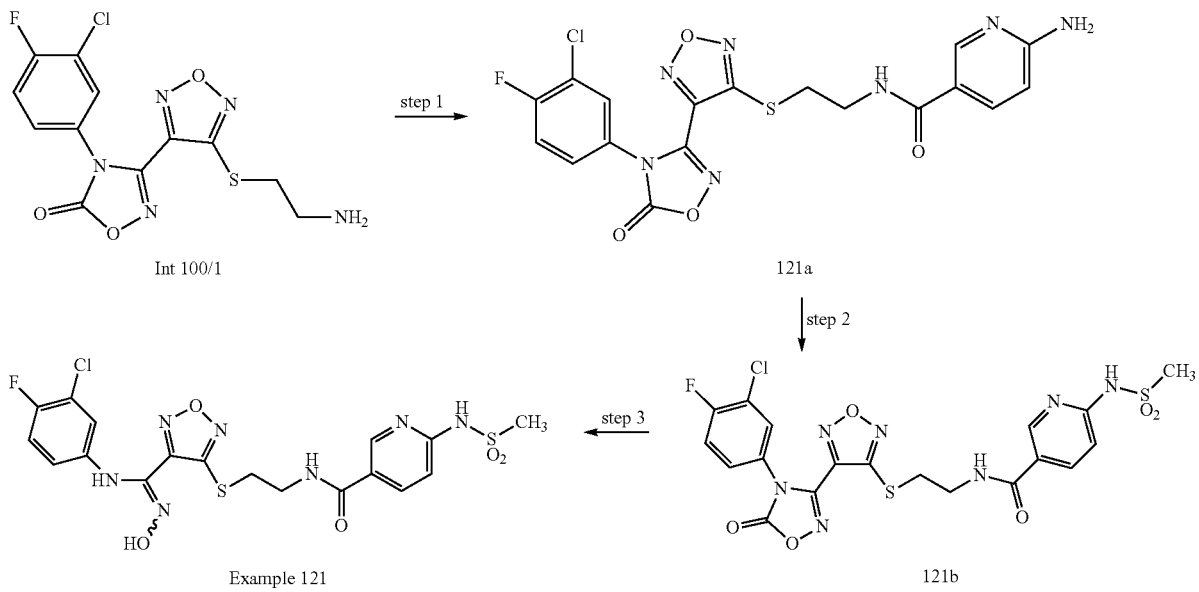

Step 1: 6-Amino-N-(2-((4-(4-(3-chloro-4-fluorophe-nyl)-5-oxo-4,5-dihydro-1,2,4-oxadiazol-3-yl)-1,2,5-oxadiazol-3-yl)thio)ethyl)nicotinamide (121a)

To a solution of 3-(4-((2-aminoethyl)thio)-1,2,5-oxadi-azol-3-yl)-4-(3-chloro-4-fluorophenyl)-1,2,4-oxadiazol-5(4H)-one (Int 100/1) (100 mg, 0.25 mmol), EDCI (72 mg, 0.38 mmol), HOBt (51 mg, 0.38 mmol) and DIPEA (132 mg, 1.02 mmol) in DMF (1.5 mL) was added 6-aminonicotinic acid (31 mg, 0.28 mmol) at rt. Then the mixture was stirred at rt for 18 h. Water (20 mL) was added and the mixture was extracted with EtOAc (20 mL). The organic layer was washed with brine (10 mL), dried over Na$_2$SO$_4$, and concentrated to give the title compound as a yellow solid (130 mg, crude).

Step 2: N-(2-((4-(4-(3-Chloro-4-fluorophenyl)-5-oxo-4,5-dihydro-1,2,4-oxadiazol-3-yl)-1,2,5-oxadi-azol-3-yl)thio)ethyl)-6-(methylsulfonamido)nicotina-mide (121b)

To a solution of 6-amino-N-(2-((4-(4-(3-chloro-4-fluorophenyl)-5-oxo-4,5-dihydro-1,2,4-oxadiazol-3-yl)-1,2,5-oxadiazol-3-yl)thio)ethyl)nicotinamide (121a) (130 mg, crude) and DIPEA (65 mg, 0.50 mmol) in DCM (5 mL) was added MsCl (43 mg, 0.38 mmol) dropwise at 0° C. Then the mixture was stirred at rt for 1 h. The solvent was removed and the residue was diluted with H$_2$O (15 mL), extracted with EtOAc (3×20 mL) and washed with brine (10 mL). The organic layer was dried over Na$_2$SO$_4$ and concentrated give the title compound as a pale yellow solid.

Step 3: N-(2-((4-(N-(3-Chloro-4-fluorophenyl)-N-hydroxycarbamimidoyl)-1,2,5-oxadiazol-3-yl)thio)ethyl)-6-(methylsulfonamido)nicotinamide (121)

To a solution of N-(2-((4-(4-(3-chloro-4-fluorophenyl)-5-oxo-4,5-dihydro-1,2,4-oxadiazol-3-yl)-1,2,5-oxadiazol-3-yl)thio)ethyl)-6-(methylsulfonamido)nicotinamide (121b) (85 mg, 0.15 mmol) in MeOH (5 mL) was added 1N NaOH (0.6 mL, 0.60 mmol), the mixture was stirred at rt for 30 min. The solvent was removed and the residue was diluted with H$_2$O (15 mL), extracted with EtOAc (3×20 mL) and washed with brine (10 mL). The organic layer was dried over Na$_2$SO$_4$ and concentrated. The residue was purified by HPLC to the title compound as a white solid. $^1$H NMR (500 MHz, DMSO-d$_6$): δ ppm11.72 (s, 1H), 11.10 (s br, 1H), 8.99 (s, 1H), 8.82-8.78 (m, 1H), 8.67 (s, 1H), 8.13-8.10 (m, 1H), 7.22-7.17 (m, 1H), 7.04-6.97 (m, 2H), 6.69-6.65 (m, 1H), 3.69-3.63 (m, 2H), 3.39-3.28 (m, 5H). MS (ESI): m/z 529.9 [M+H]$^+$.

Example 122

N-(2-((4-(N-(3-(Difluoromethyl)-4-fluorophenyl)-N-hydroxycarbamimidoyl)-1,2,5-oxadiazol-3-yl)thio)ethyl)-4-(S-methylsulfonimidoyl)benzamide (122)

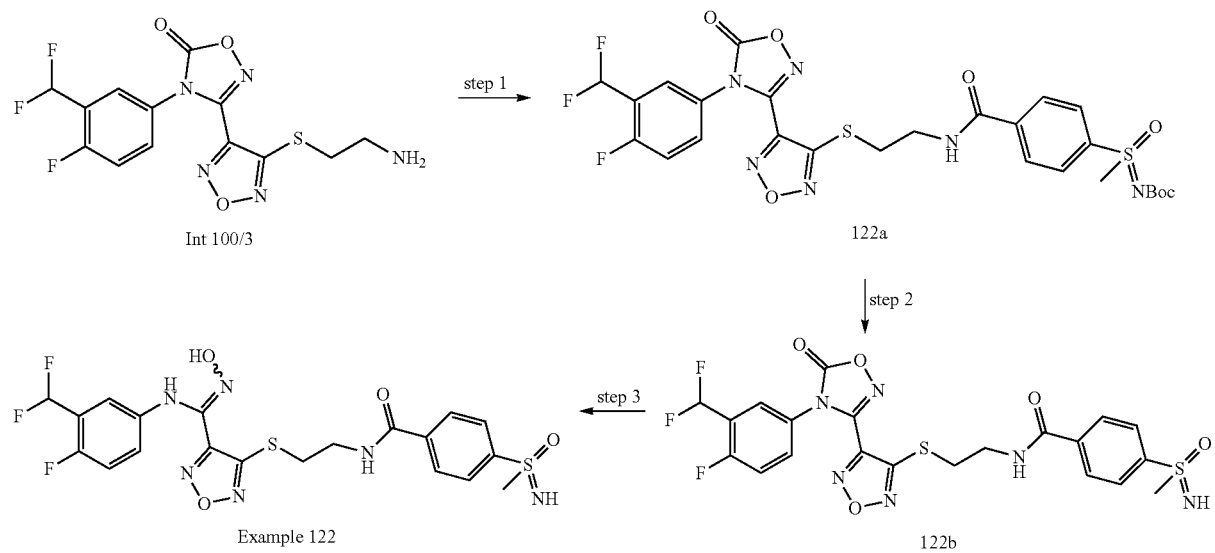

Step 1: tert-Butyl ((4-((2-((4-(4-(3-(difluoromethyl)-4-fluorophenyl)-5-oxo-4,5-dihydro-1,2,4-oxadiazol-3-yl)-1,2,5-oxadiazol-3-yl)thio)ethyl)carbamoyl)phenyl)(methyl)(oxo)—λ$^6$-sulfaneylidene)carbamate (122a)

To a solution of 4-(N-(tert-butoxycarbonyl)-S-methyl-sulfonimidoyl)benzoic acid (Int 9) (233 mg, 0.78 mmol), Et$_3$N (105 mg, 1.04 mmol), HATU (395 mg, 1.04 mmol) in DCM (20 mL) was added 3-(4-((2-aminoethyl)thio)-1,2,5-oxadiazol-3-yl)-4-(3-(difluoromethyl)-4-fluorophenyl)-1,2,4-oxadiazol-5(4H)-one (Int 100/3) (194 mg, 0.52 mmol) and the mixture was stirred at rt overnight. Then the mixture was concentrated to get an oil, which was resolved in DCM (30 mL) and washed with water (30 mL) twice, the organic layer was dried over Na$_2$SO$_4$, the combined organic layer was concentrated under vacuum, and then purified by column chromatography (EtOAc: PE=1: 2) to give the title compound as a yellow solid.

Step 2: N-(2-((4-(4-(3-(Difluoromethyl)-4-fluorophenyl)-5-oxo-4,5-dihydro-1,2,4-oxadiazol-3-yl)-1,2,5-oxadiazol-3-yl)thio)ethyl)-4-(S-methylsulfonimidoyl)benzamide (122b)

To a solution of tert-butyl ((4-((2-((4-(4-(3-(difluoromethyl)-4-fluorophenyl)-5-oxo-4,5-dihydro-1,2,4-oxadiazol-3-yl)-1,2,5-oxadiazol-3-yl)thio)ethyl)carbamoyl)-phenyl)(methyl)(oxo)—λ$^6$-sulfaneylidene)carbamate (122a) (190 mg, 0.29 mmol) in DCM (20 mL) was added TFA (1 mL) and the mixture was stirred at rt overnight. The mixture was concentrated to dryness to give the title compound as a yellow oil.

Step 3: N-(2-((4-(N-(3-(Difluoromethyl)-4-fluorophenyl)-N'-hydroxycarbamimidoyl)-1,2,5-oxadiazol-3-yl)thio)ethyl)-4-(S-methylsulfonimidoyl)benzamide (122)

To a solution of N-(2-((4-(4-(3-(difluoromethyl)-4-fluorophenyl)-5-oxo-4,5-dihydro-1,2,4-oxadiazol-3-yl)-1,2,5-oxadiazol-3-yl)thio)ethyl)-4-(S-methylsulfonimidoyl)benzamide (122b) (160 mg, 0.39 mmol) in MeOH (3 mL) was added NaOH (1N, 0.5 mL) and the mixture was stirred at rt overnight. Then water was added, and the mixture was extracted with EtOAc (20 mL). The organic layer was washed with brine (20 mL), dried over Na$_2$SO$_4$ filtered and concentrated. The residue was purified by HPLC to give the title compound as a white solid. $^1$H NMR (500 MHz, DMSO-d$_6$): δ ppm 11.69 (s, 1H), 9.07-9.03 (m, 2H), 8.12-8.07 (m, 4H), 7.23-7.00 (m, 4H), 6.91-6.88 (m, 1H), 3.72-3.69 (m, 2H), 3.45 (s, 3H), 3.41-3.39 (m, 2H). MS (ESI): m/z 529.1 [M+H]$^+$.

Example 123

N-(2-((4-(N-(3-Chloro-4-fluorophenyl)-N'-hydroxycarbamimidoyl)-1,2,5-oxadiazol-3-yl)thio)ethyl)-3-hydroxyazetidine-3-carboxamide (123)

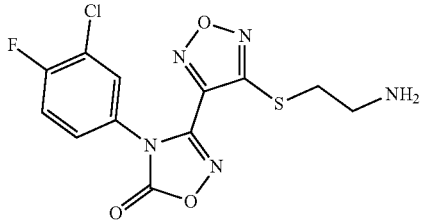
Int 100/1

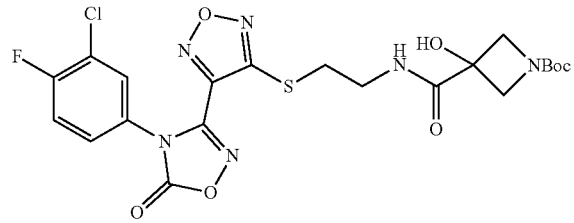
123a

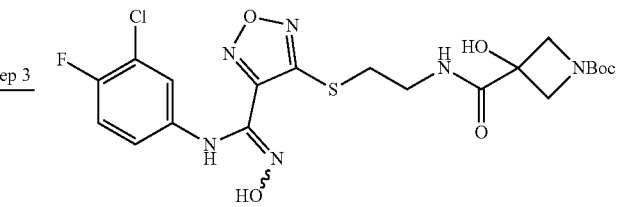
123b

Example 123

Step 1: tert-Butyl 3-((2-((4-(4-(3-chloro-4-fluorophenyl)-5-oxo-4,5-dihydro-1,2,4-oxadiazol-3-yl)-1,2,5-oxadiazol-3-yl)thio)ethyl)carbamoyl)-3-hydroxyazetidine-1-carboxylate (123a)

To a solution of 1-(tert-butoxycarbonyl)-3-hydroxyazetidine-3-carboxylic acid (35 mg, 0.24 mmol), EDCI (72 mg, 0.38 mmol), HOBt (51 mg, 0.38 mmol) and DIPEA (132 mg, 1.02 mmol) in DMF (1.5 mL) was added 3-(4-((2-aminoethyl)thio)-1,2,5-oxadiazol-3-yl)-4-(3-chloro-4-fluorophenyl)-1,2,4-oxadiazol-5(4H)-one (Int 100/1) (100 mg, 0.23 mmol) at rt, then the mixture stirred at this temperature for 18 h. Water (20 mL) was added and the mixture was extracted with EtOAc (20 mL). The organic layer was washed with brine (10 mL), dried over Na$_2$SO$_4$, and concentrated to give the crude title compound as a yellow solid.

Step 2: tert-Butyl 3-((2-((4-(N-(3-chloro-4-fluorophenyl)-N'-hydroxycarbamimidoyl)-1,2,5-oxadiazol-3-yl)thio)ethyl)carbamoyl)-3-hydroxyazetidine-1-carboxylate (123b)

To a solution of tert-butyl 3-((2-((4-(4-(3-chloro-4-fluorophenyl)-5-oxo-4,5-dihydro-1,2,4-oxadiazol-3-yl)-1,2,5-oxadiazol-3-yl)thio)ethyl)carbamoyl)-3-hydroxyazetidine-1-carboxylate (123a) (150 mg, 0.23 mmol) in MeOH (5 mL) was added aqueous NaOH (1N, 0.6 mL), the mixture was stirred at rt for 30 min. The solvent was removed, the residue was diluted with H₂O (15 mL) and the mixture was extracted with EtOAc (3×20 mL). The organic layer was washed with brine (20 mL), dried over Na₂SO₄, concentrated and purified by column chromatography on silica gel (DCM: MeOH=20:1) to give the title compound as a white solid.

Step 3: N-(2-((4-(N-(3-Chloro-4-fluorophenyl)-N'-hydroxycarbamimidoyl)-1,2,5-oxadiazol-3-yl)thio)ethyl)-3-hydroxyazetidine-3-carboxamide (123)

To a solution of tert-butyl 3-((2-((4-(N-(3-chloro-4-fluorophenyl)-N'-hydroxycarbamimidoyl)-1,2,5-oxadiazol-3-yl)thio)ethyl)carbamoyl)-3-hydroxyazetidine-1-carboxylate (123b) (80 mg, 0.14 mmol) in DCM (3 mL) was added TFA (0.5 mL) and the mixture was stirred at rt for 2 h. The solvent was removed and the residue was purified by HPLC to give the title compound as a white solid. ¹H NMR (500 MHz, CD3OD): δ ppm 7.10-7.07 (m, 1H), 6.98-6.96 (m, 1H), 6.75-6.71 (m, 1H), 4.38 (d, 2H, J=12 Hz), 4.05 (d, 2H, J=12 Hz), 3.68-3.65 (m, 2H), 3.37-3.35 (m, 2H). MS (ESI): m/z 431.1 [M+H]⁺.

Examples 123/1 to 123/8

The following Examples were prepared similar as described for Example 123 using the appropriate Intermediates and building blocks.

| # | Int. # | Structure | Analytical data |
|---|--------|-----------|-----------------|
| 123/1 | Int 100/2 | 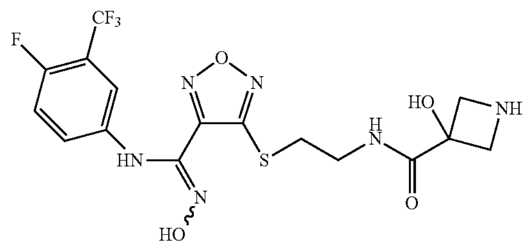 [SMILES: O=C(NCCSc1nonc1C(=NO)Nc1ccc(F)c(C(F)(F)F)c1)C1(O)CNC1] | ¹H NMR (500 MHz, CD₃OD): δ ppm 7.20-7.11 (m, 2H), 7.06-7.02 (m, 1H), 4.38 (d, J = 11.5 Hz, 2H), 4.05 (d, J = 11.5 Hz, 2H), 3.68-3.66 (m, 2H), 3.37-3.34 (m, 2H). MS (ESI): m/z 465.1 [M + H]⁺. |
| 123/2 | Int 100/3, step 1 | 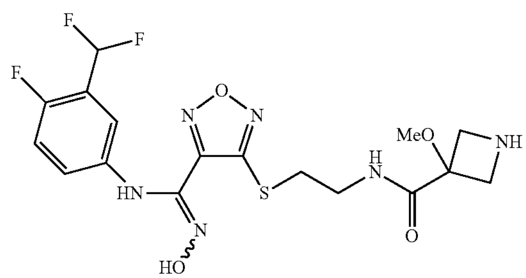 [SMILES: COC1(C(=O)NCCSc2nonc2C(=NO)Nc2ccc(F)c(C(F)F)c2)CNC1] | ¹H NMR (500 MHz, CD₃OD): δ ppm 7.12-6.98 (m, 3H), 6.92 (t, J = 54 Hz, 1H), 4.36 (d, 2H, J = 11.5 Hz), 4.20 (d, 2H, J = 11.5 Hz), 3.69-3.67 (m, 2H), 3.41 (s, 3H), 3.38-3.36 (m, 2H). MS (ESI): m/z 461.0 [M + H]⁺. |
| 123/3 | Int 100/3, step 1 | 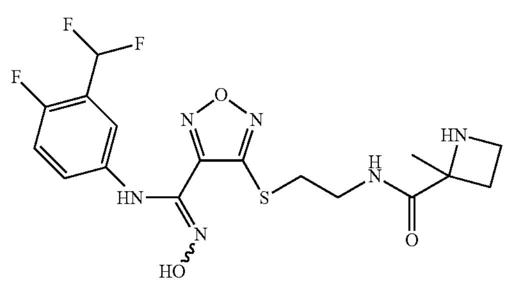 [SMILES: CC1(C(=O)NCCSc2nonc2C(=NO)Nc2ccc(F)c(C(F)F)c2)CCN1] | ¹H NMR (500 MHz, DMSO-d₆): δ ppm 11.69 (s br, 1H), 9.01 (s, 1H), 8.32-8.30 (m, 1H), 7.22-6.90 (m, 4H), 3.55-3.44 (m, 4H), 3.29-3.32 (m, 1H), 3.08-3.04 (m, 1H), 2.26-2.21 (m, 1H), 2.09-2.04 (m, 1H), 1.38 (s, 3H). MS (ESI): m/z 445.0 [M + H]⁺. |
| 123/4 | Int 100/3, step 1 | 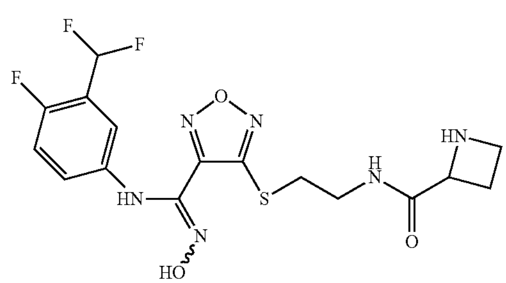 [SMILES: O=C(NCCSc1nonc1C(=NO)Nc1ccc(F)c(C(F)F)c1)C1CCN1] | ¹H NMR (500 MHz, CD₃OD): δ ppm 7.11-6.96 (m, 3H), 6.92 (t, J = 54 Hz, 1H), 4.36-4.33 (m, 1H), 3.72-3.69 (m, 1H), 3.66-3.62 (m, 2H), 3.46-3.42 (m, 1H), 3.39-3.33 (m, 2H), 2.66-2.62 (m, 1H), 2.36-2.32 (m, 1H). MS (ESI): m/z 430.9 [M + H]⁺. |

| # | Int. # | Structure | Analytical data |
|---|---|---|---|
| 123/5 | Int 100/3, Boc-azetidine-3-methyl-3-carboxylic acid, step 1 | [structure] | $^1$H NMR (500 MHz, CD$_3$OD): δ ppm 7.11-6.81 (m, 4H), 4.35 (d, 2H, J = 11.0 Hz), 3.61 (d, 2H, J = 11.0 Hz), 3.65-3.62 (m, 2H), 3.36-3.33 (m, 2H), 1.60 (s, 3H). MS (ESI): m/z 445.0 [M + H]$^+$. |
| 123/6 | Int 100/3, Boc-3-fluoroazetidine-3-carboxylic acid, step 1 | [structure] | $^1$H NMR (500 MHz, DMSO-d$_6$): δ ppm 11.72 (s, 1H), 9.03 (s, 1H), 8.46-8.45 (m, 1H), 7.23-6.89 (m, 4H), 3.89-3.81 (m, 2H), 3.60-3.50 (m, 4H), 3.33-3.28 (m, 2H). MS (ESI): m/z 449.0 [M + H]$^+$. |
| 123/7 | Int 100/3, 4,4,4-trifluoro-3-(Boc-amino)butanoic acid, step 1 | [structure] | $^1$H NMR (500 MHz, DMSO-d$_6$): δ ppm 11.70 (s br, 1H), 9.03 (s, 1H), 8.35-8.33 (m, 1H), 7.23-6.89 (m, 4H), 3.62 (s br, 1H), 3.48-3.43 (m, 2H), 3.27-3.23 (m, 2H), 2.42-2.38 (m, 1H), 2.25-2.20 (m, 1H), 1.99 (s, 2H). MS (ESI): m/z 487.0 [M + H]$^+$. |
| 123/8 | Int 100/3, 2-(3-(Boc-amino)-1,1-dioxothietan-3-yl)acetic acid, step 1 | [structure] | $^1$H NMR (500 MHz, DMSO-d$_6$): δ ppm 11.71 (s br, 1H), 9.03 (s, 1H), 8.40-8.37 (m, 1H), 7.23-6.89 (m, 4H), 4.21-4.18 (m, 2H), 3.96-3.92 (m, 2H), 3.47-3.43 (m, 2H), 3.28-3.23 (m, 2H), 2.63 (s, 2H). MS (ESI): m/z 509.0 [M + H]$^+$. |

Example 124

1-Ethyl-N-(2-((4-(N-(4-fluoro-3-(trifluoromethyl)phenyl)-N'-hydroxycarbamimidoyl)-1,2,5-oxadiazol-3-yl)thio)ethyl)-3-hydroxyazetidine-3-carboxamide (124)

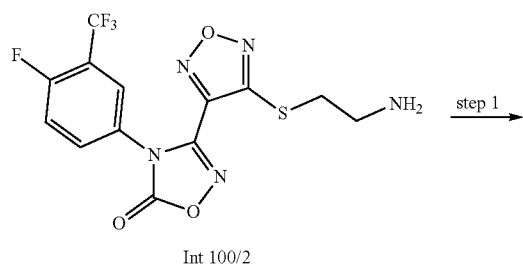

Int 100/2 step 1

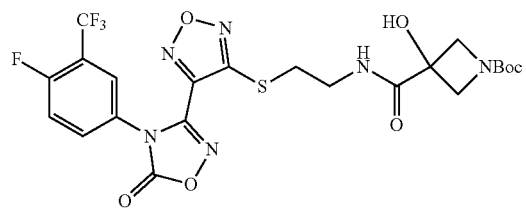

124a

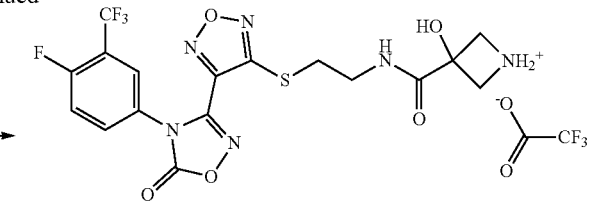

124b

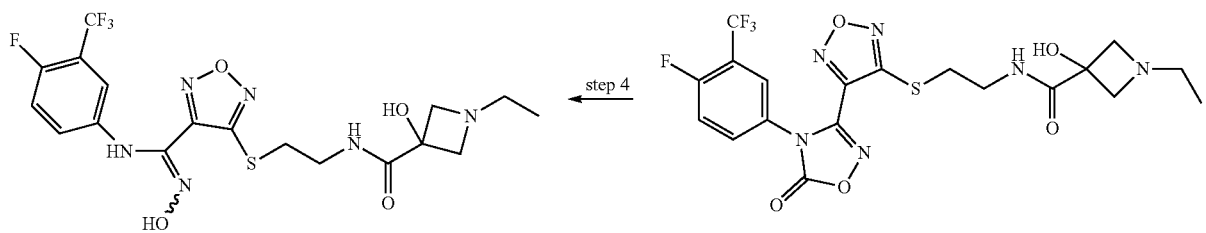

Example 124
124c

Step 1: tert-Butyl 3-((2-((4-(4-(4-fluoro-3-(trifluoromethyl)phenyl)-5-oxo-4,5-dihydro-1,2,4-oxadiazol-3-yl)-1,2,5-oxadiazol-3-yl)thio)ethyl)carbamoyl)-3-hydroxyazetidine-1-carboxylate (124a)

To a solution of 1-(tert-butoxycarbonyl)-3-hydroxyazetidine-3-carboxylic acid (35 mg, 0.24 mmol), EDCI (72 mg, 0.38 mmol), HOBt (51 mg, 0.38 mmol) and DIPEA (132 mg, 1.02 mmol) in DMF (1.5 mL) was added 3-(4-((2-aminoethyl)thio)-1,2,5-oxadiazol-3-yl)-4-(4-fluoro-3-(trifluoromethyl)phenyl)-1,2,4-oxadiazol-5(4H)-one (Int 100/2) (135 mg, 0.23 mmol) at rt, then the mixture was stirred at this temperature for 18 h. Water (20 mL) was added and the mixture was extracted with EtOAc (20 mL). The organic layer was washed with brine (10 mL), dried over $Na_2SO_4$, and concentrated to give the crude title compound as a yellow solid.

Step 2: 3-((2-((4-(4-(4-Fluoro-3-(trifluoromethyl)phenyl)-5-oxo-4,5-dihydro-1,2,4-oxadiazol-3-yl)-1,2,5-oxadiazol-3-yl)thio)ethyl)carbamoyl)-3-hydroxyazetidin-1-ium 2,2,2-trifluoroacetate (124b)

To a solution of tert-butyl 3-((2-((4-(4-(4-fluoro-3-(trifluoromethyl)phenyl)-5-oxo-4,5-dihydro-1,2,4-oxadiazol-3-yl)-1,2,5-oxadiazol-3-yl)thio)ethyl)carbamoyl)-3-hydroxyazetidine-1-carboxylate (124a) (120 mg, 0.24 mmol) in DCM (3 mL) was added TFA (1 mL) and the mixture was stirred at rt for 2 h. The solvent was removed to give the title compound as pale yellow solid.

Step 3: 1-Ethyl-N-(2-((4-(4-(4-fluoro-3-(trifluoromethyl)phenyl)-5-oxo-4,5-dihydro-1,2,4-oxadiazol-3-yl)-1,2,5-oxadiazol-3-yl)thio)ethyl)-3-hydroxyazetidine-3-carboxamide (124c)

To a solution of 3-((2-((4-(4-(4-fluoro-3-(trifluoromethyl)phenyl)-5-oxo-4,5-dihydro-1,2,4-oxadiazol-3-yl)-1,2,5-oxadiazol-3-yl)thio)ethyl)carbamoyl)-3-hydroxyazetidin-1-ium 2,2,2-trifluoroacetate (124b) (145 mg, 0.24 mmol) in MeOH (3 mL) was added acetaldehyde (0.5 mL) the mixture was stirred at rt for 20 minutes. Then $NaBH_3CN$ (22 mg, 0.36 mmol) was added and the mixture was stirred at rt for another 0.5 h. The solvent was removed, the residue was diluted with $NaHCO_3$ (25 mL) and extracted with EtOAc (3×20 mL). After concentration to dryness the title compound was obtained as a pale yellow solid.

Step 4: 1-Ethyl-N-(2-((4-(N-(4-fluoro-3-(trifluoromethyl)phenyl)—N'-hydroxy-carbamimidoyl)-1,2,5-oxadiazol-3-Athio)ethyl)-3-hydroxyazetidine-3-carboxamide (124)

To a solution of 1-ethyl-N-(2-((4-(4-(4-fluoro-3-(trifluoromethyl)phenyl)-5-oxo-4,5-dihydro-1,2,4-oxadiazol-3-yl)-1,2,5-oxadiazol-3-yl)thio)ethyl)-3-hydroxyazetidine-3-carboxamide (124c) (140 mg, 0.24 mmol) in MeOH (5 mL) was added NaOH (1N, 0.6 mL) and the mixture was stirred at rt for 30 min. The solvent was removed, the residue was diluted with $H_2O$ (15 mL), extracted with EtOAc (3×20 mL) and washed with brine (10 mL). The organic layer was dried over $Na_2SO_4$, concentrated and the residue was purified by HPLC to give the title compound as a white solid. $^1H$ NMR (500 MHz, DMSO-$d_6$): δ ppm 11.82 (s, 1H), 9.11 (s, 1H), 8.04-8.02 (m, 1H), 7.33-7.28 (m, 1H), 7.19-7.16 (m, 1H), 7.03-7.00 (m, 1H), 6.26 (s, 1H), 3.51-3.47 (m, 2H), 3.38-3.34 (m, 2H), 3.29-3.28 (m, 2H), 3.06 (d, J=8.0 Hz, 2H), 2.40-2.36 (m, 2H), 0.84-0.81 (m, 3H). MS (ESI): m/z 493.0 $[M+H]^+$.

Example 124/1

N-(2-((4-(N-(3-(Difluoromethyl)-4-fluorophenyl)-N'-hydroxycarbamimidoyl)-1,2,5-oxadiazol-3-yl)thio)ethyl)-1-methylazetidine-2-carboxamide (124/1)

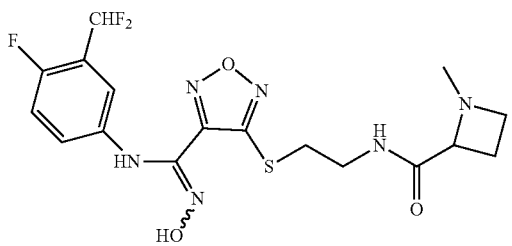 [SMILES: CN1CCC1C(=O)NCCSc1nonc1C(=NO)Nc1ccc(F)c(C(F)F)c1]

The title compound was prepared similar as described for Example 124 using in step 1 3-(4-((2-aminoethyl)thio)-1,2,5-oxadiazol-3-yl)-4-(3-(difluoromethyl)-4-fluorophenyl)-1,2,4-oxadiazol-5(4H)-one (Int 100/3) in place of 3-(4-((2-aminoethyl)thio)-1,2,5-oxadiazol-3-yl)-4-(4-fluoro-3-(trifluoromethyl)phenyl)-1,2,4-oxadiazol-5(4H)-one (Int 100/2) and 1-(tert-butoxycarbonyl)azetidine-2-carboxylic acid in place of 1-(tert-butoxycarbonyl)-3-hydroxyazetidine-3-carboxylic acid, and in step 3 formaldehyde in place of acetaldehyde. $^1$H NMR (500 MHz, DMSO-$d_6$): δ ppm 11.70 (s, 1H), 9.02 (s, 1H), 8.05-8.02 (m, 1H), 7.23-6.98 (m, 3H), 6.90-6.88 (m, 1H), 3.54-3.50 (m, 2H), 3.49-3.33 (m, 3H), 3.25-3.22 (m, 1H), 2.85-2.80 (m, 1H), 2.22 (s, 3H), 2.19-2.13 (m, 1H), 1.96-1.90 (m, 1H). MS (ESI): m/z 445.0 [M+H]$^+$.

Example 125

3-Cyano-N-(2-((4-(N-(3-(difluoromethyl)-4-fluorophenyl)-N'-hydroxycarbamimidoyl)-1,2,5-oxadiazol-3-yl)thio)ethyl)azetidine-3-carboxamide (125)

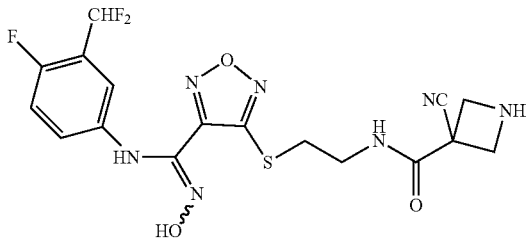 [SMILES: N#CC1(C(=O)NCCSc2nonc2C(=NO)Nc2ccc(F)c(C(F)F)c2)CNC1]

The title compound was prepared similar as described for Example 123 using in step 1 3-(4-((2-aminoethyl)thio)-1,2,5-oxadiazol-3-yl)-4-(3-(difluoromethyl)-4-fluorophenyl)-1,2,4-oxadiazol-5(4H)-one (Int 100/3) in place of 3-(4-((2-aminoethyl)thio)-1,2,5-oxadiazol-3-yl)-4-(4-fluoro-3-chlorophenyl)-1,2,4-oxadiazol-5(4H)-one (Int 100/1) and 1-(tert-butoxycarbonyl)-3-cyanoazetidine-3-carboxylic acid in place of 1-(tert-butoxycarbonyl)-3-hydroxyazetidine-3-carboxylic acid and in step 3 0.5 N aqueous HCl for 30 min in place of TFA in DCM for 2 h. $^1$H NMR (500 MHz, DMSO-$d_6$): δ ppm 11.74 (s, 1H), 9.04 (s, 1H), 8.74-8.72 (m, 1H), 7.23-6.88 (m, 4H), 3.86 (d, J=8.0 Hz, 2H), 3.74 (d, J=8.0 Hz, 2H), 3.56-3.52 (m, 2H), 3.32-3.29 (m, 2H). MS (ESI): m/z 456.0 [M+H]$^+$.

Example 126

N-(2-((4-(N-(3-(difluoromethyl)-4-fluorophenyl)-N'-hydroxycarbamimidoyl)-1,2,5-oxadiazol-3-Athio)ethyl)azetidine-3,3-dicarboxamide (126)

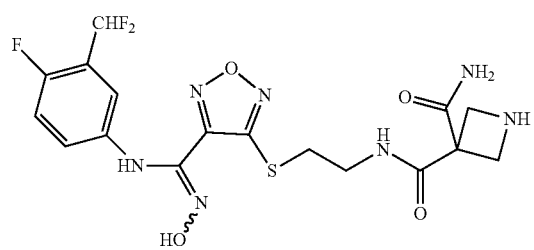 [SMILES: NC(=O)C1(C(=O)NCCSc2nonc2C(=NO)Nc2ccc(F)c(C(F)F)c2)CNC1]

The title compound was prepared similar as described for Example 123 using in step 1 3-(4-((2-aminoethyl)thio)-1,2,5-oxadiazol-3-yl)-4-(3-(difluoromethyl)-4-fluorophenyl)-1,2,4-oxadiazol-5(4H)-one (Int 100/3) in place of 3-(4-((2-aminoethyl)thio)-1,2,5-oxadiazol-3-yl)-4-(4-fluoro-3-chlorophenyl)-1,2,4-oxadiazol-5(4H)-one (Int 100/1) and 1-(tert-butoxycarbonyl)-3-cyanoazetidine-3-carboxylic acid in place of 1-(tert-butoxycarbonyl)-3-hydroxyazetidine-3-carboxylic acid and in step 3 HCl/Dioxane (4M) for 5 h in place of TFA in DCM for 2 h. $^1$H NMR (500 MHz, CD$_3$OD): δ ppm 7.11-6.81 (m, 4H), 4.00 (s, 4H), 3.65-3.62 (m, 2H), 3.36-3.33 (m, 2H). MS (ESI): m/z 474.0 [M+H]$^+$.

Example 127

N-(2-((4-(N-(3-Bromo-4-fluorophenyl)-N'-hydroxycarbamimidoyl)-1,2,5-oxadiazol-3-yl)thio)ethyl)-2-(S-methylsulfonimidoyl)acetamide (127)

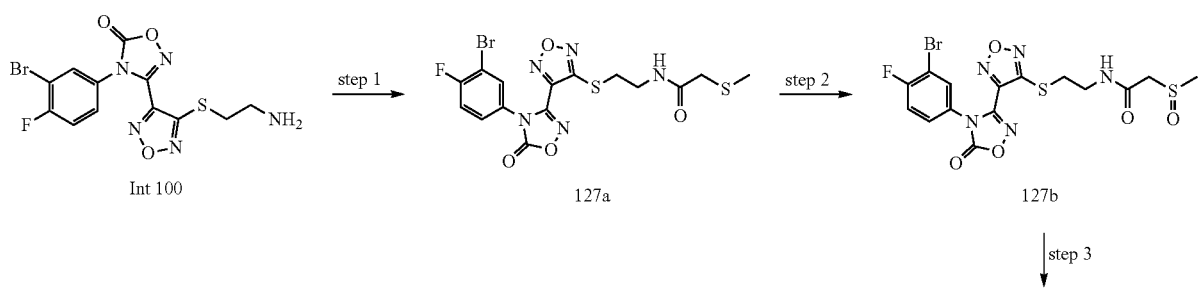

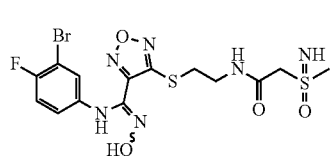 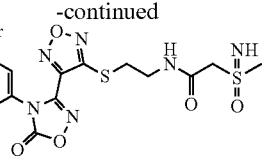

Example 127    127d    127c

Step 1: N-(2-((4-(4-(3-Bromo-4-fluorophenyl)-5-oxo-4,5-dihydro-1,2,4-oxadiazol-3-yl)-1,2,5-oxadiazol-3-yl)thio)ethyl)-2-(methylthio)acetamide (127a)

To a solution of 2-(methylthio)acetic acid (165 mg, 1.56 mmol), HATU (592 mg, 1.56 mmol) and Et$_3$N (210 mg, 2.08 mmol) in DCM (20 mL) was added 3-(4-((2-aminoethypthio)-1,2,5-oxadiazol-3-yl)-4-(3-bromo-4-fluorophenyl)-1,2,4-oxadiazol-5(4H)-one (Int 100) (417 mg, 1.04 mmol) at rt. After stirring overnight, the mixture was concentrated and the residue was resolved in DCM (50 mL) and the mixture was washed with water (2×50 mL). The organic layer was dried over Na$_2$SO$_4$, concentrated and the residue was purified by column chromatography on silica gel (EtOAc: PE=1:2) to give the title compound as a yellow solid.

Step 2: N-(2-((4-(4-(3-Bromo-4-fluorophenyl)-5-oxo-4,5-dihydro-1,2,4-oxadiazol-3-yl)-1,2,5-oxadiazol-3-yl)thio)ethyl)-2-(methylsulfinyl)acetamide (127b)

To a solution of N-(2-((4-(4-(3-bromo-4-fluorophenyl)-5-oxo-4,5-dihydro-1,2,4-oxadiazol-3-yl)-1,2,5-oxadiazol-3-yl)thio)ethyl)-2-(methylthio)acetamide (127a) (371 mg, 0.76 mmol) in DCM (20 mL) was added MCPBA (174 mg, 75%) at rt and the mixture was stirred at rt for 30 min. The mixture was washed with saturated aqueous NaHCO$_3$ (20 mL) and extracted with DCM (2×20 mL). The combined organic phase was washed with brine (20 mL), dried over Na$_2$SO$_4$, and concentrated to dryness under vacuum. The residue was purified by column chromatography on silica gel (EtOAc: PE=1:4) to give the title compound as a yellow solid.

Step 3: tert-Butyl ((2-((2-((4-(4-(3-bromo-4-fluorophenyl)-5-oxo-4,5-dihydro-1,2,4-oxadiazol-3-yl)-1,2,5-oxadiazol-3-yl)thio)ethyl)amino)-2-oxoethyl)(methyl)(oxo)—λ$^6$-sulfaneylidene)carbamate (127c)

To a solution of N-(2-((4-(4-(3-bromo-4-fluorophenyl)-5-oxo-4,5-dihydro-1,2,4-oxadiazol-3-yl)-1,2,5-oxadiazol-3-yl)thio)ethyl)-2-(methylsulfinyl)acetamide (127b) (363 mg, 0.72 mmol), MgO (115 mg, 2.88 mmol), PhI(OAc)$_2$ (348 mg, 1.08 mmol) and Rh$_2$(OAc)$_4$ (31 mg, 0.07 mmol) in DCM (20 mL) was added tert-butyl carbamate (168 mg, 1.44 mmol) at rt and the mixture was stirred at 45° C. for 8 h. The mixture was washed with water (20 mL), extracted with DCM (2×20 mL). The combined organic phase was washed with brine (20 mL), dried over Na$_2$SO$_4$, and concentrated to dryness under vacuum. The residue was purified by column chromatography on silica gel (EtOAc: PE=1:1) to give the title compound as a yellow oil.

Step 4: N-(2-((4-(4-(3-Bromo-4-fluorophenyl)-5-oxo-4,5-dihydro-1,2,4-oxadiazol-3-yl)-1,2,5-oxadiazol-3-yl)thio)ethyl)-2-(S-methylsulfonimidoyl)acetamide (127d)

To a solution of tert-butyl ((2-((2-((4-(4-(3-bromo-4-fluorophenyl)-5-oxo-4,5-dihydro-1,2,4-oxadiazol-3-yl)-1,2,5-oxadiazol-3-yl)thio)ethyl)amino)-2-oxoethyl)(methyl)(oxo)-16-sulfaneylidene)carbamate (127c) (66 mg, 0.10 mmol) in dioxane (20 mL) was added HCl in dioxane (3M, 2 mL) at rt. After stirring overnight, the mixture was evaporated to dryness under vacuum to get the title compound as a yellow solid.

Step 5: N-(2-((4-(N-(3-bromo-4-fluorophenyl)-N'-hydroxycarbamimidoyl)-1,2,5-oxadiazol-3-yl)thio)ethyl)-2-(S-methylsulfonimidoyl)acetamide (127)

To a solution of N-(2-((4-(4-(3-bromo-4-fluorophenyl)-5-oxo-4,5-dihydro-1,2,4-oxadiazol-3-yl)-1,2,5-oxadiazol-3-yl)thio)ethyl)-2-(S-methylsulfonimidoyl)acetamide (127d) (50 mg, 0.10 mmol) in MeOH (3 mL) was added NaOH (1N, 0.5 mL) at rt and the mixture was stirred overnight. Then water was added and the mixture was extracted with EtOAc (20 mL). The organic phase was washed with brine (20 mL), dried over Na$_2$SO$_4$, filtered and concentrated to dryness. The residue was purified by HPLC to give the title compound as a white solid. $^1$H NMR (500 MHz, DMSO-d$_6$): δ ppm 11.74 (s, 1H), 8.98 (s, 1 H), 8.69 (s, 1H), 7.19-7.09 (m, 2H), 6.73-6.69 (m, 1H), 4.20-4.16 (m, 2H), 3.51-3.47 (m, 2H), 3.27-3.18 (m, 5H). MS (ESI): m/z 495.0 [M+H]$^+$.

Examples 127/1 to 127/4

The following Examples were prepared similar as described for Example 127 using the appropriate Intermediates and building blocks.

| # | Int. # | Structure | analytical data |
|---|---|---|---|
| 127/1 | Int 100/3 | 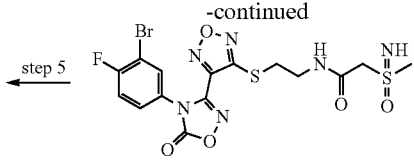 | $^1$H NMR (500 MHz, DMSO-d$_6$): δ ppm 11.73 (s, 1H), 9.04 (s, 1H), 8.76-8.73 (m, 1H) 7.23-6.89 (m, 4H), 4.26 (s, 2H), 3.53-3.49 (m, 2H), 3.29-3.24 (m, 5H). MS (ESI): m/z 466.8 [M + H]$^+$. |

-continued
| # | Int. # | Structure | analytical data |
|---|---|---|---|
| 127/2 | Int 100/2 | 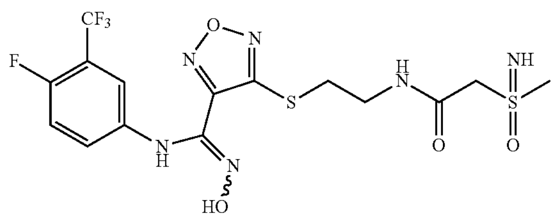 [SMILES: CS(=N)(=O)CC(=O)NCCSc1nonc1C(=NO)Nc1ccc(F)c(C(F)(F)F)c1] | ¹H NMR (500 MHz, DMSO-d₆): δ ppm 11.86 (s, 1H), 9.14 (s, 1H), 8.66-8-63 (m, 1H), 7.33-7.28 (m, 1H), 7.16-7.12 (m, 1H), 7.01-6.97 (m, 1H), 4.10 (s, 2H), 3.51-3.47 (m, 2H), 3.27-3.14 (m, 5H). MS (ESI): m/z 485.0 [M + H]⁺. |
| 127/3 | Int 100/5 | 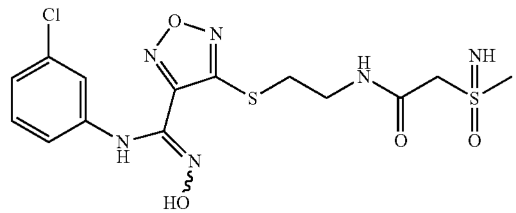 | ¹H NMR (500 MHz, DMSO-d₆): δ ppm 11.81 (s, 1H), 9.05 (s, 1H), 8.81-8.79 (m, 1H), 7.19-7.15 (m, 1H), 6.95-6.92 (m, 1H), 6.83 (s, 1H), 6.61-6.58 (m, 1H), 4.44-4.40 (m, 2H), 3.54-3.50 (m, 2H), 3.39-3.253.36 (m, 3H), 3.29-3.26 (m, 2H). MS (ESI): m/z 433.0 [M + H]⁺. |
| 127/4 | Int 100/6 | 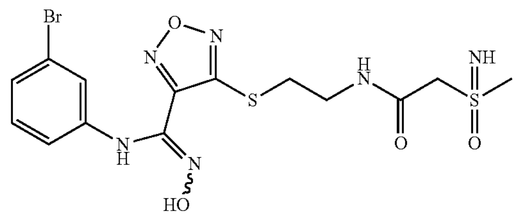 [SMILES: CS(=N)(=O)CC(=O)NCCSc1nonc1C(=NO)Nc1cccc(Br)c1] | ¹H NMR (500 MHz, DMSO-d₆): δ ppm 11.81 (s, 1H), 9.03 (s, 1H), 8.79-8.77 (m, 1H), 7.12-7.05 (m, 2H), 6.97 (s, 1H), 6.64-6.61 (m, 1H), 4.40-4.35 (m, 2H), 3.53-3.47 (m, 2H), 3.36-3.25 (m, 5H). MS (ESI): m/z 477.0 [M + H]⁺. |
Example 128
N-(2-((4-(N-(3-(Difluoromethyl)-4-fluorophenyl)-N'-hydroxycarbamimidoyl)-1,2,5-oxadiazol-3-yl)thio)ethyl)-2-(sulfamoylamino)acetamide (128)
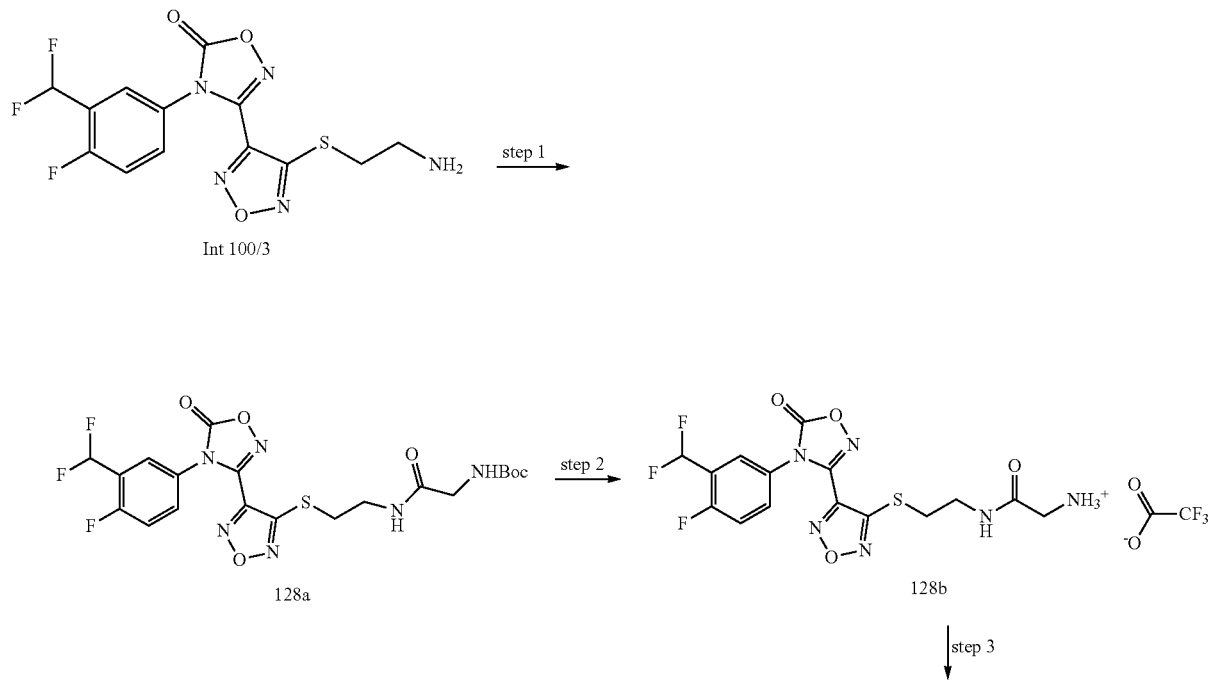

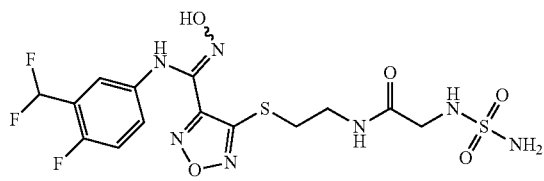

Example 128

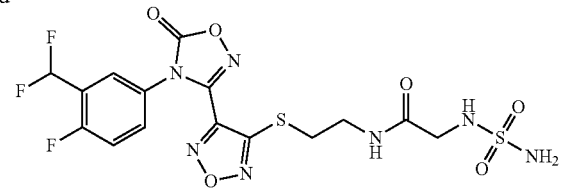

128c

Step 1: tert-Butyl (2-((2-((4-(4-(3-(difluoromethyl)-4-fluorophenyl)-5-oxo-4,5-dihydro-1,2,4-oxadiazol-3-yl)-1,2,5-oxadiazol-3-Athio)ethyl)amino)-2-oxoethyl)carbamate (128a)

A solution of 2-(tert-butoxycarbonylamino)acetic acid (90 mg, 0.78 mmol), HATU (296 mg, 0.78 mmol) and Et₃N (105 mg, 1.04 mmol) in DCM (20 mL) was added 3-(4-((2-aminoethyl)thio)-1,2,5-oxadiazol-3-yl)-4-(3-(difluoromethyl)-4-fluorophenyl)-1,2,4-oxadiazol-5(4H)-one (Int 100/3) (194 mg, 0.52 mmol) at rt. After stirring overnight, the mixture was concentrated to get an oil and resolved in DCM (50 mL). The mixture was washed with water (2×50 mL). The organic layer was dried over Na₂SO₄, concentrated and the residue was purified by column chromatography on silica gel to give the title compound as a yellow solid.

Step 2: 2-((2-((4-(4-(3-(Difluoromethyl)-4-fluorophenyl)-5-oxo-4,5-dihydro-1,2,4-oxadiazol-3-yl)-1,2,5-oxadiazol-3-Athio)ethyl)amino)-2-oxoethan-1-aminium 2,2,2-trifluoroacetate (128b)

To a solution of tert-butyl (2-((2-((4-(4-(3-(difluoromethyl)-4-fluorophenyl)-5-oxo-4,5-dihydro-1,2,4-oxadiazol-3-yl)-1,2,5-oxadiazol-3-yl)thio)ethyl)amino)-2-oxoethyl)carbamate (128a) (200 mg, 0.38 mmol) in DCM (20 mL) was added TFA (2 mL) at rt. After stirring overnight, the mixture was concentrated to dryness under vacuum to get the title compound as yellow solid.

Step 3: N-(2-((4-(4-(3-(Difluoromethyl)-4-fluorophenyl)-5-oxo-4,5-dihydro-1,2,4-oxadiazol-3-yl)-1,2,5-oxadiazol-3-Athio)ethyl)-2-(sulfamoylamino)acetamide (128c)

To a solution 2-((2-((4-(4-(3-(difluoromethyl)-4-fluorophenyl)-5-oxo-4,5-dihydro-1,2,4-oxadiazol-3-yl)-1,2,5-oxadiazol-3-Athio)ethyl)amino)-2-oxoethan-1-aminium 2,2,2-trifluoroacetate (128b) (154 mg, 0.29 mmol) and Et₃N (73 mg, 0.72 mmol) in DCM (20 mL) was added sulfamoyl chloride (55 mg, 0.48 mmol) at rt. After stirring overnight, the mixture was concentrated to get an oil and resolved in DCM (50 mL). The mixture was washed with water (2×50 mL). The organic layer was dried over Na₂SO₄, concentrated and the residue was purified by column chromatography on silica gel (EA: PE=1:1) to give the title compound as a yellow solid.

Step 4: N-(2-((4-(N-(3-(Difluoromethyl)-4-fluorophenyl)-N'-hydroxycarbamimidoyl)-1,2,5-oxadiazol-3-yl)thio)ethyl)-2-(sulfamoylamino)acetamide (128)

To a solution of N-(2-((4-(4-(3-(difluoromethyl)-4-fluorophenyl)-5-oxo-4,5-dihydro-1,2,4-oxadiazol-3-yl)-1,2,5-oxadiazol-3-Athio)ethyl)-2-(sulfamoylamino)acetamide (128c) (100 mg, 0.20 mmol) in MeOH (3 mL) was added NaOH (1N, 0.5 mL) at rt, and stirred overnight. Then water was added and the mixture was extracted with EtOAc (20 mL). The organic phase was washed with brine (20 mL), dried over Na₂SO₄, filtered and concentrated to dryness. The residue was purified by HPLC to give the title compound as a white solid. $^1$H NMR (500 MHz, DMSO-d₆): δ ppm 11.70 (s, 1H), 9.02 (s, 1H), 8.10-8.08 (m, 1H), 7.23-6.99 (m, 3H), 6.90-6.88 (m, 1H), 6.79 (s br, 1H), 6.65 (s br, 1H), 3.50-3.28 (m, 4H), 3.27-3.25 (m, 2H). MS (ESI): m/z 484.1 [M+H]⁺.

Examples 128/1 to 128/7

The following Examples were prepared similar as described for Example 128 using the appropriate Intermediates and building blocks.

| # | Int. # | Structure | analytical data |
|---|---|---|---|
| 128/1 | Int 100/2 | 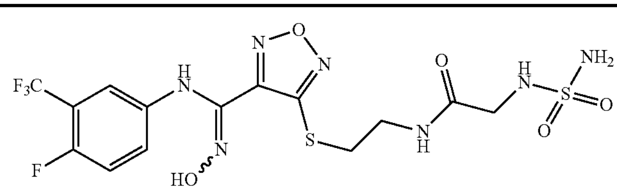 | $^1$H NMR (500 MHz, DMSO-d₆): δ ppm 11.86 (s, 1H), 9.14 (s, 1H), 8.12-8.10 (m, 1H) 7.33-7.28 (m, 1H), 7.16-7.13 (m, 1H), 7.01-6.96 (m, 1H), 6.83-6.80 (m, 1H), 6.66 (s, 2H), 3.50-3.45 (m, 4H), 3.30-3.25 (m, 2H). MS (ESI): m/z 502.0 [M + H]⁺. |
| 128/2 | Int 100/3, MsCl, step 3 | 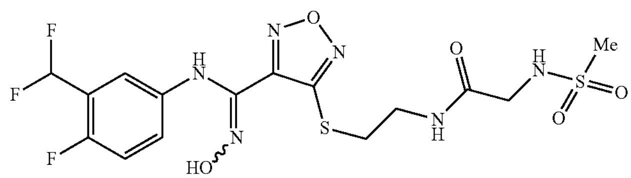 [SMILES: CS(=O)(=O)NCC(=O)NCCSc1nonc1C(=NO)Nc1ccc(F)c(C(F)F)c1] | $^1$H NMR (500 MHz, DMSO-d₆): δ ppm 11.72 (s, 1H), 9.04 (s, 1H), 8.27-8.25 (m, 1H), 7.40-7.37 (m, 1H), 7.23-6.87 (m, 4H), 3.61-3.60 (m, 2H), 3.50-3.46 (m, 2H), 3.27-3.24 (m, 2H), 2.92 (s, 3H). MS (ESI): m/z 483.1 [M + H]⁺. |

| # | Int. # | Structure | analytical data |
|---|---|---|---|
| 128/3 | Int 100/3, [Boc-azetidine-OH-COOH], step 1, [acetyl chloride], step 3 | [structure] | $^1$H NMR (500 MHz, DMSO-d$_6$): δ ppm 11.70 (s, 1H), 9.03 (s, 1H), 8.25-8.23 (m, 1H), 7.19-7.14 (m, 1H), 7.11 (t, J = 54 Hz, 1H), 7.03-7.00 (m, 1H), 6.92-6.89 (m, 1H), 6.83 (s, 1H), 4.31 (d, 1H, J = 9.0 Hz), 4.03 (d, 1H, J = 9.0 Hz), 3.95 (d, 1H, J = 9.0 Hz), 3.68 (d, 1H, J = 9.0 Hz), 3.54-3.49 (m, 2H), 3.31-3.27 (m, 2H), 1.73 (s, 3H). MS (ESI): m/z 489.1 [M + H]$^+$. |
| 128/4 | Int 100/3, [Boc-azetidine-OH-COOH], step 1, [TMS-isocyanate], step 3 | [structure] | $^1$H NMR (500 MHz, DMSO-d$_6$): δ ppm 11.71 (s br, 1H), 9.02 (s, 1H), 8.17-8.15 (m, 1H), 7.23-7.00 (m, 3H), 6.89-6.87 (m, 1H), 6.69 (s, 1H), 5.87 (s, 2H), 4.02 (d, J = 8.5 Hz, 2H), 3.65 (d, J = 8.5 Hz, 2H), 3.52-3.49 (m, 2H), 3.31-3.27 (m, 2H). MS (ESI): m/z 490.0 [M + H]$^+$. |
| 128/5 | Int 100/3, [Boc-azetidine-OH-COOH], step 1, MsCl, step 3 | [structure] | $^1$H NMR (500 MHz, DMSO-d$_6$): δ ppm 11.70 (s, 1H), 9.03 (s, 1H), 8.29-8.27 (m, 1H), 7.23-6.89 (m, 5H), 4.14 (d, 2H, J = 8.5 Hz), 3.78 (d, 2H, J = 8.5 Hz), 3.52-3.49 (m, 2H), 3.31-3.27 (m, 2H), 2.99 (s, 3H). MS (ESI): m/z 525.0 [M + H]$^+$. |
| 128/6 | Int 100/3, [Boc-azetidine-OH-COOH], step 1, | [structure] | $^1$H NMR (500 MHz, DMSO-d$_6$): δ ppm 11.70 (s, 1H), 9.01 (s, 1H), 8.22-8.20 (m, 1H), 7.23-6.87 (m, 6H), 6.71 (s, 1H), 3.97 (d, J = 8.5 Hz, 2H), 3.61 (d, J = 8.5 Hz, 2H), 3.52-3.49 (m, 2H), 3.31-3.27 (m, 2H). MS (ESI): m/z 525.8 [M + H]$^+$. |

| # | Int. # | Structure | analytical data |
|---|---|---|---|
| 128/7 | Int 100/3, [sulfamoyl chloride, step 3] [Boc-azetidine-carboxylic acid, step 1], [sulfamoyl chloride, step 3] | [structure] | $^1$H NMR (500 MHz, DMSO-d$_6$): δ ppm 11.71 (s, 1H), 9.01 (s, 1H), 8.30-8.27 (m, 1H), 7.23-6.88 (m, 6H), 3.80-3.71 (m, 4H), 3.49-3.43 (m, 2H) 3.27-3.19 (m, 3H). MS (ESI): m/z 510.0 [M + H]$^+$. |

Example 129

2-(3-Aminooxetan-3-yl)-N-(2-((4-(N-(3-(difluoromethyl)-4-fluorophenyl)-N'-hydroxycarbamimidoyl)-1,2,5-oxadiazol-3-yl)thio)ethyl)acetamide (129)

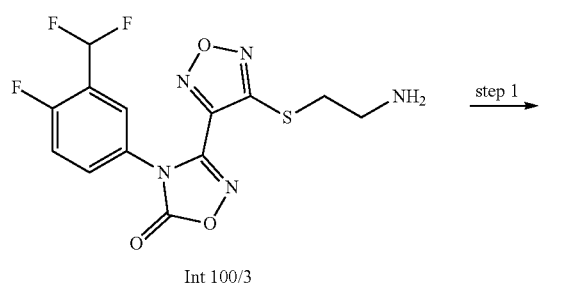

Int 100/3

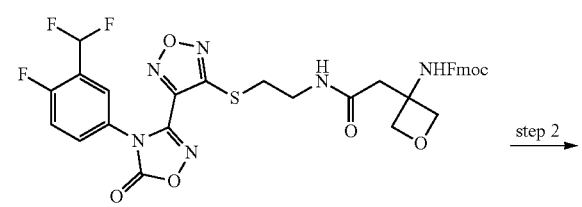

129 a

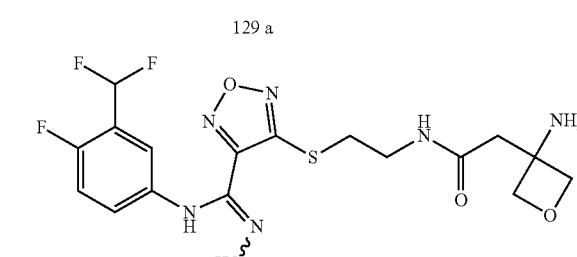

129

Step 1: (9H-Fluoren-9-yl)methyl (3-(2-((2-((4-(4-(3-(difluoromethyl)-4-fluorophenyl)-5-oxo-4,5-dihydro-1,2,4-oxadiazol-3-yl)-1,2,5-oxadiazol-3-yl)thio)ethyl)amino)-2-oxoethyl)oxetan-3-yl)carbamate (129a)

A mixture of 2-(3-((((9H-fluoren-9-yl)methoxy)carbonyl)amino)oxetan-3-yl)acetic acid (Int 107) (70 mg, 0.20 mmol), 3-(4-((2-aminoethyl)thio)-1,2,5-oxadiazol-3-yl)-4-(3-(difluoromethyl)-4-fluorophenyl)-1,2,4-oxadiazol-5(4H)-one (Int 100/3) (74 mg, 0.20 mmol) and EDCI (78 mg, 0.40 mmol) in DMF (6 mL) was stirred at rt for 18 h. Water was added and the mixture was extracted with EtOAc (2×30 mL). The organic layer was washed with water (2×25 mL) and brine (20 mL), dried over (Na$_2$SO$_4$) and concentrated. The residue was purified by chromatography on silica gel (MeOH in DCM=0~15%) to give the title compound as an oil.

Step 2: 2-(3-Aminooxetan-3-yl)-N-(2-((4-(N-(3-(difluoromethyl)-4-fluorophenyl)-N'-hydroxycarbamimidoyl)-1,2,5-oxadiazol-3-yl)thio)ethyl)acetamide (129)

To a mixture of (9H-fluoren-9-yl)methyl (3-(2-((2-((4-(4-(3-(difluoromethyl)-4-fluorophenyl)-5-oxo-4,5-dihydro-1,2,4-oxadiazol-3-yl)-1,2,5-oxadiazol-3-yl)thio)ethyl)amino)-2-oxoethyl)oxetan-3-yl)carbamate (129a) (100 mg, 0.14 mmol) in MeOH (5 mL) was added NaOH (2 N, 0.2 mL, 0.40 mmol). After stirring for 2 h, the reaction mixture was concentrated and the residue was purified by preparative TLC (DCM: MeOH=10: 1) to give the title compound as a white solid (15 mg, yield: 24%). $^1$H NMR (400 MHz, DMSO-d$_6$): δ ppm 11.69 (s br, 1H), 9.03 (s, 1H), 8.44-8.41 (m, 1H), 7.25-6.88 (m, 4H), 4.40-4.34 (m, 4H), 3.47-3.42 (m, 2H), 3.27-3.22 (m, 2H), 2.62 (s, 2H). MS (ESI): m/z=461.2 [M+1]$^+$.

If one were to use similar procedures as described above, the following compounds can be prepared:
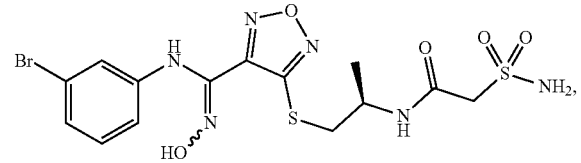
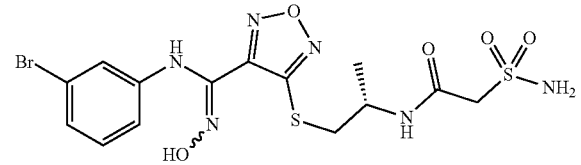
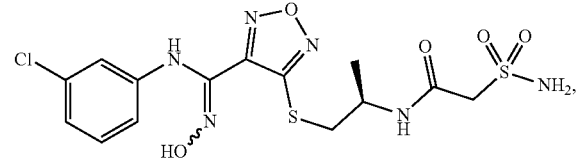
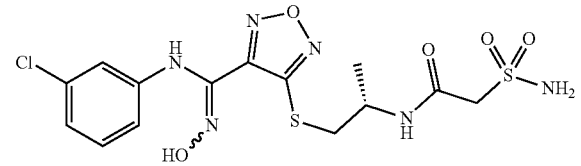
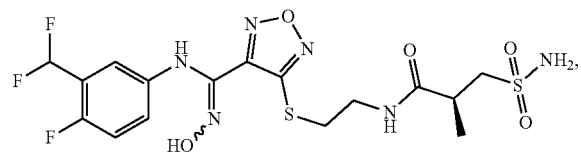
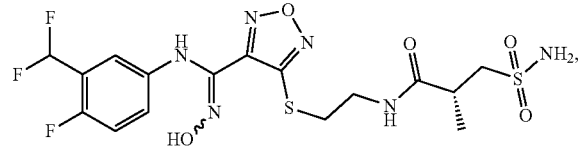
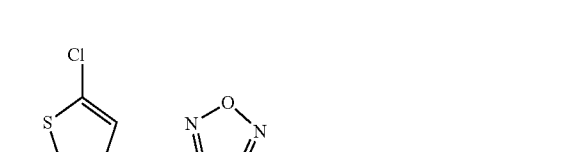
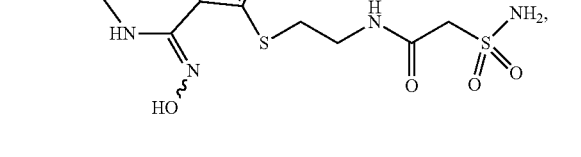
-continued
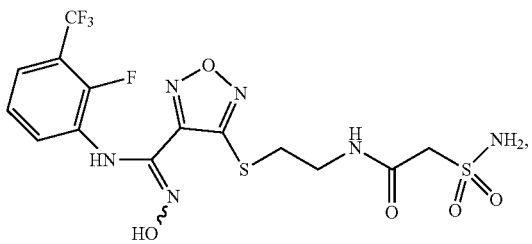
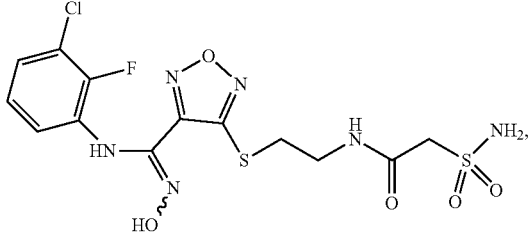
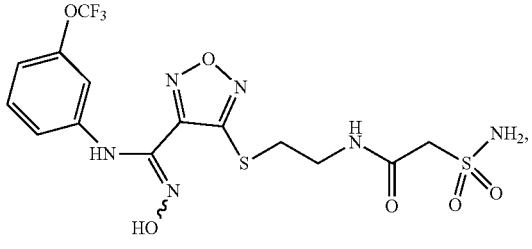
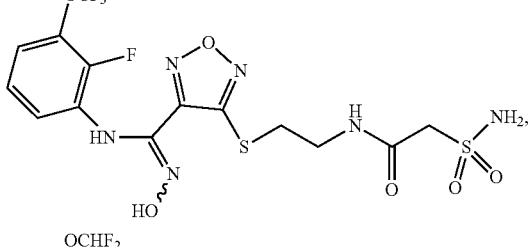
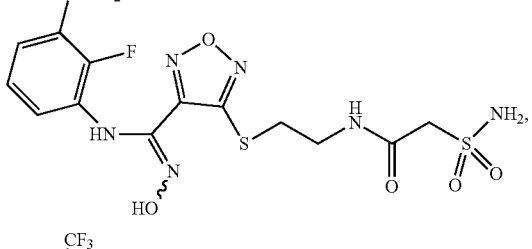
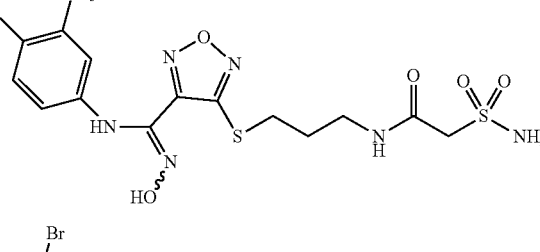
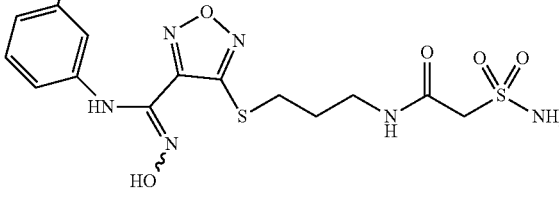

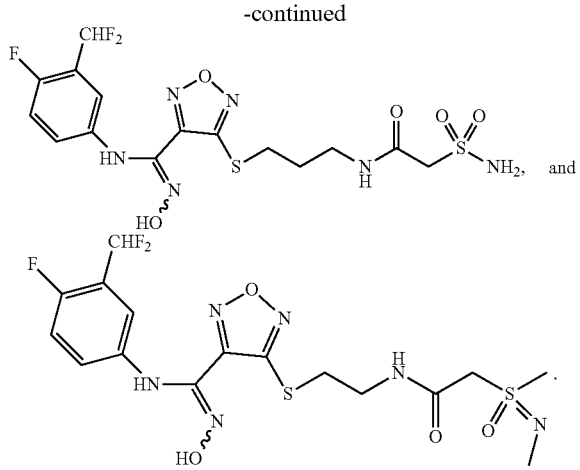

Biological Assays

SKOV-3 cellular Indoleamine 2,3-dioxygenase assay

SKOV-3 cells were obtained from the American Type Culture Collection (ATCC® HTB-77™) and maintained in McCoy's medium (Pan Biotech) supplemented with 10% fetal bovine serum and 1% Penicilin/Streptomycin. Cells were kept at 37° C. in a humidified incubator with 5% $CO_2$. For assay preparation, cells were seeded at a density of $2*10^5$/ml into black clear bottom 96 well plates in 100 µl medium/well supplemented with 50 ng/ml Interferon gamma (eBioscience, Thermo Fisher Scientific). After cells fully adhered to the plate, dilution series of compounds were added in medium containing additional L-Tryptophan to a final L-Tryptophan concentration of 100 µM. The cells were incubated for 24 hours. Detection of produced N-Formylkynurenin was performed by addition of 3-Methylpiperidine to a final concentration of 200 mM. The plates were sealed and heated to 65° C. for 20 minutes in a water bath. After cooling the fluorescence of each well was recorded with a Victor™X4 (PerkinElmer) plate reader at an emission wavelength of 535 nm and excitation at 405 nm (Tomek et al.; Anal Bioanal Chem (2013) 405:2515-2524., Tomek et al.; Biochim Biophys Acta. 2015 September; 1850(9):1772-80).

The $IC_{50}$ values of the example compounds are shown in Table 1 below (A=$IC_{50}$<100 nM, B=100 nM≤$IC_{50}$≤1 µM, C=$IC_{50}$>1 µM).

TABLE 1

| Example # | cell based activity |
| --- | --- |
| 1 | A |
| 1/1 | A |
| 1/2 | C |
| 1/3 | A |
| 1/4 | B |
| 2 | A |
| 2/1 | A |
| 2 | A |
| 2/3 | A |
| 2/4 | A |
| 2/5 | A |
| 2/6 | A |
| 2/7 | B |
| 3 | B |
| 3/1 | B |
| 3/2 | B |
| 3/3 | B |

TABLE 1-continued

| Example # | cell based activity |
| --- | --- |
| 3/4 | A |
| 4 | B |
| 4/1 | A |
| 4/2 | A |
| 5 | A |
| 6 | A |
| 6/1 | A |
| 6/2 | A |
| 6/3 | B |
| 6/4 | B |
| 6/5 | B |
| 6/6 | A |
| 7 | A |
| 7/1 | A |
| 8 | C |
| 8/1 | A |
| 8/2 | B |
| 8/3 | B |
| 9 | C |
| 9/1 | B |
| 9/2 | B |
| 9/3 | A |
| 9/4 | B |
| 9/5 | B |
| 9/6 | C |
| 9/7 | B |
| 9/8 | C |
| 9/9 | C |
| 9/10 | C |
| 9/11 | C |
| 9/12 | B |
| 9/13 | C |
| 9/14 | B |
| 9/15 | A |
| 9/16 | B |
| 9/17 | B |
| 9/18 | C |
| 9/19 | B |
| 9/20 | B |
| 9/21 | A |
| 9/22 | B |
| 10 | B |
| 10/1 | B |
| 11 | B |
| 12 | B |
| 13 | C |
| 14 | B |
| 15 | B |
| 16 | C |
| 16/1 | C |
| 17 | B |
| 18 | B |
| 19 | B |
| 20 | C |
| 20/1 | B |
| 21 | B |
| 22 | C |
| 100 | A |
| 100/1 | A |
| 101 | A |
| 101/1 | A |
| 102 | A |
| 102/1 | A |
| 102/2 | B |
| 103 | B |
| 103/1 | A |
| 103/2 | A |
| 103/3 | A |
| 104 | C |
| 105 | B |
| 106 | C |
| 107 | A |
| 107/1 | A |
| 107/2 | A |
| 107/3 | A |
| 107/4 | A |

TABLE 1-continued

| Example # | cell based activity |
|---|---|
| 107/5 | A |
| 107/6 | A |
| 107/7 | A |
| 107/8 | A |
| 107/9 | A |
| 107/10 | A |
| 107/11 | A |
| 107/12 | A |
| 107/13 | A |
| 107/14 | A |
| 107/15 | A |
| 107/16 | A |
| 107/17 | A |
| 107/18 | A |
| 107/19 | A |
| 107/20 | B |
| 107/21 | A |
| 107/22 | A |
| 107/23 | A |
| 107/24 | A |
| 107/25 | A |
| 107/26 | B |
| 107/27 | A |
| 107/28 | A |
| 107/29 | A |
| 107/30 | A |
| 107/31 | A |
| 107/32 | A |
| 107/33 | A |
| 107/34 | C |
| 107/35 | A |
| 107/36 | A |
| 107/37 | A |
| 107/38 | A |
| 107/39 | A |
| 107/40 | A |
| 107/41 | A |
| 108 | A |
| 108/1 | C |
| 108/2 | B |
| 109 | B |
| 109/1 | C |
| 109/2 | B |
| 109/3 | C |
| 110 | B |
| 111 | A |
| 112 | A |
| 112/1 | B |
| 113 | A |
| 113/1 | A |
| 114 | A |
| 114/1 | A |
| 114/2 | A |
| 114/3 | A |
| 114/4 | A |
| 114/5 | A |
| 115 | A |
| 115/1 | A |
| 116 | A |
| 117 | B |
| 117/1 | B |
| 117/2 | C |
| 117/3 | A |
| 117/4 | B |
| 117/5 | C |
| 117/6 | B |
| 117/7 | A |
| 117/8 | A |
| 117/9 | A |
| 117/10 | A |
| 117/11 | C |
| 117/12 | A |
| 117/13 | A |
| 117/14 | A |
| 117/15 | A |
| 117/16 | A |

TABLE 1-continued

| Example # | cell based activity |
|---|---|
| 117/17 | B |
| 117/18 | B |
| 117/19 | A |
| 117/20 | A |
| 117/21 | A |
| 117/22 | A |
| 117/23 | A |
| 117/24 | A |
| 118 | A |
| 119 | A |
| 119/1 | A |
| 119/2 | A |
| 119/3 | A |
| 119/4 | A |
| 119/5 | A |
| 119/6 | A |
| 120 | A |
| 120/1 | A |
| 121 | B |
| 122 | A |
| 123 | B |
| 123/1 | B |
| 123/2 | A |
| 123/3 | A |
| 123/4 | A |
| 123/5 | A |
| 123/6 | A |
| 123/7 | A |
| 124 | A |
| 124/1 | A |
| 125 | B |
| 126 | B |
| 127 | A |
| 127/1 | A |
| 127/2 | A |
| 127/3 | A |
| 127/4 | A |
| 128 | A |
| 128/1 | A |
| 128/2 | A |
| 128/3 | A |
| 128/4 | B |
| 128/5 | A |
| 128/6 | A |
| 128/7 | A |

The invention claimed is:
1. A compound represented by Formula (I)

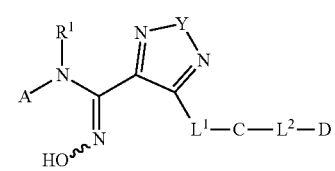

or an enantiomer, diastereomer, tautomer or pharmaceutically acceptable salt thereof
wherein
A is $C_{3-10}$-cycloalkyl, 3 to 10-membered heterocycloalkyl containing 1 to 5 heteroatoms independently selected from the group consisting of N, O and S, or 6- to 10-membered mono- or bicyclic aryl,
wherein cycloalkyl, heterocycloalkyl and aryl are unsubstituted or substituted with 1 to 7 substituents independently selected from the group consisting of halogen, OH, oxo, CN, $C_{1-6}$-alkyl, O—$C_{1-6}$-alkyl, C(O)OR², S(O)—C₁₋₆-alkyl, S(O)₂—C₁₋₆-alkyl, N(R²)₂, C(O)N(R²)₂, S(O)₂N(R²)₂ and C₃₋₆-cycloalkyl,
   wherein alkyl and cycloalkyl are unsubstituted or substituted with 1 to 3 substituents independently selected from
the group consisting of halogen, C₁₋₃-alkyl, OH, CN, oxo and OS(O)₂CH₃, or
wherein two adjacent substituents complete a 3- to 8-membered saturated or partially unsaturated ring containing carbon atoms and optionally containing 1 to 3 heteroatoms selected from O, S, N, S(0), S(O)₂ or NR², wherein the ring is unsubstituted or substituted with 1 to 7 substituents independently selected from the group consisting of halogen, OH, oxo, CN, C₁₋₆-alkyl, O—C₁₋₆-alkyl, C(O)OR², S(O)—C₁₋₆-alkyl, S(O)₂—C₁₋₆-alkyl, N(R²)₂, C(O)N(R²)₂, S(O)₂ N(R²)₂ and C₃₋₆-cycloalkyl,
wherein alkyl and cycloalkyl are unsubstituted or substituted with 1 to 3 substituents independently selected from the group consisting of halogen, C₁₋₃-alkyl, OH, CN, oxo and OS(O)₂CH₃;
R¹ is hydrogen or C₁₋₆-alkyl;
R² is independently selected from the group consisting of hydrogen, C₁₋₆-alkyl, halo-C₁₋₆-alkyl and hydroxy-C₁₋₆-alkyl;
Y is O or S;
L¹ is —O—, —S—, —S(O)—, —S(O)₂—or —S(O)(=NR³)-;
R³ is hydrogen or C₁₋₆-alkyl;
C is a bond, C₁₋₆-alkylene, C₂₋₆-alkenylene, C₂₋₆-alkynylene, C₀₋₆-alkylene-C₃₋₆-cycloalkylene, C₀₋₆-alkylene-3 to 10-membered-heterocycloalkylene, C₀₋₆-alkylene-C₆₋₁₀-aryl, or C₀₋₆-alkylene-5-to 14-membered mono- or bicyclic heteroaryl,
   wherein alkylene, alkenylene and alkynylene are unsubstituted or substituted with 1 to 3 substituents independently selected from C₁₋₆-alkyl, halo-C₁₋₆-alkyl, halogen, OH, OR², N(R²)₂, C₃₋₆-cycloalkyl, and 3- to 8-membered heterocycloalkyl; and
L²-D is selected from

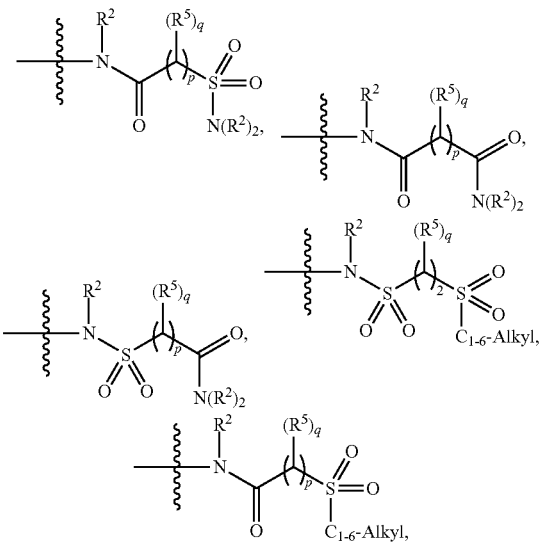

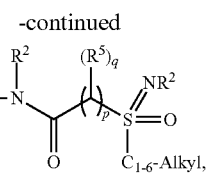

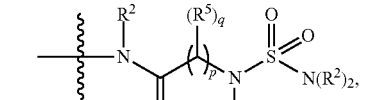

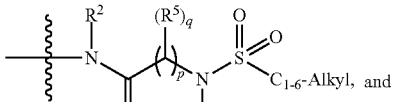

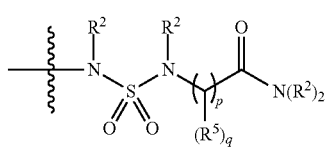

wherein
   R⁵ is independently selected from the group consisting of halogen, C1-6-alkyl, halo-C1-6-alkyl, or two R⁵ form a 3- to 6-membered cycloalkyl ring;
   p is 1 or 2; and
   q is 0, 1, 2 or 3.

2. The compound according to claim 1, or an enantiomer, diastereomer, tautomer, or pharmaceutically acceptable salt thereof, wherein Y is O.

3. The compound according to claim 1, or an enantiomer, diastereomer, tautomer, or pharmaceutically acceptable salt thereof, wherein A is phenyl, unsubstituted or substituted with 1 to 4 substituents independently selected from the group consisting of F, Cl, Br, CH₃, CH₂CH₃, CH₂F, CHF₂, CF₃, OCH₃, OCH₂F, OCHF₂, OCF₃, CH₂OH and C₃₋₆-cycloalkyl which is unsubstituted or substituted with halogen or C₁₋₃-alkyl.

4. The compound according to claim 1, or an enantiomer, diastereomer, tautomer, or pharmaceutically acceptable salt thereof, wherein A is selected from

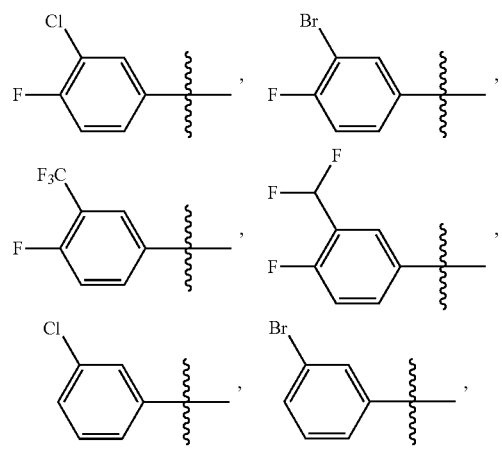

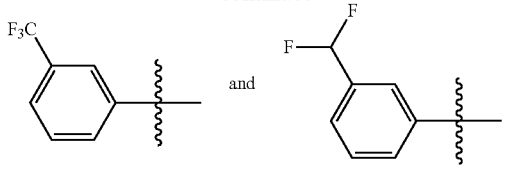

5. The compound according to claim 1, or an enantiomer, diastereomer, tautomer, or pharmaceutically acceptable salt thereof, wherein L²-D is selected from

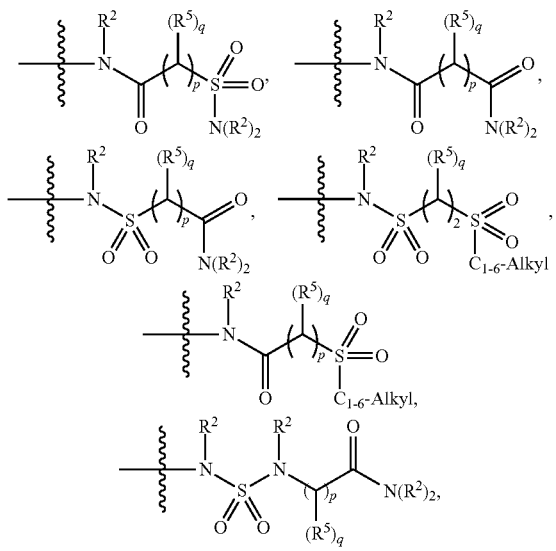

wherein
R⁵ is independently selected from the group consisting of halogen,
C$_{1-6}$-alkyl, halo-C$_{1-6}$-alkyl, or two R⁵ form a 3- to 6-membered cycloalkyl ring;
p is 1 or 2; and
q is 0, 1, 2 or 3.

6. The compound according to claim 1, or an enantiomer, diastereomer, tautomer, or pharmaceutically acceptable salt thereof, wherein –L²-D is selected from

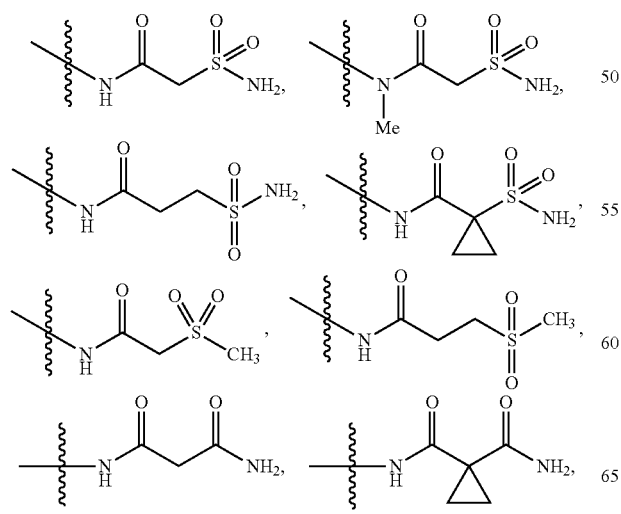

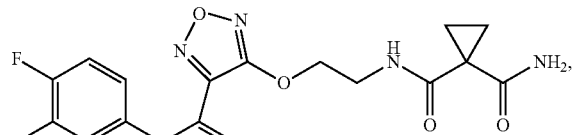

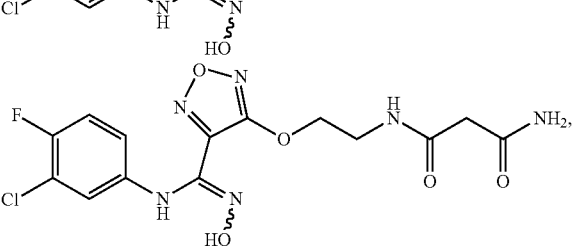

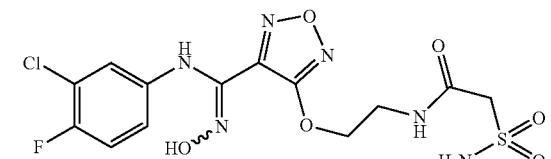

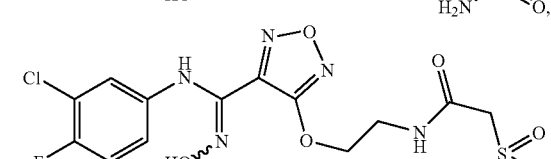

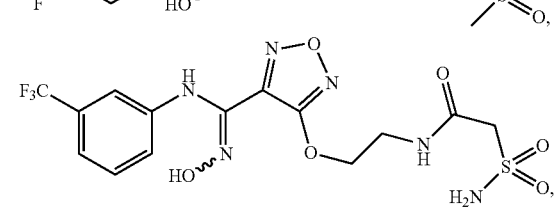

7. The compound according to claim 1 selected from the group consisting of

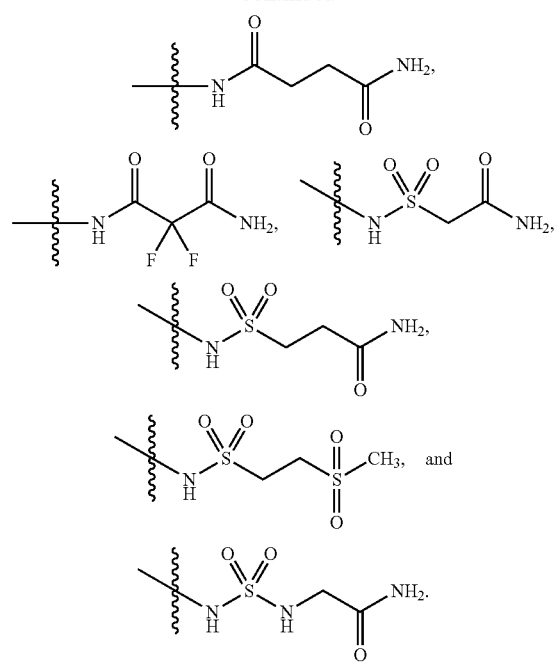

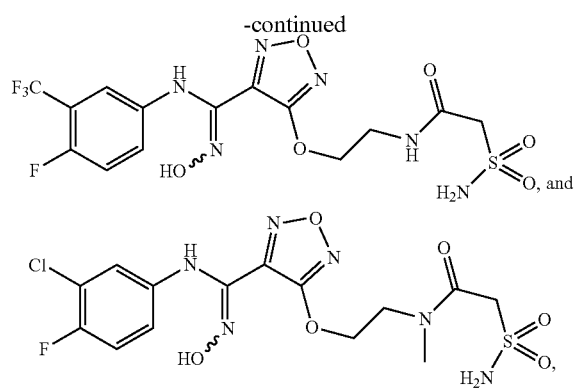
and
an enantiomer, diastereomer, tautomer, or pharmaceutically acceptable salt thereof.
8. The compound according to claim 1 selected from the group consisting of
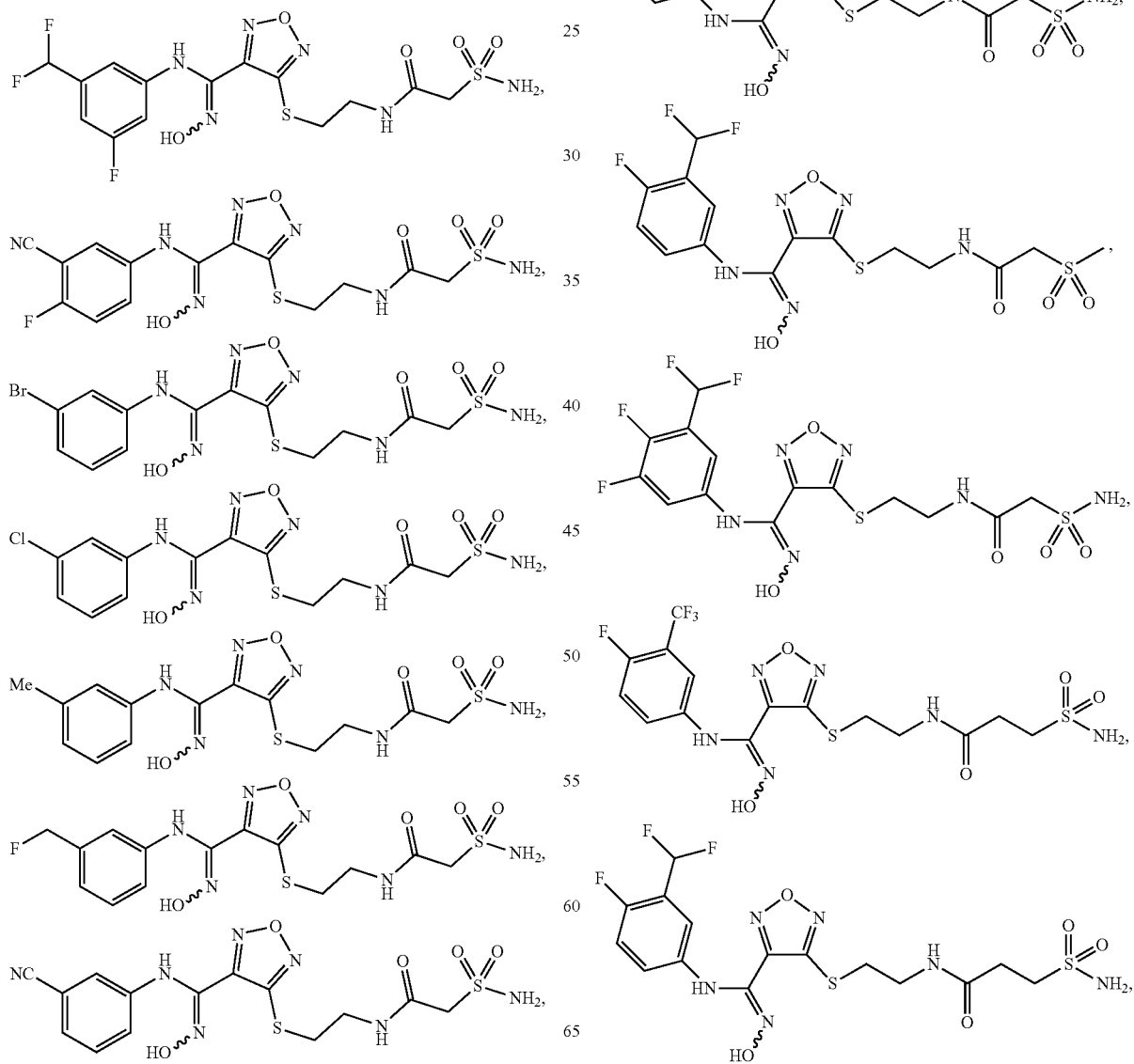
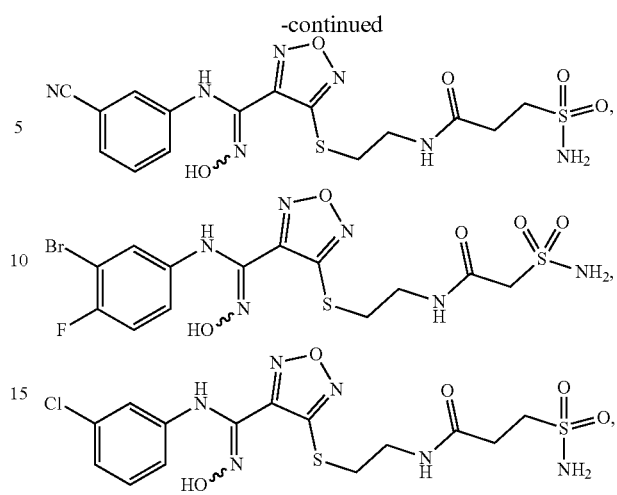

223

-continued

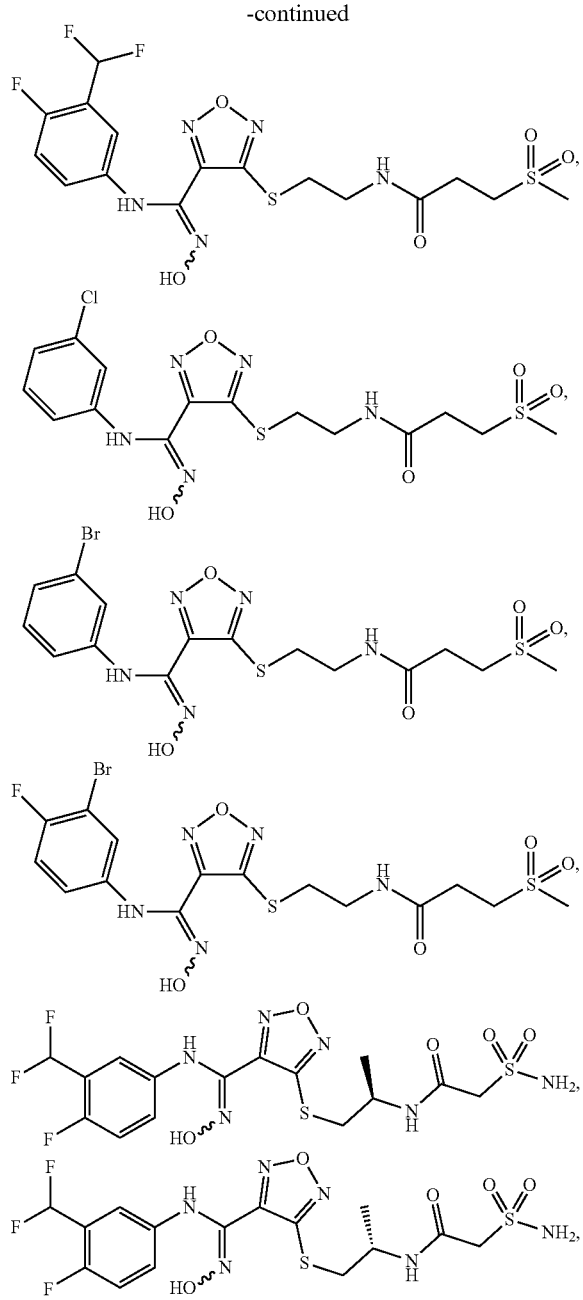

and an enantiomer, diastereomer, tautomer, or pharmaceutically acceptable salt thereof.

9. The compound according to claim 1 selected from the group consisting of

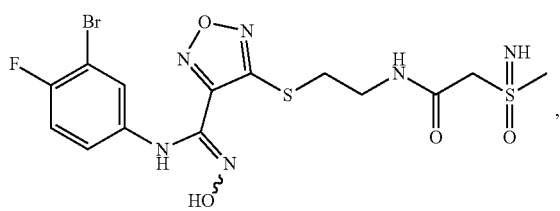

224

-continued

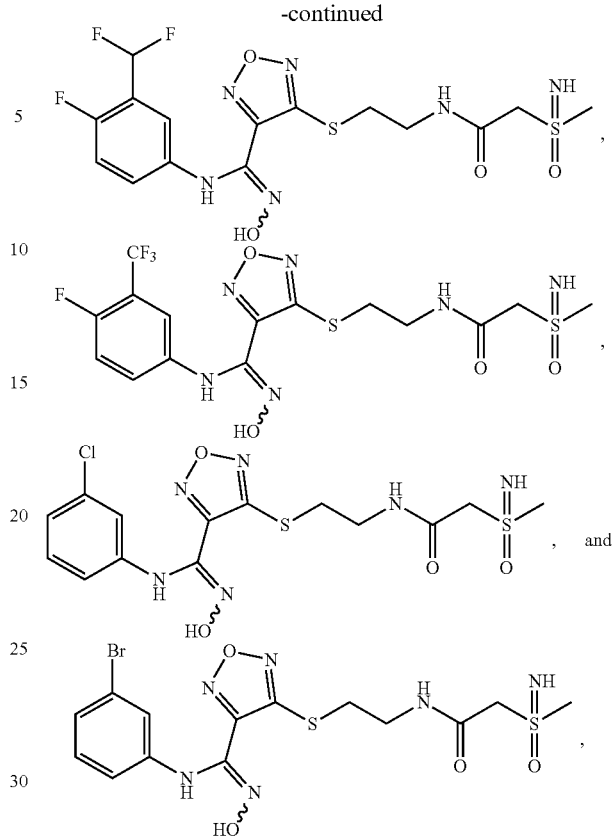

and an enantiomer, diastereomer, tautomer, or pharmaceutically acceptable salt thereof.

10. A method for treatment of a disease or condition mediated by indoleamine 2,3-dioxygenase, comprising administering to a subject in need thereof a therapeutically effective amount of a compound of claim 1, or an enantiomer, diastereomer, tautomer, or pharmaceutically acceptable salt thereof.

11. The method according to claim 10, wherein the disease or condition is selected from the group consisting of cancer, viral and bacterial infections, depression, neurodegenerative diseases, age-related cataracts, asthma, rheumatoid arthritis, multiple sclerosis, inflammatory bowel disease, psoriasis, and systemic lupus erythematosus.

12. The method according to claim 11, wherein the disease or condition is cancer.

13. The method according to claim 11, wherein the compound is administered with one or more therapeutic agents for cancer selected from the group consisting of PD-1 agent, PD-L1 agent, CTLA-4 agent, chemotherapeutic agent, anticancer vaccine, and cytokine therapy, or wherein the compound is administered under irradiation therapy.

14. A pharmaceutical composition comprising a compound according to claim 1, or an enantiomer, diastereomer, tautomer, or pharmaceutically acceptable salt thereof, and one or more pharmaceutically acceptable excipients.

15. The method of claim 11, wherein the viral infection is HIV infection.

16. The method of claim 11, wherein the neurodegenerative disease is Alzheimer's disease or Huntington's disease.

17. A method for inhibiting indoleamine 2,3-dioxygenase in a subject, comprising administering to a subject in need thereof an effective amount of a compound of claim 1, or an enantiomer, diastereomer, tautomer, or pharmaceutically acceptable salt thereof.

* * * * *

UNITED STATES PATENT AND TRADEMARK OFFICE
CERTIFICATE OF CORRECTION

PATENT NO. : 11,078,168 B2
APPLICATION NO. : 16/346505
DATED : August 3, 2021
INVENTOR(S) : C. Steeneck et al.

It is certified that error appears in the above-identified patent and that said Letters Patent is hereby corrected as shown below:

In the Claims

| Column | Line | |
|---|---|---|
| 217 | 12 | Claim 1, change "S(0)" to -- S(O) -- |
| 217 | 28 | Claim 1, change "S(O)$_2$-or" to -- S(O)$_2$- or -- |
| 219 | 12 | Claim 5, change "wherein L" to -- wherein –L -- |

Signed and Sealed this
Eleventh Day of July, 2023

Katherine Kelly Vidal
*Director of the United States Patent and Trademark Office*